US006225054B1

(12) United States Patent
Frudakis et al.

(10) Patent No.: US 6,225,054 B1
(45) Date of Patent: May 1, 2001

(54) COMPOSITIONS AND METHODS FOR THE TREATMENT AND DIAGNOSIS OF BREAST CANCER

(75) Inventors: Tony N. Frudakis, Seattle; John M. Smith, Everett; Steven G. Reed, Bellevue, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 08/991,789

(22) Filed: Dec. 11, 1997

Related U.S. Application Data

(63) Continuation-in-part of application No. 08/838,762, filed as application No. PCT/US97/00485 on Jan. 10, 1997, now abandoned, and a continuation-in-part of application No. 08/700,014, filed on Aug. 20, 1996, now abandoned, which is a continuation-in-part of application No. 08/585,392, filed on Jan. 1, 1996, now abandoned.

(51) Int. Cl.$^7$ .............................. C12Q 1/68; C12N 15/00; C12N 5/00; C07H 21/04
(52) U.S. Cl. ........................... 435/6; 435/320.1; 435/325; 536/23.5; 536/24.31; 536/24.33
(58) Field of Search ................................ 536/23.5, 24.31, 536/24.33; 435/325, 320.1, 6; 514/44

(56) References Cited

U.S. PATENT DOCUMENTS

| 5,231,012 | 7/1993 | Mosmann et al. | 435/69.52 |
|---|---|---|---|
| 5,428,145 | 6/1995 | Okamoto et al. | 536/23.72 |
| 5,516,650 | 5/1996 | Foster et al. | 435/68.1 |
| 5,523,225 | * 6/1996 | Kraus | 435/358 |
| 5,585,270 | 12/1996 | Grotendorst et al. | 435/252.3 |

FOREIGN PATENT DOCUMENTS

| 2 273 099 | 6/1994 | (GB) . |
|---|---|---|
| WO 91/02062 | 2/1991 | (WO) . |
| WO 95/10777 | 4/1995 | (WO) . |
| WO 95/19369 | 7/1995 | (WO) . |
| WO 95/32311 | 11/1995 | (WO) . |
| WO 96/38463 | 12/1996 | (WO) . |
| WO 97/06256 | 2/1997 | (WO) . |
| WO 97/25426 | 7/1997 | (WO) . |
| WO 97/25431 | 7/1997 | (WO) . |
| WO 98/45328 | 10/1998 | (WO) . |

OTHER PUBLICATIONS

JC Venter et al Trends in Biotechnology 10:8–11, 1992.*
DS Charnock–Jones et al J Biotechnology 35:205–215, 1994.*
Anderson et al., "Sequence and organization of the human mitochondrial genome," *Nature* 290:457–465, 1981.
Bauer et al., "Identification of differentially expressed mRNA species by an improved display technique (DDRT–PCR)," *Nucleic Acids Research* 21(18):4272–4280, 1993.
Bratthauer et al., "Expression of Line–1 Retrotransposons in Human Breast Cancer," *Cancer* 73:2333–2336, 1994.
Byrne et al., "A Screening Method to Identify Genes Commonly Overexpressed in Carcinomas and the Identification of a Novel Complementary DNA Sequence," *Cancer Research* 55:2869–2903, 1995.
Chen and Sager, "Differential Expression of Human Tissue Factor in Normal Mammary Epithelial Cells and in Carcinomas," *Molecular Medicine* 1(2):153–160, 1995.
Cordonnier et al., "Isolation of Novel Human Endogenous Retrovirus–Like Elements with Foamy Virus–Related pol Sequence," *Journal of Virology* 69(9):5890–5897, 1995.
Databank Genebank Accession No. Z34289, 1995.
Ezzell, "Cancer "Vaccines": An Idea Whose Time Has Come?," *The Journal of NIH Research* 7:46–49, 1995.
Gura, "Systems for Identifying New Drugs Are Often Faulty," *Science* 278:1041–1042, 1997.
Haltmeier et al., "Identification of S71–Related Human Endogenous Retroviral Sequences with Full–Length pol Genes," *Virology* 209:550–560, 1995.
Keydar et al., "Properties of retrovirus–like particles produced by a human breast carcinoma cell line: Immunological relationship with mouse mammary tumor virus proteins," *Proc. Natl. Acad. Sci.* USA 81:4188–92, 1984.
Leib–Mösch and Seifarth, "Evolution and Biological Significance Human Retroelements," *Virus Genes* 11(2/3):133–145, 1996.
Leib–Mösch et al., "Endogenous Retroviral Elements in Human DNA," *Cancer Research* 50:5636s–5642s, 1994.
Leib–Mösch et al., "Genomic Distribution and Transcription of Solitary HERV–K LTRs," *Genomics* 18:261–269, 1993.
Liang et al., "Differential Display of Eukaryotic Messenger RNA by Means of the Polymerase Chain Reaction," *Science* 257:967–971, 1992.
Wang et al., "Detection of Mammary Tumor Virus ENV Gene–like Sequences in Human Breast Cancer," *Cancer Research* 55:5173–5179, 1995.
Watson and Fleming, "Isolation of Differentially Expressed Sequence Tags from Human Breast Cancer," *Cancer Research* 54(17):4598–4602, 1994.
Werner et al., "S71 Is a Phylogenetically Distinct Human Endogenous Retroviral Element with Structural and Sequence Homology to Simian Sarcoma Virus (SSV)," *Virology* 174:225–238, 1990.

(List continued on next page.)

*Primary Examiner*—Scott D. Priebe
(74) *Attorney, Agent, or Firm*—Seed Intellectual Property Law Group PLLC

(57) ABSTRACT

Compositions and methods for the detection and therapy of breast cancer are disclosed. The compounds provided include nucleotide sequences that are preferentially expressed in breast tumor tissue, as well as polypeptides encoded by such nucleotide sequences. Vaccines and pharmaceutical compositions comprising such compounds are also provided and may be used, for example, for the prevention and treatment of breast cancer. The polypeptides may also be used for the production of antibodies, which are useful for diagnosing and monitoring the progression of breast cancer in a patient.

13 Claims, 22 Drawing Sheets

OTHER PUBLICATIONS

Critical Synergy: The Biotechnology Industry and Intellectual Property Protection, Presentations of the Intellectual Property Committee of the Biotechnology Industry Organization at the Oct. 17, 1994, Hearing of the U.S. Patent and Trademark Office, San Diego, CA, published by the Biotechnology Industry Organization, Washington, D.C., pp. 75, 100–107.
M Bernard et al (1988) J Biol Chem 263: 17159–17166.*
H Yoshioka et al (1990) J BIol Chem 265: 6423–6426.*
Hillier et al (1995) GenBank Accession No. R55637.*
Hillier et al (1995) GenBank Accession No. R60426.*
Hillier et al (1995) GenBank Accession No. R19532.*
Hillier et al (1995) GenBank Accession No. T83348.*
Hillier et al (1995) Genbank Accession No. R35308.*
Hillier et al (1995) GenBank Accession No. H80165.*
Adams et al (1993) GenBank Accession No. Q60347.*
Frank et al (1994) GenBank Accession No. Q70049.*
Adams et al (1993) GenBank Accession No. Q61250.*
Chai et al (1994) GenBank Accession No. U03644.*
Matsubara et al (1995) GenBank Accession No. T24124.*

* cited by examiner-

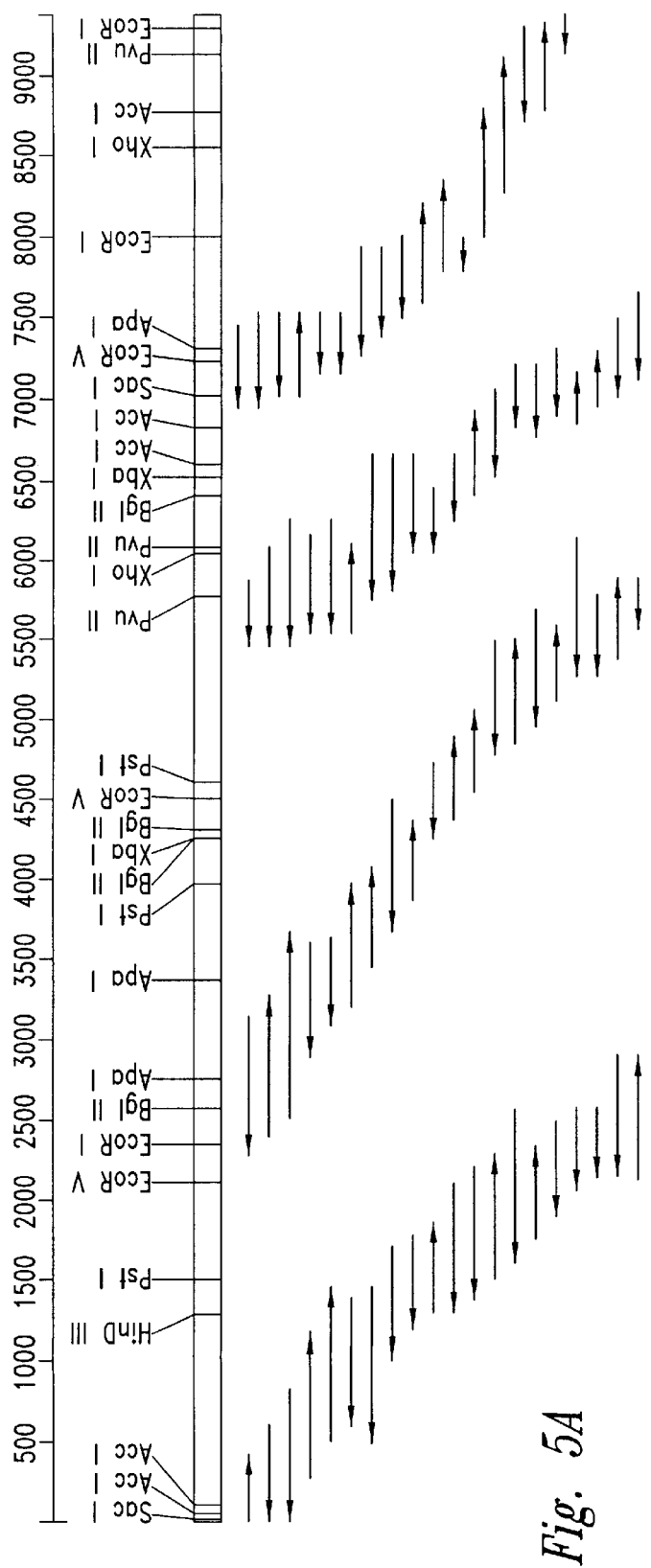
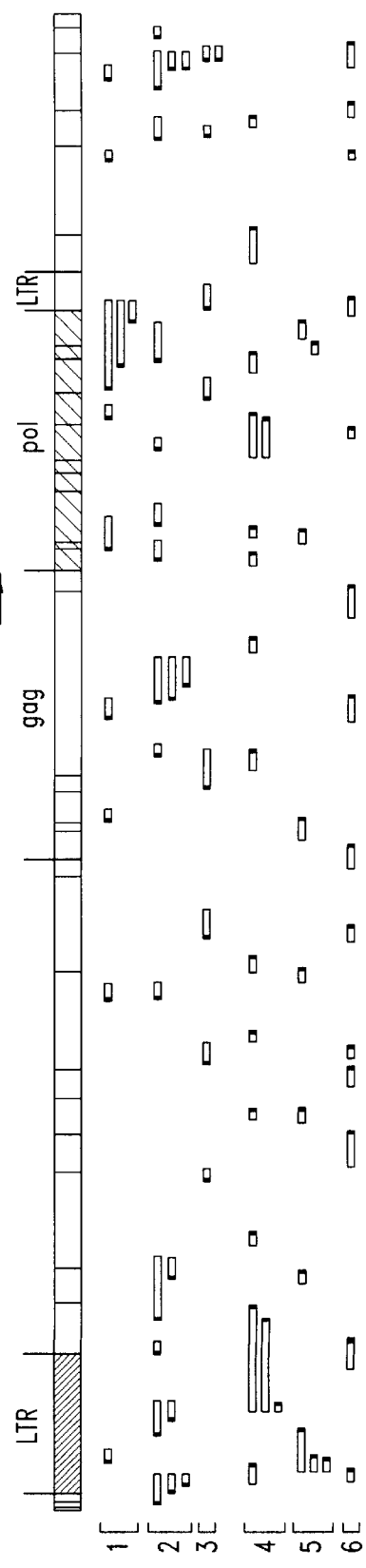
Fig. 5A
Fig. 5B

NUCLEOTIDE SEQUENCE OF THE REPRESENTATIVE
BREAST-TUMOR SPECIFIC cDNA B18Ag1

| | | | | | | | | | | | | | | | | |
|---|---|---|---|---|---|---|---|---|---|---|---|---|---|---|---|---|
| TTA | GAG | ACC | CAA | TTG | GGA | CCT | AAT | TGG | GAC | CCA | AAT | TTC | TCA | AGT | GGA | 48 |
| Leu | Glu | Thr | Gln | Leu | Gly | Pro | Asn | Trp | Asp | Pro | Asn | Phe | Ser | Ser | Gly | |
| 1 | | | | 5 | | | | 10 | | | | | | 15 | | |

| | | | | | | | | | | | | | | | | |
|---|---|---|---|---|---|---|---|---|---|---|---|---|---|---|---|---|
| GGG | AGA | ACT | TTT | GAC | GAT | TTC | CAC | CGG | TAT | CTC | CTC | GTG | GGT | ATT | CAG | 96 |
| Gly | Arg | Thr | Phe | Asp | Asp | Phe | His | Arg | Tyr | Leu | Leu | Val | Gly | Ile | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| GGA | GCT | GCC | CAG | AAA | CCT | ATA | AAC | TTG | TCT | AAG | GCG | ATT | GAA | GTC | GTC | 144 |
| Gly | Ala | Ala | Gln | Lys | Pro | Ile | Asn | Leu | Ser | Lys | Ala | Ile | Glu | Val | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| CAG | GGG | CAT | GAT | GAG | TCA | CCA | GGA | GTG | TTT | TTA | GAG | CAC | CTC | CAG | GAG | 192 |
| Gln | Gly | His | Asp | Glu | Ser | Pro | Gly | Val | Phe | Leu | Glu | His | Leu | Gln | Glu | |
| | 50 | | | | | 55 | | | | | | 60 | | | | |

| | | | | | | | | | | | | | | | | |
|---|---|---|---|---|---|---|---|---|---|---|---|---|---|---|---|---|
| GCT | TAT | CGG | ATT | TAC | ACC | CCT | TTT | GAC | CTG | GCA | GCC | CCC | GAA | AAT | AGC | 240 |
| Ala | Tyr | Arg | Ile | Tyr | Thr | Pro | Phe | Asp | Leu | Ala | Ala | Pro | Glu | Asn | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CAT | GCT | CTT | AAT | TTG | GCA | TTT | GTG | GCT | CAG | GCA | GCC | CCA | GAT | AGT | AAA | 288 |
| His | Ala | Leu | Asn | Leu | Ala | Phe | Val | Ala | Gln | Ala | Ala | Pro | Asp | Ser | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| AGG | AAA | CTC | CAA | AAA | CTA | GAG | GGA | TTT | TGC | TGG | AAT | GAA | TAC | CAG | TCA | 336 |
| Arg | Lys | Leu | Gln | Lys | Leu | Glu | Gly | Phe | Cys | Trp | Asn | Glu | Tyr | Gln | Ser | |
| | | | 100 | | | | | 105 | | | | | 110 | | | |

| | | | | | | | |
|---|---|---|---|---|---|---|---|
| GCT | TTT | AGA | GAT | AGC | CTA | AAA | GGT | TTT | 363 |
| Ala | Phe | Arg | Asp | Ser | Leu | Lys | Gly | Phe | |
| | | 115 | | | | | 120 | | |

*Fig. 6*

NUCLEOTIDE SEQUENCE OF THE REPRESENTATIVE
BREAST-TUMOR SPECIFIC cDNA B17Ag1

| | | | | | |
|---|---|---|---|---|---|
| GC | TGGGCACAGT | GGCTCATACC | TGTAATCCTG | ACCGTTTCAG | AGGCTCAGGT | 60 |
| CG | CTTGAGCCCA | AGATTTCAAG | ACTAGTCTGG | GTAACATAGT | GAGACCCTAT | 120 |
| AA | AAATAAAAAA | ATGAGCCTGG | TGTAGTGGCA | CACACCAGCT | GAGGAGGGAG | 180 |
| CT | AGGAGA | | | | | 196 |

*Fig. 7*

NUCLEOTIDE SEQUENCE OF THE REPRESENTATIVE
BREAST-TUMOR SPECIFIC cDNA B17Ag2

```
GC TTGGGGGCTC TGACTAGAAA TTCAAGGAAC CTGGGATTCA AGTCCAACTG      60
AC TTACACTGTG GNCTCCAATA AACTGCTTCT TTCCTATTCC CTCTCTATTA     120
AA GGAAAACGAT GTCTGTGTAT AGCCAAGTCA GNTATCCTAA AAGGAGATAC     180
AT TAAATATCAG AATGTAAAAC CTGGGAACCA GGTTCCCAGC CTGGGATTAA     240
CA AGAAGACTGA ACAGTACTAC TGTGAAAAGC CCGAAGNGGC AATATGTTCA     300
TT GAAGGATGGC TGGGAGAATG AATGCTCTGT CCCCCAGTCC CAAGCTCACT     360
CT CCTTTATAGC CTAGGAGA                                        388
```

*Fig. 8*

NUCLEOTIDE SEQUENCE OF THE REPRESENTATIVE
BREAST-TUMOR SPECIFIC cDNA B13Ag2a

```
GC CTATAATCAT GTTCTCATT ATTTTCACAT TTTATTAACC AATTTCTGTT      60

AA AATATGAGGG AAATATATGA AACAGGGAGG CAATGTTCAG ATAATTGATC    120

TG ATTTCTACAT CAGATGCTCT TTCCTTTCCT GTTTATTTCC TTTTTATTTC    180

GG TCGAATGTAA TAGCTTTGTT TCAAGAGAGA GTTTTGGCAG TTTCTGTAGC    240

CT GCTCATGTCT CCAGGCATCT ATTTGCACTT TAGGAGGTGT CGTGGGAGAC    300

CT ATTTTTTCCA TATTTGGGCA ACTACTA                              337
```

*Fig. 9*

NUCLEOTIDE SEQUENCE OF THE REPRESENTATIVE
BREAST-TUMOR SPECIFIC cDNA B13Ag1b

| | | | | | |
|---|---|---|---|---|---|
| GC | CATACAGTGC | CTTTCCATTT | ATTTAACCCC | CACCTGAACG | GCATAAACTG | 60 |
| GC | TGGTGTTTTT | TACTGTAAAC | AATAAGGAGA | CTTTGCTCTT | CATTTAAACC | 120 |
| AT | TTCATATTTT | ACGCTCGAGG | GTTTTTACCG | GTTCCTTTTT | ACACTCCTTA | 180 |
| TT | TAAGTCGTTT | GGAACAAGAT | ATTTTTTCTT | TCCTGGCAGC | TTTTAACATT | 240 |
| TT | TGTGTCTGGG | GGACTGCTGG | TCACTGTTTC | TCACAGTTGC | AAATCAAGGC | 300 |
| CC | AAGAAAAAAA | AATTTTTTTG | TTTTATTTGA | AACTGGACCG | GATAAACGGT | 360 |
| CG | GCTGCTGTAT | ATAGTTTTAA | ATGGTTTATT | GCACCTCCTT | AAGTTGCACT | 420 |
| GG | GGGGNTTTTG | NATAGAAAGT | NTTTANTCAC | ANAGTCACAG | GGACTTTTNT | 480 |
| NA | CTGAGCTAAA | AAGGGCTGNT | TTTCGGGTGG | GGGCAGATGA | AGGCTCACAG | 540 |
| TC | TCTTAGAGGG | GGGAACTNCT | A | | | 571 |

*Fig. 10*

NUCLEOTIDE SEQUENCE OF THE REPRESENTATIVE
BREAST-TUMOR SPECIFIC cDNA B13Ag1a

```
TA ATAACTTAAA TATATTTTGA TCACCCACTG GGGTGATAAG ACAATAGATA      60

TT TCCAAAAAGC ATAAAACCAA AGTATCATAC CAAACCAAAT TCATACTGCT     120

CC GCACTGAAAC TTCACCTTCT AACTGTCTAC CTAACCAAAT TCTACCCTTC     180

GG TGCGTGCTCA CTACTCTTTT TTTTTTTTT TTTNTTTTGG AGATGGAGTC      240

CA GCCCAGGGGT GGAGTACAAT GGCACAACCT CAGCTCACTG NAACCTCCGC     300

TT CATGAGATTC TCCTGNTTCA GCCTTCCCAG TAGCTGGGAC TACAGGTGTG     360

TG CCTGGNTAAT CTTTTTTNGT TTTNGGGTAG AGATGGGGGT TTTACATGTT     420

TG GTNTCGAACT CCTGACCTCA AGTGATCCAC CCACCTCAGG CTCCCAAAGT     480

TA CAGACATGAG CCACTGNGCC CAGNCCTGGT GCATGCTCAC TTCTCTAGGC     540

NUCLEOTIDE SEQUENCE OF THE REPRESENTATIVE
BREAST-TUMOR SPECIFIC cDNA B11Ag1

| | | | | | |
|---|---|---|---|---|---|
| TG | CACATGCAGA | ATATTCTATC | GGTACTTCAG | CTATTACTCA | TTTTGATGGC | 60 |
| AG | CCTATCCTCA | AGATGAGTAT | TTAGAAAGAA | TTGATTTAGC | GATAGACCAA | 120 |
| GC | ACTCTGACTA | CACGAAATTG | TTCAGATGTG | ATGGATTTAT | GACAGTTGAT | 180 |
| GA | GATTATTAAG | TGATTATTTT | AAAGGGAATC | CATTAATTCC | AGAATATCTT | 240 |
| TC | AAGATGATAT | AGAAATAGAA | CAGAAAGAGA | CTACAAATGA | AGATGTATCA | 300 |
| TA | TTGAAGAGCC | TATAGTAGAA | AATGAATTAG | CTGCATTTAT | TAGCCTTACA | 360 |
| TT | TTCCTGATGA | ATCTTATATT | CAGCCATCGA | CATAGCATTA | CCTGATGGGC | 420 |
| GA | ATAATAGAAA | CTGGGTGCGG | GGCTATTGAT | GAATTCATCC | NCAGTAAATT | 480 |
| AC | AAAATATAAC | TCGATTGCAT | TTGGATGATG | GAATACTAAA | TCTGGCAAAA | 540 |
| GG | AGCTACTAGT | AACCTCTCTT | TTTGAGATGC | AAAATTTTCT | TTTAGGGTTT | 600 |
| CT | ACTTTACGGA | TATTGGAGCA | TAACGGGA | | | 638 |

*Fig. 12*

NUCLEOTIDE SEQUENCE OF THE REPRESENTATIVE
BREAST-TUMOR SPECIFIC cDNA B3CA3c

```
ACTGATGGAT GTCGCCGGAG GCGAGGGGCC TTATCTGATG CTCGGCTGCC TGTTCGTGAT    60
GTGCGCGGCG ATTGGGCTGT TTATCTCAAA CACCGCCACG GCGGTGCTGA TGGCGCCTAT   120
TGCCTTAGCG GCGGCGAAGT CAATGGGCGT CTCACCCTAT CCTTTTGCCA TGGTGGTGGC   180
GATGGCGGCT TCGGCGGCGT TTATGACCCC GGTCTCCTCG CCGGTTAACA CCCTGGTGCT   240
TGGCCCTGGC AAGTACTCAT TTAGCGATTT TGTCAAAATA GGCGTG                  286
```

*Fig. 13*

NUCLEOTIDE SEQUENCE OF THE REPRESENTATIVE
BREAST-TUMOR SPECIFIC cDNA B9CG1

```
AG CAGCCCCTTC TTCTCAATTT CATCTGTCAC TACCCTGGTG TAGTATCTCA      60

CA TTTTTATAGC CTCCTCCCTG GTCTGTCTTT TGATTTTCCT GCCTGTAATC     120

AC ATAACTGCAA GTAAACATTT CTAAAGTGTG GTTATGCTCA TGTCACTCCT     180

AA ATAGTTTCCA TTACCGTCTT AATAAAATTC GGATTTGTTC TTTNCTATTN     240

CA CCTATGACCG AA                                              262
```

Fig. 14

NUCLEOTIDE SEQUENCE OF THE REPRESENTATIVE
BREAST-TUMOR SPECIFIC cDNA B9CG3

| | | | | | |
|---|---|---|---|---|---|
| AG | CAAAGCCAGT | GGTTTGAGCT | CTCTACTGTG | TAAACTCCTA | AACCAAGGCC | 60 |
| TA | AATGGTGGCA | GGATTTTTAT | TATAAACATG | TACCCATGCA | AATTTCCTAT | 120 |
| GA | TATATTCTTC | TACATTTAAA | CAATAAAAAT | AATCTATTTT | TAAAAGCCTA | 180 |
| AG | TTAGGTAAGA | GTGTTTAATG | AGAGGGTATA | AGGTATAAAT | CACCAGTCAA | 240 |
| TG | CCTATGACCG | A | | | | 261 |

*Fig. 15*

NUCLEOTIDE SEQUENCE OF THE REPRESENTATIVE
BREAST-TUMOR SPECIFIC cDNA B2CA2

| | | | | | |
|---|---|---|---|---|---|
| GG | GCATGGACGC | AGACGCCTGA | CGTTTGGCTG | AAAATCTTTC | ATTGATTCGT | 60 |
| AT | AGGAAAATTC | CCAAAGAGGG | AATGTCCTGT | TGCTCGCCAG | TTTTTNTGTT | 120 |
| GG | ANAAGGCAAN | GAGCTCTTCA | GACTATTGGN | ATTNTCGTTC | GGTCTTCTGC | 180 |
| CG | NCTTGCNANG | ATCTTCAT | | | | 208 |

Fig. 16

NUCLEOTIDE SEQUENCE OF THE REPRESENTATIVE
BREAST-TUMOR SPECIFIC cDNA B3CA1

| | |
|---|---|
| GG GCATGGACGC AGACGCCTGA CGTTTGGCTG AAAATCTTTC ATTGATTCGT | 60 |
| AT AGGAAAATTC CCAAAGAGGG AATGTCCTGT TGCTCGCCAG TTTTTNTGTT | 120 |
| GG ANAAGGCAAN GAGCTCTTCA GACTATTGGN ATTNTCGTTC GGTCTTCTGC | 180 |
| CG NCTTGCNANG ATCTTCAT | 208 |

*Fig. 17*

NUCLEOTIDE SEQUENCE OF THE REPRESENTATIVE
BREAST-TUMOR SPECIFIC cDNA B3CA2

| | | | | | |
|---|---|---|---|---|---|
| GG | GCATGGACGC | AGACGCCTGA | CGTTTGGCTG | AAAATCTTTC | ATTGATTCGT | 60 |
| AT | AGGAAAATTC | CCAAAGAGGG | AATGTCCTGT | TGCTCGCCAG | TTTTTNTGTT | 120 |
| GG | ANAAGGCAAN | GAGCTCTTCA | GACTATTGGN | ATTNTCGTTC | GGTCTTCTGC | 180 |
| CG | NCTTGCNANG | ATCTTCAT | | | | 208 |

Fig. 18

NUCLEOTIDE SEQUENCE OF THE REPRESENTATIVE
BREAST-TUMOR SPECIFIC cDNA B3CA3

| | | | | | |
|---|---|---|---|---|---|
| AG | GGAGCAAGGA | GAAGGCATGG | AGAGGCTCAN | GCTGGTCCTG | GCCTACGACT | 60 |
| CT | GTCGCCGGGG | ATGGTGGAGA | ACTGAAGCGG | GACCTCCTCG | AGGTCCTCCG | 120 |
| TC | NCCGTCCAGG | AGGAGGGTCT | TTCCGTGGTC | TNGGAGGAGC | GGGGGGAGAA | 180 |
| TC | ATGGTCNACA | TCCC | | | | 204 |

*Fig. 19*

NUCLEOTIDE SEQUENCE OF THE REPRESENTATIVE
BREAST-TUMOR SPECIFIC cDNA B4CA1

```
TC AGGAGCGGGT AGAGTGGCAC CATTGAGGGG ATATTCAAAA ATATTATTTT        60

TG ATAGTTGCTG AGTTTTTCTT TGACCCATGA GTTATATTGG AGTTTATTTT       120

CC AATCGCATGG ACATGTTAGA CTTATTTTCT GTTAATGATT NCTATTTTTA       180

GA TTTGAGAAAT TGGTTNTTAT TATATCAATT TTTGGTATTT GTTGAGTTTG       240

GC TTAGTATGTG ACCA                                              264
```

*Fig. 20*

# COMPOSITIONS AND METHODS FOR THE TREATMENT AND DIAGNOSIS OF BREAST CANCER

CROSS REFERENCE TO RELATED APPLICATIONS

This application is a continuation-in-part of U.S. patent application Ser. No. 08/838,762, filed Apr. 9, 1997, now abandoned, which claims priority from International Patent Application No. PCT/US97/00485, filed Jan. 10, 1997, and is a continuation-in-part of U.S. patent application Ser. No. 08/700,014, now abandoned, filed Aug. 20, 1996, which is a continuation-in-part of U.S. patent application Ser. No. 08/585,392, filed Jan. 1, 1996, now abandoned.

TECHNICAL FIELD

The present invention relates generally to the detection and therapy of breast cancer. The invention is more specifically related to nucleotide sequences that are preferentially expressed in breast tumor tissue and to polypeptides encoded by such nucleotide sequences. The nucleotide sequences and polypeptides may be used in vaccines and pharmaceutical compositions for the prevention and treatment of breast cancer. The polypeptides may also be used for the production of compounds, such as antibodies, useful for diagnosing and monitoring the progression of breast cancer in a patient.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

Briefly stated, the subject invention provides compositions and methods for the diagnosis and therapy of breast cancer. In one aspect, isolated DNA molecules are provided, comprising (a) a nucleotide sequence preferentially expressed in breast cancer tissue, relative to normal tissue; (b) a variant of such a sequence that contains one or more nucleotide substitutions, deletions, insertions and/or modifications at no more than 20% (preferably no more than 5%) of the nucleotide positions, such that the antigenic and/or immunogenic properties of the polypeptide encoded by the nucleotide sequence are retained; or (c) a nucleotide sequence encoding an epitope of a polypeptide encoded by at least one of the above sequences. In one embodiment, the isolated DNA molecule comprises a human endogenous retroviral sequence recited in SEQ ID NO: 1. In other embodiments, the isolated DNA molecule comprises a nucleotide sequence recited in any one of SEQ ID NO: 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284 288 and 291.

In related embodiments, the isolated DNA molecule encodes an epitope of a polypeptide, wherein the polypeptide is encoded by a nucleotide sequence that: (a) hybridizes to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284 288 and 291 under stringent conditions; and (b) is at least 80% identical to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284 288 and 291; and wherein RNA corresponding to said nucleotide sequence is expressed at a greater level in human breast tumor tissue than in normal breast tissue.

In another embodiment, the present invention provides an isolated DNA molecule encoding an epitope of a polypeptide, the polypeptide being encoded by: (a) a nucleotide sequence transcribed from the sequence of SEQ ID NO: 141; or (b) a variant of said nucleotide sequence that contains one or more nucleotide substitutions, deletions, insertions and/or modifications at no more than 20% of the nucleotide positions, such that the antigenic and/or immunogenic properties of the polypeptide encoded by the nucleotide sequence are retained. Isolated DNA and RNA molecules comprising a nucleotide sequence complementary to a DNA molecule as described above are also provided.

In related aspects, the present invention provides recombinant expression vectors comprising a DNA molecule as described above and host cells transformed or transfected with such expression vectors.

In further aspects, polypeptides, comprising an amino acid sequence encoded by a DNA molecule as described above, and monoclonal antibodies that bind to such polypeptides are provided.

In yet another aspect, methods are provided for determining the presence of breast cancer in a patient. In one embodiment, the method comprises detecting, within a biological sample, a polypeptide as described above. In another embodiment, the method comprises detecting, within a biological sample, an RNA molecule encoding a polypeptide as described above. In yet another embodiment, the method comprises (a) intradermally injecting a patient with a polypeptide as described above; and (b) detecting an immune response on the patient's skin and therefrom detecting the presence of breast cancer in the patient. In further embodiments, the present invention provides methods for determining the presence of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In a related aspect, diagnostic kits useful in the determination of breast cancer are provided. The diagnostic kits generally comprise either one or more monoclonal antibodies as described above, or one or more monoclonal antibodies that bind to a polypeptide encoded by a nucleotide sequence selected from the group consisting of sequences provided in SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and a detection reagent.

Within a related aspect, the diagnostic kit comprises a first polymerase chain reaction primer and a second polymerase chain reaction primer, at least one of the primers being specific for an RNA molecule described herein. In one embodiment, at least one of the primers comprises at least about 10 contiguous nucleotides of an RNA molecule as described above, or an RNA molecule encoding a polypeptide encoded by a nucleotide sequence selected from the group consisting of SEQ ID NO: 78–86, 144, 145, 153, 167, 177, 193, 199, 205, 208, 215, 217, 220, 241, 242 246, 248, 249, 252, 256, 267, 270, 274, 277, 279, 282, 283, 285–287, 289 and 290.

Within another related aspect, the diagnostic kit comprises at least one oligonucleotide probe, the probe being specific for a DNA molecule described herein. In one embodiment, the probe comprises at least about 15 contiguous nucleotides of a DNA molecule as described above, or a DNA molecule selected from the group consisting of SEQ ID NO: 78–86, 144, 145, 153, 167, 177, 193, 199, 205, 208, 215, 217, 220, 241, 242 246, 248, 249, 252, 256, 267, 270, 274, 277, 279, 282, 283, 285–287, 289 and 290.

In another related aspect, the present invention provides methods for monitoring the progression of breast cancer in a patient. In one embodiment, the method comprises: (a) detecting an amount, in a biological sample, of a polypeptide as described above at a first point in time; (b) repeating step (a) at a subsequent point in time; and (c) comparing the amounts of polypeptide detected in steps (a) and (b), and therefrom monitoring the progression of breast cancer in the patient. In another embodiment, the method comprises (a) detecting an amount, within a biological sample, of an RNA molecule encoding a polypeptide as described above at a first point in time; (b) repeating step (a) at a subsequent point in time; and (c) comparing the amounts of RNA molecules detected in steps (a) and (b), and therefrom monitoring the progression of breast cancer in the patient. In yet other embodiments, the present invention provides methods for monitoring the progression of breast cancer in a patient as described above wherein the polypeptide is encoded by a nucleotide sequence selected form the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In still other aspects, pharmaceutical compositions, which comprise a polypeptide as described above in combination with a physiologically acceptable carrier, and vaccines, which comprise a polypeptide as described above in combination with an immune response enhancer or adjuvant, are provided. In yet other aspects, the present invention provides pharmaceutical compositions and vaccines comprising a polypeptide encoded by a nucleotide sequence selected from the group consisting of SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and sequences that hybridize thereto under stringent conditions.

In related aspects, the present invention provides methods for inhibiting the development of breast cancer in a patient, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 5A and 5B show the sequencing strategy, genomic organization and predicted open reading frame for the retroviral element containing B18Ag1.

FIG. 6 shows the nucleotide sequence of the representative breast tumor-specific cDNA B18Ag1 (SEQ ID NO: 1 and 2).

FIG. 7 shows the nucleotide sequence of the representative breast tumor-specific cDNA B17Ag1 (SEQ ID NO: 11).

FIG. 8 shows the nucleotide sequence of the representative breast tumor-specific cDNA B17Ag2 (SEQ ID NO: 12).

FIG. 9 shows the nucleotide sequence of the representative breast tumor-specific cDNA B13Ag2a (SEQ ID NO: 13).

FIG. 10 shows the nucleotide sequence of the representative breast tumor-specific cDNA B13Ag1b (SEQ ID NO: 14).

FIG. 11 shows the nucleotide sequence of the representative breast tumor-specific cDNA B13Ag1a (SEQ ID NO: 15).

FIG. 12 shows the nucleotide sequence of the representative breast tumor-specific cDNA B11Ag1(SEQ ID NO: 16).

FIG. 13 shows the nucleotide sequence of the representative breast tumor-specific cDNA B3CA3c (SEQ ID NO: 292).

FIG. 14 shows the nucleotide sequence of the representative breast tumor-specific cDNA B9CG1 (SEQ ID NO: 18).

FIG. 15 shows the nucleotide sequence of the representative breast tumor-specific cDNA B9CG3 (SEQ ID NO: 19).

FIG. 16 shows the nucleotide sequence of the representative breast tumor-specific cDNA B2CA2 (SEQ ID NO: (SEQ ID NO: 20).

FIG. 17 shows the nucleotide sequence of the representative breast tumor-specific cDNA B3CA1 (SEQ ID NO: 21).

FIG. 18 shows the nucleotide sequence of the representative breast tumor-specific cDNA B3CA2 (SEQ ID NO: 22).

FIG. 19 shows the nucleotide sequence of the representative breast tumor-specific cDNA B3CA3 (SEQ ID NO: 23).

FIG. 20 shows the nucleotide sequence of the representative breast tumor-specific cDNA B4CA1 (SEQ ID NO: 24).

DETAILED DESCRIPTION OF THE INVENTION

Figure 1:
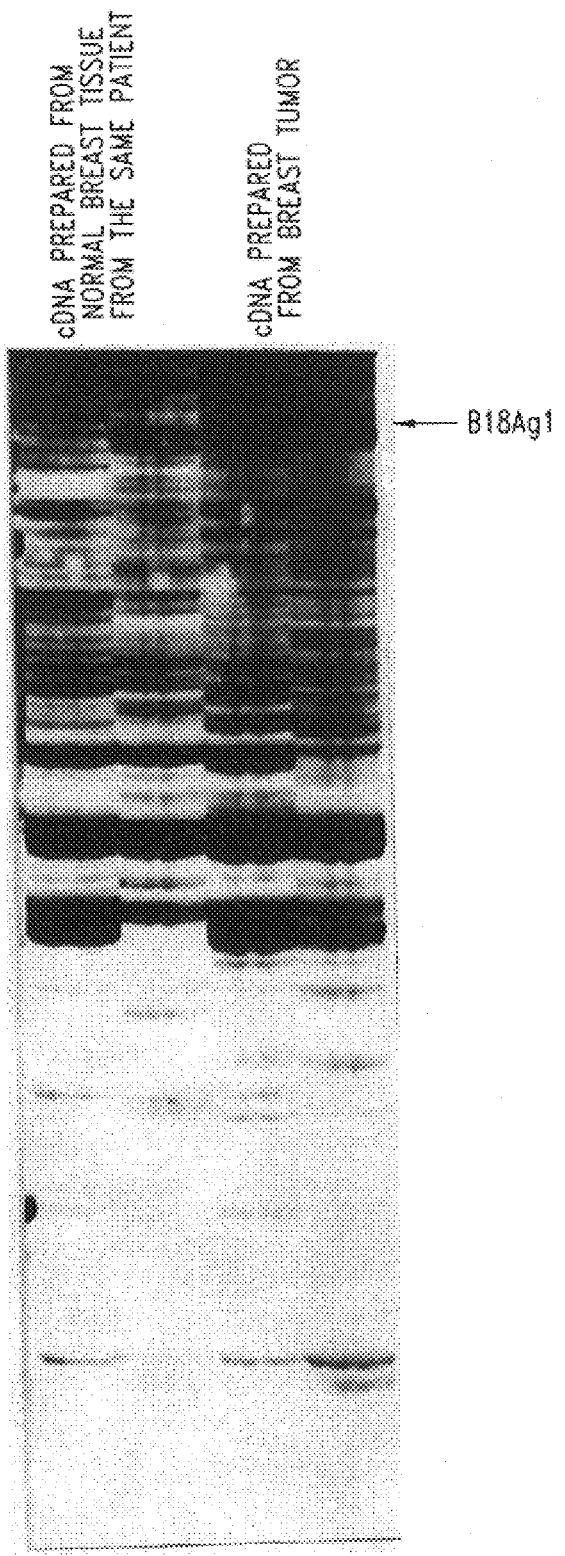
FIG. 1 shows the differential display PCR products, separated by gel electrophoresis, obtained from cDNA prepared from normal breast tissue (lanes 1 and 2) and from cDNA prepared from breast tumor tissue from the same patient (lanes 3 and 4). The arrow indicates the band corresponding to B18Ag1.

As noted above, the present invention is generally directed to compositions and methods for the diagnosis, monitoring and therapy of breast cancer. The compositions described herein include polypeptides, nucleic acid sequences and antibodies. Polypeptides of the present invention generally comprise at least a portion of a protein that is expressed at a greater level in human breast tumor tissue than in normal breast tissue (i.e., the level of RNA encoding the polypeptide is at least 2-fold higher in tumor tissue). Such polypeptides are referred to herein as breast tumor-specific polypeptides, and cDNA molecules encoding such polypeptides are referred to as breast tumor-specific cDNAs. Nucleic acid sequences of the subject invention generally comprise a DNA or RNA sequence that encodes all or a portion of a polypeptide as described above, or that is complementary to such a sequence. Antibodies are generally immune system proteins, or fragments thereof, that are capable of binding to a portion of a polypeptide as described above. Antibodies can be produced by cell culture techniques, including the generation of monoclonal antibodies as described herein, or via transfection of antibody genes into suitable bacterial or mammalian cell hosts, in order to allow for the production of recombinant antibodies.

Polypeptides within the scope of this invention include, but are not limited to, polypeptides (and epitopes thereof) encoded by a human endogenous retroviral sequence, such as the sequence designated B18Ag1 (FIG. 5 and SEQ ID NO:1). Also within the scope of the present invention are polypeptides encoded by other sequences within the retroviral genome containing B18Ag1 (SEQ ID NO: 141). Such sequences include, but are not limited to, the sequences recited in SEQ ID NO:3–SEQ ID NO: 10. B18Ag1 has homology to the gag p30 gene of the endogenous human retroviral element S71, as described in Werner et al., *Virology* 174:225–238 (1990) and also shows homology to about thirty other retroviral gag genes. As discussed in more detail below, the present invention also includes a number of additional breast tumor-specific polypeptides, such as those encoded by the nucleotide sequences recited in SEQ ID NO: 11–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284 288 and 291. As used herein, the term "polypeptide" encompasses amino acid chains of any length, including full length proteins containing the sequences recited herein. A polypeptide comprising an epitope of a protein containing a sequence as described herein may consist entirely of the epitope, or may contain additional sequences. The additional sequences may be derived from the native protein or may be heterologous, and such sequences may (but need not) possess immunogenic or antigenic properties.

An "epitope," as used herein is a portion of a polypeptide that is recognized (i.e., specifically bound) by a B-cell and/or T-cell surface antigen receptor. Epitopes may generally be identified using well known techniques, such as those summarized in Paul, *Fundamental Immunology*, 3rd ed., 243–247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, *Antibodies: A Laboratory Manual*, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

The compositions and methods of the present invention also encompass variants of the above polypeptides and nucleic acid sequences encoding such polypeptides. A polypeptide "variant," as used herein, is a polypeptide that differs from the native polypeptide in substitutions and/or modifications, such that the antigenic and/or immunogenic properties of the polypeptide are retained. Such variants may generally be identified by modifying one of the above polypeptide sequences and evaluating the reactivity of the modified polypeptide with antisera and/or T-cells as described above. Nucleic acid variants may contain one or more substitutions, deletions, insertions and/or modifications such that the antigenic and/or immunogenic properties of the encoded polypeptide are retained. One preferred variant of the polypeptides described herein is a variant that contains nucleotide substitutions, deletions, insertions and/or modifications at no more than 20% of the nucleotide positions.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr;

(2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the immunogenic or antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, nucleotide sequences encoding all or a portion of the polypeptides described herein may be prepared using any of several techniques. For example, cDNA molecules encoding such polypeptides may be cloned on the basis of the breast tumor-specific expression of the corresponding mRNAs, using differential display PCR. This technique compares the amplified products from RNA template prepared from normal and breast tumor tissue. cDNA may be prepared by reverse transcription of RNA using a $(dT)_{12}AG$ primer. Following amplification of the cDNA using a random primer, a band corresponding to an amplified product specific to the tumor RNA may be cut out from a silver stained gel and subcloned into a suitable vector (e.g., the T-vector, Novagen, Madison, Wis.). Nucleotide sequences encoding all or a portion of the breast tumor-specific polypeptides disclosed herein may be amplified from cDNA prepared as described above using the random primers shown in SEQ ID NO.:87–125.

Alternatively, a gene encoding a polypeptide as described herein (or a portion thereof) may be amplified from human genomic DNA, or from breast tumor cDNA, via polymerase chain reaction. For this approach, B18Ag1 sequence-specific primers may be designed based on the sequence provided in SEQ ID NO: 1, and may be purchased or synthesized. One suitable primer pair for amplification from breast tumor cDNA is (5'ATG GCT ATT TTC GGG GGC TGA CA) (SEQ ID NO.:126) and (5'CCG GTA TCT CCT CGT GGG TAT T) (SEQ ID NO.: 127). An amplified portion of B18Ag1 may then be used to isolate the full length gene from a human genomic DNA library or from a breast tumor cDNA library, using well known techniques, such as those described in Sambrook et al., *Molecular Cloning: A Laboratory Manual*, Cold Spring Harbor Laboratories, Cold Spring Harbor, N.Y. (1989). Other sequences within the retroviral genome of which B18Ag1 is a part may be similarly prepared by screening human genomic libraries using B18Ag1-specific sequences as probes. Nucleotides translated into protein from the retroviral genome shown in SEQ ID NO: 141 may then be determined by cloning the corresponding cDNAs, predicting the open reading frames and cloning the appropriate cDNAs into a vector containing a viral promoter, such as T7. The resulting constructs can be employed in a translation reaction, using techniques known to those of skill in the art, to identify nucleotide sequences which result in expressed protein. Similarly, primers specific for the remaining breast tumor-specific polypeptides described herein may be designed based on the nucleotide sequences provided in SEQ ID NO:11–SEQ ID NO:86 and SEQ ID NO:142–SEQ ID NO:290.

Recombinant polypeptides encoded by the DNA sequences described above may be readily prepared from the DNA sequences. For example, supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

In general, any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO.

Such techniques may also be used to prepare polypeptides comprising epitopes or variants of the native polypeptides. For example, variants of a native polypeptide may generally be prepared using standard mutagenesis techniques, such as oligonucleotide-directed site-specific mutagenesis, and sections of the DNA sequence may be removed to permit preparation of truncated polypeptides. Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J Am. Chem. Soc.* 85:2149–2146 (1963). Equipment for automated synthesis of polypeptides is commercially available from suppliers such as Perkin Elmer/Applied BioSystems Division, Foster City, Calif., and may be operated according to the manufacturer's instructions.

In specific embodiments, polypeptides of the present invention encompass amino acid sequences encoded by a DNA molecule having a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284 288 and 291, variants of such polypeptides that are encoded by DNA molecules containing one or more nucleotide substitutions, deletions, insertions and/or modifications at no more than 20% of the nucleotide positions, and epitopes of the above polypeptides. Polypeptides within the scope of the present invention also include polypeptides (and epitopes thereof) encoded by DNA sequences that hybridize to a DNA molecule having a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284 288 and 291 under stringent conditions, wherein the DNA sequences are at least 80% identical in overall sequence to a recited sequence and wherein RNA corresponding to the nucleotide sequence is expressed at a greater level in human breast tumor tissue than in normal breast tissue. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2 ×SSC, 0.1% SDS at 65° C. DNA molecules according to the present invention include molecules that encode any of the above polypeptides.

In another aspect of the present invention, antibodies are provided. Such antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519 (1976), and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used, for example, in methods for detecting breast cancer in a patient. Such methods involve using an antibody to detect the presence or absence of a breast tumor-specific polypeptide as described herein in a suitable biological sample. As used herein, suitable biological samples include tumor or normal tissue biopsy, mastectomy, blood, lymph node, serum or urine samples, or other tissue, homogenate, or extract thereof obtained from a patient.

There are a variety of assay formats known to those of ordinary skill in the art for using an antibody to detect polypeptide markers in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the polypeptide and remove it from the remainder of the sample. The bound polypeptide may then be detected using a second antibody or reagent that contains a reporter group. Alternatively, a competitive assay may be utilized, in which a polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the concentration of polypeptide in the sample.

The solid support may be any material known to those of ordinary skill in the art to which the antibody may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be immobilized on the solid support using a variety of techniques known to those in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of antibody ranging from about 10 ng to about 1 μg, and preferably about 100–200 ng, is sufficient to immobilize an adequate amount of polypeptide.

Covalent attachment of antibody to a solid support may also generally be achieved by first reacting the support with a bifunctional reagent that will react with both the support and a functional group, such as a hydroxyl or amino group, on the antibody. For example, the antibody may be covalently attached to supports having an appropriate polymer coating using benzoquinone or by condensation of an aldehyde group on the support with an amine and an active hydrogen on the binding partner (see, e.g., Pierce Immunotechnology Catalog and Handbook (1991) at A12–A13).

In certain embodiments, the assay for detection of polypeptide in a sample is a two-antibody sandwich assay. This assay may be performed by first contacting an antibody that has been immobilized on a solid support, commonly the well of a microtiter plate, with the biological sample, such that the polypeptide within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 2™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value established from non-tumor tissue. In one preferred embodiment, the cut-off value is the average mean signal obtained when the immobilized antibody is incubated with samples from patients without breast cancer. In general, a sample generating a signal that is three standard deviations above the predetermined cut-off value may be considered positive for breast cancer. In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, the polypeptide within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 µg, and more preferably from about 50 ng to about 1 µg. Such tests can typically be performed with a very small amount of biological sample.

The presence or absence of breast cancer in a patient may also be determined by evaluating the level of mRNA encoding a breast tumor-specific polypeptide as described herein within the biological sample (e.g., a biopsy, mastectomy and/or blood sample from a patient) relative to a predetermined cut-off value. Such an evaluation may be achieved using any of a variety of methods known to those of ordinary skill in the art such as, for example, in situ hybridization and amplification by polymerase chain reaction.

For example, polymerase chain reaction may be used to amplify sequences from cDNA prepared from RNA that is isolated from one of the above biological samples. Sequence-specific primers for use in such amplification may be designed based on the sequences provided in any one of SEQ ID NO: 1, 11–86 and 142–247, and may be purchased or synthesized. In the case of B18Ag 1, as noted herein, one suitable primer pair is B18Ag1-2 (5'ATG GCT ATT TTC GGG GGC TGA CA) (SEQ ID NO.:126) and B18Ag1-3 (5'CCG GTA TCT CCT CGT GGG TAT T) (SEQ ID NO.:127). The PCR reaction products may then be separated by gel electrophoresis and visualized according to methods well known to those of ordinary skill in the art. Amplification is typically performed on samples obtained from matched pairs of tissue (tumor and non-tumor tissue from the same individual) or from unmatched pairs of tissue (tumor and non-tumor tissue from different individuals). The amplification reaction is preferably performed on several dilutions of CDNA spanning two orders of magnitude. A two-fold or greater increase in expression in several dilutions of the tumor sample as compared to the same dilution of the non-tumor sample is considered positive.

As used herein, the term "primer/probe specific for a DNA/RNA molecule" means an oligonucleotide sequence that has at least about 80% identity, preferably at least about 90% and more preferably at least about 95%, identity to the DNA/RNA molecule in question. Primers and/or probes which may be usefully employed in the inventive diagnostic methods preferably have at least about 10–40 nucleotides. In a preferred embodiment, the polymerase chain reaction primers comprise at least about 10 contiguous nucleotides of a DNA/RNA molecule encoding one of the polypeptides disclosed herein. Preferably, oligonucleotide probes for use in the inventive diagnostic methods comprise at least about 15 contiguous oligonucleotides of a DNA/RNA molecule encoding one of the polypeptides disclosed herein. Techniques for both PCR based assays and in situ hybridization assays are well known in the art.

Conventional RT-PCR protocols using agarose and ethidium bromide staining while important in defining gene specificity do not lend themselves to diagnostic kit development because of the time and effort required in making them quantitative (i.e., construction of saturation and/or titration curves), and their sample throughput. This problem is overcome by the development of procedures such as real time RT-PCR which allows for assays to be performed in single tubes, and in turn can be modified for use in 96 well plate formats. Instrumentation to perform such methodologies are available from Perkin Elmer/Applied Biosystems Division. Alternatively, other high throughput assays using labeled probes (e.g., digoxygenin) in combination with labeled (e.g., enzyme fluorescent, radioactive) antibodies to such probes can also be used in the development of 96 well plate assays.

In yet another method for determining the presence or absence of breast cancer in a patient, one or more of the breast tumor-specific polypeptides described may be used in a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, a response that is greater than about 0.5 cm in diameter, preferably greater than about 5.0 cm in diameter, is a positive response, indicative of breast cancer.

The breast tumor-specific polypeptides described herein are preferably formulated, for use in a skin test, as pharmaceutical compositions containing at least one polypeptide and a physiologically acceptable carrier, such as water, saline, alcohol, or a buffer. Such compositions typically contain one or more of the above polypeptides in an amount ranging from about 1 µg to 100 µg, preferably from about 10 µg to 50 µg in a volume of 0.1 mL. Preferably, the carrier employed in such pharmaceutical compositions is a saline solution with appropriate preservatives, such as phenol and/or Tween 80™.

In other aspects of the present invention, the progression and/or response to treatment of a breast cancer may be monitored by performing any of the above assays over a period of time, and evaluating the change in the level of the response (i.e., the amount of polypeptide or mRNA detected or, in the case of a skin test, the extent of the immune response detected). For example, the assays may be performed every month to every other month for a period of 1 to 2 years. In general, breast cancer is progressing in those patients in whom the level of the response increases over time. In contrast, breast cancer is not progressing when the signal detected either remains constant or decreases with time.

In further aspects of the present invention, the compounds described herein may be used for the immunotherapy of breast cancer. In these aspects, the compounds (which may be polypeptides, antibodies or nucleic acid molecules) are preferably incorporated into pharmaceutical compositions or vaccines. Pharmaceutical compositions comprise one or more such compounds and a physiologically acceptable carrier. Vaccines may comprise one or more polypeptides and an immune response enhancer, such as an adjuvant or a liposome (into which the compound is incorporated). Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, including one or more separate polypeptides.

Alternatively, a vaccine may contain DNA encoding one or more of the polypeptides as described above, such that the polypeptide is generated in situ. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993), and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a stimulator of immune responses, such as lipid A, Bortadella pertussis or Mycobacterium tuberculosis derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The above pharmaceutical compositions and vaccines may be used, for example, for the therapy of breast cancer in a patient. As used herein, a "patient" refers to any warm-blooded animal, preferably a human. A patient may or may not be afflicted with breast cancer. Accordingly, the above pharmaceutical compositions and vaccines may be used to prevent the development of breast cancer or to treat a patient afflicted with breast cancer. To prevent the development of breast cancer, a pharmaceutical composition or vaccine comprising one or more polypeptides as described herein may be administered to a patient. Alternatively, naked DNA or plasmid or viral vector encoding the polypeptide may be administered. For treating a patient with breast cancer, the pharmaceutical composition or vaccine may comprise one or more polypeptides, antibodies or nucleotide sequences complementary to DNA encoding a polypeptide as described herein (e.g., antisense RNA or antisense deoxyribonucleotide oligonucleotides).

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered for a 52-week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 µg to 5 mg. Suitable dose sizes will vary with the size of the patient, but will typically range from about 0.1 mL to about 5 mL.

The following Examples are offered by way of illustration and not by way of limitation.

EXAMPLES

Example 1

Preparation of Breast Tumor-Specific cDNAs Using Differential Display RT-PCR

This Example illustrates the preparation of cDNA molecules encoding breast tumor-specific polypeptides using a differential display screen.

A. Preparation of B18Ag1 cDNA and Characterization of mRNA Expression

Tissue samples were prepared from breast tumor and normal tissue of a patient with breast cancer that was confirmed by pathology after removal from the patient. Normal RNA and tumor RNA was extracted from the samples and mRNA was isolated and converted into cDNA using a $(dT)_{12}AG$ (SEQ ID NO.:130) anchored 3' primer. Differential display PCR was then executed using a randomly chosen primer (CTTCAACCTC) (SEQ ID NO.:103). Amplification conditions were standard buffer containing 1.5 mM $MgCl_2$, 20 pmol of primer, 500 pmol dNTP, and 1 unit of Taq DNA polymerase (Perkin-Elmer, Branchburg, N.J.). Forty cycles of amplification were performed using 94° C. denaturation for 30 seconds, 42° C. annealing for 1 minute, and 72° C. extension for 30 seconds. An RNA fingerprint containing 76 amplified products was obtained. Although the RNA fingerprint of breast tumor tissue was over 98% identical to that of the normal breast tissue, a band was repeatedly observed to be specific to the RNA fingerprint pattern of the tumor. This band was cut out of a silver stained gel, subcloned into the T-vector (Novagen, Madison, Wis.) and sequenced.

The sequence of the cDNA, referred to as B18Ag1, is provided in SEQ ID NO:1. A database search of GENBANK and EMBL revealed that the B18Ag1 fragment initially cloned is 77% identical to the endogenous human retroviral element S71, which is a truncated retroviral element homologous to the Simian Sarcoma Virus (SSV). S71 contains an incomplete gag gene, a portion of the pol gene and an LTR-like structure at the 3' terminus (see Werner et al., Virology 174:225–238 (1990)). B18Ag1 is also 64% identical to SSV in the region corresponding to the P30 (gag) locus. B18Ag1 contains three separate and incomplete reading frames covering a region which shares considerable homology to a wide variety of gag proteins of retroviruses which infect mammals. In addition, the homology to S71 is not just within the gag gene, but spans several kb of sequence including an LTR.

Figure 2:
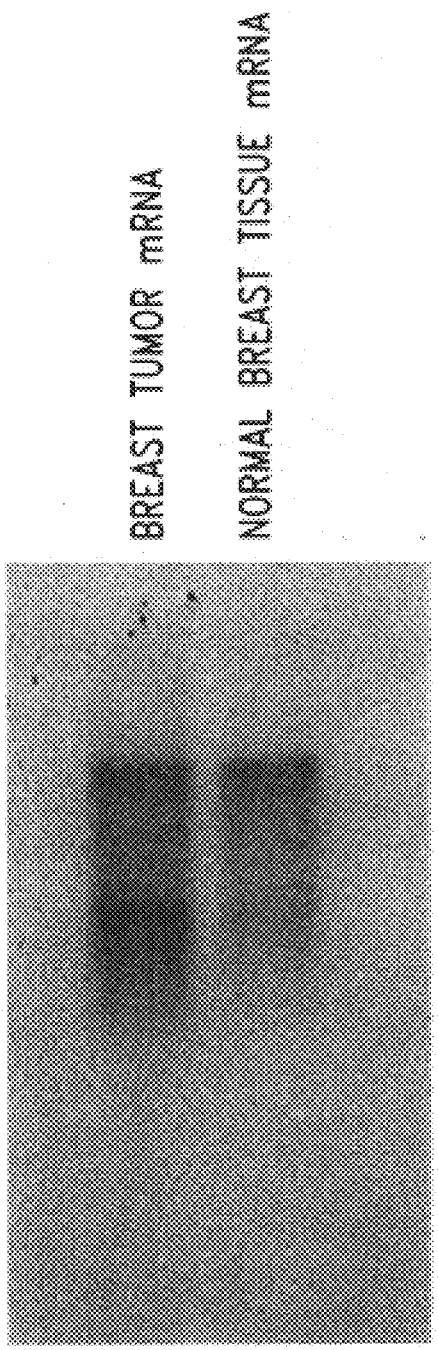
FIG. 2 is a northern blot comparing the level of B18Ag1 mRNA in breast tumor tissue (lane 1) with the level in normal breast tissue.

B18Ag1-specific PCR primers were synthesized using computer analysis guidelines. RT-PCR amplification (94° C., 30 seconds; 60° C.→42° C., 30 seconds; 72° C., 30 seconds for 40 cycles) confirmed that B18Ag1 represents an actual mRNA sequence present at relatively high levels in the patient's breast tumor tissue. The primers used in amplification were B18Ag1-1 (CTG CCT GAG CCA CAA ATG) (SEQ ID NO.:128) and B18Ag1-4 (CCG GAG GAG GAA GCT AGA GGA ATA) (SEQ ID NO.:129) at a 3.5 mM magnesium concentration and a pH of 8.5, and B18Ag1-2 (ATG GCT ATT TTC GGG GCC TGA CA) (SEQ ID NO.:126) and B18Ag1-3 (CCG GTA TCT CCT CGT GGG TAT T) (SEQ ID NO.:127) at 2 mM magnesium at pH 9.5. The same experiments showed exceedingly low to nonexistent levels of expression in this patient's normal breast tissue (see FIG. 1). RT-PCR experiments were then used to show that B18Ag1 mRNA is present in nine other breast tumor samples (from Brazilian and American patients) but absent in, or at exceedingly low levels in, the normal breast tissue corresponding to each cancer patient. RT-PCR analysis has also shown that the B18Ag1 transcript is not present in various normal tissues (including lymph node, myocardium and liver) and present at relatively low levels in PBMC and lung tissue. The presence of B18Ag1 mRNA in breast tumor samples, and its absence from normal breast tissue, has been confirmed by Northern blot analysis, as shown in FIG. 2.

Figure 3:
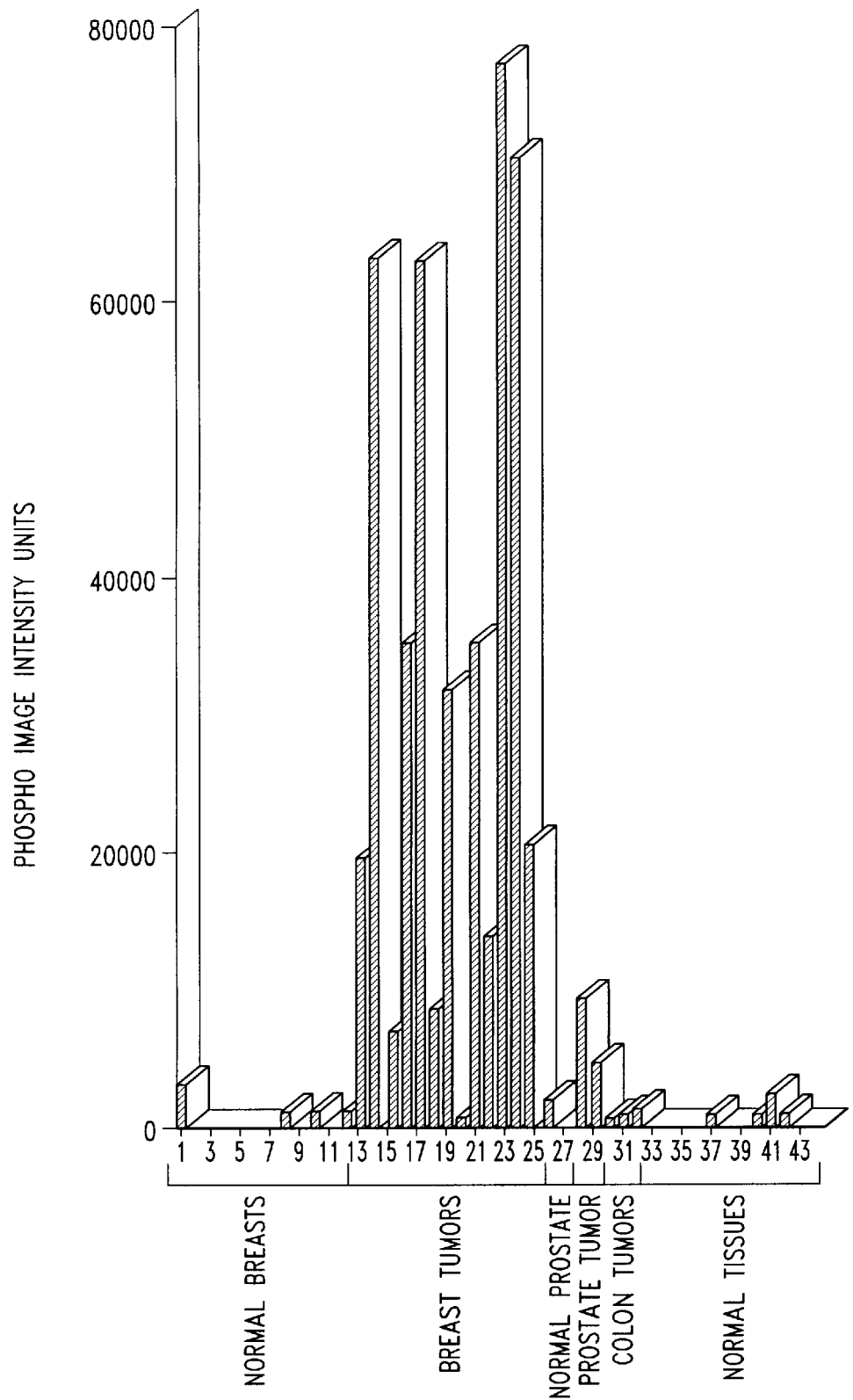
FIG. 3 shows the level of B18Ag1 mRNA in breast tumor tissue compared to that in various normal and non-breast tumor tissues as determined by RNase protection assays.

The differential expression of B18Ag1 in breast tumor tissue was also confirmed by RNase protection assays. FIG. 3 shows the level of B18Ag1 mRNA in various tissue types as determined in four different RNase protection assays. Lanes 1–12 represent various normal breast tissue samples, lanes 13–25 represent various breast tumor samples; lanes 26–27 represent normal prostate samples; lanes 28–29 represent prostate tumor samples; lanes 30–32 represent colon tumor samples; lane 33 represents normal aorta; lane 34 represents normal small intestine; lane 35 represents normal skin, lane 36 represents normal lymph node; lane 37 represents normal ovary; lane 38 represents normal liver; lane 39 represents normal skeletal muscle; lane 40 represents a first normal stomach sample, lane 41 represents a second normal stomach sample; lane 42 represents a normal lung; lane 43 represents normal kidney; and lane 44 represents normal pancreas. Interexperimental comparison was facilitated by including a positive control RNA of known β-actin message abundance in each assay and normalizing the results of the different assays with respect to this positive control.

Figure 4:
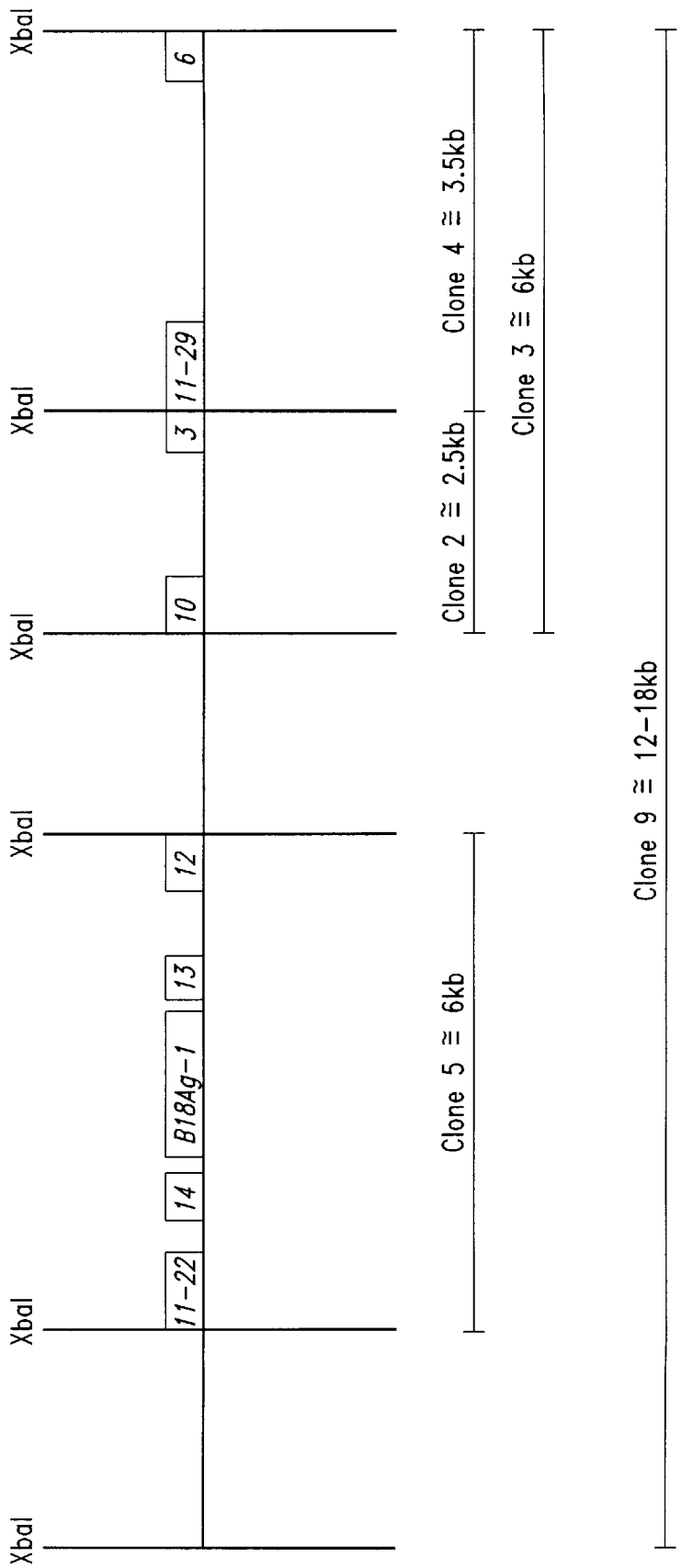
FIG. 4 is a genomic clone map showing the location of additional retroviral sequences obtained from ends of XbaI restriction digests (provided in SEQ ID NO:3–SEQ ID NO: 10) relative to B18Ag1.

RT-PCR and Southern Blot analysis has shown the B18Ag1 locus to be present in human genomic DNA as a single copy endogenous retroviral element. A genomic clone of approximately 12–18 kb was isolated using the initial B18Ag1 sequence as a probe. Four additional subclones were also isolated by XbaI digestion. Additional retroviral sequences obtained from the ends of the XbaI digests of these clones (located as shown in FIG. 4) are shown as SEQ ID NO:3–SEQ ID NO:10, where SEQ ID NO:3 shows the location of the sequence labeled 10 in FIG. 4, SEQ ID NO:4 shows the location of the sequence labeled 11–29, SEQ ID NO:5 shows the location of the sequence labeled 3, SEQ ID NO:6 shows the location of the sequence labeled 6, SEQ ID NO:7 shows the location of the sequence labeled 12, SEQ ID NO:8 shows the location of the sequence labeled 13, SEQ ID NO:9 shows the location of the sequence labeled 14 and SEQ ID NO:10 shows the location of the sequence labeled 11–22.

Subsequent studies demonstrated that the 12–18 kb genomic clone contains a retroviral element of about 7.75 kb, as shown in FIGS. 5A and 5B. The sequence of this retroviral element is shown in SEQ ID NO: 141. The numbered line at the top of FIG. 5A represents the sense strand sequence of the retroviral genomic clone. The box below this line shows the position of selected restriction sites. The arrows depict the different overlapping clones used to sequence the retroviral element. The direction of the arrow shows whether the single-pass subclone sequence corresponded to the sense or anti-sense strand. FIG. 5B is a schematic diagram of the retroviral element containing B18Ag1 depicting the organization of viral genes within the element. The open boxes correspond to predicted reading frames, starting with a methionine, found throughout the element. Each of the six likely reading frames is shown, as indicated to the left of the boxes, with frames 1–3 corresponding to those found on the sense strand.

Using the CDNA of SEQ ID NO:1 as a probe, a longer CDNA was obtained (SEQ ID NO:227) which contains minor nucleotide differences (less than 1%) compared to the genomic sequence shown in SEQ ID NO:141.

B. Preparation of cDNA Molecules Encoding Other Breast Tumor-Specific Polypeptides Normal RNA and tumor RNA was prepared and mRNA was isolated and converted into cDNA using a $(dT)_{12}AG$ anchored 3' primer, as described above. Differential display PCR was then executed using the randomly chosen primers SEQ ID NO.:87–125. Amplification conditions were as noted above, and bands observed to be specific to the RNA fingerprint pattern of the tumor were cut out of a silver stained gel, subcloned into either the T-vector (Novagen, Madison, Wis.) or the pCRII vector (Invitrogen, San Diego, Calif.) and sequenced. The sequences are provided in SEQ ID NO:11–SEQ ID NO:86. Of the 79 sequences isolated, 67 were found to be novel (SEQ ID NO.:11–26 and 28–77) (see also FIGS. 6–20).

An extended DNA sequence (SEQ ID NO: 290) for the antigen B15Ag1 (originally identified partial sequence provided in SEQ ID NO: 27) was obtained in further studies. Comparison of the sequence of SEQ ID NO: 290 with those in the gene bank as described above, revealed homology to the known human β-A activin gene.

Subsequent studies identified an additional 146 sequences (SEQ ID NOS:142–289), of which 115 appeared to be novel (SEQ ID NOS:142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291). To the best of the inventors' knowledge none of the previously identified sequences have heretofore been shown to be expressed at a greater level in human breast tumor tissue than in normal breast tissue.

Example 2

Preparation of B18Ag1 DNA from Human Genomic DNA

This Example illustrates the preparation of B18Ag1 DNA by amplification from human genomic DNA.

B18Ag1 DNA may be prepared from 250 ng human genomic DNA using 20 pmol of B18Ag1 specific primers, 500 pmol dNTPS and 1 unit of Taq DNA polymerase (Perkin Elmer, Branchburg, N.J.) using the following amplification parameters: 94° C. for 30 seconds denaturing, 30 seconds 60° C. to 42° C. touchdown annealing in 2° C. increments every two cycles and 72° C. extension for 30 seconds. The last increment (a 42° C. annealing temperature) should cycle times. Primers were selected using computer analysis. Primers synthesized were B18Ag1-1, B18Ag1-2, B18Ag1-3, and B18Ag1-4. Primer pairs that may be used are 1+3, 1+4, 2+3, and 2+4.

Following gel electrophoresis, the band corresponding to B18Ag1 DNA may be excised and cloned into a suitable vector.

Example 3

Preparation of B18Ag1 DNA from Breast Tumor cDNA

This Example illustrates the preparation of B18Ag1 DNA by amplification from human breast tumor cDNA.

First strand cDNA is synthesized from RNA prepared from human breast tumor tissue in a reaction mixture containing 500 ng poly A+ RNA, 200 pmol of the primer $(T)_{12}AG$ (i.e., TTT TTT TTT TTT AG) (SEQ ID NO: 130), 1× first strand reverse transcriptase buffer, 6.7 mM DTT, 500 mmol dNTPs, and 1 unit AMV or MMLV reverse transcriptase (from any supplier, such as Gibco-BRL (Grand Island, N.Y.)) in a final volume of 30 μl. After first strand synthesis, the cDNA is diluted approximately 25 fold and 1 μl is used for amplification as described in Example 2. While some primer pairs can result in a heterogeneous population of transcripts, the primers B18Ag1-2 (5'ATG GCT ATT TTC GGG GGC TGA CA) (SEQ ID NO: 126) and B18Ag1-3 (5'CCG GTA TCT CCT CGT GGG TAT T) (SEQ ID NO: 127) yield a single 151 bp amplification product.

Example 4

Identification of B-cell and T-cell Epitopes of B18Ag1

This Example illustrates the identification of B18Ag1 epitopes.

The B18Ag1 sequence can be screened using a variety of computer algorithms. To determine B-cell epitopes, the sequence can be screened for hydrophobicity and hydrophilicity values using the method of Hopp, *Prog. Clin. Biol. Res.* 172B:367–77 (1985) or, alternatively, Cease et al., *J. Exp. Med.* 164:1779–84 (1986) or Spouge et al., *J Immunol.* 138:204–12 (1987). Additional Class II MHC (antibody or B-cell) epitopes can be predicted using programs such as AMPHI (e.g., Margalit et al., *J Immunol.* 138:2213 (1987)) or the methods of Rothbard and Taylor (e.g., *EMBO J.* 7:93 (1988)).

Once peptides (15–20 amino acids long) are identified using these techniques, individual peptides can be synthesized using automated peptide synthesis equipment (available from manufacturers such as Perkin Elmer/Applied Biosystems Division, Foster City, Calif.) and techniques such as Merrifield synthesis. Following synthesis, the peptides can used to screen sera harvested from either normal or breast cancer patients to determine whether patients with breast cancer possess antibodies reactive with the peptides. Presence of such antibodies in breast cancer patient would confirm the immunogenicity of the specific B-cell epitope in question. The peptides can also be tested for their ability to generate a serologic or humoral immune in animals (mice, rats, rabbits, chimps etc.) following immunization in vivo. Generation of a peptide-specific antiserum following such immunization further confirms the immunogenicity of the specific B-cell epitope in question.

To identify T-cell epitopes, the B18Ag1 sequence can be screened using different computer algorithms which are useful in identifying 8–10 amino acid motifs within the B18Ag1 sequence which are capable of binding to HLA Class I MHC molecules. (see, e.g., Rammensee et al., *Immunogenetics* 41:178–228 (1995)). Following synthesis such peptides can be tested for their ability to bind to class I MHC using standard binding assays (e.g., Sette et al., *J Immunol.* 153:5586–92 (1994)) and more importantly can be tested for their ability to generate antigen reactive cytotoxic T-cells following in vitro stimulation of patient or normal peripheral mononuclear cells using, for example, the methods of Bakker et al., *Cancer Res.* 55:5330–34 (1995); Visseren et al., *J Immunol.* 154:3991–98 (1995); Kawakami et al., *J Immunol.* 154:3961–68 (1995); and Kast et al., *J Immunol.* 152:3904–12 (1994). Successful in vitro generation of T-cells capable of killing autologous (bearing the same Class I MHC molecules) tumor cells following in vitro peptide stimulation further confirms the immunogenicity of the B18Ag1 antigen. Furthermore, such peptides may be used to generate murine peptide and B18Ag1 reactive cytotoxic T-cells following in vivo immunization in mice rendered transgenic for expression of a particular human MHC Class I haplotype (Vitiello et al., *J Exp. Med.* 173:1007–15 (1991).

A representative list of predicted B18Ag1 B-cell and T-cell epitopes, broken down according to predicted HLA Class I MHC binding antigen, is shown below:

Predicted Th Motifs (B-cell epitopes) (SEQ ID NOS.: 131–133)

SSGGRTFDDFHRYLLVGI

QGAAQKPINLSKXIEVVQGHDE

SPGVFLEHLQEAYRIYTPFDLSA

Predicted HLA A2.1 Motifs (T-cell epitopes) (SEQ ID NOS.: 134–140)

YLLVGIQGA

GAAQKPINL

NLSKXIEVV

EVVQGHDES

HLQEAYRIY

NLAFVAQAA

FVAQAAPDS

Example 5

Characterization of Breast Tumor Genes Discovered by Differential Display PCR

The specificity and sensitivity of the breast tumor genes discovered by differential display PCR were determined using RT-PCR. This procedure enabled the rapid evaluation of breast tumor gene mRNA expression semiquantitatively without using large amounts of RNA. Using gene specific primers, mRNA expression levels in a variety of tissues were examined, including 8 breast tumors, 5 normal breasts, 2 prostate tumors, 2 colon tumors, 1 lung tumor, and 14 other normal adult human tissues, including normal prostate, colon, kidney, liver, lung, ovary, pancreas, skeletal muscle, skin, stomach and testes.

To ensure the semiquantitative nature of the RT-PCR, β-actin was used as internal control for each of the tissues examined. Serial dilutions of the first strand cDNAs were prepared and RT-PCR assays performed using β-actin specific primers. A dilution was then selected that enabled the linear range amplification of β-actin template, and which was sensitive enough to reflect the difference in the initial copy number. Using this condition, the β-actin levels were determined for each reverse transcription reaction from each tissue. DNA contamination was minimized by DNase treatment and by assuring a negative result when using first strand cDNA that was prepared without adding reverse transcriptase.

Using gene specific primers, the mRNA expression levels were determined in a variety of tissues. To date, 38 genes have been successfully examined by RT-PCR, five of which exhibit good specificity and sensitivity for breast tumors (B15AG-1, B31GA1b, B38GA2a, B11A1a and B18AG1a).

Figure 21A:
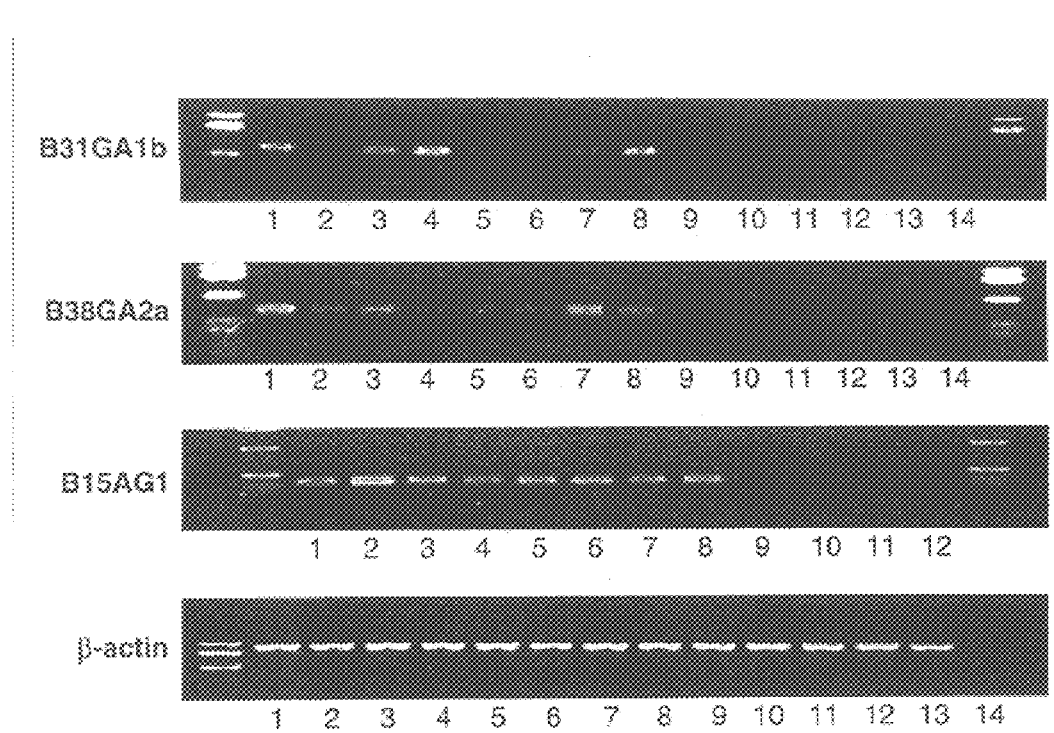
FIG. 21A depicts RT-PCR analysis of breast tumor genes in breast tumor tissues (lanes 1–8) and normal breast tissues (lanes 9–13) and $H_2O$ (lane 14).
Figure 21B:
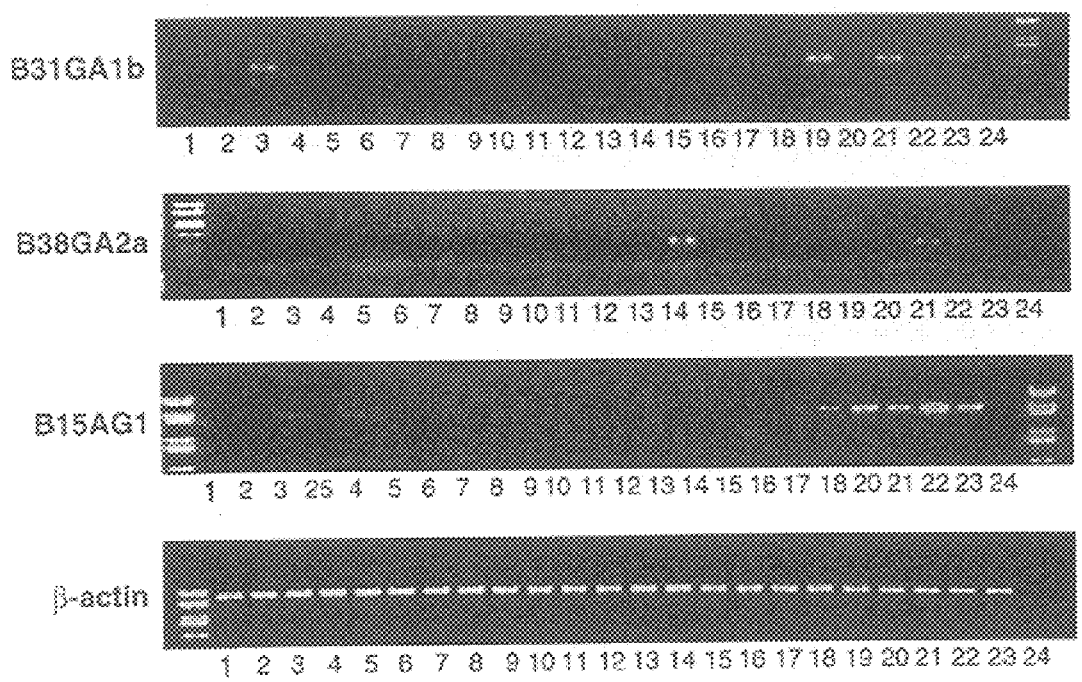
FIG. 21B depicts RT-PCR analysis of breast tumor genes in prostate tumors (lane 1,2), colon tumors (lane 3), lung tumor (lane 4), normal prostate (lane 5), normal colon (lane 6), normal kidney (lane 7), normal liver (lane 8), normal lung (lane 9), normal ovary (lanes 10, 18), normal pancreases (lanes 11, 12), normal skeletal muscle (lane 13), normal skin (lane 14), normal stomach (lane 15), normal testes (lane 16), normal small intestine (lane 17), HBL-100 (lane 19), MCF-12A (lane 20), breast tumors (lanes 21–23), $H_2O$ (lane 24), and colon tumor (lane 25).

FIGS. 21A and 21B depict the results for three of these genes: B15AG-1 (SEQ ID NO:27), B31GA1b (SEQ ID NO:148) and B38GA2a (SEQ ID NO:157). Table I summarizes the expression level of all the genes tested in normal breast tissue and breast tumors, and also in other tissues.

TABLE I

Percentage of Breast Cancer Antigens that are Expressed in Various Tissues

Breast Tissues

| | |
|---|---|
| Over-expressed in Breast Tumors | 84% |
| Equally Expressed in Normals and Tumor | 16% |
| Over-expressed in Breast Tumors but not in any Normal Tissues | 9% |

TABLE I-continued

Percentage of Breast Cancer Antigens that are Expressed in Various Tissues

Other Tissues

| | |
|---|---|
| Over-expressed in Breast Tumors but Expressed in Some Normal Tissues | 30% |
| Over-expressed in Breast Tumors but Equally Expressed in All Other Tissues | 61% |

From the foregoing, it will be appreciated that, although specific embodiments of the invention have been described herein for the purpose of illustration, various modifications may be made without deviating from the spirit and scope of the invention.

SEQUENCE LISTING (1) GENERAL INFORMATION:

(iii) NUMBER OF SEQUENCES: 292

(2) INFORMATION FOR SEQ ID NO: 1:

(i) SEQUENCE CHARACTERISTICS:
      (A) LENGTH: 363 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..363

(xi) SEQUENCE DESCRIPTION: SEQ ID NO: 1:

```
TTA GAG ACC CAA TTG GGA CCT AAT TGG GAC CCA AAT TTC TCA AGT GGA        48
Leu Glu Thr Gln Leu Gly Pro Asn Trp Asp Pro Asn Phe Ser Ser Gly
 1               5                  10                  15

GGG AGA ACT TTT GAC GAT TTC CAC CGG TAT CTC CTC GTG GGT ATT CAG        96
Gly Arg Thr Phe Asp Asp Phe His Arg Tyr Leu Leu Val Gly Ile Gln
                20                  25                  30

GGA GCT GCC CAG AAA CCT ATA AAC TTG TCT AAG GCG ATT GAA GTC GTC       144
Gly Ala Ala Gln Lys Pro Ile Asn Leu Ser Lys Ala Ile Glu Val Val
            35                  40                  45

CAG GGG CAT GAT GAG TCA CCA GGA GTG TTT TTA GAG CAC CTC CAG GAG       192
Gln Gly His Asp Glu Ser Pro Gly Val Phe Leu Glu His Leu Gln Glu
        50                  55                  60

GCT TAT CGG ATT TAC ACC CCT TTT GAC CTG GCA GCC CCC GAA AAT AGC       240
Ala Tyr Arg Ile Tyr Thr Pro Phe Asp Leu Ala Ala Pro Glu Asn Ser
 65                 70                  75                  80

CAT GCT CTT AAT TTG GCA TTT GTG GCT CAG GCA GCC CCA GAT AGT AAA       288
His Ala Leu Asn Leu Ala Phe Val Ala Gln Ala Ala Pro Asp Ser Lys
                85                  90                  95

AGG AAA CTC CAA AAA CTA GAG GGA TTT TGC TGG AAT GAA TAC CAG TCA       336
Arg Lys Leu Gln Lys Leu Glu Gly Phe Cys Trp Asn Glu Tyr Gln Ser
               100                 105                 110

GCT TTT AGA GAT AGC CTA AAA GGT TTT                                   363
Ala Phe Arg Asp Ser Leu Lys Gly Phe
           115                 120
```

(2) INFORMATION FOR SEQ ID NO: 2:

(i) SEQUENCE CHARACTERISTICS:

(A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO: 2:

```
Leu Glu Thr Gln Leu Gly Pro Asn Trp Asp Pro Asn Phe Ser Ser Gly
 1               5                  10                  15

Gly Arg Thr Phe Asp Asp Phe His Arg Tyr Leu Leu Val Gly Ile Gln
                20                  25                  30

Gly Ala Ala Gln Lys Pro Ile Asn Leu Ser Lys Ala Ile Glu Val Val
            35                  40                  45

Gln Gly His Asp Glu Ser Pro Gly Val Phe Leu Glu His Leu Gln Glu
        50                  55                  60

Ala Tyr Arg Ile Tyr Thr Pro Phe Asp Leu Ala Ala Pro Glu Asn Ser
65                  70                  75                  80

His Ala Leu Asn Leu Ala Phe Val Ala Gln Ala Ala Pro Asp Ser Lys
                85                  90                  95

Arg Lys Leu Gln Lys Leu Glu Gly Phe Cys Trp Asn Glu Tyr Gln Ser
            100                 105                 110

Ala Phe Arg Asp Ser Leu Lys Gly Phe
        115                 120
```

(2) INFORMATION FOR SEQ ID NO: 3:

(i) SEQUENCE CHARACTERISTICS:
        (A) LENGTH: 1101 base pairs
        (B) TYPE: nucleic acid
        (C) STRANDEDNESS: single
        (D) TOPOLOGY: linear (xi) SEQUENCE DESCRIPTION: SEQ ID NO: 3:

```
TCTTAGAATC TTCATACCCC GAACTCTTGG GAAAACTTTA ATCAGTCACC TACAGTCTAC      60

CACCCATTTA GGAGGAGCAA AGCTACCTCA GCTCCTCCGG AGCCGTTTTA AGATCCCCCA     120

TCTTCAAAGC CTAACAGATC AAGCAGCTCT CCGGTGCACA ACCTGCGCCC AGGTAAATGC     180

CAAAAAAGGT CCTAAACCCA GCCCAGGCCA CCGTCTCCAA GAAAACTCAC CAGGAGAAAA     240

GTGGGAAATT GACTTTACAG AAGTAAAACC ACACCGGGCT GGGTACAAAT ACCTTCTAGT     300

ACTGGTAGAC ACCTTCTCTG GATGGACTGA AGCATTTGCT ACCAAAAACG AAACTGTCAA     360

TATGGTAGTT AAGTTTTTAC TCAATGAAAT CATCCCTCGA CGTGGGCTGC CTGTTGCCAT     420

AGGGTCTGAT AATGGAACGG CCTTCGCCTT GTCTATAGTT TAATCAGTCA GTAAGGCGTT     480

AAACATTCAA TGGAAGCTCC ATTGTGCCTA TCGACCCAGA GCTCTGGGCA GTAGAACGC     540

ATGAACTGCA CCCTAAAAAA ACACTCTTAC AAAATTAATC TTAAAAACCG GTGTTAATTG     600

TGTTAGTCTC CTTCCCTTAG CCCTACTTAG AGTTAAGGTG CACCCCTTAC TGGGCTGGGT     660

TCTTTACCTT TTGAAATCAT NTTTNGGAAG GGGCTGCCTA TCTTTNCTTA ACTAAAAAAN     720

GCCCATTTGG CAAAAATTTC NCAACTAATT TNTACGTNCC TACGTCTCCC CAACAGGTAN     780

AAAAATCTNC TGCCCTTTTC AAGGAACCAT CCCATCCATT CCTNAACAAA AGGCCTGCCN     840

TTCTTCCCCC AGTTAACTNT TTTTTNTTAA AATTCCCAAA AAANGAACCN CCTGCTGGAA     900

AAACNCCCCC CTCCAANCCC CGGCCNAAGN GGAAGGTTCC CTTGAATCCC NCCCCNCNA     960

ANGGCCCGGA ACCNTTAAAN TNGTTCCNGG GGGTNNGGCC TAAAAGNCCN ATTTGGTAAA    1020

CCTANAAATT TTTTCTTTTN TAAAAACCAC NNTTTNNTTT TTCTTAAACA AAACCCTNTT    1080
```

(2) INFORMATION FOR SEQ ID NO: 4:

(i) SEQUENCE CHARACTERISTICS:
        (A) LENGTH: 1087 base pairs
        (B) TYPE: nucleic acid
        (C) STRANDEDNESS: single
        (D) TOPOLOGY: linear (xi) SEQUENCE DESCRIPTION: SEQ ID NO: 4:

```
TNTAGNACN  TATTTCCCNC  C                                               1101

TCTAGAGCTG  CGCCTGGATC  CCGCCACAGT  GAGGAGACCT  GAAGACCAGA  GAAAACACAG   60

CAAGTAGGCC  CTTTAAACTA  CTCACCTGTG  TTGTCTTCTA  ATTTATTCTG  TTTTATTTTG  120

TTTCCATCAT  TTTAAGGGGT  TAAAATCATC  TTGTTCAGAC  CTCAGCATAT  AAAATGACCC  180

ATCTGTAGAC  CTCAGGCTCC  AACCATACCC  CAAGAGTTGT  CTGGTTTTGT  TTAAATTACT  240

GCCAGGTTTC  AGCTGCAGAT  ATCCCTGGAA  GGAATATTCC  AGATTCCCTG  AGTAGTTTCC  300

AGGTTAAAAT  CCTATAGGCT  TCTTCTGTTT  TGAGGAAGAG  TTCCTGTCAG  AGAAAAACAT  360

GATTTTGGAT  TTTTAACTTT  AATGCTTGTG  AAACGCTATA  AAAAAAATTT  TCTACCCCTA  420

GCTTTAAAGT  ACTGTTAGTG  AGAAATTAAA  ATTCCTTCAG  GAGGATTAAA  CTGCCATTTC  480

AGTTACCCTA  ATTCCAAATG  TTTTGGTGGT  TAGAATCTTC  TTTAATGTTC  TTGAAGAAGT  540

GTTTTATATT  TTCCCATCNA  GATAAATTCT  CTCNCNCCTT  NNTTTTNTNT  CTNNTTTTTT  600

AAAACGGANT  CTTGCTCCGT  TGTCCANGCT  GGGAATTTTN  TTTTGGCCAA  TCTCCGCTNC  660

CTTGCAANAA  TNCTGCNTCC  CAAAATTACC  NCCTTTTTCC  CACCTCCACC  CCNNGGAATT  720

ACCTGGAATT  ANAGGCCCCC  NCCCCCCCCC  CGGCTAATTT  GTTTTTGTTT  TTAGTAAAAA  780

ACGGGTTTCC  TGTTTTAGTT  AGGATGGCCC  ANNTCTGACC  CCNTATCNT   CCCCCTCNGC  840

CCTCNAATNT  TNGGNNTANG  GCTTACCCCC  CCCNGNNGTT  TTTCCTCCAT  TNAAATTTTC  900

TNTGGANTCT  TGAATNNCGG  GTTTTCCCTT  TTAAACCNAT  TTTTTTTTN   NNCCCCCAN   960

TTTTNCCTCC  CCCNTNTNTA  ANGGGGGTTT  CCCAANCCGG  GTCCNCCCCC  ANGTCCCCAA  1020

TTTTTCTCCC  CCCCCCTCTT  TTTTCTTTNC  CCCAAAANTC  CTATCTTTTC  CTNNAAATAT  1080

CNANTNT                                                                1087
```

(2) INFORMATION FOR SEQ ID NO: 5:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear (xi) SEQUENCE DESCRIPTION: SEQ ID NO: 5:

```
TCTAGACCAA  GAAATGGGAG  GATTTTAGAG  TGACTGATGA  TTTCTCTATC  ATCTGCAGTT   60

AGTAAACATT  CTCCACAGTT  TATGCAAAAA  GTAACAAAAC  CACTGCAGAT  GACAAACACT  120

AGGTAACACA  CATACTATCT  CCCAAATACC  TACCCACAAG  CTCAACAATT  TTAAACTGTT  180

AGGATCACTG  GCTCTAATCA  CCATGACATG  AGGTCACCAC  CAAACCATCA  AGCGCTAAAC  240

AGACAGAATG  TTTCCACTCC  TGATCCACTG  TGTGGGAAGA  AGCACCGAAC  TTACCCACTG  300

GGGGGCCTGC  NTCANAANAA  AAGCCCATGC  CCCCGGGTNT  NCCTTTNAAC  CGGAACGAAT  360

NAACCCACCA  TCCCCACANC  TCCTCTGTTC  NTGGGCCCTG  CATCTTGTGG  CCTCNTNTNC  420

TTTNGGGGAN  ACNTGGGGAA  GGTACCCCAT  TTCNTTGACC  CCNCNANAAA  ACCCCNGTGG  480

CCCTTTGCCC  TGATTCNCNT  GGGCCTTTTC  TCTTTTCCCT  TTTGGGTTGT  TTAAATTCCC  540
```

```
AATGTCCCCN GAACCCTCTC CNTNCTGCCC AAAACCTACC TAAATTNCTC NCTANGNNTT      600

TTCTTGGTGT TNCTTTTCAA AGGTNACCTT NCCTGTTCAN NCCCNACNAA AATTTNTTCC      660

NTATNNTGGN CCCNNAAAAA NNNATCNNCC CNAATTGCCC GAATTGGTTN GGTTTTTCCT      720

NCTGGGGGAA ACCCTTTAAA TTTCCCCCTT GGCCGGCCCC CCTTTTTTCC CCCCTTTNGA      780

AGGCAGGNGG TTCTTCCCGA ACTTCCAATT NCAACAGCCN TGCCCATTGN TGAAACCCTT      840

TTCCTAAAAT TAAAAAATAN CCGGTTNNGG NNGGCCTCTT TCCCCTCCNG GNGGGNNGNG      900

AAANTCCTTA CCCCNAAAAA GGTTGCTTAG CCCCCNGTCC CCACTCCCCC NGGAAAAATN      960

AACCTTTTCN AAAAAAGGAA TATAANTTTN CCACTCCTTN GTTCTCTTCC                1010

(2) INFORMATION FOR SEQ ID NO: 6:

(i) SEQUENCE CHARACTERISTICS:
        (A) LENGTH: 950 base pairs
        (B) TYPE: nucleic acid
        (C) STRANDEDNESS: single
        (D) TOPOLOGY: linear (xi) SEQUENCE DESCRIPTION: SEQ ID NO: 6:

TCTAGAGCTC GCGGCCGCGA GCTCTAATAC GACTCACTAT AGGGCGTCGA CTCGATCTCA       60

GCTCACTGCA ATCTCTGCCC CCGGGGTCAT GCGATTCTCC TGCCTCAGCC TTCCAAGTAG      120

CTGGGATTAC AGGCGTGCAA CACCACACCC GGCTAATTTT GTATTTTTAA TAGAGATGGG      180

GTTTTCCCTT GTTGGCCANN ATGGTCTCNA ACCCCTGACC TCNNGTGATC CCCCCNCCCN      240

NGANCTCNNA CTGCTGGGGA TNNCCGNNNN NNNCCTCCCN NCNCNNNNNN NCNCNNTCCN      300

TNNTCCTTNC TCNNNNNNNN CNNTCNNTCC NNCTTCTCNC CNNNTNTTNT CNNCNNCCNN      360

CNNNCCNCNT NCCCNCNNNT TCNCNTNCNN TNTCCNNCNN NNTCNNCNNN CNNNNCNTNN      420

CCNNTACNTC NTNNNCNNNT CCNTCTNTNN CCTCNNCNNT CNCTCNCNT TNTCTCCTCN      480

NTNNNNNNCT CCNNNNNTCT CNTCNCNNCN TNCCTCNNTN NCCNCNCCCC NCCTCNCNNC      540

CTNNTTTNNN CNNCNNNTCC NTNCCNTTCN NNTCCNNTNN CNNCNTCNCN NNCNTTNTTC      600

CCNCCNNTTC CTTNCNCNTN NNNTNTCNNN CNCNTCNNTC NTTTNCTCCT NNNTCCCNNC      660

TCNNTTCNCC CNNNTCCNCC CCCCNCCTNT CTCTCNCCCN NNTNNNTNTN NNNCNTCCNC      720

TNTCNCNTTC NTCNNTNCNT TNCTNTCNNC NNCNNTNCNC TNCCNTNTNT CTNNNTCNCN      780

TCNCNTNTCN CCNTCCNTTN CTNTCTCCTN TNTCCTTCCC CTCNCCTNCT CNTTCNCCNC      840

CCNNTNTNTN TNNCNCCNNT NCTNNNCNNC CNTCNTTTCN TCTCTNCTNN NNNTNNCCTC      900

NNCCCNTNCC CTNNTNCNCT NCTNNTACCN TNCTNCTCCN TCTTCCTTCC                 950

(2) INFORMATION FOR SEQ ID NO: 7:

(i) SEQUENCE CHARACTERISTICS:
        (A) LENGTH: 1086 base pairs
        (B) TYPE: nucleic acid
        (C) STRANDEDNESS: single
        (D) TOPOLOGY: linear (xi) SEQUENCE DESCRIPTION: SEQ ID NO: 7:

TCTAGAGCTC GCGGCCGCGA GCTCAATTAA CCCTCACTAA AGGGAGTCGA CTCGATCAGA       60

CTGTTACTGT GTCTATGTAG AAAGAAGTAG ACATAAGAGA TTCCATTTTG TTCTGTACTA      120

AGAAAAATTC TTCTGCCTTG AGATGCTGTT AATCTGTAAC CCTAGCCCCA ACCCTGTGCT      180

CACAGAGACA TGTGCTGTGT TGACTCAAGG TTCAATGGAT TTAGGGCTAT GCTTTGTTAA      240
```

-continued

```
AAAAGTGCTT GAAGATAATA TGCTTGTTAA AAGTCATCAC CATTCTCTAA TCTCAAGTAC      300

CCAGGGACAC AATACACTGC GGAAGGCCGC AGGGACCTCT GTCTAGGAAA GCCAGGTATT      360

GTCCAAGATT TCTCCCCATG TGATAGCCTG AGATATGGCC TCATGGGAAG GGTAAGACCT      420

GACTGTCCCC CAGCCCGACA TCCCCCAGCC CGACATCCCC CAGCCCGACA CCCGAAAAGG      480

GTCTGTGCTG AGGAAGATTA NTAAAAGAGG AAGGCTCTTT GCATTGAAGT AAGAAGAAGG      540

CTCTGTCTCC TGCTCGTCCC TGGGCAATAA AATGTCTTGG TGTTAAACCC GAATGTATGT      600

TCTACTTACT GAGAATAGGA GAAACATCC  TTAGGGCTGG AGGTGAGACA CCCTGGCGGC      660

ATACTGCTCT TTAATGCACG AGATGTTTGT NTAATTGCCA TCCAGGGCCA NCCCCTTTCC      720

TTAACTTTTT ATGANACAAA AACTTTGTTC NCTTTTCCTG CGAACCTCTC CCCCTATTAN      780

CCTATTGGCC TGCCCATCCC CTCCCCAAAN GGTGAAAANA TGTTCNTAAA TNCGAGGGAA      840

TCCAAAACNT TTTCCCGTTG GTCCCCTTTC CAACCCCGTC CCTGGGCCNN TTTCCTCCCC      900

AACNTGTCCC GGNTCCTTCN TTCCCNCCCC CTTCCCNGAN AAAAAACCCC GTNTGANGGN      960

GCCCCCTCAA ATTATAACCT TTCCNAAACA AANNGGTTCN AAGGTGGTTT GNTTCCGGTG     1020

CGGCTGGCCT TGAGGTCCCC CCTNCACCCC AATTTGGAAN CCNGTTTTTT TTATTGCCCN     1080

NTCCCC                                                                1086
```

(2) INFORMATION FOR SEQ ID NO: 8:

(i) SEQUENCE CHARACTERISTICS:
        (A) LENGTH: 1177 base pairs
        (B) TYPE: nucleic acid
        (C) STRANDEDNESS: single
        (D) TOPOLOGY: linear (xi) SEQUENCE DESCRIPTION: SEQ ID NO: 8:

```
NCCNTTTAGA TGTTGACAAN NTAAACAAGC NGCTCAGGCA GCTGAAAAAA GCCACTGATA       60

AAGCATCCTG GAGTATCAGA GTTTACTGTT AGATCAGCCT CATTTGACTT CCCCTCCCAC      120

ATGGTGTTTA AATCCAGCTA CACTACTTCC TGACTCAAAC TCCACTATTC CTGTTCATGA      180

CTGTCAGGAA CTGTTGGAAA CTACTGAAAC TGGCCGACCT GATCTTCAAA ATGTGCCCCT      240

AGGAAAGGTG GATGCCACCG TGTTCACAGA CAGTACCNCC TTCCTCGAGA AGGGACTACG      300

AGGGGCCGGT GCANCTGTTA CCAAGGAGAC TNATGTGTTG TGGGCTCAGG CTTTACCANC      360

AAACACCTCA NCNCNNAAGG CTGAATTGAT CGCCCTCACT CAGGCTCTCG GATGGGGTAA      420

GGGATATTAA CGTTAACACT GACAGCAGGT ACGCCTTTGC TACTGTGCAT GTACGTGGAG      480

CCATCTACCA GGAGCGTGGG CTACTCACTC GGCAGGTGGC TGTNATCCAC TGTAAANGGA      540

CATCAAAAGG AAAACNNGGC TGTTGCCCGT GGTAACCANA AANCTGATCN NCAGCTCNAA      600

GATGCTGTGT TGACTTTCAC TCNCNCCTCT TAAACTTGCT GCCCACANTC TCCTTTCCCA      660

ACCAGATCTG CCTGACAATC CCCATACTCA AAAAAAAAAN AANACTGGCC CCGAACCCNA      720

ACCAATAAAA ACGGGGANGG TNGGTNGANC NNCCTGACCC AAAAATAATG GATCCCCCGG      780

GCTGCAGGAA TTCAATTCAN CCTTATCNAT ACCCCCAACN GGNGGGGGG  GGCCNGTNCC      840

CATTNCCCCT NTATTNATTC TTTNNCCCCC CCCCCGGCNT CCTTTTTNAA CTCGTGAAAG      900

GGAAAACCTG NCTTACCAAN TTATCNCCTG GACCNTCCCC TTCCNCGGTN GNTTANAAAA      960

AAAAGCCCNC ANTCCCNTCC NAAATTTGCA CNGAAAGGNA AGGAATTTAA CCTTTATTTT     1020

TTNNTCCTTT ANTTTGTNNN CCCCCTTTTA CCCAGGCGAA CNGCCATCNT TTAANAAAAA     1080

AAANAGAAAG TTTATTTTTC CTTNGAACCA TCCCAATANA AANCACCCGC NGGGGAACGG     1140
```

```
GGNGGNAGGC CNCTCACCCC CTTTNTGTNG GNGGGNC                      1177
```

(2) INFORMATION FOR SEQ ID NO: 9:

(i) SEQUENCE CHARACTERISTICS:
        (A) LENGTH: 1146 base pairs
        (B) TYPE: nucleic acid
        (C) STRANDEDNESS: single
        (D) TOPOLOGY: linear (xi) SEQUENCE DESCRIPTION: SEQ ID NO: 9:

```
NCCNNTTNNT GATGTTGTCT TTTTGGCCTC TCTTTGGATA CTTTCCCTCT CTTCAGAGGT    60

GAAAAGGGTC AAAAGGAGCT GTTGACAGTC ATCCCAGGTG GGCCAATGTG TCCAGAGTAC   120

AGACTCCATC AGTGAGGTCA AAGCCTGGGG CTTTTCAGAG AAGGGAGGAT TATGGGTTTT   180

CCAATTATAC AAGTCAGAAG TAGAAAGAAG GGACATAAAC CAGGAAGGGG GTGGAGCACT   240

CATCACCCAG AGGGACTTGT GCCTCTCTCA GTGGTAGTAG AGGGGCTACT TCCTCCCACC   300

ACGGTTGCAA CCAAGAGGCA ATGGGTGATG AGCCTACAGG GGACATANCC GAGGAGACAT   360

GGGATGACCC TAAGGGAGTA GGCTGGTTTT AAGGCGGTGG GACTGGGTGA GGGAAACTCT   420

CCTCTTCTTC AGAGAGAAGC AGTACAGGGC GAGCTGAACC GGCTGAAGGT CGAGGCGAAA   480

ACACGGTCTG GCTCAGGAAG ACCTTGGAAG TAAAATTATG AATGGTGCAT GAATGGAGCC   540

ATGGAAGGGG TGCTCCTGAC CAAACTCAGC CATTGATCAA TGTTAGGGAA ACTGATCAGG   600

GAAGCCGGGA ATTTCATTAA CAACCCGCCA CACAGCTTGA ACATTGTGAG GTTCAGTGAC   660

CCTTCAAGGG GCCACTCCAC TCCAACTTTG GCCATTCTAC TTTGCNAAAT TTCCAAAACT   720

TCCTTTTTTA AGGCCGAATC CNTANTCCCT NAAAAACNAA AAAAAATCTG CNCCTATTCT   780

GGAAAAGGCC CANCCCTTAC CAGGCTGGAA GAAATTTTNC CTTTTTTTTT TTTTTGAAGG   840

CNTTTNTTAA ATTGAACCTN AATTCNCCCC CCCAAAAAAA AACCCNCCNG GGGGCGGAT    900

TTCCAAAAAC NAATTCCCTT ACCAAAAAAC AAAAACCCNC CCTTNTTCCC TTCCNCCCTN   960

TTCTTTTAAT TAGGGAGAGA TNAAGCCCCC CAATTTCCNG GNCTNGATNN GTTTCCCCCC  1020

CCCCCATTTT CCNAAACTTT TTCCCANCNA GGAANCCNCC CTTTTTTTNG GTCNGATTNA  1080

NCAACCTTCC AAACCATTTT TCCNNAAAAA NTTTGNTNGG NGGGAAAAAN ACCTNNTTTT  1140

ATAGAN                                                             1146
```

(2) INFORMATION FOR SEQ ID NO: 10:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (xi) SEQUENCE DESCRIPTION: SEQ ID NO: 10:

```
CTTCATTGGG TACGGGCCCC CTCGAGGTCG ACGGTATCGA TAAGCTTGAT ATCGAATTCC    60

TGCAGCCCGG GGGATCCACT AGTTCTAGAG TCAGGAAGAA CCACCAACCT TCCTGATTTT   120

TATTGGCTCT GAGTTCTGAG GCCAGTTTTC TTCTTCTGTT GAGTATGCGG GATTGTCAGG   180

CAGATCTGGC TGTGGAAAGG AGACTGTGGG CAGCAAGTTT AGAGGCGTGA CTGAAAGTCA   240

CACTGCATCT TGAGCTGCTG AATCAGCTTT CTGGTTACCA CGGGCAACAG CCGTGTTTTC   300

CTTTTGATGT CCTTTACAGT GGATTACAGC CACCTGCTGA GGTGAGTAGC CCACGCTCCT   360

GGTAGATGGC TCCACGTACA TGCACAGTAG CAAAGGCGTA CCTGCTGTCA GTGTTAACGT   420

TAATATCCTT ACCCCATCGG AGAGCCTGAG TGAGGGCGAT CAATTCAGCC CTTTTGTGCT   480
```

GAGGTGTTTG CTGGTTAAGC CCTGAACCCA CAACACATCT GTCTCCATGG TAACAGCTGC      540

ACCGG                                                                 545

(2) INFORMATION FOR SEQ ID NO: 11:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (xi) SEQUENCE DESCRIPTION: SEQ ID NO: 11:

TCTCCTAGGC TGGGCACAGT GGCTCATACC TGTAATCCTG ACCGTTTCAG AGGCTCAGGT       60

GGGGGGATCG CTTGAGCCCA AGATTTCAAG ACTAGTCTGG GTAACATAGT GAGACCCTAT      120

CTCTACGAAA AATAAAAAA ATGAGCCTGG TGTAGTGGCA CACACCAGCT GAGGAGGGAG      180

AATCGAGCCT AGGAGA                                                     196

(2) INFORMATION FOR SEQ ID NO: 12:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (xi) SEQUENCE DESCRIPTION: SEQ ID NO: 12:

TCTCCTAGGC TTGGGGGCTC TGACTAGAAA TTCAAGGAAC CTGGGATTCA AGTCCAACTG       60

TGACACCAAC TTACACTGTG GNCTCCAATA AACTGCTTCT TTCCTATTCC CTCTCTATTA      120

AATAAAATAA GGAAAACGAT GTCTGTGTAT AGCCAAGTCA GNTATCCTAA AAGGAGATAC      180

TAAGTGACAT TAAATATCAG AATGTAAAAC CTGGGAACCA GGTTCCCAGC CTGGGATTAA      240

ACTGACAGCA AGAAGACTGA ACAGTACTAC TGTGAAAAGC CCGAAGNGGC AATATGTTCA      300

CTCTACCGTT GAAGGATGGC TGGGAGAATG AATGCTCTGT CCCCCAGTCC CAAGCTCACT      360

TACTATACCT CCTTTATAGC CTAGGAGA                                        388

(2) INFORMATION FOR SEQ ID NO: 13:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (xi) SEQUENCE DESCRIPTION: SEQ ID NO: 13:

TAGTAGTTGC CTATAATCAT GTTTCTCATT ATTTTCACAT TTTATTAACC AATTTCTGTT       60

TACCCTGAAA AATATGAGGG AAATATATGA AACAGGGAGG CAATGTTCAG ATAATTGATC      120

ACAAGATATG ATTTCTACAT CAGATGCTCT TTCCTTTCCT GTTTATTTCC TTTTTATTTC      180

GGTTGTGGGG TCGAATGTAA TAGCTTTGTT TCAAGAGAGA GTTTTGGCAG TTTCTGTAGC      240

TTCTGACACT GCTCATGTCT CCAGGCATCT ATTTGCACTT TAGGAGGTGT CGTGGGAGAC      300

TGAGAGGTCT ATTTTTTCCA TATTTGGGCA ACTACTA                              337

(2) INFORMATION FOR SEQ ID NO: 14:

(i) SEQUENCE CHARACTERISTICS:
        (A) LENGTH: 571 base pairs
        (B) TYPE: nucleic acid
        (C) STRANDEDNESS: single (D) TOPOLOGY: linear (xi) SEQUENCE DESCRIPTION: SEQ ID NO: 14:

| | | | | | |
|---|---|---|---|---|---|
| TAGTAGTTGC | CATACAGTGC | CTTTCCATTT | ATTTAACCCC | CACCTGAACG | GCATAAACTG | 60 |
| AGTGTTCAGC | TGGTGTTTTT | TACTGTAAAC | AATAAGGAGA | CTTTGCTCTT | CATTTAAACC | 120 |
| AAAATCATAT | TTCATATTTT | ACGCTCGAGG | GTTTTTACCG | GTTCCTTTTT | ACACTCCTTA | 180 |
| AAACAGTTTT | TAAGTCGTTT | GGAACAAGAT | ATTTTTTCTT | TCCTGGCAGC | TTTTAACATT | 240 |
| ATAGCAAATT | TGTGTCTGGG | GGACTGCTGG | TCACTGTTTC | TCACAGTTGC | AAATCAAGGC | 300 |
| ATTTGCAACC | AAGAAAAAAA | AATTTTTTTG | TTTTATTTGA | AACTGGACCG | GATAAACGGT | 360 |
| GTTTGGAGCG | GCTGCTGTAT | ATAGTTTTAA | ATGGTTTATT | GCACCTCCTT | AAGTTGCACT | 420 |
| TATGTGGGGG | GGGGNTTTTG | NATAGAAAGT | NTTTANTCAC | ANAGTCACAG | GGACTTTTNT | 480 |
| CTTTTGGNNA | CTGAGCTAAA | AAGGGCTGNT | TTTCGGGTGG | GGGCAGATGA | AGGCTCACAG | 540 |
| GAGGCCTTTC | TCTTAGAGGG | GGGAACTNCT | A | | | 571 |

(2) INFORMATION FOR SEQ ID NO: 15:

(i) SEQUENCE CHARACTERISTICS:
        (A) LENGTH: 548 base pairs
        (B) TYPE: nucleic acid
        (C) STRANDEDNESS: single
        (D) TOPOLOGY: linear (xi) SEQUENCE DESCRIPTION: SEQ ID NO: 15:

| | | | | | |
|---|---|---|---|---|---|
| TATATATTTA | ATAACTTAAA | TATATTTTGA | TCACCCACTG | GGGTGATAAG | ACAATAGATA | 60 |
| TAAAAGTATT | TCCAAAAAGC | ATAAAACCAA | AGTATCATAC | CAAACCAAAT | TCATACTGCT | 120 |
| TCCCCCACCC | GCACTGAAAC | TTCACCTTCT | AACTGTCTAC | CTAACCAAAT | TCTACCCTTC | 180 |
| AAGTCTTTGG | TGCGTGCTCA | CTACTCTTTT | TTTTTTTTTT | TTTNTTTTGG | AGATGGAGTC | 240 |
| TGGCTGTGCA | GCCCAGGGGT | GGAGTACAAT | GGCACAACCT | CAGCTCACTG | NAACCTCCGC | 300 |
| CTCCCAGGTT | CATGAGATTC | TCCTGNTTCA | GCCTTCCCAG | TAGCTGGGAC | TACAGGTGTG | 360 |
| CATCACCATG | CCTGGNTAAT | CTTTTTTNGT | TTTNGGGTAG | AGATGGGGGT | TTTACATGTT | 420 |
| GGCCAGGNTG | GTNTCGAACT | CCTGACCTCA | AGTGATCCAC | CCACCTCAGG | CTCCCAAAGT | 480 |
| GCTAGGATTA | CAGACATGAG | CCACTGNGCC | CAGNCCTGGT | GCATGCTCAC | TTCTCTAGGC | 540 |
| AACTACTA | | | | | | 548 |

(2) INFORMATION FOR SEQ ID NO: 16:

(i) SEQUENCE CHARACTERISTICS:
        (A) LENGTH: 638 base pairs
        (B) TYPE: nucleic acid
        (C) STRANDEDNESS: single
        (D) TOPOLOGY: linear (xi) SEQUENCE DESCRIPTION: SEQ ID NO: 16:

| | | | | | |
|---|---|---|---|---|---|
| TTCCGTTATG | CACATGCAGA | ATATTCTATC | GGTACTTCAG | CTATTACTCA | TTTTGATGGC | 60 |
| GCAATCCGAG | CCTATCCTCA | AGATGAGTAT | TTAGAAAGAA | TTGATTTAGC | GATAGACCAA | 120 |
| GCTGGTAAGC | ACTCTGACTA | CACGAAATTG | TTCAGATGTG | ATGGATTTAT | GACAGTTGAT | 180 |
| CTTTGGAAGA | GATTATTAAG | TGATTATTTT | AAAGGGAATC | CATTAATTCC | AGAATATCTT | 240 |
| GGTTTAGCTC | AAGATGATAT | AGAAATAGAA | CAGAAAGAGA | CTACAAATGA | AGATGTATCA | 300 |
| CCAACTGATA | TTGAAGAGCC | TATAGTAGAA | AATGAATTAG | CTGCATTTAT | TAGCCTTACA | 360 |
| CATAGCGATT | TCCTGATGA | ATCTTATATT | CAGCCATCGA | CATAGCATTA | CCTGATGGGC | 420 |

```
AACCTTACGA ATAATAGAAA CTGGGTGCGG GGCTATTGAT GAATTCATCC NCAGTAAATT      480

TGGATATNAC AAAATATAAC TCGATTGCAT TTGGATGATG GAATACTAAA TCTGGCAAAA      540

GTAACTTTGG AGCTACTAGT AACCTCTCTT TTTGAGATGC AAAATTTTCT TTTAGGGTTT      600

CTTATTCTCT ACTTTACGGA TATTGGAGCA TAACGGGA                              638

(2) INFORMATION FOR SEQ ID NO: 17:

(i) SEQUENCE CHARACTERISTICS:
         (A) LENGTH: 286 base pairs
         (B) TYPE: nucleic acid
         (C) STRANDEDNESS: single
         (D) TOPOLOGY: linear (xi) SEQUENCE DESCRIPTION: SEQ ID NO: 17:

ACTGATGGAT GTCGCCGGAG GCGAGGGGCC TTATCTGATG CTCGGCTGCC TGTTCGTGAT       60

GTGCGCGGCG ATTGGGCTGT TTATCTCAAA CACCGCCACG GCGGTGCTGA TGGCGCCTAT      120

TGCCTTAGCG GCGGCGAAGT CAATGGGCGT CTCACCCTAT CCTTTTGCCA TGGTGGTGGC      180

GATGGCGGCT TCGGCGGCGT TTATGACCCC GGTCTCCTCG CCGGTTAACA CCCTGGTGCT      240

TGGCCCTGGC AAGTACTCAT TTAGCGATTT TGTCAAAATA GGCGTG                    286

(2) INFORMATION FOR SEQ ID NO: 18:

(i) SEQUENCE CHARACTERISTICS:
         (A) LENGTH: 262 base pairs
         (B) TYPE: nucleic acid
         (C) STRANDEDNESS: single
         (D) TOPOLOGY: linear (xi) SEQUENCE DESCRIPTION: SEQ ID NO: 18:

TCGGTCATAG CAGCCCCTTC TTCTCAATTT CATCTGTCAC TACCCTGGTG TAGTATCTCA       60

TAGCCTTACA TTTTTATAGC CTCCTCCCTG GTCTGTCTTT TGATTTTCCT GCCTGTAATC     120

CATATCACAC ATAACTGCAA GTAAACATTT CTAAAGTGTG GTTATGCTCA TGTCACTCCT     180

GTGNCAAGAA ATAGTTTCCA TTACCGTCTT AATAAAATTC GGATTTGTTC TTTNCTATTN     240

TCACTCTTCA CCTATGACCG AA                                              262

(2) INFORMATION FOR SEQ ID NO: 19:

(i) SEQUENCE CHARACTERISTICS:
         (A) LENGTH: 261 base pairs
         (B) TYPE: nucleic acid
         (C) STRANDEDNESS: single
         (D) TOPOLOGY: linear (xi) SEQUENCE DESCRIPTION: SEQ ID NO: 19:

TCGGTCATAG CAAAGCCAGT GGTTTGAGCT CTCTACTGTG TAAACTCCTA AACCAAGGCC       60

ATTTATGATA AATGGTGGCA GGATTTTTAT TATAAACATG TACCCATGCA AATTTCCTAT     120

AACTCTGAGA TATATTCTTC TACATTTAAA CAATAAAAAT AATCTATTTT TAAAAGCCTA     180

ATTTGCGTAG TTAGGTAAGA GTGTTTAATG AGAGGGTATA AGGTATAAAT CACCAGTCAA     240

CGTTTCTCTG CCTATGACCG A                                               261

(2) INFORMATION FOR SEQ ID NO: 20:

(i) SEQUENCE CHARACTERISTICS:
         (A) LENGTH: 294 base pairs
         (B) TYPE: nucleic acid
         (C) STRANDEDNESS: single
```

-continued (D) TOPOLOGY: linear (xi) SEQUENCE DESCRIPTION: SEQ ID NO: 20:

```
TACAACGAGG CGACGTCGGT AAAATCGGAC ATGAAGCCAC CGCTGGTCTT TTCGTCCGAG      60
CGATAGGCGC CGGCCAGCCA GCGGAACGGT TGCCCGGATG GCGAAGCGAG CCGGAGTTCT     120
TCGGACTGAG TATGAATCTT GTTGTGAAAA TACTCGCCGC CTTCGTTCGA CGACGTCGCG     180
TCGAAATCTT CGANCTCCTT ACGATCGAAG TCTTCGTGGG CGACGATCGC GGTCAGTTCC     240
GCCCCACCGA AATCATGGTT GAGCCGGATG CTGNCCCCGA AGNCCTCGTT TGTN           294
```

(2) INFORMATION FOR SEQ ID NO: 21:

(i) SEQUENCE CHARACTERISTICS:
          (A) LENGTH: 208 base pairs
          (B) TYPE: nucleic acid
          (C) STRANDEDNESS: single
          (D) TOPOLOGY: linear (xi) SEQUENCE DESCRIPTION: SEQ ID NO: 21:

```
TTGGTAAAGG GCATGGACGC AGACGCCTGA CGTTTGGCTG AAAATCTTTC ATTGATTCGT      60
ATCAATGAAT AGGAAAATTC CCAAAGAGGG AATGTCCTGT TGCTCGCCAG TTTTTNTGTTY    120
GTTCTCATGG ANAAGGCAAN GAGCTCTTCA GACTATTGGN ATTNTCGTTC GGTCTTCTGC     180
CAACTAGTCG NCTTGCNANG ATCTTCAT                                        208
```

(2) INFORMATION FOR SEQ ID NO: 22:

(i) SEQUENCE CHARACTERISTICS:
          (A) LENGTH: 287 base pairs
          (B) TYPE: nucleic acid
          (C) STRANDEDNESS: single
          (D) TOPOLOGY: linear (xi) SEQUENCE DESCRIPTION: SEQ ID NO: 22:

```
NCCNTTGAGC TGAGTGATTG AGATNTGTAA TGGTTGTAAG GGTGATTCAG GCGGATTAGG      60
GTGGCGGGTC ACCCGGCAGT GGGTCTCCCG ACAGGCCAGC AGGATTTGGG GCAGGTACGG     120
NGTGCGCATC GCTCGACTAT ATGCTATGGC AGGCGAGCCG TGGAAGGNGG ATCAGGTCAC     180
GGCGCTGGAG CTTTCCACGG TCCATGNATT GNGATGGCTG TTCTAGGCGG CTGTTGCCAA    240
GCGTGATGGT ACGCTGGCTG GAGCATTGAT TTCTGGTGCC AAGGTGG                   287
```

(2) INFORMATION FOR SEQ ID NO: 23:

(i) SEQUENCE CHARACTERISTICS:
          (A) LENGTH: 204 base pairs
          (B) TYPE: nucleic acid
          (C) STRANDEDNESS: single
          (D) TOPOLOGY: linear (xi) SEQUENCE DESCRIPTION: SEQ ID NO: 23:

```
TTGGGTAAAG GGAGCAAGGA GAAGGCATGG AGAGGCTCAN GCTGGTCCTG GCCTACGACT      60
GGGCCAAGCT GTCGCCGGGG ATGGTGGAGA ACTGAAGCGG GACCTCCTCG AGGTCCTCCG     120
NCGTTACTTC NCCGTCCAGG AGGAGGGTCT TTCCGTGGTC TNGGAGGAGC GGGGGGAGAA     180
GATNCTCCTC ATGGTCNACA TCCC                                            204
```

(2) INFORMATION FOR SEQ ID NO: 24:

(i) SEQUENCE CHARACTERISTICS:
          (A) LENGTH: 264 base pairs
          (B) TYPE: nucleic acid (C) STRANDEDNESS: single
        (D) TOPOLOGY: linear (xi) SEQUENCE DESCRIPTION: SEQ ID NO: 24:

TGGATTGGTC AGGAGCGGGT AGAGTGGCAC CATTGAGGGG ATATTCAAAA ATATTATTTT      60

GTCCTAAATG ATAGTTGCTG AGTTTTTCTT TGACCCATGA GTTATATTGG AGTTTATTTT     120

TTAACTTTCC AATCGCATGG ACATGTTAGA CTTATTTTCT GTTAATGATT NCTATTTTTA     180

TTAAATTGGA TTTGAGAAAT TGGTTNTTAT TATATCAATT TTTGGTATTT GTTGAGTTTG     240

ACATTATAGC TTAGTATGTG ACCA                                            264

(2) INFORMATION FOR SEQ ID NO: 25:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (xi) SEQUENCE DESCRIPTION: SEQ ID NO: 25:

TTACAACGAG GGGAAACTCC GTCTCTACAA AAATTAAAAA ATTAGCCAGG TGTGGTGGTG      60

TGCACCCGCA ATCCCAGCTA CTTGGGAGGT TGAGACACAA GANTCACCTA NATGTGGGAG     120

GTCAAGGTTG CATGAGTCAT GATTGTGCCA CTGCACTCCA GCCTGGGTGA CAGACCGAGA     180

CCCTGCCTCA ANAGANAANG AATAGGAAGT TCAGAAATCN TGGNTGTGGN GCCCAGCAAT     240

CTGCATCTAT NCAACCCCTG CAGGCAANGC TGATGCAGCC TANGTTCAAG AGCTGCTGTT     300

TCTGGAGGCA GCAGTTNGGG CTTCCATCCA GTATCACGGC CACACTCGCA CNAGCCATCT     360

GTCCTCCGTN TGTNAC                                                     376

(2) INFORMATION FOR SEQ ID NO: 26:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (xi) SEQUENCE DESCRIPTION: SEQ ID NO: 26:

TTACAACGAG GGGAAACTCC GTCTCTACAA AAATTAAAAA ATTAGCCAGG TGTGGTGGTG      60

TGCACCTGTA ATCCCAGCTA CTTGGGCGGC TGAGACACAA GAACCACCTA AATGTGGGAG     120

GGTCAAGGTT GCATGAGTCA TGATCGCGCC ACTGCACTCC AGCCTGGGTG ACAGACTGAG     180

ACCCTGCCTC AAAAGAAAAA GAATAGGAAG TTCAGAAACC CTGGGTGTGG NGCCCAGCAA     240

TCTGCATTTA AACAATCCCT GCAGGCAATG CTGATGCAGC CTAAGTTCAA GAGCTGCTGT     300

TCTGGAGGCA GNAGTAAGGG CTTCCATCCA GCATCACGGN CAACACTGCA AAAGCACCTG     360

TCCTCGTTGG TA                                                         372

(2) INFORMATION FOR SEQ ID NO: 27:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (xi) SEQUENCE DESCRIPTION: SEQ ID NO: 27:

TTCTGTCCAC ATCTACAAGT TTTATTTATT TTGTGGGTTT TCAGGGTGAC TAAGTTTTTC      60

CCTACATTGA AAAGAGAAGT TGCTAAAAGG TGCACAGGAA ATCATTTTTT TAAGTGAATA     120

TGATAATATG GGTCCGTGCT TAATACAACT GAGACATATT TGTTCTCTGT TTTTTTAGAG    180

TCACCTCTTA AAGTCCAATC CCACAATGGT GAAAAAAAAA TAGAAAGTAT TTGTTCTACC    240

TTTAAGGAGA CTGCAGGGAT TCTCCTTGAA AACGGAGTAT GGAATCAATC TTAAATAAAT    300

ATGAAATTGG TTGGTCTTCT GGGATAAGAA ATTCCCAACT CAGTGTGCTG AAATTCACCT    360

GACTTTTTTT GGGAAAAAAT AGTCGAAAAT GTCAATTTGG TCCATAAAAT ACATGTTACT    420

ATTAAAAGAT ATTTAAAGAC AAATTCTTTC AGAGCTCTAA GATTGGTGTG GACAGAA       477

(2) INFORMATION FOR SEQ ID NO: 28:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (xi) SEQUENCE DESCRIPTION: SEQ ID NO: 28:

TCTNCAACCT CTTGANTGTC AAAAACCTTN TAGGCTATCT CTAAAAGCTG ACTGGTATTC     60

ATTCCAGCAA AATCCCTCTA GTTTTTGGAG TTTCCTTTTA CTATCTGGGG CTGCCTGAGC    120

CACAAATGCC AAATTAAGAG CATGGCTATT TTCGGGGGCT GACAGGTCAA AAGGGGTGTA    180

AATCCGATAA GCCTCCTGGA GGTGCTCTAA AAACACTCCT GGTGACTCAT CATGCCCCTG    240

GACGACTTCA ATCGNCTTAG ACAAGTTTAT AGGTTTCTGG GCAGCTCCCT GAATACCCAC    300

GAGGAGATAC CGGTGGAAAT CGTCAAAAGT TCTCCCTCCA CTTGAGAAAT TTGGGTCCCA    360

ATTAGGTCCC AATTGGGTCT CTAATCACTA TTCCTCTAGC TTCCTCCTCC GGNCTATTGG    420

TTGATGTGAG GTTGAAGA                                                  438

(2) INFORMATION FOR SEQ ID NO: 29:

(i) SEQUENCE CHARACTERISTICS:
        (A) LENGTH: 620 base pairs
        (B) TYPE: nucleic acid
        (C) STRANDEDNESS: single
        (D) TOPOLOGY: linear (xi) SEQUENCE DESCRIPTION: SEQ ID NO: 29:

AAGAGGGTAC CAGCCCCAAG CCTTGACAAC TTCCATAGGG TGTCAAGCCT GTGGGTGCAC     60

AGAAGTCAAA AATTGAGTTT TGGGATCCTC AGCCTAGATT TCAGAGGATA TAAAGAAACA    120

CCTAACACCT AGATATTCAG ACAAAAGTTT ACTACAGGGA TGAAGCTTTC ACGGAAAACC    180

TCTACTAGGA AAGTACAGAA GAGAAATGTG GGTTTGGAGC CCCCAAACAG AATCCCCTCT    240

AGAACACTGC CTAATGAAAC TGTGAGAAGA TGGCCACTGT CATCCAGACA CCAGAATGAT    300

AGACCCACCA AAAACTTATG CCATATTGCC TATAAAACCT ACAGACACTC AATGCCAGCC    360

CCATGAAAAA AAAACTGAGA AGAAGACTGT NCCCTACAAT GCCACCGGAG CAGAACTGCC    420

CCAGGCCATG GAAGCACAGC TCTTATATCA ATGTGACCTG GATGTTGAGA CATGGAATCC    480

NANGAAATCN TTTTAANACT TCCACGGTTN AATGACTGCC CTATTANATT CNGAACTTAN    540

ATCCNGGCCT GTGACCTCTT TGCTTTGGCC ATTCCCCCTT TTTGGAATGG CTNTTTTTTT    600

CCCATGCCTG TNCCCTCTTA                                                620

(2) INFORMATION FOR SEQ ID NO: 30:

(i) SEQUENCE CHARACTERISTICS:
        (A) LENGTH: 100 base pairs
        (B) TYPE: nucleic acid (C) STRANDEDNESS: single
        (D) TOPOLOGY: linear (xi) SEQUENCE DESCRIPTION: SEQ ID NO: 30:

TTACAACGAG GGGGTCAATG TCATAAATGT CACAATAAAA CAATCTCTTC TTTTTTTTTT      60

TTTTTTTTTT TTTTTTTTTT TTTTTTTTTT TTTTTTTTTT                          100

(2) INFORMATION FOR SEQ ID NO: 31:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (xi) SEQUENCE DESCRIPTION: SEQ ID NO: 31:

TAGTCTATGC GCCGGACAGA GCAGAATTAA ATTGGAAGTT GCCCTCCGGA CTTTCTACCC      60

ACACTCTTCC TGAAAAGAGA AAGAAAAGAG GCAGGAAAGA GGTTAGGATT TCATTTTCAA     120

GAGTCAGCTA ATTAGGAGAG CAGAGTTTAG ACAGCAGTAG GCACCCCATG ATACAAACCA     180

TGGACAAAGT CCCTGTTTAG TAACTGCCAG ACATGATCCT GCTCAGGTTT TGAAATCTCT     240

CTGCCCATAA AAGATGGAGA GCAGGAGTGC CATCCACATC AACACGTGTC CAAGAAAGAG     300

TCTCAGGGAG ACAAGGGTAT CAAAAAACAA GATTCTTAAT GGGAAGGAAA TCAAACCAAA     360

AAATTAGATT TTTCTCTACA TATATATAAT ATACAGATAT TTAACACATT ATTCCAGAGG     420

TGGCTCCAGT CCTTGGGGCT TGAGAGATGG TGAAAACTTT TGTTCCACAT TAACTTCTGC     480

TCTCAAATTC TGAAGTATAT CAGAATGGGA CAGGCAATGT TTTGCTCCAC ACTGGGGCAC     540

AGACCCAAAT GGTTCTGTGC CCGAAGAAGA GAAGCCCGAA AGACATGAAG GATGCTTAAG     600

GGGGGTTGGG AAAGCCAAAT TGGTANTATC TTTTCCTCCT GCCTGTGTTC CNGAAGTCTC     660

CNCTGAAGGA ATTCTTAAAA CCCTTTGTGA GGAAATGCCC CCTTACCATG ACAANTGGTC     720

CCATTGCTTT TAGGGNGATG GAAACACCAA GGGTTTTGAT CC                       762

(2) INFORMATION FOR SEQ ID NO: 32:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (xi) SEQUENCE DESCRIPTION: SEQ ID NO: 32:

TAGTCTATGC GTGTATTAAC CTCCCCTCCC TCAGTAACAA CCAAAGAGGC AGGAGCTGTT      60

ATTACCAACC CCATTTTACA GATGCATCAA TAATGACAGA GAAGTGAAGT GACTTGCGCA     120

CACAACCAGT AAATTGGCAG AGTCAGATTT GAATCCATGG AGTCTGGTCT GCACTTTCAA     180

TCACCGAATA CCCTTTCTAA GAAACGTGTG CTGAATGAGT GCATGGATAA ATCAGTGTCT     240

ACTCAACATC TTTGCCTAGA TATCCCGCAT AGACTA                              276

(2) INFORMATION FOR SEQ ID NO: 33:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (xi) SEQUENCE DESCRIPTION: SEQ ID NO: 33:

TAGTAGTTGC CAAATATTTG AAAATTTACC CAGAAGTGAT TGAAAACTTT TTGGAAACAA      60

```
AAACAAATAA AGCCAAAAGG TAAAATAAAA ATATCTTTGC ACTCTCGTTA TTACCTATCC      120

ATAACTTTTT CACCGTAAGC TCTCCTGCTT GTTAGTGTAG TGTGGTTATA TTAAACTTTT      180

TAGTTATTAT TTTTTATTCA CTTTTCCACT AGAAAGTCAT TATTGATTTA GCACACATGT      240

TGATCTCATT TCATTTTTTC TTTTTATAGG CAAAATTTGA TGCTATGCAA CAAAAATACT      300

CAAGCCCATT ATCTTTTTTC CCCCCGAAAT CTGAAAATTG CAGGGGACAG AGGGAAGTTA      360

TCCCATTAAA AAATTGTAAA TATGTTCAGT TTATGTTTAA AAATGCACAA AACATAAGAA      420

AATTGTGTTT ACTTGAGCTG CTGATTGTAA GCAGTTTTAT CTCAGGGGCA ACTACTA        477

(2) INFORMATION FOR SEQ ID NO: 34:

(i) SEQUENCE CHARACTERISTICS:
        (A) LENGTH: 631 base pairs
        (B) TYPE: nucleic acid
        (C) STRANDEDNESS: single
        (D) TOPOLOGY: linear (xi) SEQUENCE DESCRIPTION: SEQ ID NO: 34:

TAGTAGTTGC CAATTCAGAT GATCAGAAAT GCTGCTTTCC TCAGCATTGT CTTGTTAAAC       60

CGCATGCCAT TTGGAACTTT GGCAGTGAGA AGCCAAAAGG AAGAGGTGAA TGACATATAT      120

ATATATATAT ATTCAATGAA AGTAAAATGT ATATGCTCAT ATACTTTCTA GTTATCAGAA      180

TGAGTTAAGC TTTATGCCAT TGGGCTGCTG CATATTTTAA TCAGAAGATA AAAGAAAATC      240

TGGGCATTTT TAGAATGTGA TACATGTTTT TTTAAAACTG TTAAATATTA TTTCGATATT      300

TGTCTAAGAA CCGGAATGTT CTTAAAATTT ACTAAAACAG TATTGTTTGA GGAAGAGAAA      360

ACTGTACTGT TTGCCATTAT TACAGTCGTA CAAGTGCATG TCAAGTCACC CACTCTCTCA      420

GGCATCAGTA TCCACCTCAT AGCTTTACAC ATTTTGACGG GGAATATTGC AGCATCCTCA      480

GGCCTGACAT CTGGGAAAGG CTCAGATCCA CCTACTGCTC CTTGCTCGTT GATTTGTTTT      540

AAAATATTGT GCCTGGTGTC ACTTTTAAGC CACAGCCCTG CCTAAAAGCC AGCAGAGAAC      600

AGAACCCGCA CCATTCTATA GGCAACTACT A                                    631

(2) INFORMATION FOR SEQ ID NO: 35:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO: 35:

TAGTAGTTGC CATCCCATAT TACAGAAGGC TCTGTATACA TGACTTATTT GGAAGTGATC       60

TGTTTTCTCT CCAAACCCAT TTATCGTAAT TTCACCAGTC TTGGATCAAT CTTGGTTTCC      120

ACTGATACCA TGAAACCTAC TTGGAGCAGA CATTGCACAG TTTTCTGTGG TAAAAACTAA      180

AGGTTTATTT GCTAAGCTGT CATCTTATGC TTAGTATTTT TTTTTACAG TGGGGAATTG      240

CTGAGATTAC ATTTTGTTAT TCATTAGATA CTTTGGGATA ACTTGACACT GTCTTCTTTT      300

TTTCGCTTTT AATTGCTATC ATCATGCTTT TGAAACAAGA ACACATTAGT CCTCAAGTAT      360

TACATAAGCT TGCTTGTTAC GCCTGGTGGT TTAAAGGACT ATCTTTGGCC TCAGGTTCAC      420

AAGAATGGGC AAAGTGTTTC CTTATGTTCT GTAGTTCTCA ATAAAAGATT GCCAGGGGCC      480

GGGTACTGTG GCTCGCACTG TAATCCCAGC ACTTTGGGAA GCTGAGGCTG GCGGATCATG      540

TTAGGGCAGG TGTTCGAAAC CAGCCTGGGC AACTACTA                             578
```

(2) INFORMATION FOR SEQ ID NO: 36:

(i) SEQUENCE CHARACTERISTICS:
        (A) LENGTH: 583 base pairs
        (B) TYPE: nucleic acid
        (C) STRANDEDNESS: single
        (D) TOPOLOGY: linear (xi) SEQUENCE DESCRIPTION: SEQ ID NO: 36:

```
TAGTAGTTGC CTGTAATCCC AGCAACTCAG GAGGCTGGGG CAGGAGAATC AGTTGAACCT      60

GGGAGGCAGA AGTTGTAATT AGCAAAGATC GCACCATTGC ACTTCAGCCT GGGCAACAAG     120

AGTGAGATTC CATCTCAAAA ACAAAAAAAA GAAAAAGAAA AGAAAAGGAA AAAACGTATA     180

AACCCAGCCA AAACAAAATG ATCATTCTTT TAATAAGCAA GACTAATTTA ATGTGTTTAT     240

TTAATCAAAG CAGTTGAATC TTCTGAGTTA TTGGTGAAAA TACCCATGTA GTTAATTTAG     300

GGTTCTTACT TGGGTGAACG TTTGATGTTC ACAGGTTATA AAATGGTTAA CAAGGAAAAT     360

GATGCATAAA GAATCTTATA AACTACTAAA AATAAATAAA ATATAAATGG ATAGGTGCTA     420

TGGATGGAGT TTTTGTGTAA TTTAAAATCT TGAAGTCATT TTGGATGCTC ATTGGTTGTC     480

TGGTAATTTC CATTAGGAAA AGGTTATGAT ATGGGGAAAC TGTTTCTGGA AATTGCGGAA     540

TGTTTCTCAT CTGTAAAATG CTAGTATCTC AGGGCAACTA CTA                      583
```

(2) INFORMATION FOR SEQ ID NO: 37:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (xi) SEQUENCE DESCRIPTION: SEQ ID NO: 37:

```
GATCTACTAG TCATNTGGAT TCTATCCATG GCAGCTAAGC CTTTCTGAAT GGATTCTACT      60

GCTTTCTTGT TCTTTAATCC AGACCCTTAT ATATGTTTAT GTTCACAGGC AGGGCAATGT     120

TTAGTGAAAA CAATTCTAAA TTTTTTATTT TGCATTTTCA TGCTAATTTC CGTCACACTC     180

CAGCAGGCTT CCTGGGAGAA TAAGGAGAAA TACAGCTAAA GACATTGTCC CTGCTTACTT     240

ACAGCCTAAT GGTATGCAAA ACCACTTCAA TAAAGTAACA GGAAAAGTAC TAACCAGGTA     300

GAATGGACCA AAACTGATAT AGAAAAATCA GAGGAAGAGA GGAACAAATA TTTACTGAGT     360

CCTAGAATGT ACAAGGCTTT TTAATTACAT ATTTTATGTA AGGCCTGCAA AAAACAGGTG     420

AGTAATCAAC ATTTGTCCCA TTTTACATAT AAGGAAACTG AAGCTTAAAT TGAATAATTT     480

AATGCATAGA TTTTATAGTT AGACCATGTT CAGGTCCCTA TGTTATACTT ACTAGCTGTA     540

TGAATATGAG AAAATAATTT TGTTATTTTC TTGGCATCAG TATTTTCATC TGCAAAATAA     600

AGCTAAAGTT ATTTAGCAAA CAGTCAGCAT AGTGCCTGAT ACATAGTAGG TGCTCCAAAC     660

ATGATTACNC TANTATTNGG TATTANAAAA ATCCAATATA GGCNTGGATA AAACCG        716
```

(2) INFORMATION FOR SEQ ID NO: 38:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (xi) SEQUENCE DESCRIPTION: SEQ ID NO: 38:

```
TTCTGTCCAC ATATCATCCC ACTTTAATTG TTAATCAGCA AAACTTTCAA TGAAAAATCA      60
```

```
TCCATTTTAA CCAGGATCAC ACCAGGAAAC TGAAGGTGTA TTTTTTTTTA CCTTAAAAAA      120

AAAAAAAAAA ACCAAACAAA CCAAAACAGA TTAACAGCAA AGAGTTCTAA AAAATTTACA      180

TTTCTCTTAC AACTGTCATT CAGAGAACAA TAGTTCTTAA GTCTGTTAAA TCTTGGCATT      240

AACAGAGAAA CTTGATGAAN AGTTGTACTT GGAATATTGT GGATTTTTTT TTTTGTCTAA      300

TCTCCCCCTA TTGTTTTGCC AACAGTAATT TAAGTTTGTG TGGAACATCC CCGTAGTTGA      360

AGTGTAAACA ATGTATAGGA AGGAATATAT GATAAGATGA TGCATCACAT ATGCATTACA      420

TGTAGGGACC TTCACAACTT CATGCACTCA GAAAACATGC TTGAAGAGGA GGAGAGGACG      480

GCCCAGGGTC ACCATCCAGG TGCCTTGAGG ACAGAGAATG CAGAAGTGGC ACTGTTGAAA      540

TTTAGAAGAC CATGTGTGAA TGGTTTCAGG CCTGGGATGT TGCCACCAA GAAGTGCCTC       600

CGAGAAATTT CTTTCCCATT TGGAATACAG GGTGGCTTGA TGGGTACGGT GGGTGACCCA      660

ACGAAGAAAA TGAAATTCTG CCCTTTCC                                        688
```

(2) INFORMATION FOR SEQ ID NO: 39:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (xi) SEQUENCE DESCRIPTION: SEQ ID NO: 39:

```
TAGTAGTTGC CGCNNACCTA AAANTTGGAA AGCATGATGT CTAGGAAACA TANTAAAATA       60

GGGTATGCCT ATGTGCTACA GAGAGATGTT AGCATTTAAA GTGCATANTT TTATGTATTT      120

TGACAAATGC ATATNCCTCT ATAATCCACA ACTGATTACG AAGCTATTAC AATTAAAAAG      180

TTTGGCCGGG CGTGGTGGGC GGTGGCTGAC GCCTGTAATC CCAGCACTTT GGGAGGCCGA      240

GGCACGCGGA TCACGAGGTC GGGAGTTCAA GACCATCCTG GCTAACACGG TGAAAGTCCA      300

TCTCTACTAA AAATACGAAA AAATTACCCC GGCGTGGTGG CGGGCGCCTG TAGTCCCAGC      360

TACTCCGGAG GCTGAGGCAG GAGAATGGCG TGAACCCAGG ACACGGAGCT TGCAGTGTGC      420

CAACATCACG TCACTGCCCT CCAGCCTGGG GGACAGGAAC AAGANTCCCG TCCTCANAAA      480

AGAAAAATAC TACTNATANT TTCNACTTTA TTTTAANTTA CACAGAACTN CCTCTTGGTA      540

CCCCCTTACC ATTCATCTCA CCCACCTCCT ATAGGGCACN NCTAA                     585
```

(2) INFORMATION FOR SEQ ID NO: 40:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (xi) SEQUENCE DESCRIPTION: SEQ ID NO: 40:

```
TCTGTCCACA CCAATCTTAG AAGCTCTGAA AAGAATTTGT CTTTAAATAT CTTTTAATAG       60

TAACATGTAT TTTATGGACC AAATTGACAT TTTCGACTGT TTTTTCCAAA AAAGTCAGGT      120

GAATTTCAGC ACACTGAGTT GGGAATTTCT TATCCCAGAA GACCAACCAA TTTCATATTT      180

ATTTAAGATT GATTCCATAC TCCGTTTTCA AGGAGAATCC CTGCAGTCTC CTTAAAGGTA      240

GAACAAATAC TTCCTATTTT TTTTTCACCA TTGTGGGATT GGACTTTAAG AGGTGACTCT      300

AAAAAAACAG AGAACAAATA TGTCTCAGTT GTATTAAGCA CGGACCCATA TTATCATATT      360

CACTTAAAAA AATGATTTCC TGTGCACCTT TTGGCAACTT CTCTTTTCAA TGTAGGGAAA      420

AACTTAGTCA CCCTGAAAAC CCACAAAATA AATAAAACTT GTAGATGTGG ACAGA          475
```

(2) INFORMATION FOR SEQ ID NO: 41:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (xi) SEQUENCE DESCRIPTION: SEQ ID NO: 41:

```
TAAGAGGGTA CATCGGGTAA GAACGTAGGC ACATCTAGAG CTTAGAGAAG TCTGGGGTAG      60

GAAAAAAATC TAAGTATTTA TAAGGGTATA GGTAACATTT AAAAGTAGGG CTAGCTGACA     120

TTATTTAGAA AGAACACATA CGGAGAGATA AGGGCAAAGG ACTAAGACCA GAGGAACACT     180

AATATTTAGT GATCACTTCC ATTCTTGGTA AAAATAGTAA CTTTTAAGTT AGCTTCAAGG     240

AAGATTTTTG GCCATGATTA GTTGTCAAAA GTTAGTTCTC TTGGGTTTAT ATTACTAATT     300

TTGTTTTAAG ATCCTTGTTA GTGCTTTAAT AAAGTCATGT TATATCAAAC GCTCTAAAAC     360

ATTGTAGCAT GTTAAATGTC ACAATATACT TACCATTTGT TGTATATGGC TGTACCCTCT     420

CTA                                                                   423
```

(2) INFORMATION FOR SEQ ID NO: 42:

(i) SEQUENCE CHARACTERISTICS:
        (A) LENGTH: 527 base pairs
        (B) TYPE: nucleic acid
        (C) STRANDEDNESS: single
        (D) TOPOLOGY: linear (xi) SEQUENCE DESCRIPTION: SEQ ID NO: 42:

```
TCTCCTAGGC TAATGTGTGT GTTTCTGTAA AAGTAAAAAG TTAAAAATTT TAAAAATAGA      60

AAAAAGCTTA TAGAATAAGA ATATGAAGAA AGAAAATATT TTTGTACATT TGCACAATGA     120

GTTTATGTTT TAAGCTAAGT GTTATTACAA AAGAGCCAAA AAGGTTTTAA AAATTAAAAC     180

GTTTGTAAAG TTACAGTACC CTTATGTTAA TTTATAATTG AAGAAAGAAA AACTTTTTTT     240

TATAAATGTA GTGTAGCCTA AGCATACAGT ATTTATAAAG TCTGGCAGTG TTCAATAATG     300

TCCTAGGCCT TCACATTCAC TCACTGACTC ACCCAGAGCA ACTTCCAGTC CTGTAAGCTC     360

CATTCGTGGT AAGTGCCCTA TACAGGTGCA CCATTTATTT TACAGTATTT TTACTGTACC     420

TTCTCTATGT TTCCATATGT TTCGATATAC AAATACCACT GGTTACTATN GCCCNACAGG     480

TAATTCCAGT AACACGGCCT GTATACGTCT GGTANCCCTA GNGAAGA                   527
```

(2) INFORMATION FOR SEQ ID NO: 43:

(i) SEQUENCE CHARACTERISTICS:
        (A) LENGTH: 331 base pairs
        (B) TYPE: nucleic acid
        (C) STRANDEDNESS: single
        (D) TOPOLOGY: linear (xi) SEQUENCE DESCRIPTION: SEQ ID NO: 43:

```
TCTTCAACCT CGTAGGACAA CTCTCATATG CCTGGGCACT ATTTTAGGT TACTACCTTG       60

GCTGCCCTTC TTTAAGAAAA AAAAAAGAAG AAAAAAGAAC TTTTCCACAA GTTTCTCTTC     120

CTCTAGTTGG AAAATTAGAG AAATCATGTT TTTAATTTTG TGTTATTTCA GATCACAAAT     180

TCAAACACTT GTAAACATTA AGCTTCTGTT CAATCCCCTG GGAAGAGGAT TCATTCTGAT     240

ATTTACGGTT CAAAAGAAGT TGTAATATTG TGCTTGGAAC ACAGAGAACC AGTTATTAAC     300

TTCCTACTAC TATTATATAA TAAATAATAA C                                    331
```

(2) INFORMATION FOR SEQ ID NO: 44:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (xi) SEQUENCE DESCRIPTION: SEQ ID NO: 44:

```
GGCTTAGTAG TTGCCAGGCA AAATARCGTT GATTCTCCTC AGGAGCCACC CCCAACACCC      60

CTGTTTGCTT CTAGACCTAT ACCTAGACTA AAGTCCCAGC AGACCCCTAG AGGTGAGGTT     120

CAGAGTGACC CTTGAGGAGA TGTGCTACAC TAGAAAAGAA CTGCTTGAGT TTTCTAATTT     180

ATATAAGCAG AAATCTGGAG AAGAGTCATA GGAATGGATA TTAAGGGTGT GAGATAATGG     240

CGGAAGGAAT ATAGAGTTGG ATCAGGCTGG ACTTATTGAT TTGAACCCAC TAAGTAGAGA     300

TTCTGCTTTT GATGTTGCAG CTCAGGGAGT TAAAAAAGGT TTTAATGGTT CTAATAGTTT     360

ATTTGCTTGG TTAGCTGAAA TATGGATAAA AGATGGCCCA CTGTGAGCAA GCTGGAAATG     420

CCTGATCTCT CTCAGTTTAA TGTAGAGGAA GGGATCCAAA AGTTTAGGGA GANTTGGATG     480

CTGGRAKTGG ATTGGTCACT TTGRGACCTA CCCWTCCCAG CTGGGAGGGT CCAGAAGATA     540

CACCCTTGAC CAACGCTTTG CGAAATGGAT TTGTGATGGC GGCAACTACT AA            592
```

(2) INFORMATION FOR SEQ ID NO: 45:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (xi) SEQUENCE DESCRIPTION: SEQ ID NO: 45:

```
GGCTTAGTAG TTGCCATTGC GAGTGCTTGC TCAACGAGCG TTGAACATGG CGGATTGTCT      60

AGATTCAACG GATTTGAGTT TTACCAGCAA AGCGAACCAA GCGCGGCCCA GAGAATTATG     120

GGTTGGTTGG CTTTGAAAAG ATGGAAATCC TGTAGGCCTA GTCAGAAAAG CCTTCTTGCA     180

GAACAGTTGG TTCTCGGGCG AACGCTCATC AAGATGCCCA TTGGAAAGGC TAGCGTGTAT     240

TTGGGAGAGC CTGATAGCGT GTCTTCTGAT GATGTTTGTG CTTGGACAGT GACAAAAGAT     300

ATGCAAAGCA AGTCCGAACT AGACGTCAAG CTTCGTGAGC AAATTATTGT AGACTCCTAC     360

TTATACTGTG AGGAATGATA GCCAAGGGTG GGGACTTTAA GACTAAGGTG GTTTGTACTT     420

GCGCCGATGA TCCCAGGCAG AAAGAMCTGA TCGCTAGTTT TATACGGGCA ACTACTAAGC     480

CGAATTCCAG CACACTGGCG GCCGTTACTA ATTGGATCCG ANCTCGGTAC CAGCTTGATG     540

CATASCTTGA GTTWTCTATA NTGTCNC                                        567
```

(2) INFORMATION FOR SEQ ID NO: 46:

(i) SEQUENCE CHARACTERISTICS:
        (A) LENGTH: 908 base pairs
        (B) TYPE: nucleic acid
        (C) STRANDEDNESS: single
        (D) TOPOLOGY: linear (xi) SEQUENCE DESCRIPTION: SEQ ID NO: 46:

```
GAGCGAAAGA CCGAGGGCAG NGNNTANGNG CGANGAAGCG GAGAGGGCCA AAAAGCAACC      60

GCTTTCCCCG GGGGGTGCCG ATTCATTAAG GCAGGTGGAG GACAGGTTTC CCGATGGAAG     120

GCGGCAGGGG CGCAAGCAAT TAATGTGAGT AGGCCATTCA TTAGCACCCG GGCTTAACAT     180
```

```
TTAAGCTTCG GGTTGGTATG TGGTGGGAAT TGTGAGCGGA TAACAATTTC ACACAGGAAA      240

CAGCTATGAC CATGATTACG CCAAGCTATT TAGGTGACAT TATAGAATAA CTCAAGTTAT      300

GCATCAAGCT TGGTACCGAG TTCGGATCCA CTAGTAACGG CCGCCAGTGT GTGGAATTCG      360

GCTTAGTAGT TGCCGACCAT GGAGTGCTAC CTAGGCTAGA ATACCTGAGY TCCTCCCTAG      420

CCTCACTCAC ATTAAATTGT ATCTTTTCTA CATTAGATGT CCTCAGCGCC TTATTTCTGC      480

TGGACWATCG ATAAATTAAT CCTGATAGGA TGATAGCAGC AGATTAATTA CTGAGAGTAT      540

GTTAATGTGT CATCCCTCCT ATATAACGTA TTTGCATTTT AATGGAGCAA TTCTGGAGAT      600

AATCCCTGAA GGCAAAGGAA TGAATCTTGA GGGTGAGAAA GCCAGAATCA GTGTCCAGCT      660

GCAGTTGTGG GAGAAGGTGA TATTATGTAT GTCTCAGAAG TGACACCATA TGGGCAACTA      720

CTAAGCCCGA ATTCCAGCAC ACTGGCGGGC GTTACTAATG GATCCGAGCT CGGTACCAAG      780

CTTGATGCAT AGCTTGAGTA TCTATAGTGT CACTAAATAG CCTGGCGTTA TCATGGTCAT      840

AGCTGTTTCC TGTGTGAAAT TGTTATCCGC TCCCAATTCC CCCCACCATA CGAGCCGGAA      900

CATAAAGT                                                               908

(2) INFORMATION FOR SEQ ID NO: 47:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (xi) SEQUENCE DESCRIPTION: SEQ ID NO: 47:

TGCCAACAAG GAAAGTTTTA AATTTCCCCT TGAGGATTCT TGGTGATCAT CAAATTCAGT       60

GGTTTTTAAG GTTGTTTTCT GTCAAATAAC TCTAACTTTA AGCCAAACAG TATATGGAAG      120

CACAGATAKA ATATTACACA GATAAAAGAG GAGTTGATCT AAAGTARAGA TAGTTGGGGG      180

CTTTAATTTC TGGAACCTAG GTCTCCCCAT CTTCTTCTGT GCTGAGGAAC TTCTTGGAAG      240

CGGGGATTCT AAAGTTCTTT GGAAGACAGT TTGAAAACCA CCATGTTGTT CTCAGTACCT      300

TTATTTTTAA AAAGTAGGTG AACATTTTGA GAGAGAAAAG GGCTTGGTTG AGATGAAGTC      360

CCCCCCCCCC CTTTTTTTTT TTTTAGCTGA AATAGATACC CTATGTTNAA RGAARGGATT      420

ATTATTTACC ATGCCAYTAR SCACATGCTC TTTGATGGGC NYCTCCSTAC CCTCCTTAAG      480

(2) INFORMATION FOR SEQ ID NO: 48:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (xi) SEQUENCE DESCRIPTION: SEQ ID NO: 48:

AAGAGGGTAC CGAGTGGAAT TTCCGCTTCA CTAGTCTGGT GTGGCTAGTC GGTTTCGTGG       60

TGGCCAACAT TACGAACTTC CAACTCAACC GTTCTTGGAC GTTCAAGCGG GAGTACCGGC      120

GAGGATGGTG GCGTGAATTC TGGCCTTTCT TTGCCGTGGG ATCGGTAGCC GCCATCATCG      180

GTATGTTTAT CAAGATCTTC TTTACTAACC CGACCTCTCC GATTTACCTG CCCGAGCCGT      240

GGTTTAACGA GGGGAGGGGG ATCCAGTCAC GCGAGTACTG GTCCCAGATC TTCGCCATCG      300

TCGTGACAAT GCCTATCAAC TTCGTCGTCA ATAAGTTGTG GACCTTCCGA ACGGTGAAGC      360

ACTCCGAAAA CGTCCGGTGG CTGCTGTGCG GTGACTCCCA AAATCTTGAT AACAACAAGG      420
```

```
TAACCGAATC GCGCTAAGGA ACCCCGGCAT CTCGGGTACT CTGCATATGC GTACCCCTTA      480

AGCCGAATTC CAGCACACTG GCGGCCGTTA CTAATTGGAT CCGAACTCCG TAACCAAGCC      540

TGATGCGTAA CTTGAGTTAT TCTATAGTGT CCCTAAAATA ACCTGGCGTT A               591

(2) INFORMATION FOR SEQ ID NO: 49:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (xi) SEQUENCE DESCRIPTION: SEQ ID NO: 49:

AAGAGGGTAC CTGCCTTGAA ATTTAAATGT CTAAGGAAAR TGGGAGATGA TTAAGAGTTG       60

GTGTGGCYTA GTCACACCAA AATGTATTTA TTACATCCTG CTCCTTTCTA GTTGACAGGA     120

AAGAAAGCTG CTGTGGGGAA AGGAGGGATA AATACTGAAG GGATTTACTA AACAAATGTC     180

CATCACAGAG TTTTCCTTTT TTTTTTTTTG AGACAGAGTC TTGCTCTGTC ACCCAGGCTG     240

GAATGAAGWG GTATGATCTC AGTTGAATGC AACCTCTACC TCCTAGGTTC AAGCGATTCT     300

CATGCCTCAG CCTCCTGAGC AGCTGGGACT ATAGGCGCAT GCTACCATGC CAGGCTAATT     360

TTTATATTTT TATTAGAGAC GGGGTGTTGC CATGTTGGCC AGGCAGGTCT CGAACTCCTG     420

GGCCTCAGAT GATCTGCCCC ACCGTACCCT CTTA                                 454

(2) INFORMATION FOR SEQ ID NO: 50:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (xi) SEQUENCE DESCRIPTION: SEQ ID NO: 50:

AAGAGGGTAC CAAAAAAAG AAAAAGGAAA AAAAGAAAAA CAACTTGTAT AAGGCTTTCT       60

GCTGCATACA GCTTTTTTTT TTTAAATAAA TGGTGCCAAC AAATGTTTTT GCATTCACAC     120

CAATTGCTGG TTTTGAAATC GTACTCTTCA AAGGTATTTG TGCAGATCAA TCCAATAGTG     180

ATGCCCCGTA GGTTTTGTGG ACTGCCCACG TTGTCTACCT TCTCATGTAG GAGCCATTGA     240

GAGACTGTTT GGACATGCCT GTGTTCATGT AGCCGTGATG TCCGGGGCC GTGTACATCA     300

TGTTACCGTG GGGTGGGGTC TGCATTGGCT GCTGGGCATA TGGCTGGGTG CCCATCATGC     360

CCATCTGCAT CTGCATAGGG TATTGGGGCG TTTGATCCAT ATAGCCATGA TTGCTGTGGT     420

AGCCACTGTT CATCATTGGC TGGGACATGC TGTTACCCTC TTA                       463

(2) INFORMATION FOR SEQ ID NO: 51:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (xi) SEQUENCE DESCRIPTION: SEQ ID NO: 51:

CTTCAACCTC CCAAAGTGCT GGGATTACAG GACTGAGCCA CCACGCTCAG CCTAAGCCTC      60

TTTTTCACTA CCCTCTAAGC GATCTACCAC AGTGATGAGG GGCTAAAGAG CAGTGCAATT     120

TGATTACAAT AATGGAACTT AGATTTATTA ATTAACAATT TTTCCTTAGC ATGTTGGTTC     180

CATAATTATT AAGAGTATGG ACTTACTTAG AAATGAGCTT TCATTTTAAG AATTTCATCT     240
```

```
TTGACCTTCT CTATTAGTCT GAGCAGTATG ACACTATACG TATTTTATTT AACTAACCTA        300

CCTTGAGCTA TTACTTTTTA AAAGGCTATA TACATGAATG TGTATTGTCA ACTGTAAAGC        360

CCCACAGTAT TTAATTATAT CATGATGTCT TTGAGGTTG                               399

(2) INFORMATION FOR SEQ ID NO: 52:

(i) SEQUENCE CHARACTERISTICS:
          (A) LENGTH: 392 base pairs
          (B) TYPE: nucleic acid
          (C) STRANDEDNESS: single
          (D) TOPOLOGY: linear (xi) SEQUENCE DESCRIPTION: SEQ ID NO: 52:

CTTCAACCTC AATCAACCTT GGTAATTGAT AAAATCATCA CTTAACTTTC TGATATAATG         60

GCAATAATTA TCTGAGAAAA AAAAGTGGTG AAAGATTAAA CTTGCATTTC TCTCAGAATC        120

TTGAAGGATA TTTGAATAAT TCAAAAGCGG AATCAGTAGT ATCAGCCGAA GAAACTCACT        180

TAGCTAGAAC GTTGGACCCA TGGATCTAAG TCCCTGCCCT TCCACTAACC AGCTGATTGG        240

TTTTGTGTAA ACCTCCTACA CGCTTGGGCT TGGTCGCCTC ATTTGTCAAA GTAAAGGCTG        300

AAATAGGAAG ATAATGAACC GTGTCTTTTT GGTCTCTTTT CCATCCATTA CTCTGATTTT        360

ACAAAGAGGC CTGTATTCCC CTGGTGAGGT TG                                     392

(2) INFORMATION FOR SEQ ID NO: 53:

(i) SEQUENCE CHARACTERISTICS:
          (A) LENGTH: 179 base pairs
          (B) TYPE: nucleic acid
          (C) STRANDEDNESS: single
          (D) TOPOLOGY: linear (xi) SEQUENCE DESCRIPTION: SEQ ID NO: 53:

TTCGGGTGAT GCCTCCTCAG GCTACAGTGA AGACTGGATT ACAGAAAGGT GCCAGCGAGA         60

TTTCAGATTC CTGTAAACCT CTAAAGAAAA GGAGTCGCGC CTCAACTGAT GTAGAAATGA        120

CTAGTTCAGC ATACNGAGAC ACNTCTGACT CCGATTCTAG AGGACTGAGT GACCTGCAN        179

(2) INFORMATION FOR SEQ ID NO: 54:

(i) SEQUENCE CHARACTERISTICS:
          (A) LENGTH: 112 base pairs
          (B) TYPE: nucleic acid
          (C) STRANDEDNESS: single
          (D) TOPOLOGY: linear (xi) SEQUENCE DESCRIPTION: SEQ ID NO: 54:

TTCGGGTGAT GCCTCCTCAG GCTACATCAT NATAGAAGCA AAGTAGAANA ATCNNGTTTG         60

TGCATTTTCC CACANACAAA ATTCAAATGA NTGGAAGAAA TTGGGANAGT AT               112

(2) INFORMATION FOR SEQ ID NO: 55:

(i) SEQUENCE CHARACTERISTICS:
          (A) LENGTH: 225 base pairs
          (B) TYPE: nucleic acid
          (C) STRANDEDNESS: single
          (D) TOPOLOGY: linear (xi) SEQUENCE DESCRIPTION: SEQ ID NO: 55:

TGAGCTTCCG CTTCTGACAA CTCAATAGAT AATCAAAGGA CAACTTTAAC AGGGATTCAC         60

AAAGGAGTAT ATCCAAATGC CAATAAACAT ATAAAAAGGA ATTCAGCTTC ATCATCATCA        120

GAAGWATGCA AATTAAAACC ATAATGAGAA ACCACTATGT CCCACTAGAA TAGATAAAAT        180
```

CTTAAAAGAC TGGTAAAACC AAGTGTTGGT AAGGCAAGAG GAGCA                    225

(2) INFORMATION FOR SEQ ID NO: 56:

(i) SEQUENCE CHARACTERISTICS:
          (A) LENGTH: 175 base pairs
          (B) TYPE: nucleic acid
          (C) STRANDEDNESS: single
          (D) TOPOLOGY: linear (xi) SEQUENCE DESCRIPTION: SEQ ID NO: 56:

GCTCCTCTTG CCTTACCAAC ACATTCTCAA AAACCTGTTA GAGTCCTAAG CATTCTCCTG     60

TTAGTATTGG GATTTTACCC CTGTCCTATA AAGATGTTAT GTACCAAAAA TGAAGTGGAG    120

GGCCATACCC TGAGGGAGGG GAGGGATCTC TAGTGTTGTC AGAAGCGGAA GCTCA         175

(2) INFORMATION FOR SEQ ID NO: 57:

(i) SEQUENCE CHARACTERISTICS:
          (A) LENGTH: 223 base pairs
          (B) TYPE: nucleic acid
          (C) STRANDEDNESS: single
          (D) TOPOLOGY: linear (xi) SEQUENCE DESCRIPTION: SEQ ID NO: 57:

AGCCATTTAC CACCCATGGA TGAATGGATT TTGTAATTCT AGCTGTTGTA TTTTGTGAAT     60

TTGTTAATTT TGTTGTTTTT CTGTGAAACA CATACATTGG ATATGGGAGG TAAAGGAGTG    120

TCCCAGTTGC TCCTGGTCAC TCCCTTTATA GCCATTACTG TCTTGTTTCT TGTAACTCAG    180

GTTAGGTTTT GGTCTCTCTT GCTCCACTGC AAAAAAAAAA AAA                     223

(2) INFORMATION FOR SEQ ID NO: 58:

(i) SEQUENCE CHARACTERISTICS:
          (A) LENGTH: 211 base pairs
          (B) TYPE: nucleic acid
          (C) STRANDEDNESS: single
          (D) TOPOLOGY: linear (xi) SEQUENCE DESCRIPTION: SEQ ID NO: 58:

GTTCGAAGGT GAACGTGTAG GTAGCGGATC TCACAACTGG GGAACTGTCA AAGACGAATT     60

AACTGACTTG GATCAATCAA ATGTGACTGA GGAAACACCT GAAGGTGAAG AACATCATCC    120

AGTGGCAGAC ACTGAAAATA GGAGAATGA AGTTGAAGAG GTAAAAGAGG AGGGTCCAAA     180

AGAGATGACT TTGGATGGGT GGTAAATGGC T                                   211

(2) INFORMATION FOR SEQ ID NO: 59:

(i) SEQUENCE CHARACTERISTICS:
          (A) LENGTH: 208 base pairs
          (B) TYPE: nucleic acid
          (C) STRANDEDNESS: single
          (D) TOPOLOGY: linear (xi) SEQUENCE DESCRIPTION: SEQ ID NO: 59:

GCTCCTCTTG CCTTACCAAC TTTGCACCCA TCATCAACCA TGTGGCCAGG TTTGCAGCCC     60

AGGCTGCACA TCAGGGGACT GCCTCGCAAT ACTTCATGCT GTTGCTGCTG ACTGATGGTG    120

CTGTGACGGA TGTGGAAGCC ACACGTGAGG CTGTGGTGCG TGCCTCGAAC CTGCCCATGT    180

CAGTGATCAT TATGGGTGGT AAATGGCT                                      208

(2) INFORMATION FOR SEQ ID NO: 60:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (xi) SEQUENCE DESCRIPTION: SEQ ID NO: 60:

AGCCATTTAC CACCCATACT AAATTCTAGT TCAAACTCCA ACTTCTTCCA TAAAACATCT        60

AACCACTGAC ACCAGTTGGC AATAGCTTCT TCCTTCTTTA ACCTCTTAGA GTATTTATGG       120

TCAATGCCAC ACATTTCTGC AACTGAATAA AGTTGGTAAG GCAAGAGGAG C                171

(2) INFORMATION FOR SEQ ID NO: 61:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (xi) SEQUENCE DESCRIPTION: SEQ ID NO: 61:

CGGGTGATGC CTCCTCAGGC TTTGGTGTGT CCACTCNACT CACTGGCCTC TTCTCCAGCA        60

ACTGGTGAAN ATGTCCTCAN GAAAANCNCC ACACGCNGCT CAGGGTGGGG TGGGAANCAT       120

CANAATCATC NGGC                                                        134

(2) INFORMATION FOR SEQ ID NO: 62:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (xi) SEQUENCE DESCRIPTION: SEQ ID NO: 62:

AGAGGGTACA TATGCAACAG TATATAAAGG AAGAAGTGCA CTGAGAGGAA CTTCATCAAG        60

GCCATTTAAT CAATAAGTGA TAGAGTCAAG GCTCAACCCA GGTGTGACGG ATTCCAGGTC       120

CCAAGCTCCT TACTGGTACC CTCTT                                            145

(2) INFORMATION FOR SEQ ID NO: 63:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO: 63:

TGCACTGAGA GGAATTCAAA GGGTTTATGC CAAAGAACAA ACCAGTCCTC TGCAGCCTAA        60

CTCATTTGTT TTTGGGCTGC GAAGCCATGT AGAGGGCGAT CAGGCAGTAG ATGGTCCCTC       120

CCACAGTCAG CGCCATGGTG GTCCGGTAAA GCATTTGGTC AGGCAGGCCT CGTTTCAGGT       180

AGACGGGCAC ACATCAGCTT TCTGGAAAAA CTTTTGTAGC TCTGGAGCTT TGTTTTTCCC       240

AGCATAATCA TACACTGTGG AATCGGAGGT CAGTTTAGTT GGTAAGGCAA GAGGAGC          297

(2) INFORMATION FOR SEQ ID NO: 64:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (xi) SEQUENCE DESCRIPTION: SEQ ID NO: 64:

```
GCACTGAGAG GAACTTCCAA TACTATGTTG AATAGGAGTG GTGAGAGAGG GCATCCTTGT        60

CTTGTGCCGG TTTTCAAAGG GAATGCTTCC AGCTTTTGCC CATTCAGTAT AATATTAAAG       120

AATGTTTTAC CATTTTCTGT CTTGCCTGTT TTTCTGTGTT TTTGTTGGTC TCTTCATTCT       180

CCATTTTTAG GCCTTTACAT GTTAGGAATA TATTTCTTTT AATGATACTT CACCTTTGGT       240

ATCTTTTGTG AGACTCTACT CATAGTGTGA TAAGCACTGG GTTGGTAAGG CAAGAGGAGC       300
```

(2) INFORMATION FOR SEQ ID NO: 65:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (xi) SEQUENCE DESCRIPTION: SEQ ID NO: 65:

```
GCTCCTCTTG CCTTACCAAC TCACCCAGTA TGTCAGCAAT TTTATCRGCT TTACCTACGA        60

AACAGCCTGT ATCCAAACAC TTAACACACT CACCTGAAAA GTTCAGGCAA CAATCGCCTT       120

CTCATGGGTC TCTCTGCTCC AGTTCTGAAC CTTTCTCTTT TCCTAGAACA TGCATTTARG       180

TCGATAGAAG TTCCTCTCAG TGC                                               203
```

(2) INFORMATION FOR SEQ ID NO: 66:

(i) SEQUENCE CHARACTERISTICS:
        (A) LENGTH: 344 base pairs
        (B) TYPE: nucleic acid
        (C) STRANDEDNESS: single
        (D) TOPOLOGY: linear (xi) SEQUENCE DESCRIPTION: SEQ ID NO: 66:

```
TACGGGGACC CCTGCATTGA GAAAGCGAGA CTCACTCTGA AGCTGAAATG CTGTTGCCCT        60

TGCAGTGCTG GTAGCAGGAG TTCTGTGCTT TGTGGGCTAA GGCTCCTGGA TGACCCCTGA       120

CATGGAGAAG GCAGAGTTGT GTGCCCCTTC TCATGGCCTC GTCAAGGCAT CATGGACTGC       180

CACACACAAA ATGCCGTTTT TATTAACGAC ATGAAATTGA AGGAGAGAAC ACAATTCACT       240

GATGTGGCTC GTAACCATGG ATATGGTCAC ATACAGAGGT GTGATTATGT AAAGGTTAAT       300

TCCACCCACC TCATGTGGAA ACTAGCCTCA ATGCAGGGGT CCCA                        344
```

(2) INFORMATION FOR SEQ ID NO: 67:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (xi) SEQUENCE DESCRIPTION: SEQ ID NO: 67:

```
GCACTGAGAG GAACTTCGTA GGGAGGTTGA ACTGGCTGCT GAGGAGGGGG AACAACAGGG        60

TAACCAGACT GATAGCCATT GGATGGATAA TATGGTGGTT GAGGAGGGAC ACTACTTATA       120

GCAGAGGGTT GTGTATAGCC TGAGGAGGCA TCACCCG                                157
```

(2) INFORMATION FOR SEQ ID NO: 68:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (xi) SEQUENCE DESCRIPTION: SEQ ID NO: 68:

| | |
|---|---|
| GCACTGAGAG GAACTTCTAG AAAGTGAAAG TCTAGACATA AAATAAAATA AAAATTTAAA | 60 |
| ACTCAGGAGA GACAGCCCAG CACGGTGGCT CACGCCTGTA ATCCCAGAAC TTTGGGAGCC | 120 |
| TGAGGAGGCA TCACCCG | 137 |

(2) INFORMATION FOR SEQ ID NO: 69:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (xi) SEQUENCE DESCRIPTION: SEQ ID NO: 69:

| | |
|---|---|
| CGGGTGATGC CTCCTCAGGC TGTATTTTGA AGACTATCGA CTGGACTTCT TATCAACTGA | 60 |
| AGAATCCGTT AAAAATACCA GTTGTATTAT TTCTACCTGT CAAAATCCAT TTCAAATGTT | 120 |
| GAAGTTCCTC TCAGTGC | 137 |

(2) INFORMATION FOR SEQ ID NO: 70:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (xi) SEQUENCE DESCRIPTION: SEQ ID NO: 70:

| | |
|---|---|
| AGCATGTTGA GCCCAGACAC GCAATCTGAA TGAGTGTGCA CCTCAAGTAA ATGTCTACAC | 60 |
| GCTGCCTGGT CTGACATGGC ACACCATCNC GTGGAGGGCA CASCTCTGCT CNGCCTACWA | 120 |
| CGAGGGCANT CTCATWGACA GGTTCCACCC ACCAAACTGC AAGAGGCTCA NNAAGTACTR | 180 |
| CCAGGGTMYA SGGACMASGG TGGGAYTYCA YCACWCATCT | 220 |

(2) INFORMATION FOR SEQ ID NO: 71:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (xi) SEQUENCE DESCRIPTION: SEQ ID NO: 71:

| | |
|---|---|
| CGTTAGGGTC TCTATCCACT GCTAAACCAT ACACCTGGGT AAACAGGGAC CATTTAACAT | 60 |
| TCCCANCTAA ATATGCCAAG TGACTTCACA TGTTTATCTT AAAGATGTCC AAAACGCAAC | 120 |
| TGATTTTCTC CCCTAAACCT GTGATGGTGG GATGATTAAN CCTGAGTGGT CTACAGCAAG | 180 |
| TTAAGTGCAA GGTGCTAAAT GAANGTGACC TGAGATACAG CATCTACAAG GCAGTACCTC | 240 |
| TCAACNCAGG GCAACTTTGC TTCTCANAGG GCATTTAGCA GTGTCTGAAG TAATTTCTGT | 300 |
| ATTACAACTC ACGGGCGGG GGGTGAATAT CTANTGGANA GNAGACCCTA ACG | 353 |

(2) INFORMATION FOR SEQ ID NO: 72:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (xi) SEQUENCE DESCRIPTION: SEQ ID NO: 72:

```
GCACTGAGAG GAACTTCCAA TACYATKATC AGAGTGAACA RGCARCCYAC AGAACAGGAG      60

AAAATGTTYG CAATCTCTCC ATCTGACAAA AGGCTAATAT CCAGAWTCTA AWAGGAACTT     120

AAACAAATTT ATGAGAAAAG AACARACAAC CTCAWCAAAA AGTGGGTGAA GGAWATGCTS     180

AAARGAAGAC ATYTATTCAG CCAGTAAACA YATGAAAAAA AGGCTCATSA TCACTGAWCA     240

TTAGAGAAAT GCAAATCAAA ACCACAATGA GATACCATCT YAYRCCAGTT AGAAYGGTGA    300

TCATTAAAAR STCAGGAAAC AACAGATGCT GGACAAGGTG TCA                      343
```

(2) INFORMATION FOR SEQ ID NO: 73:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO: 73:

```
GCACTGAGAG GAACTTCAGA GAGAGAGAGA GAGTTCCACC CTGTACTTGG GGAGAGAAAC     60

AGAAGGTGAG AAAGTCTTTG GTTCTGAAGC AGCTTCTAAG ATCTTTTCAT TTGCTTCATT    120

TCAAAGTTCC CATGCTGCCA AAGTGCCATC CTTTGGGGTA CTGTTTTCTG AGCTCCAGTG    180

ATAACTCATT TATACAAGGG AGATACCCAG AAAAAAAGTG AGCAAATCTT AAAAAGGTGG    240

CTTGAGTTCA GCCTTAAATA CCATCTTGAA ATGACACAGA GAAAGAANGA TGTTGGGTGG    300

GAGTGGATAG AGACCCTAAC G                                             321
```

(2) INFORMATION FOR SEQ ID NO: 74:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO: 74:

```
GCACTGAGAG GAACTTCAGA GAGAGAGAGA GAGTTCCACC CTGTACTTGG GGAGAGAAAC     60

AGAAGGTGAG AAAGTCTTTG GTTCTGAAGC AGCTTCTAAG ATCTTTTCAT TTGCTTCATT    120

TCAAAGTTCC CATGCTGCCA AAGTGCCATC CTTTGGGGTA CTGTTTTCTG AGCTCCAGTG    180

ATAACTCATT TATACAAGGG AGATACCCAG AAAAAAAGTG AGCAAATCTT AAAAAGGTGG    240

CTTGAGTTCA GYCTTAAATA CCATCTTGAA ATGAMACAGA GAAAGAAGGA TGTTGGGTGG    300

GAGTGGATAG AGACCCTAAC G                                             321
```

(2) INFORMATION FOR SEQ ID NO: 75:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (xi) SEQUENCE DESCRIPTION: SEQ ID NO: 75:

```
GCACTGAGAG GAACTTCCAC ATGCACTGAG AAATGCATGT TCACAAGGAC TGAAGTCTGG     60

AACTCAGTTT CTCAGTTCCA ATCCTGATTC AGGTGTTTAC CAGCTACACA ACCTTAAGCA    120

AGTCAGATAA CCTTAGCTTC CTCATATGCA AAATGAGAAT GAAAAGTACT CATCGCTGAA    180

TTGTTTTGAG GATTAGAAAA ACATCTGGCA TGCAGTAGAA ATTCAATTAG TATTCATTTT    240

CATTCTTCTA AATTAAACAA ATAGGATTTT TAGTGGTGGA ACTTCAGACA CCAGAAATGG    300
```

```
GAGTGGATAG AGACCCT                                                    317

(2) INFORMATION FOR SEQ ID NO: 76:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (xi) SEQUENCE DESCRIPTION: SEQ ID NO: 76:

CGTTAGGGTC TCTATCCACT CCCACTACTG ATCAAACTCT ATTTATTTAA TTATTTTTAT     60

CATACTTTAA GTTCTGGGAT ACACGTGCAG CATGCGCAGG TTTGTTGCAT AGGTATACAC    120

TTGCCATGGT GGTTTGCTGC ACCCATCAGT CCATCATCTA CATTAGGTAT TTCTCCTAAT    180

GCTATCCCTC CCCTAGCCCC TTACACCCCC AACAGGCTCT AGTGTGTGAA GTTCCTCTCA    240

GTGC                                                                 244

(2) INFORMATION FOR SEQ ID NO: 77:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (xi) SEQUENCE DESCRIPTION: SEQ ID NO: 77:

CGTTAGGGTC TCTATCCACT GAAATCTGAA GCACAGGAGG AAGAGAAGCA GTYCTAGTGA     60

GATGGCAAGT TCWTTTACCA CACTCTTTAA CATTTYGTTT AGTTTTAACC TTTATTTATG    120

GATAATAAAG GTTAATATTA ATAATGATTT ATTTTAAGGC ATTCCCRAAT TTGCATAATT    180

CTCCTTTTGG AGATACCCTT TTATCTCCAG TGCAAGTCTG GATCAAAGTG ATASAMAGAA    240

GTTCCTCTCA GTGC                                                      254

(2) INFORMATION FOR SEQ ID NO: 78:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (xi) SEQUENCE DESCRIPTION: SEQ ID NO: 78:

TTCGATACAG GCAAACATGA ACTGCAGGAG GGTGGTGACG ATCATGATGT TGCCGATGGT     60

CCGGATGGNC ACGAAGACGC ACTGGANCAC GTGCTTACGT CCTTTTGCTC TGTTGATGGC    120

CCTGAGGGGA CGCAGGACCC TTATGACCCT CAGAATCTTC ACAACGGGAG ATGGCACTGG    180

ATTGANTCCC ANTGCACCA GAGACACCCC AACCACCAGN ATATCANTAT ATTGATGTAG    240

TTCCTGTAGA NGGCCCCCTT GTGGAGGAAA GCTCCATNAG TTGGTCATCT TCAACAGGAT    300

CTCAACAGTT TCCGATGGCT GTGATGGGCA TAGTCATANT TAACCNTGTN TCGAA         355

(2) INFORMATION FOR SEQ ID NO: 79:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (xi) SEQUENCE DESCRIPTION: SEQ ID NO: 79:

TAAGAGGGTA CCAGCAGAAA GGTTAGTATC ATCAGATAGC ATCTTATACG AGTAATATGC     60
```

```
CTGCTATTTG AAGTGTAATT GAGAAGGAAA ATTTTAGCGT GCTCACTGAC CTGCCTGTAG    120

CCCCAGTGAC AGCTAGGATG TGCATTCTCC AGCCATCAAG AGACTGAGTC AAGTTGTTCG    180

TTAAGTCAGA ACAGCAGACT CAGCTCTGAC ATTCTGATTC GAATGACACT GTTCAGGAAC    240

CGGAATCCTG TCGATTAGAC TGGACAGCTT GTGGCAAGTG AATTTGCCTG TAACAAGCCT    300

GATTTTTTAA AATTTATATT GTAAATAATG TGTGTGTGTG TGTGTGTATA TATATATATA    360

TGTACAGTTA TCTAAGTTAA TTTAAAAGTT GTTTGGTACC CTCTTA                   406

(2) INFORMATION FOR SEQ ID NO: 80:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (xi) SEQUENCE DESCRIPTION: SEQ ID NO: 80:

TTTTTTTTTT TTTACTCGGC TCAGTCTAAT CCTTTTTGTA GTCACTCATA GGCCAGACTT     60

AGGGCTAGGA TGATGATTAA TAAGAGGGAT GACATAACTA TTAGTGGCAG GTTAGTTGTT    120

TGTAGGGCTC ATGGTAGGGG TAAAAGGAGG GCAATTTCTA GATCAAATAA TAAGAAGGTA    180

ATAGCTACTA AGAAGAATTT TATGGAGAAA GGGACGCGGG CGGGGGATAT AGGGTCGAAG    240

CCGCACTCGT AAGGGGTGGA TTTTTCTATG TAGCCGTTGA GTTGTGGTAG TCAAAATGTA    300

ATAATTATTA GTAGTAAGCC TAGGAGA                                        327

(2) INFORMATION FOR SEQ ID NO: 81:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (xi) SEQUENCE DESCRIPTION: SEQ ID NO: 81:

TAGTCTATGC GGTTGATTCG GCAATCCATT ATTTGCTGGA TTTTGTCATG TGTTTTGCCA     60

ATTGCATTCA TAATTTATTA TGCATTTATG CTTGTATCTC CTAAGTCATG GTATATAATC    120

CATGCTTTTT ATGTTTTGTC TGACATAAAC TCTTATCAGA GCCCTTTGCA CACAGGGATT    180

CAATAAATAT TAACACAGTC TACATTTATT TGGTGAATAT TGCATATCTG CTGTACTGAA    240

AGCACATTAA GTAACAAAGG CAAGTGAGAA GAATGAAAAG CACTACTCAC AACAGTTATC    300

ATGATTGCGC ATAGACTA                                                  318

(2) INFORMATION FOR SEQ ID NO: 82:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (xi) SEQUENCE DESCRIPTION: SEQ ID NO: 82:

TCTTCAACCT CTACTCCCAC TAATAGCTTT TTGATGACTT CTAGCAAGCC TCGCTAACCT     60

CGCCTTACCC CCCACTATTA ACCTACTGGG AGAACTCTCT GTGCTAGTAA CCACGTTCTC    120

CTGATCAAAT ATCACTCTCC TACTTACAGG ACTCAACATA CTAGTCACAG CCCTATACTC    180

CCTCTACATA TTTACCACAA CACAATGGGG CTCACTCACC CACCACATTA ACAACATAAA    240

ACCCTCATTC ACACGAGAAA ACACCCTCAT GTTCATACAC CTATCCCCCA TTCTCCTCCT    300
```

ATCCCTCAAC CCCGACATCA TTACCGGGTT TTCCTCTT                                    338

(2) INFORMATION FOR SEQ ID NO: 83:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO: 83:

AGCCATTTAC CACCCATCCA CAAAAAAAAA AAAAAAAAG AAAAATATCA AGGAATAAAA             60

ATAGACTTTG AACAAAAAGG AACATTTGCT GGCCTGAGGA GGCATCACCC G                    111

(2) INFORMATION FOR SEQ ID NO: 84:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (xi) SEQUENCE DESCRIPTION: SEQ ID NO: 84:

TCGGGTGATG CCTCCTCAGG CCAAGAAGAT AAAGCTTCAG ACCCCTAACA CATTTCCAAA            60

AAGGAAGAAA GGAGAAAAAA GGGCATCATC CCCGTTCCGA AGGGTCAGGG AGGAGGAAAT           120

TGAGGTGGAT TCACGAGTTG CGGACAACTC CTTTGATGCC AAGCGAGGTG CAGCCGGAGA           180

CTGGGGAGAG CGAGCCAATC AGGTTTTGAA GTTCCTCTCA GTGC                           224

(2) INFORMATION FOR SEQ ID NO: 85:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (xi) SEQUENCE DESCRIPTION: SEQ ID NO: 85:

GCACTGAGAG GAACTTCGTT GGAAACGGGT TTTTTTCATG TAAGGCTAGA CAGAAGAATT            60

CTCAGTAACT TCCTTGTGTT GTGTGTATTC AACTCACASA GTTGAACGAT CCTTTACACA           120

GAGCAGACTT GTAACACTCT TWTTGTGGAA TTTGCAAGTG GAGATTTCAG SCGCTTTGAA           180

GTSAAAGGTA GAAAAGGAAA TATCTTCCTA TAAAAACTAG ACAGAATGAT TCTCAGAAAC           240

TCCTTTGTGA TGTGTGCGTT CAACTCACAG AGTTTAACCT TTCWTTTCAT AGAAGCAGTT           300

AGGAAACACT CTGTTTGTAA AGTCTGCAAG TGGATAGAGA CCCTAACG                       348

(2) INFORMATION FOR SEQ ID NO: 86:

(i) SEQUENCE CHARACTERISTICS:
        (A) LENGTH: 293 base pairs
        (B) TYPE: nucleic acid
        (C) STRANDEDNESS: single
        (D) TOPOLOGY: linear (xi) SEQUENCE DESCRIPTION: SEQ ID NO: 86:

GCACTGAGAG GAACTTCYTT GTGWTGTKTG YATTCAACTC ACAGAGTTGA ASSWTSMTTT            60

ACABAGWKCA GGCTTKCAAA CACTCTTTTT GTMGAATYTG CAAGWGGAKA TTTSRRCCRC           120

TTTGWGGYCW WYSKTMGAAW MGGRWATATC TTCWYATMRA AMCTAGACAG AAKSATTCTC           180

AKAAWSTYYY YTGTGAWGWS TGCRTTCAAC TCACAGAGKT KAACMWTYCT KYTSATRGAG           240

```
CAGTTWKGAA ACTCTMTTTC TTTGGATTCT GCAAGTGGAT AGAGACCCTA ACG         293
```

(2) INFORMATION FOR SEQ ID NO: 87:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 87:

```
CTCCTAGGCT                                                         10
```

(2) INFORMATION FOR SEQ ID NO: 88:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 88:

```
AGTAGTTGCC                                                         10
```

(2) INFORMATION FOR SEQ ID NO: 89:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO: 89:

```
TTCCGTTATG C                                                       11
```

(2) INFORMATION FOR SEQ ID NO: 90:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 90:

```
TGGTAAAGGG                                                         10
```

(2) INFORMATION FOR SEQ ID NO: 91:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 91:

```
TCGGTCATAG                                                         10
```

(2) INFORMATION FOR SEQ ID NO: 92:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 92:

```
TACAACGAGG                                                         10
```

-continued (2) INFORMATION FOR SEQ ID NO: 93:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 93:

TGGATTGGTC    10

(2) INFORMATION FOR SEQ ID NO: 94:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 94:

CTTTCTACCC    10

(2) INFORMATION FOR SEQ ID NO: 95:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 95:

TTTTGGCTCC    10

(2) INFORMATION FOR SEQ ID NO: 96:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 96:

GGAACCAATC    10

(2) INFORMATION FOR SEQ ID NO: 97:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 97:

TCGATACAGG    10

(2) INFORMATION FOR SEQ ID NO: 98:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 98:

GGTACTAAGG    10

(2) INFORMATION FOR SEQ ID NO: 99:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 99:

AGTCTATGCG                          10

(2) INFORMATION FOR SEQ ID NO: 100:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 100:

CTATCCATGG                          10

(2) INFORMATION FOR SEQ ID NO: 101:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 101:

TCTGTCCACA                          10

(2) INFORMATION FOR SEQ ID NO: 102:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 102:

AAGAGGGTAC                          10

(2) INFORMATION FOR SEQ ID NO: 103:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 103:

CTTCAACCTC                          10

(2) INFORMATION FOR SEQ ID NO: 104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 104:

GCTCCTCTTG CCTTACCAAC                20

(2) INFORMATION FOR SEQ ID NO: 105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 105:

GTAAGTCGAG CAGTGTGATG        20

(2) INFORMATION FOR SEQ ID NO: 106:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 106:

GTAAGTCGAG CAGTCTGATG        20

(2) INFORMATION FOR SEQ ID NO: 107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 107:

GACTTAGTGG AAAGAATGTA        20

(2) INFORMATION FOR SEQ ID NO: 108:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 108:

GTAATTCCGC CAACCGTAGT        20

(2) INFORMATION FOR SEQ ID NO: 109:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 109:

ATGGTTGATC GATAGTGGAA        20

(2) INFORMATION FOR SEQ ID NO: 110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 110:

ACGGGGACCC CTGCATTGAG        20

(2) INFORMATION FOR SEQ ID NO: 111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 111:

TATTCTAGAC CATTCGCTAC                                                   20

(2) INFORMATION FOR SEQ ID NO: 112:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 112:

ACATAACCAC TTTAGCGTTC                                                   20

(2) INFORMATION FOR SEQ ID NO: 113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 113:

CGGGTGATGC CTCCTCAGGC                                                   20

(2) INFORMATION FOR SEQ ID NO: 114:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 114:

AGCATGTTGA GCCCAGACAC                                                   20

(2) INFORMATION FOR SEQ ID NO: 115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 115:

GACACCTTGT CCAGCATCTG                                                   20

(2) INFORMATION FOR SEQ ID NO: 116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 116:

TACGCTGCAA CACTGTGGAG                                                   20

(2) INFORMATION FOR SEQ ID NO: 117:

```
        (i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 117:

CGTTAGGGTC TCTATCCACT                                                   20

(2) INFORMATION FOR SEQ ID NO: 118:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 118:

AGACTGACTC ATGTCCCCTA                                                   20

(2) INFORMATION FOR SEQ ID NO: 119:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 119:

TCATCGCTCG GTGACTCAAG                                                   20

(2) INFORMATION FOR SEQ ID NO: 120:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 120:

CAAGATTCCA TAGGCTGACC                                                   20

(2) INFORMATION FOR SEQ ID NO: 121:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 121:

ACGTACTGGT CTTGAAGGTC                                                   20

(2) INFORMATION FOR SEQ ID NO: 122:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 122:

GACGCTTGGC CACTTGACAC                                                   20

(2) INFORMATION FOR SEQ ID NO: 123:

(i) SEQUENCE CHARACTERISTICS:
```

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 123:

GTATCGACGT AGTGGTCTCC                                               20

(2) INFORMATION FOR SEQ ID NO: 124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 124:

TAGTGACATT ACGACGCTGG                                               20

(2) INFORMATION FOR SEQ ID NO: 125:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 125:

CGGGTGATGC CTCCTCAGGC                                               20

(2) INFORMATION FOR SEQ ID NO: 126:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 126:

ATGGCTATTT TCGGGGGCTG ACA                                           23

(2) INFORMATION FOR SEQ ID NO: 127:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 127:

CCGGTATCTC CTCGTGGGTA TT                                            22

(2) INFORMATION FOR SEQ ID NO: 128:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 128:

CTGCCTGAGC CACAAATG                                                 18

(2) INFORMATION FOR SEQ ID NO: 129:

(i) SEQUENCE CHARACTERISTICS:
        (A) LENGTH: 24 base pairs (B) TYPE: nucleic acid
        (C) STRANDEDNESS: single
        (D) TOPOLOGY: linear (xi) SEQUENCE DESCRIPTION: SEQ ID NO: 129:

CCGGAGGAGG AAGCTAGAGG AATA                                                  24

(2) INFORMATION FOR SEQ ID NO: 130:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 130:

TTTTTTTTTT TTAG                                                             14

(2) INFORMATION FOR SEQ ID NO: 131:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 131:

Ser Ser Gly Gly Arg Thr Phe Asp Asp Phe His Arg Tyr Leu Leu Va
1               5                   10                  15
Gly Ile (2) INFORMATION FOR SEQ ID NO: 132:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 132:

Gln Gly Ala Ala Gln Lys Pro Ile Asn Leu Ser Lys Xaa Ile Glu Va
1               5                   10                  15
Val Gln Gly His Asp Glu
            20

(2) INFORMATION FOR SEQ ID NO: 133:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO: 133:

Ser Pro Gly Val Phe Leu Glu His Leu Gln Glu Ala Tyr Arg Ile Ty
1               5                   10                  15
Thr Pro Phe Asp Leu Ser Ala
            20

(2) INFORMATION FOR SEQ ID NO: 134:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 134:

Tyr Leu Leu Val Gly Ile Gln Gly Ala
1               5

(2) INFORMATION FOR SEQ ID NO: 135:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 135:

Gly Ala Ala Gln Lys Pro Ile Asn Leu
1               5

(2) INFORMATION FOR SEQ ID NO: 136:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 136:

Asn Leu Ser Lys Xaa Ile Glu Val Val
1               5

(2) INFORMATION FOR SEQ ID NO: 137:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 137:

Glu Val Val Gln Gly His Asp Glu Ser
1               5

(2) INFORMATION FOR SEQ ID NO: 138:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 138:

His Leu Gln Glu Ala Tyr Arg Ile Tyr
1               5

(2) INFORMATION FOR SEQ ID NO: 139:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 139:

Asn Leu Ala Phe Val Ala Gln Ala Ala
1               5

(2) INFORMATION FOR SEQ ID NO: 140:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 140:

Phe Val Ala Gln Ala Ala Pro Asp Ser
1               5

(2) INFORMATION FOR SEQ ID NO: 141:

(i) SEQUENCE CHARACTERISTICS:
        (A) LENGTH: 9388 base pairs
        (B) TYPE: nucleic acid
        (C) STRANDEDNESS: single
        (D) TOPOLOGY: linear (xi) SEQUENCE DESCRIPTION: SEQ ID NO: 141:

| | | | | | |
|---|---|---|---|---|---|
| GCTCGCGGCC | GCGAGCTCAA | TTAACCCTCA | CTAAAGGGAG | TCGACTCGAT | CAGACTGTTA | 60 |
| CTGTGTCTAT | GTAGAAAGAA | GTAGACATAA | GAGATTCCAT | TTTGTTCTGT | ACTAAGAAAA | 120 |
| ATTCTTCTGC | CTTGAGATGC | TGTTAATCTG | TAACCCTAGC | CCCAACCCTG | TGCTCACAGA | 180 |
| GACATGTGCT | GTGTTGACTC | AAGGTTCAAT | GGATTTAGGG | CTATGCTTTG | TTAAAAAAGT | 240 |
| GCTTGAAGAT | AATATGCTTG | TTAAAAGTCA | TCACCATTCT | CTAATCTCAA | GTACCCAGGG | 300 |
| ACACAATACA | CTGCGGAAGG | CCGCAGGGAC | CTCTGTCTAG | GAAAGCCAGG | TATTGTCCAA | 360 |
| GATTTCTCCC | CATGTGATAG | CCTGAGATAT | GGCCTCATGG | GAAGGGTAAG | ACCTGACTGT | 420 |
| CCCCCAGCCC | GACATCCCCC | AGCCCGACAT | CCCCCAGCCC | GACACCCGAA | AAGGGTCTGT | 480 |
| GCTGAGGAGG | ATTAGTAAAA | GAGGAAGGCC | TCTTTGCAGT | TGAGGTAAGA | GGAAGGCATC | 540 |
| TGTCTCCTGC | TCGTCCCTGG | GCAATAGAAT | GTCTTGGTGT | AAAACCCGAT | TGTATGTTCT | 600 |
| ACTTACTGAG | ATAGGAGAAA | ACATCCTTAG | GGCTGGAGGT | GAGACACGCT | GGCGGCAATA | 660 |
| CTGCTCTTTA | ATGCACCGAG | ATGTTTGTAT | AAGTGCACAT | CAAGGCACAG | CACCTTTCCT | 720 |
| TAAACTTATT | TATGACACAG | AGACCTTTGT | TCACGTTTTC | CTGCTGACCC | TCTCCCCACT | 780 |
| ATTACCCTAT | TGGCCTGCCA | CATCCCCCTC | TCCGAGATGG | TAGAGATAAT | GATCAATAAA | 840 |
| TACTGAGGGA | ACTCAGAGAC | CAGTGTCCCT | GTAGGTCCTC | CGTGTGCTGA | GCGCCGGTCC | 900 |
| CTTGGGCTCA | CTTTTCTTTC | TCTATACTTT | GTCTCTGTGT | CTCTTTCTTT | TCTCAGTCTC | 960 |
| TCGTTCCACC | TGACGAGAAA | TACCCACAGG | TGTGGAGGGG | CAGGCCACCC | CTTCAATAAT | 1020 |
| TTACTAGCCT | GTTCGCTGAC | AACAAGACTG | GTGGTGCAGA | AGGTTGGGTC | TTGGTGTTCA | 1080 |
| CCGGGTGGCA | GGCATGGGCC | AGGTGGGAGG | GTCTCCAGCG | CCTGGTGCAA | ATCTCCAAGA | 1140 |
| AAGTGCAGGA | AACAGCACCA | AGGGTGATTG | TAAATTTTGA | TTTGGCGCGG | CAGGTAGCCA | 1200 |
| TTCCAGCGCA | AAAATGCGCA | GGAAAGCTTT | TGCTGTGCTT | GTAGGCAGGT | AGGCCCCAAG | 1260 |
| CACTTCTTAT | TGGCTAATGT | GGAGGGAACC | TGCACATCCA | TTGGCTGAAA | TCTCCGTCTA | 1320 |
| TTTGAGGCTG | ACTGAGCGCG | TTCCTTTCTT | CTGTGTTGCC | TGGAAACGGA | CTGTCTGCCT | 1380 |
| AGTAACATCT | GATCACGTTT | CCCATTGGCC | GCCGTTTCCG | GAAGCCCGCC | CTCCCATTTC | 1440 |
| CGGAAGCCTG | GCGCAAGGTT | GGTCTGCAGG | TGGCCTCCAG | GTGCAAAGTG | GAAGTGTGA | 1500 |
| GTCCTCAGTC | TTGGGCTATT | CGGCCACGTG | CCTGCCGGAC | ATGGGACGCT | GGAGGGTCAG | 1560 |
| CAGCGTGGAG | TCCTGGCCTT | TTGCGTCCAC | GGGTGGGAAA | TTGGCCATTG | CCACGGCGGG | 1620 |
| AACTGGGACT | CAGGCTGCCC | CCCGGCCGTT | TCTCATCCGT | CCACCGGACT | CGTGGGCGCT | 1680 |
| CGCACTGGCG | CTGATGTAGT | TTCCTGACCT | CTGACCCGTA | TTGTCTCCAG | ATTAAAGGTA | 1740 |

```
AAAACGGGGC TTTTTCAGCC CACTCGGGTA AAACGCCTTT TGATTTCTAG GCAGGTGTTT    1800

TGTTGCACGC CTGGGAGGGA GTGACCCGCA GGTTGAGGTT TATTAAAATA CATTCCTGGT    1860

TTATGTTATG TTTATAATAA AGCACCCCAA CCTTTACAAA ATCTCACTTT TTGCCAGTTG    1920

TATTATTTAG TGGACTGTCT CTGATAAGGA CAGCCAGTTA AAATGGAATT TTGTTGTTGC    1980

TAATTAAACC AATTTTTAGT TTTGGTGTTT GTCCTAATAG CAACAACTTC TCAGGCTTTA    2040

TAAAACCATA TTTCTTGGGG GAAATTTCTG TGTAAGGCAC AGCGAGTTAG TTTGGAATTG    2100

TTTTAAAGGA AGTAAGTTCC TGGTTTTGAT ATCTTAGTAG TGTAATGCCC AACCTGGTTT    2160

TTACTAACCC TGTTTTTAGA CTCTCCCTTT CCTTAAATCA CCTAGCCTTG TTTCCACCTG    2220

AATTGACTCT CCCTTAGCTA AGAGCGCCAG ATGGACTCCA TCTTGGCTCT TTCACTGGCA    2280

GCCCCTTCCT CAAGGACTTA ACTTGTGCAA GCTGACTCCC AGCACATCCA AGAATGCAAT    2340

TAACTGTTAA GATACTGTGG CAAGCTATAT CCGCAGTTCC GAGGAATTCA TCCGATTGAT    2400

TATGCCCAAA AGCCCCGCGT CTATCACCTT GTAATAATCT TAAAGCCCCT GCACCTGGAA    2460

CTATTAACTT TCCTGTAACC ATTTATCCTT TTAACTTTTT TGCTTACTTT ATTTCTGTAA    2520

AATTGTTTTA ACTAGACCTC CCCTCCCCTT TCTAAACCAA AGTATAAAAG AAGATCTAGC    2580

CCCTTCTTCA GAGCGGAGAG AATTTTGAGC ATTAGCCATC TCTTGGCGGC CAGCTAAATA    2640

AATGGACTTT TAATTTGTCT CAAAGTGTGG CGTTTTCTCT AACTCGCTCA GGTACGACAT    2700

TTGGAGGCCC CAGCGAGAAA CGTCACCGGG AGAAACGTCA CCGGGCGAGA GCCGGGCCCG    2760

CTGTGTGCTC CCCCGGAAGG ACAGCCAGCT TGTAGGGGGG AGTGCCACCT GAAAAAAAAA    2820

TTTCCAGGTC CCCAAAGGGT GACCGTCTTC CGGAGGACAG CGGATCGACT ACCATGCGGG    2880

TGCCCACCAA AATTCCACCT CTGAGTCCTC AACTGCTGAC CCCGGGGTCA GGTAGGTCAG    2940

ATTTGACTTT GGTTCTGGCA GAGGGAAGCG ACCCTGATGA GGGTGTCCCT CTTTTGACTC    3000

TGCCCATTTC TCTAGGATGC TAGAGGGTAG AGCCCTGGTT TTCTGTTAGA CGCCTCTGTG    3060

TCTCTGTCTG GGAGGGAAGT GGCCCTGACA GGGGCCATCC CTTGAGTCAG TCCACATCCC    3120

AGGATGCTGG GGGACTGAGT CCTGGTTTCT GGCAGACTGG TCTCTCTCTC TCTCTTTTTC    3180

TATCTCTAAT CTTTCCTTGT TCAGGTTTCT TGGAGAATCT CTGGGAAAGA AAAAAGAAAA    3240

ACTGTTATAA ACTCTGTGTG AATGGTGAAT GAATGGGGGA GGACAAGGGC TTGCGCTTGT    3300

CCTCCAGTTT GTAGCTCCAC GGCGAAAGCT ACGGAGTTCA AGTGGGCCCT CACCTGCGGT    3360

TCCGTGGCGA CCTCATAAGG CTTAAGGCAG CATCCGGCAT AGCTCGATCC GAGCCGGGGG    3420

TTTATACCGG CCTGTCAATG CTAAGAGGAG CCCAAGTCCC CTAAGGGGGA GCGGCCAGGC    3480

GGGCATCTGA CTGATCCCAT CACGGGACCC CCTCCCCTTG TTTGTCTAAA AAAAAAAAAA    3540

GAAGAAACTG TCATAACTGT TTACATGCCC TAGGGTCAAC TGTTTGTTTT ATGTTTATTG    3600

TTCTGTTCGG TGTCTATTGT CTTGTTTAGT GGTTGTCAAG GTTTTGCATG TCAGGACGTC    3660

GATATTGCCC AAGACGTCTG GGTAAGAACT TCTGCAAGGT CCTTAGTGCT GATTTTTGT     3720

CACAGGAGGT TAAATTTCTC ATCAATCATT TAGGCTGGCC ACCACAGTCC TGTCTTTTCT    3780

GCCAGAAGCA AGTCAGGTGT TGTTACGGGA ATGAGTGTAA AAAAACATTC GCCTGATTGG    3840

GATTTCTGGC ACCATGATGG TTGTATTTAG ATTGTCATAC CCCACATCCA GGTTGATTGG    3900

ACCTCCTCTA AACTAAACTG GTGGTGGGTT CAAAACAGCC ACCCTGCAGA TTTCCTTGCT    3960

CACCTCTTTG GTCATTCTGT AACTTTTCCT GTGCCCTTAA ATAGCACACT GTGTAGGGAA    4020

ACCTACCCTC GTACTGCTTT ACTTCGTTTA GATTCTTACT CTGTTCCTCT GTGGCTACTC    4080
```

-continued

```
TCCCATCTTA AAAACGATCC AAGTGGTCCT TTTCCTCCTC CCTGCCCCCT ACCCCACACA    4140

TCTCGTTTTC CAGTGCGACA GCAAGTTCAG CGTCTCCAGG ACTTGGCTCT GCTCTCACTC    4200

CTTGAACCCT TAAAAGAAAA AGCTGGGTTT GAGCTATTTG CCTTTGAGTC ATGGAGACAC    4260

AAAAGGTATT TAGGGTACAG ATCTAGAAGA AGAGAGAGAA CACCTAGATC CAACTGACCC    4320

AGGAGATCTC GGGCTGGCCT CTAGTCCTCC TCCCTCAATC TTAAAGCTAC AGTGATGTGG    4380

CAAGTGGTAT TTAGCTGTTG TGGTTTTTCT GCTCTTTCTG GTCATGTTGA TTCTGTTCTT    4440

TCGATACTCC AGCCCCCCAG GGAGTGAGTT TCTCTGTCTG TGCTGGGTTT GATATCTATG    4500

TTCAAATCTT ATTAAATTGC CTTCAAAAAA AAAAAAAAAA GGGAAACACT TCCTCCCAGC    4560

CTTGTAAGGG TTGGAGCCCT CTCCAGTATA TGCTGCAGAA TTTTTCTCTC GGTTTCTCAG    4620

AGGATTATGG AGTCCGCCTT AAAAAAGGCA AGCTCTGGAC ACTCTGCAAA GTAGAATGGC    4680

CAAAGTTTGG AGTTGAGTGG CCCCTTGAAG GGTCACTGAA CCTCACAATT GTTCAAGCTG    4740

TGTGGCGGGT TGTTACTGAA ACTCCCGGCC TCCCTGATCA GTTTCCCTAC ATTGATCAAT    4800

GGCTGAGTTT GGTCAGGAGC ACCCCTTCCA TGGCTCCACT CATGCACCAT TCATAATTTT    4860

ACCTCCAAGG TCCTCCTGAG CCAGACCGTG TTTTCGCCTC GACCCTCAGC CGGTTCAGCT    4920

CGCCCTGTAC TGCCTCTCTC TGAAGAAGAG GAGAGTCTCC CTCACCCAGT CCCACCGCCT    4980

TAAAACCAGC CTACTCCCTT AGGGTCATCC CATGTCTCCT CGGCTATGTC CCCTGTAGGC    5040

TCATCACCCA TTGCCTCTTG GTTGCAACCG TGGTGGGAGG AAGTAGCCCC TCTACTACCA    5100

CTGAGAGAGG CACAAGTCCC TCTGGGTGAT GAGTGCTCCA CCCCCTTCCT GGTTTATGTC    5160

CCTTCTTTCT ACTTCTGACT TGTATAATTG GAAAACCCAT AATCCTCCCT TCTCTGAAAA    5220

GCCCCAGGCT TTGACCTCAC TGATGGAGTC TGTACTCTGG ACACATTGGC CCACCTGGGA    5280

TGACTGTCAA CAGCTCCTTT TGACCCTTTT CACCTCTGAA GAGAGGGAAA GTATCCAAAG    5340

AGAGGCCAAA AAGTACAACC TCACATCAAC CAATAGGCCG GAGGAGGAAG CTAGAGGAAT    5400

AGTGATTAGA GACCCAATTG GGACCTAATT GGGACCCAAA TTTCTCAAGT GGAGGGAGAA    5460

CTTTTGACGA TTTCCACCGG TATCTCCTCG TGGGTATTCA GGGAGCTGCT CAGAAACCTA    5520

TAAACTTGTC TAAGGCGACT GAAGTCGTCC AGGGGCATGA TGAGTCACCA GGAGTGTTTT    5580

TAGAGCACCT CCAGGAGGCT TATCGGATTT ACACCCCTTT TGACCTGGCA GCCCCCGAAA    5640

ATAGCCATGC TCTTAATTTG GCATTTGTGG CTCAGGCAGC CCCAGATAGT AAAAGGAAAC    5700

TCCAAAAACT AGAGGGATTT TGCTGGAATG AATACCAGTC AGCTTTTAGA GATAGCCTAA    5760

AAGGTTTTTG ACAGTCAAGA GGTTGAAAAA CAAAACAAG CAGCTCAGGC AGCTGAAAAA    5820

AGCCACTGAT AAAGCATCCT GGAGTATCAG AGTTTACTGT TAGATCAGCC TCATTTGACT    5880

TCCCCTCCCA CATGGTGTTT AAATCCAGCT ACACTACTTC CTGACTCAAA CTCCACTATT    5940

CCTGTTCATG ACTGTCAGGA ACTGTTGGAA ACTACTGAAA CTGGCCGACC TGATCTTCAA    6000

AATGTGCCCC TAGGAAAGGT GGATGCCACC GTGTTCACAG ACAGTAGCAG CTTCCTCGAG    6060

AAGGGACTAC GAAAGGCCGG TGCAGCTGTT ACCATGGAGA CAGATGTGTT GTGGGCTCAG    6120

GCTTTACCAG CAAACACCTC AGCACAAAAG GCTGAATTGA TCGCCCTCAC TCAGGCTCTC    6180

CGATGGGGTA AGGATATTAA CGTTAACACT GACAGCAGGT ACGCCTTTGC TACTGTGCAT    6240

GTACGTGGAG CCATCTACCA GGAGCGTGGG CTACTCACCT CAGCAGGTGG CTGTAATCCA    6300

CTGTAAAGGA CATCAAAAGG AAAACACGGC TGTTGCCCGT GGTAACCAGA AAGCTGATTC    6360

AGCAGCTCAA GATGCAGTGT GACTTTCAGT CACGCCTCTA AACTTGCTGC CCACAGTCTC    6420

CTTTCCACAG CCAGATCTGC CTGACAATCC CGCATACTCA ACAGAAGAAG AAAACTGGCC    6480
```

-continued

```
TCAGAACTCA GAGCCAATAA AAATCAGGAA GGTTGGTGGA TTCTTCCTGA CTCTAGAATC    6540

TTCATACCCC GAACTCTTGG GAAAACTTTA ATCAGTCACC TACAGTCTAC CACCCATTTA    6600

GGAGGAGCAA AGCTACCTCA GCTCCTCCGG AGCCGTTTTA AGATCCCCCA TCTTCAAAGC    6660

CTAACAGATC AAGCAGCTCT CCGGTGCACA ACCTGCGCCC AGGTAAATGC CAAAAAAGGT    6720

CCTAAACCCA GCCCAGGCCA CCGTCTCCAA GAAAACTCAC CAGGAGAAAA GTGGGAAATT    6780

GACTTTACAG AAGTAAAACC ACACCGGGCT GGGTACAAAT ACCTTCTAGT ACTGGTAGAC    6840

ACCTTCTCTG GATGGACTGA AGCATTTGCT ACCAAAAACG AAACTGTCAA TATGGTAGTT    6900

AAGTTTTTAC TCAATGAAAT CATCCCTCGA CGTGGGCTGC CTGTTGCCAT AGGGTCTGAT    6960

AATGGACCGG CCTTCGCCTT GTCTATAGTT TAGTCAGTCA GTAAGGCGTT AAACATTCAA    7020

TGGAAGCTCC ATTGTGCCTA TCGACCCCAG AGCTCTGGGC AAGTAGAACG CATGAACTGC    7080

ACCCTAAAAA ACACTCTTAC AAAATTAATC TTAGAAACCG GTGTAAATTG TGTAAGTCTC    7140

CTTCCTTTAG CCCTACTTAG AGTAAGGTGC ACCCCTTACT GGGCTGGGTT CTTACCTTTT    7200

GAAATCATGT ATGGGAGGGC GCTGCCTATC TTGCCTAAGC TAAGAGATGC CCAATTGGCA    7260

AAAATATCAC AAACTAATTT ATTACAGTAC CTACAGTCTC CCCAACAGGT ACAAGATATC    7320

ATCCTGCCAC TTGTTCGAGG AACCCATCCC AATCCAATTC CTGAACAGAC AGGGCCCTGC    7380

CATTCATTCC CGCCAGGTGA CCTGTTGTTT GTTAAAAAGT TCCAGAGAGA AGGACTCCCT    7440

CCTGCTTGGA AGAGACCTCA CACCGTCATC ACGATGCCAA CGGCTCTGAA GGTGGATGGC    7500

ATTCCTGCGT GGATTCATCA CTCCCGCATC AAAAAGGCCA ACGGAGCCCA ACTAGAAACA    7560

TGGGTCCCCA GGGCTGGGTC AGGCCCCTTA AAACTGCACC TAAGTTGGGT GAAGCCATTA    7620

GATTAATTCT TTTTCTTAAT TTTGTAAAAC AATGCATAGC TTCTGTCAAA CTTATGTATC    7680

TTAAGACTCA ATATAACCCC CTTGTTATAA CTGAGGAATC AATGATTTGA TTCCCCAAAA    7740

ACACAAGTGG GGAATGTAGT GTCCAACCTG GTTTTTACTA ACCCTGTTTT TAGACTCTCC    7800

CTTTCCTTTA ATCACTCAGC CTTGTTTCCA CCTGAATTGA CTCTCCCTTA GCTAAGAGCG    7860

CCAGATGGAC TCCATCTTGG CTCTTTCACT GGCAGCCGCT TCCTCAAGGA CTTAACTTGT    7920

GCAAGCTGAC TCCCAGCACA TCCAAGAATG CAATTAACTG ATAAGATACT GTGGCAAGCT    7980

ATATCCGCAG TTCCCAGGAA TTCGTCCAAT TGATTACACC CAAAAGCCCC GCGTCTATCA    8040

CCTTGTAATA ATCTTAAAGC CCCTGCACCT GGAACTATTA ACGTTCCTGT AACCATTTAT    8100

CCTTTTAACT TTTTTGCCTA CTTTATTTCT GTAAAATTGT TTTAACTAGA CCCCCCCTCT    8160

CCTTTCTAAA CCAAAGTATA AAAGCAAATC TAGCCCCTTC TTCAGGCCGA GAGAATTTCG    8220

AGCGTTAGCC GTCTCTTGGC CACCAGCTAA ATAAACGGAT TCTTCATGTG TCTCAAAGTG    8280

TGGCGTTTTC TCTAACTCGC TCAGGTACGA CCGTGGTAGT ATTTTCCCCA ACGTCTTATT    8340

TTTAGGGCAC GTATGTAGAG TAACTTTTAT GAAAGAAACC AGTTAAGGAG GTTTTGGGAT    8400

TTCCTTTATC AACTGTAATA CTGGTTTTGA TTATTTATTT ATTTATTTAT TTTTTTTGAG    8460

AAGGAGTTTC ACTCTTGTTG CCCAGGCTGG AGTGCAATGG TGCGATCTTG GCTCACTGCA    8520

ACTTCCGCCT CCCAGGTTCA AGCGATTCTC CTGCCTCAGC CTCGAGAGTA GCTGGGATTA    8580

TAGGCATGCG CCACCACACC CAGCTAATTT TGTATTTTTA GTAAAGATGG GGTTTCTTCA    8640

TGTTGGTCAA GCTGGTCTGG AACTCCCCGC CTCGGGTGAT CTGCCCGCCT CGGCCTCCGA    8700

AAGTGCTGGG ATTACAGGTG TGATCCACCA CACCCAGCCG ATTTATATGT ATATAAATCA    8760

CATTCCTCTA ACCAAAATGT AGTGTTTCCT TCCATCTTGA ATATAGGCTG TAGACCCCGT    8820
```

```
GGGTATGGGA CATTGTTAAC AGTGAGACCA CAGCAGTTTT TATGTCATCT GACAGCATCT    8880

CCAAATAGCC TTCATGGTTG TCACTGCTTC CCAAGACAAT TCCAAATAAC ACTTCCCAGT    8940

GATGACTTGC TACTTGCTAT TGTTACTTAA TGTGTTAAGG TGGCTGTTAC AGACACTATT    9000

AGTATGTCAG GAATTACACC AAAATTTAGT GGCTCAAACA ATCATTTTAT TATGTATGTG    9060

GATTCTCATG GTCAGGTCAG GATTTCAGAC AGGGCACAAG GGTAGCCCAC TTGTCTCTGT    9120

CTATGATGTC TGGCCTCAGC ACAGGAGACT CAACAGCTGG GGTCTGGGAC CATTTGGAGG    9180

CTTGTTCCCT CACATCTGAT ACCTGGCTTG GGATGTTGGA AGAGGGGGTG AGCTGAGACT    9240

GAGTGCCTAT ATGTAGTGTT TCCATATGGC CTTGACTTCC TTACAGCCTG GCAGCCTCAG    9300

GGTAGTCAGA ATTCTTAGGA GGCACAGGGC TCCAGGGCAG ATGCTGAGGG GTCTTTTATG    9360

AGGTAGCACA GCAAATCCAC CCAGGATC                                       9388

(2) INFORMATION FOR SEQ ID NO: 142:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (xi) SEQUENCE DESCRIPTION: SEQ ID NO: 142:

TGTAAGTCGA GCAGTGTGAT GGAAGGAATG GTCTTTGGAG AGAGCATATC CATCTCCTCC      60

TCACTGCCTC CTAATGTCAT GAGGTACACT GAGCAGAATT AAACAGGGTA GTCTTAACCA     120

CACTATTTTT AGCTACCTTG TCAAGCTAAT GGTTAAAGAA CACTTTTGGT TTACACTTGT     180

TGGGTCATAG AAGTTGCTTT CCGCCATCAC GCAATAAGTT TGTGTGTAAT CAGAAGGAGT     240

TACCTTATGG TTTCAGTGTC ATTCTTTAGT TAACTTGGGA GCTGTGTAAT TTAGGCTTTG     300

CGTATTATTT CACTTCTGTT CTCCACTTAT GAAGTGATTG TGTGTTCGCG TGTGTGTGCG     360

TGCGCATGTG CTTCCGGCAG TTAACATAAG CAAATACCCA ACATCACACT GCTCGACTT      419

(2) INFORMATION FOR SEQ ID NO: 143:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO: 143:

TGTAAGTCGA GCAGTGTGAT GTCCACTGCA GTGTGTTGCT GGGAACAGTT AATGAGCAAA      60

TTGTATACAA TGGCTAGTAC ATTGACCGGG ATTTGTTGAA GCTGGTGAGT GTTATGACTT     120

AGCCTGTTAG ACTAGTCTAT GCACATGGCT CTGGTCAACT ACCGCTCTCT CATTTCTCCA     180

GATAAATCCC CCATGCTTTA TATTCTCTTC CAAACATACT ATCCTCATCA CCACATAGTT     240

CCTTTGTTAA TGCTTTGTTC TAGACTTTCC CTTTTCTGTT TTCTTATTCA AACCTATATC     300

TCTTTGCATA GATTGTAAAT TCAAATGCCC TCAGGGTGCA GGCAGTTCAT GTAAGGGAGG     360

GAGGCTAGCC AGTGAGATCT GCATCACACT GCTCGACTTA CA                        402

(2) INFORMATION FOR SEQ ID NO: 144:

(i) SEQUENCE CHARACTERISTICS:
        (A) LENGTH: 224 base pairs
        (B) TYPE: nucleic acid
        (C) STRANDEDNESS: single
        (D) TOPOLOGY: linear
```

(xi) SEQUENCE DESCRIPTION: SEQ ID NO: 144:

```
TCGGGTGATG CCTCCTCAGG CCAAGAAGAT AAAGCTTCAG ACCCCTAACA CATTTCCAAA        60

AAGGAAGAAA GGAGAAAAAA GGGCATCATC CCCGTTCCGA AGGGTCAGGG AGGAGGAAAT       120

TGAGGTGGAT TCACGAGTTG CGGACAACTC CTTTGATGCC AAGCGAGGTG CAGCCGGAGA       180

CTGGGGAGAG CGAGCCAATC AGGTTTTGAA GTTCCTCTCA GTGC                        224
```

(2) INFORMATION FOR SEQ ID NO: 145:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO: 145:

```
AGCCATTTAC CACCCATCCA CAAAAAAAAA AAAAAAAAAG AAAAATATCA AGGAATAAAA        60

ATAGACTTTG AACAAAAAGG AACATTTGCT GGCCTGAGGA GGCATCACCC G                111
```

(2) INFORMATION FOR SEQ ID NO: 146:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (xi) SEQUENCE DESCRIPTION: SEQ ID NO: 146:

```
TAGCATGTTG AGCCCAGACA CTTGTAGAGA GAGGAGGACA GTTAGAAGAA GAAGAAAAGT        60

TTTTAAATGC TGAAAGTTAC TATAAGAAAG CTTTGGCTTT GGATGAGACT TTTAAAGATG       120

CAGAGGATGC TTTGCAGAAA CTTCATAAAT ATATGCAGGT GATTCCTTAT TTCCTCCTAG       180

AAATTTAGTG ATATTTGAAA TAATGCCCAA ACTTAATTTT CTCCTGAGGA AAACTATTCT       240

ACATTACTTA AGTAAGGCAT TATGAAAAGT TTCTTTTTAG GTATAGTTTT TCCTAATTGG       300

GTTTGACATT GCTTCATAGT GCCTCTGTTT TTGTCCATAA TCGAAAGTAA AGATAGCTGT       360

GAGAAAACTA TTACCTAAAT TTGGTATGTT GTTTTGAGAA ATGTCCTTAT AGGGAGCTCA       420

CCTGGTGGTT TTTAAATTAT TGTTGCTACT ATAATTGAGC TAATTATAAA AACCTTTTTG       480

AGACATATTT TAAATTGTCT TTTCCTGTAA TACTGATGAT GATGTTTTCT CATGCATTTT       540

CTTCTGAATT GGGACCATTG CTGCTGTGTC TGGGCTCACA TGCTA                       585
```

(2) INFORMATION FOR SEQ ID NO: 147:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (xi) SEQUENCE DESCRIPTION: SEQ ID NO: 147:

```
TAGCATGTTG AGCCCAGACA CTGGGCAGCG GGGGTGGCCA CGGCAGCTCC TGCCGAGCCC        60

AAGCGTGTTT GTCTGTGAAG GACCCTGACG TCACCTGCCA GGCTAGGGAG GGGTCAATGT       120

GGAGTGAATG TTCACCGACT TTCGCAGGAG TGTGCAGAAG CCAGGTGCAA CTTGGTTTGC       180

TTGTGTTCAT CACCCCTCAA GATATGCACA CTGCTTTCCA AATAAAGCAT CAACTGTCAT       240

CTCCAGATGG GGAAGACTTT TTCTCCAACC AGCAGGCAGG TCCCCATCCA CTCAGACACC       300

AGCACGTCCA CCTTCTCGGG CAGCACCACG TCCTCCACCT TCTGCTGGTA CACGGTGATG       360
```

-continued

```
ATGTCAGCAA AGCCGTTCTG CANGACCAGC TGCCCCGTGT GCTGTGCCAT CTCACTGGCC      420

TCCACCGCGT ACACCGCTCT AGGCCGCGCA TANTGTGCAC AGAANAAATG ATGATCCAGT      480

CCCACAGCCC ACGTCCAAGA NGACTTTATC CGTCAGGGAT TCTTTATTCT GCAGGATGAC     540

CTGTGGTATT AATTGTTCGT GTCTGGGCTC AACATGCTA                             579
```

(2) INFORMATION FOR SEQ ID NO: 148:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (xi) SEQUENCE DESCRIPTION: SEQ ID NO: 148:

```
TGACACCTTG TCCAGCATCT GCAAGCCAGG AAGAGAGTCC TCACCAAGAT CCCCACCCCG      60

TTGGCACCAG GATCTTGGAC TTCCAATCTC CAGAACTGTG AGAAATAAGT ATTTGTCGCT     120

AAATAAATCT TTGTGGTTTC AGATATTTAG CTATAGCAGA TCAGGCTGAC TAAGAGAAAC     180

CCCATAAGAG TTACATACTC ATTAATCTCC GTCTCTATCC CCAGGTCTCA GATGCTGGAC     240

AAGGTGTCA                                                              249
```

(2) INFORMATION FOR SEQ ID NO: 149:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (xi) SEQUENCE DESCRIPTION: SEQ ID NO: 149:

```
TGACACCTTG TCCAGCATCT GCTATTTTGT GACTTTTTAA TAATAGCCAT TCTGACTGGT      60

GTGAGATGGT AACTCATTGT GGGTTTGGTC TGCATTTCTC TAATGATCAG TGATATTAAG     120

CTTTTTTTAA ATATGCTTGT TGACCACATG TATATCATCT TTTGAGAAGT GTCTGTTCAT     180

ATCCTTTGCC CACTTTTTAA TTTTTTTATC TTGTAAATTT GTTTAATTTC CTTACAGATG     240

CTGGACAAGG TGTCA                                                       255
```

(2) INFORMATION FOR SEQ ID NO: 150:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (xi) SEQUENCE DESCRIPTION: SEQ ID NO: 150:

```
TTACGCTGCA ACACTGTGGA GGCCAAGCTG GGATCACTTC TTCATTCTAA CTGGAGAGGA      60

GGGAAGTTCA AGTCCAGCAG AGGGTGGGTG GGTAGACAGT GGCACTCAGA AATGTCAGCT     120

GGACCCCTGT CCCCGCATAG GCAGGACAGC AAGGCTGTGG CTCTCCAGGG CCAGCTGAAG     180

AACAGGACAC TGTCTCCGCT GCCACAAAGC GTCAGAGACT CCCATCTTTG AAGCACGGCC     240

TTCTTGGTCT TCCTGCACTT CCCTGTTCTG TTAGAGACCT GGTTATAGAC AAGGCTTCTC     300

CACAGTGTTG CAGCGTAA                                                    318
```

(2) INFORMATION FOR SEQ ID NO: 151:

(i) SEQUENCE CHARACTERISTICS:
        (A) LENGTH: 323 base pairs
        (B) TYPE: nucleic acid

```
        (C) STRANDEDNESS: single
        (D) TOPOLOGY: linear (xi) SEQUENCE DESCRIPTION: SEQ ID NO: 151:

TNACGCNGCN ACNNTGTAGA GANGGNAAGG CNTTCCCCAC ATTNCCCCTT CATNANAGAA      60

TTATTCNACC AAGNNTGACC NATGCCNTTT ATGACTTACA TGCNNACTNC NTAATCTGTN     120

TCNNGCCTTA AAAGCNNNTC CACTACATGC NTCANCACTG TNTGTGTNAC NTCATNAACT     180

GTCNGNAATA GGGGCNCATA ACTACAGAAA TGCANTTCAT ACTGCTTCCA NTGCCATCNG     240

CGTGTGGCCT TNCCTACTCT TCTTNTATTC CAAGTAGCAT CTCTGGANTG CTTCCCCACT     300

CTCCACATTG TTGCAGCNAT AAT                                            323

(2) INFORMATION FOR SEQ ID NO: 152:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (xi) SEQUENCE DESCRIPTION: SEQ ID NO: 152:

TCAAGATTCC ATAGGCTGAC CAGTCCAAGG AGAGTTGAAA TCATGAAGGA GAGTCTATCT      60

GGAGAGAGCT GTAGTTTTGA GGGTTGCAAA GACTTAGGAT GGAGTTGGTG GGTGTGGTTA     120

GTCTCTAAGG TTGATTTTGT TCATAAATTT CATGCCCTGA ATGCCTTGCT TGCCTCACCC     180

TGGTCCAAGC CTTAGTGAAC ACCTAAAAGT CTCTGTCTTC TTGCTCTCCA AACTTCTCCT     240

GAGGATTTCC TCAGATTGTC TACATTCAGA TCGAAGCCAG TTGGCAAACA AGATGCAGTC     300

CAGAGGGTCA G                                                         311

(2) INFORMATION FOR SEQ ID NO: 153:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (xi) SEQUENCE DESCRIPTION: SEQ ID NO: 153:

CAAGATTCCA TAGGCTGACC AGGAGGCTAT TCAAGATCTC TGGCAGTTGA GGAAGTCTCT      60

TTAAGAAAAT AGTTTAAACA ATTTGTTAAA ATTTTTCTGT CTTACTTCAT TTCTGTAGCA     120

GTTGATATCT GGCTGTCCTT TTTATAATGC AGAGTGGGAA CTTTCCCTAC CATGTTTGAT     180

AAATGTTGTC CAGGCTCCAT TGCCAATAAT GTGTTGTCCA AAATGCCTGT TTAGTTTTTA     240

AAGACGGAAC TCCACCCTTT GCTTGGTCTT AAGTATGTAT GGAATGTTAT GATAGGACAT     300

AGTAGTAGCG GTGGTCAGCC TATGGAATCT TG                                  332

(2) INFORMATION FOR SEQ ID NO: 154:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO: 154:

TCAAGATTCC ATAGGCTGAC CTGGACAGAG ATCTCCTGGG TCTGGCCCAG ACAGCAGGC       60

TCAAGCTCAG TGGAGAAGGT TTCCATGACC CTCAGATTCC CCCAAACCTT GGATTGGGTG     120

ACATTGCATC TCCTCAGAGA GGGAGGAGAT GTANGTCTGG GCTTCCACAG GGACCTGGTA     180
```

```
TTTTAGGATC AGGGTACCGC TGGCCTGAGG CTTGGATCAT TCANAGCCTG GGGGTGGAAT        240

GGCTGGCAGC CTGTGGCCCC ATTGAAATAG GCTCTGGGGC ACTCCCTCTG TTCCTANTTG        300

AACTTGGGTA AGGAACAGGA ATGTGGTCAN CCTATGGAAT CTTGA                       345

(2) INFORMATION FOR SEQ ID NO: 155:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (xi) SEQUENCE DESCRIPTION: SEQ ID NO: 155:

GACGCTTGGC CACTTGACAC ATTAAACAGT TTTGCATAAT CACTANCATG TATTTCTAGT         60

TTGCTGTCTG CTGTGATGCC CTGCCCTGAT TCTCTGGCGT TAATGATGGC AAGCATAATC        120

AAACGCTGTT CTGTTAATTC CAAGTTATAA CTGGCATTGA TTAAAGCATT ATCTTTCACA        180

ACTAAACTGT TCTTCATANA ACAGCCCATA TTATTATCAA ATTAAGAGAC AATGTATTCC        240

AATATCCTTT ANGGCCAATA TATTTNATGT CCCTTAATTA AGAGCTACTG TCCGT            295

(2) INFORMATION FOR SEQ ID NO: 156:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (xi) SEQUENCE DESCRIPTION: SEQ ID NO: 156:

GACGCTTGGC CACTTGACAC TGCAGTGGGA AAACCAGCAT GAGCCGCTGC CCCCAAGGAA         60

CCTCGAAGCC CAGGCAGAGG ACCAGCCATC CCAGCCTGCA GGTAAAGTGT GTCACCTGTC        120

AGGTGGGCTT GGGGTGAGTG GGTGGGGGAA GTGTGTGTGC AAAGGGGGTG TNAATGTNTA        180

TGCGTGTGAG CATGAGTGAT GGCTAGTGTG ACTGCATGTC AGGGAGTGTG AACAAGCGTG        240

CGGGGGTGTG TGTGCAAGTG CGTATGCATA TGAGAATATG TGTCTGTGGA TGAGTGCATT        300

TGAAAGTCTG TGTGTGTGCG TGTGGTCATG ANGGTAANTT ANTGACTGCG CAGGATGTGT        360

GAGTGTGCAT GGAACACTCA NTGTGTGTGT CAAGTGGCCN ANCGTC                      406

(2) INFORMATION FOR SEQ ID NO: 157:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (xi) SEQUENCE DESCRIPTION: SEQ ID NO: 157:

TGACGCTTGG CCACTTGACA CACTAAAGGG TGTTACTCAT CACTTTCTTC TCTCCTCGGT         60

GGCATGTGAG TGCATCTATT CACTTGGCAC TCATTTGTTT GGCAGTGACT GTAANCCANA        120

TCTGATGCAT ACACCAGCTT GTAAATTGAA TAAATGTCTC TAATACTATG TGCTCACAAT        180

ANGGTANGGG TGAGGAGAAG GGGAGAGA                                          208

(2) INFORMATION FOR SEQ ID NO: 158:

(i) SEQUENCE CHARACTERISTICS:
        (A) LENGTH: 547 base pairs
        (B) TYPE: nucleic acid
        (C) STRANDEDNESS: single
```

(D) TOPOLOGY: linear (xi) SEQUENCE DESCRIPTION: SEQ ID NO: 158:

| | | | | | |
|---|---|---|---|---|---|
| CTTCAACCTC | CTTCAACCTC | CTTCAACCTC | CTGGATTCAA | ACAATCATCC | CACCTCAGAC | 60
| TCCTTAGTAG | CTGAGACTAC | AGACTCACGC | CACTACATCT | GGCTAAATTT | TTGTAGAGAT | 120
| AGGGTTTCAT | CATGTTGCCC | TGGCTGGTCT | CAAACTCCTG | ACCTCAAGCA | ATGTGCCCAC | 180
| CTCAGCCTCC | CAAAGTGCTG | GGATTACAGG | CATAAGCCAC | CATGCCCAGT | CCATNTTTAA | 240
| TCTTTCCTAC | CACATTCTTA | CCACACTTTC | TTTTATGTTT | AGATACATAA | ATGCTTACCA | 300
| TTATGATACA | ATTGCCCACA | GTATTAAGAC | AGTAACATGC | TGCACAGGTT | TGTAGCCTAG | 360
| GAACAGTAGG | CAATACCACA | TAGCTTAGGT | GTGTGGTAGA | CTATACCATC | TAGGTTTGTG | 420
| TAAGTTACAC | TTTATGCTGT | TTACACAATG | ACAAAACCAT | CTAATGATGC | ATTTCTCAGA | 480
| ATGTATCCTT | GTCAGTAAGC | TATGATGTAC | AGGGAACACT | GCCCAAGGAC | ACAGATATTG | 540
| TACCTGT | | | | | | 547

(2) INFORMATION FOR SEQ ID NO: 159:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (xi) SEQUENCE DESCRIPTION: SEQ ID NO: 159:

| | | | | | |
|---|---|---|---|---|---|
| GCTCCTCTTG | CCTTACCAAC | TCACCCAGTA | TGTCAGCAAT | TTTATCRGCT | TTACCTACGA | 60
| AACAGCCTGT | ATCCAAACAC | TTAACACACT | CACCTGAAAA | GTTCAGGCAA | CAATCGCCTT | 120
| CTCATGGGTC | TCTCTGCTCC | AGTTCTGAAC | CTTTCTCTTT | TCCTAGAACA | TGCATTTARG | 180
| TCGATAGAAG | TTCCTCTCAG | TGC | | | | 203

(2) INFORMATION FOR SEQ ID NO: 160:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO: 160:

| | | | | | |
|---|---|---|---|---|---|
| TGTAAGTCGA | GCAGTGTGAT | GGGTGGAACA | GGGTTGTAAG | CAGTAATTGC | AAACTGTATT | 60
| TAAACAATAA | TAATAATATT | TAGCATTTAT | AGAGCACTTT | ATATCTTCAA | AGTACTTGCA | 120
| AACATTAYCT | AATTAAATAC | CCTCTCTGAT | TATAATCTGG | ATACAAATGC | ACTTAAACTC | 180
| AGGACAGGGT | CATGAGARAA | GTATGCATTT | GAAAGTTGGT | GCTAGCTATG | CTTTAAAAAC | 240
| CTATACAATG | ATGGGRAAGT | TAGAGTTCAG | ATTCTGTTGG | ACTGTTTTTG | TGCATTTCAG | 300
| TTCAGCCTGA | TGGCAGAATT | AGATCATATC | TGCACTCGAT | GACTYTGCTT | GATAACTTAT | 360
| CACTGAAATC | TGAGTGTTGA | TCATCACACT | GCTCGACTTA | CA | | 402

(2) INFORMATION FOR SEQ ID NO: 161:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (xi) SEQUENCE DESCRIPTION: SEQ ID NO: 161:

```
AGCATGTTGA GCCCAGACAC TGACCAGGAG AAAAACCAAC CAATAGAAAC ACGCCCAGAC        60

ACTGACCAGG AGAAAAACCA ACCAATAAAA ACAGGCCCGG ACATAAGACA AATAATAAAA       120

TTAGCGGACA AGGACATGAA AACAGCTATT GTAAGAGCGG ATATAGTGGT GTGTGTCTGG       180

GCTCAACATG CTA                                                         193

(2) INFORMATION FOR SEQ ID NO: 162:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (xi) SEQUENCE DESCRIPTION: SEQ ID NO: 162:

TGTTGAGCCC AGACACTGAC CAGGAGAAAA ACCAACCAAT AAAAACAGGC CCGGACATAA        60

GACAAATAAT AAAATTAGCG GACAAGGACA TGAAACAGC TATTGTAAGA GCGGATATAG       120

TGGTGTGTGT CTGGGCTCAA CATGCTA                                         147

(2) INFORMATION FOR SEQ ID NO: 163:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO: 163:

TAGCATGTTG AGCCCAGACA CAAATCTTTC CTTAAGCAAT AAATCATTTC TGCATATGTT        60

TTTAAAACCA CAGCTAAGCC ATGATTATTC AAAAGGACTA TTGTATTGGG TATTTTGATT      120

TGGGTTCTTA TCTCCCTCAC ATTATCTTCA TTTCTATCAT TGACCTCTTA TCCCAGAGAC      180

TCTCAAACTT TTATGTTATA CAAATCACAT TCTGTCTCAA AAAATATCTC ACCCACTTCT      240

CTTCTGTTTC TGCGTGTGTA TGTGTGTGTG TGTGTGTCTG GGCTCAACAT GCTA            294

(2) INFORMATION FOR SEQ ID NO: 164:

(i) SEQUENCE CHARACTERISTICS:
        (A) LENGTH: 412 base pairs
        (B) TYPE: nucleic acid
        (C) STRANDEDNESS: single
        (D) TOPOLOGY: linear (xi) SEQUENCE DESCRIPTION: SEQ ID NO: 164:

CGGGATTGGC TTTGAGCTGC AGATGCTGCC TGTGACCGCA CCCGGCGTGG AACAGAAAGC        60

CACCTGGCTG CAAGTGCGCC AGAGCCGCCC TGACTACGTG CTGCTGTGGG GCTGGGGCGT      120

GATGAACTCC ACCGCCCTGA AGGAAGCCCA GGCCACCGGA TACCCCCGCG ACAAGATGTA      180

CGGCGTGTGG TGGGCCGGTG CGGAGCCCGA TGTGCGTGAC GTGGGCGAAG GCGCCAAGGG      240

CTACAACGCG CTGGCTCTGA ACGGCTACGG CACGCAGTCC AAGGTGATCC ANGACATCCT      300

GAAACACGTG CACGACAAGG GCCAGGGCAC GGGGCCCAAA GACGAAGTGG GCTCGGTGCT      360

GTACACCCGC GGCGTGATCA TCCAGATGCT GGACAAGGTG TCAATCACTA AT              412

(2) INFORMATION FOR SEQ ID NO: 165:

(i) SEQUENCE CHARACTERISTICS:
        (A) LENGTH: 361 base pairs
        (B) TYPE: nucleic acid
        (C) STRANDEDNESS: single
        (D) TOPOLOGY: linear
```

(xi) SEQUENCE DESCRIPTION: SEQ ID NO: 165:

| | |
|---|---|
| TTGACACCTT GTCCAGCATC TGCATCTGAT GAGAGCCTCA GATGGCTACC ACTAATGGCA | 60 |
| GAAGGCAAAG GAGAACAGGC ATTGTATGGC AAGAAAGGAA GAAAGAGAGA GGGGAGAAAG | 120 |
| GTGCTAGGTT CTTTTCAACA ACCAGTTCTT GATGGAACTG AGAGTAAGAG CTCAAGGCCA | 180 |
| GGTGTGGTGA CTCCAACCAG TAATCCCAAC ATTTTAGGAG GCTGAGGCAG GCAGATGTCT | 240 |
| TGACCCCATG AGTTTGTGAC CAGCCTGAAC AACATCATGA GACTCCATCT CTACAATAAT | 300 |
| TACAAAAATT AATCAGGCAT TGTGGTATGC CCTGTAGTCC CAGATGCTGG ACAAGGTGTC | 360 |
| A | 361 |

(2) INFORMATION FOR SEQ ID NO: 166:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (xi) SEQUENCE DESCRIPTION: SEQ ID NO: 166:

| | |
|---|---|
| TWGACTGACT CATGTCCCCT ACACCCAACT ATCTTCTCCA GGTGGCCAGG CATGATAGAA | 60 |
| TCTGATCCTG ACTTAGGGGA ATATTTTCTT TTTACTTCCC ATCTTGATTC CCTGCCGGTG | 120 |
| AGTTTCCTGG TTCAGGGTAA GAAAGGAGCT CAGGCCAAAG TAATGAACAA ATCCATCCTC | 180 |
| ACAGACGTAC AGAATAAGAG AACWTGGACW TAGCCAGCAG AACMCAAKTG AAAMCAGAAC | 240 |
| MCTTAMCTAG GATRACAAMC MCRRARATAR KTGCYCMCMC WTATAATAGA AACCAAACTT | 300 |
| GTATCTAATT AAATATTTAT CCACYGTCAG GGCATTAGTG GTTTTGATAA ATACGCTTTG | 360 |
| GCTAGGATTC CTGAGGTTAG AATGGAARAA CAATTGCAMC GAGGGTAGGG GACATGAGTC | 420 |
| AKTCTAA | 427 |

(2) INFORMATION FOR SEQ ID NO: 167:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (xi) SEQUENCE DESCRIPTION: SEQ ID NO: 167:

| | |
|---|---|
| AACGTCGCAT GCTCCCGGCC GCCATGGCCG CGGGATAGAC TGACTCATGT CCCCTAAGAT | 60 |
| AGAGGAGACA CCTGCTAGGT GTAAGGAGAA GATGGTTAGG TCTACGGAGG CTCCAGGGTG | 120 |
| GGAGTAGTTC CCTGCTAAGG GAGGGTAGAC TGTTCAACCT GTTCCTGCTC CGGCCTCCAC | 180 |
| TATAGCAGAT GCGAGCAGGA GTAGGAGAGA GGGAGGTAAG AGTCAGAAGC TTATGTTGTT | 240 |
| TATGCGGGGA AACGCCRTAT CGGGGGCAGC CRAGTTATTA GGGGACANTR TAGWYARTCW | 300 |
| AGNTAGCATC CAAAGCGNGG GAGTTNTCCC ATATGGTTGG ACCTGCAGGC GGCCGCATTA | 360 |
| GTGATTAGCA TGTGAGCCCC AGACACGCAT AGCAACAAGG ACCTAAACTC AGATCCTGTG | 420 |
| CTGATTACTT AACATGAATT ATTGTATTTA TTTAACAACT TTGAGTTATG AGGCATATTA | 480 |
| TTAGGTCCAT ATTACCTGGA | 500 |

(2) INFORMATION FOR SEQ ID NO: 168:

(i) SEQUENCE CHARACTERISTICS:
        (A) LENGTH: 358 base pairs
        (B) TYPE: nucleic acid (C) STRANDEDNESS: single
        (D) TOPOLOGY: linear (xi) SEQUENCE DESCRIPTION: SEQ ID NO: 168:

TTCATCGCTC GGTGACTCAA GCCTGTAATC CCAGAACTTT GGGAGGCCGA GGGGAGCAGA    60

TCACCTGAGG TTGGGAGTTT GAGACCAGCC TGGCCAACAT GGTGACAACC CGTCTCTGCT    120

AAAAATACAA AAATTAGCCA AGCATGGTGG CATGCACTTG TAATCCCAGC TACTCGGGAG    180

GCTGAGGCAG GAGAATCACT TGAGGCCAGG AGGCAGAGGT TGCAGTGAGG CAGAGGTTGG    240

GATCATGCCA CTGCACTCCA GCCTGGGCAA CAGAGTAAGA CTCCATCTCA AAAAAAAAAA    300

AAAAAAGAA TGATCAGAGC CACAAATACA GAAAACCTTG AGTCACCGAG CGATGAAA    358

(2) INFORMATION FOR SEQ ID NO: 169:

(i) SEQUENCE CHARACTERISTICS:
        (A) LENGTH: 1265 base pairs
        (B) TYPE: nucleic acid
        (C) STRANDEDNESS: single
        (D) TOPOLOGY: linear (xi) SEQUENCE DESCRIPTION: SEQ ID NO: 169:

TTCTGTCCAC ACCAATCTTA GAGCTCTGAA AGAATTTGTC TTTAAATATC TTTTAATAGT    60

AACATGTATT TTATGGACCA AATTGACATT TTCGACTATT TTTTCCCAAA AAAAGTCAGG    120

TGAATTTCAG CACACTGAGT TGGGAATTTC TTATCCCAGA AGWCGGCACG AGCAATTTCA    180

TATTTATTTA AGATTGATTC CATACTCCGT TTTCAAGGAG AATCCCTGCA GTCTCCTTAA    240

AGGTAGAACA AATACTTTCT ATTTTTTTTT CACCATTGTG GGATTGGACT TTAAGAGGTG    300

ACTCTAAAAA AACAGAGAAC AAATATGTCT CAGTTGTATT AAGCACGGAC CCATATTATC    360

ATATTCACTT AAAAAAATGA TTTCCTGTGC ACCTTTTGGC AACTTCTCTT TTCAATGTAG    420

GGAAAAACTT AGTCACCCTG AAAACCCACA AAATAAATAA AACTTGTAGA TGTGGGCAGA    480

ARGTTTGGGG GTGGACATTG TATGTGTTTA AATTAAACCC TGTATCACTG AGAAGCTGTT    540

GTATGGGTCA GAGAAAATGA ATGCTTAGAA GCTGTTCACA TCTTCAAGAG CAGAAGCAAA    600

CCACATGTCT CAGCTATATT ATTATTTATT TTTTATGCAT AAAGTGAATC ATTTCTTCTG    660

TATTAATTTC CAAAGGGTTT TACCCTCTAT TTAAATGCTT TGAAAAACAG TGCATTGACA    720

ATGGGTTGAT ATTTTTCTTT AAAAGAAAAA TATAATTATG AAAGCCAAGA TAATCTGAAG    780

CCTGTTTTAT TTTAAAACTT TTTATGTTCT GTGGTTGATG TTGTTTGTTT GTTTGTTTCT    840

ATTTTGTTGG TTTTTTACTT TGTTTTTTGT TTTGTTTTGT TTTGGTTTDG CATACTACAT    900

GCAGTTTCTT TAACCAATGT CTGTTTGGCT AATGTAATTA AAGTTGTTAA TTTATATGAG    960

TGCATTTCAA CTATGTCAAT GGTTTCTTAA TATTTATTGT GTAGAAGTAC TGGTAATTTT    1020

TTTATTTACA ATATGTTTAA AGAGATAACA GTTTGATATG TTTTCATGTG TTTATAGCAG    1080

AAGTTATTTA TTTCTATGGC ATTCCAGCGG ATATTTTGGT GTTTGCGAGG CATGCAGTCA    1140

ATATTTGTA CAGTTAGTGG ACAGTATTCA GCAACGCCTG ATAGCTTCTT TGGCCTTATG    1200

TTAAATAAAA AGACCTGTTT GGGATGTAAA AAAAAAAAAA AAAAAAAAA AAAAAAAAAA    1260

AAAAA                                                               1265

(2) INFORMATION FOR SEQ ID NO: 170:

(i) SEQUENCE CHARACTERISTICS:
        (A) LENGTH: 383 base pairs
        (B) TYPE: nucleic acid
        (C) STRANDEDNESS: single (D) TOPOLOGY: linear (xi) SEQUENCE DESCRIPTION: SEQ ID NO: 170:

| | | | | | |
|---|---|---|---|---|---|
| TGTAAGTCGA | GCAGTGTGAT | GACGATATTC | TTCTTATTAA | TGTGGTAATT | GAACAAATGA | 60 |
| TCTGTGATAC | TGATCCTGAG | CTAGGAGGCG | CTGTTCAGTT | AATGGGACTT | CTTCGTACTC | 120 |
| TAATTGATCC | AGAGAACATG | CTGGCTACAA | CTAATAAAAC | CGAAAAAAGT | GAATTTCTAA | 180 |
| ATTTTTTCTA | CAACCATTGT | ATGCATGTTC | TCACAGCACC | ACTTTTGACC | AATACTTCAG | 240 |
| AAGACAAATG | TGAAAAGGAT | AATATAGTTG | GATCAAACAA | AAACAACACA | ATTTGTCCCG | 300 |
| ATAATTATCA | AACAGCACAG | CTACTTGCCT | TAATTTTAGA | GTTACTCACA | TTTTGTGTGG | 360 |
| AACATCACAC | TGCTCGACTT | ACA | | | | 383 |

(2) INFORMATION FOR SEQ ID NO: 171:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (xi) SEQUENCE DESCRIPTION: SEQ ID NO: 171:

| | | | | | |
|---|---|---|---|---|---|
| TGGGCACCTT | CAATATCGCA | AGTTAAAAAT | AATGTTGAGT | TTATTATACT | TTTGACCTGT | 60 |
| TTAGCTCAAC | AGGGTGAAGG | CATGTAAAGA | ATGTGGACTT | CTGAGGAATT | TTCTTTTAAA | 120 |
| AAGAACATAA | TGAAGTAACA | TTTTAATTAC | TCAAGGACTA | CTTTTGGTTG | AAGTTTATAA | 180 |
| TCTAGATACC | TCTACTTTTT | GTTTTTGCTG | TTCGACAGTT | CACAAAGACC | TTCAGCAATT | 240 |
| TACAGGGTAA | AATCGTTGAA | GTAGTGGAGG | TGAAACTGAA | ATTTAAAATT | ATTCTGTAAA | 300 |
| TACTATAGGG | AAAGAGGCTG | AGCTTAGAAT | CTTTTGGTTG | TTCATGTGTT | CTGTGCTCTT | 360 |
| ATCATCACAC | TGCTCGACTT | ACA | | | | 383 |

(2) INFORMATION FOR SEQ ID NO: 172:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (xi) SEQUENCE DESCRIPTION: SEQ ID NO: 172:

| | | | | | |
|---|---|---|---|---|---|
| TCGGGTGATG | CCTCCTCAGG | CTTGTCGTTA | GTGTACACAG | AGCTGCTCAT | GAAGCGACAG | 60 |
| CGGCTGCCCC | TGGCACTTCA | GAACCTCTTC | CTCTACACTT | TTGGTGCGCT | TCTGAATCTA | 120 |
| GGTCTGCATG | CTGGCGGCGG | CTCTGGCCCA | GGCCTCCTGG | AAAGTTTCTC | AGGATGGGCA | 180 |
| GCACTCGTGG | TGCTGAGCCA | GGCACTAAAT | GGACTGCTCA | TGTCTGCTGT | CATGGAGCAT | 240 |
| GGCAGCAGCA | TCACACGCCT | CTTTGTGGTG | TCCTGCTCGC | TGGTGGTCAA | CGCCGTGCTC | 300 |
| TCAGCAGTCC | TGCTACGGCT | GCAGCTCACA | GCCGCCTTCT | TCCTGGCCAC | ATTGCTCATT | 360 |
| GGCCTGGCCA | TGCGCCTGTA | CTATGGCAGC | CGCTAGTCCC | TGACAACTTC | CACCCTGATT | 420 |
| CCGGACCCTG | TAGATTGGGC | GCCACCACCA | GATCCCCCTC | CCAGGCCTTC | CTCCCTCTCC | 480 |
| CATCAGCGGC | CCTGTAACAA | GTGCCTTGTG | AGAAAAGCTG | GAGAAGTGAG | GGCAGCCAGG | 540 |
| TTATTCTCTG | GAGGTTGGTG | GATGAAGGGG | TACCCCTAGG | AGATGTGAAG | TGTGGGTTTG | 600 |
| GTTAAGGAAA | TGCTTACCAT | CCCCCACCCC | CAACCAAGTT | NTTCCAGACT | AAAGAATTAA | 660 |
| GGTAACATCA | ATACCTAGGC | CTGAGGAGGC | ATCACCCGA | | | 699 |

(2) INFORMATION FOR SEQ ID NO: 173:

(i) SEQUENCE CHARACTERISTICS:
        (A) LENGTH: 701 base pairs
        (B) TYPE: nucleic acid
        (C) STRANDEDNESS: single
        (D) TOPOLOGY: linear (xi) SEQUENCE DESCRIPTION: SEQ ID NO: 173:

```
TCGGGTGATG CCTCCTCAGG CCAGATCAAA CTTGGGGTTG AAAACTGTGC AAAGAAATCA      60

ATGTCGGAGA AAGAATTTTG CAAAAGAAAA ATGCCTAATC AGTACTAATT TAATAGGTCA     120

CATTAGCAGT GGAAGAAGAA ATGTTGATAT TTTATGTCAG CTATTTTATA ATCACCAGAG     180

TGCTTAGCTT CATGTAAGCC ATCTCGTATT CATTAGAAAT AAGAACAATT TTATTCGTCG     240

GAAAGAACTT TTCAATTTAT AGCATCTTAA TTGCTCAGGA TTTTAAATTT TGATAAAGAA     300

AGCTCCACTT TTGGCAGGAG TAGGGGGCAG GGAGAGAGGA GGCTCCATCC ACAAGGACAG     360

AGACACCAGG GCCAGTAGGG TAGCTGGTGG CTGGATCAGT CACAACGGAC TGACTTATGC     420

CATGAGAAGA AACAACCTCC AAATCTCAGT TGCTTAATAC AACACAAGCT CATTTCTTGC     480

TCACGTTACA TGTCCTATGT AGATCAACAG CAGGTGACTC AGGGACCCAG GCTCCATCTC     540

CATATGAGCT TCCATAGTCA CCAGGACACG GGCTCTGAAA GTGTCCTCCA TGCAGGGACA     600

CATGCCTCTT CCTTTCATTG GGCAGAGCAA GTCACTTATG GCCAGAAGTC ACACTGCAGG     660

GCAGTGCCAT CCTGCTGTAT GCCTGAGGAG GCATCACCCG A                        701
```

(2) INFORMATION FOR SEQ ID NO: 174:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (xi) SEQUENCE DESCRIPTION: SEQ ID NO: 174:

```
TCGGGTGATG CCTCCTCANG CCCCTAAATC AGAGTCCAGG GTCAGAGCCA CAGGAGACAG      60

GGAAAGACAT AGATTTTAAC CGGCCCCCTT CAGGAGATTC TGAGGCTCAG TTCACTTTGT     120

TGCAGTTTGA ACAGAGGCAG CAAGGCTAGT GGTTAGGGGC ACGGTCTCTA AAGCTGCACT     180

GCCTGGATCT GCCTCCCAGC TCTGCCAGGA ACCAGCTGCG TGGCCTTGAG CTGCTGACAC     240

GCAGAAAGCC CCCTGTGGAC CCAGTCTCCT CGTCTGTAAG ATGAGGACAG GACTCTAGGA     300

ACCCTTTCCC TTGGTTTGGC CTCACTTTCA CAGGCTCCCA TCTTGAACTC TATCTACTCT     360

TTTCCTGAAA CCTTGTAAAA GAAAAAAGTG CTAGCCTGGG CAACATGGCA AAACCCTGTC     420

TCTACAAAAA ATACAAAAAT TAGTTGGGTG TGGTGGCATG TGCCTGTAGT CCCAGCCACT     480

TGGGAGGTGC TGAGGTGGGA GGATCACTTG AGCCCGGGAG GTGGAGGTTG CAGTGAGCCA     540

AGATCATGCC ACTGCACTCC AGCCTGAGTA ATAGAGTAAG ACTCTGTCTC AAAAACAACA     600

ACAACAACAG TGAGTGTGCC TCTGTTTCCG GGTTGGATGG GGCACCACAT TTATGCATCT     660

CTCAGATTTG GACGCTGCAG CCTGAGGAGG CATCACCCGA                           700
```

(2) INFORMATION FOR SEQ ID NO: 175:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (xi) SEQUENCE DESCRIPTION: SEQ ID NO: 175:

TATAGGGCGA ATTGGGCCCG AGTTGCATGN TCCCGGCCGC CATGGCCGCG GGATTCGGGT      60

GATGCCTCCT CAGGCTTGTC TGCCACAAGC TACTTCTCTG AGCTCAGAAA GTGCCCCTTG     120

ATGAGGGAAA ATGTCCTACT GCACTGCGAA TTTCTCAGTT CCATTTTACC TCCCAGTCCT     180

CCTTCTAAAC CAGTTAATAA ATTCATTCCA CAAGTATTTA CTGATTACCT GCTTGTGCCA     240

GGGACTATTC TCAGGCTGAA GAAGGTGGGA GGGGAGGGCG GAACCTGAGG AGCCACCTGA     300

GCCAGCTTTA TATTTCAACC ATGGCTGGCC CATCTGAGAG CATCTCCCCA CTCTCGCCAA     360

CCTATCGGGG CATAGCCCAG GGATGCCCCC AGGCGGCCCA GGTTAGATGC GTCCCTTTGG     420

CTTGTCAGTG ATGACATACA CCTTAGCTGC TTAGCTGGTG CTGGCCTGAG GAGGCATCAC     480

CCGA                                                                  484

(2) INFORMATION FOR SEQ ID NO: 176:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (xi) SEQUENCE DESCRIPTION: SEQ ID NO: 176:

TCGGGTGATG CCTCCTCAGG GCTCAAGGGA TGAGAAGTGA CTTCTTTCTG GAGGGACCGT      60

TCATGCCACC CAGGATGAAA ATGGATAGGG ACCCACTTGG AGGACTTGCT GATATGTTTG     120

GACAAATGCC AGGTAGCGGA ATTGGTACTG GTCCAGGAGT TATCCAGGAT AGATTTTCAC     180

CCACCATGGG ACGTCATCGT TCAAATCAAC TCTTCAATGG CCATGGGGGA CACATCATGC     240

CTCCCACACA ATCGCAGTTT GGAGAGATGG GAGGCAAGTT TATGAAAAGC CAGGGGCTAA     300

GCCAGCTCTA CCATAACCAG AGTCAGGGAC TCTTATCCCA GCTGCAAGGA CAGTCGAAGG     360

ATATGCCACC TCGGTTTTCT AAGAAAGGAC AGCTTAATGC AGATGAGATT AGCCTGAGGA     420

GGCATCACCC GA                                                         432

(2) INFORMATION FOR SEQ ID NO: 177:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (xi) SEQUENCE DESCRIPTION: SEQ ID NO: 177:

TAGCATGTTG AGCCCAGACA CAGTAGCATT TGTGCCAATT TCTGGTTGGA ATGGTGACAA      60

CATGCTGGAG CCAAGTGCTA ACATGCCTTG GTTCAAGGGA TGGAAAGTCA CCCGTAAGGA     120

TGGCAATGCC AGTGGAACCA CGCTGCTTGA GGCTCTGGAC TGCATCCTAC CACCAACTCG     180

CCCAACTGAC AAGCCCTTGC GCCTGCCTCT CCAGGATGTC TACAAAATTG GTGGTATTGG     240

TACTGTTCCT GTTGGCCGAG TGGAGACTGG TGTTCTCAAA CCCGGTATGG TGGTCACCTT     300

TGCTCCAGTC AACGTTACAA CGGAAGTAAA ATCGTCGAA ATGCACCATG AAGCTTTGAG     360

TGAAGCTCTT CCTGGGGACA ATGTGGGCTT CAATGTCAAG AATGTGTCTG TCAAGGATGT     420

TCGTCGTGGC AACGTTGCTG GTGACAGCAA AAATGACCCA CCAATGGAAG CAGCTGGCTT     480

CACTGCTCAG GTGATTATCC TGAACCATCC AGGCCAAATA AGTGCCGGCT ATGCCCCTGT     540

ATTGGATTGC CACACGGCTC ACATTGCATG CAAGTTTGCT GAGCTGAAGG AAAAGATTGA     600

TCGCCGTTCT GGTAAAAAGC TGGAAGATGG CCCTAAATTC TTGAAGTCTG GTGATGCTGC     660

| | | |
|---|---|---|
| CATTGTTGAT ATGGTTCCTG GCAAGCCCAT GTGTGTTGAG AGCTTCTCAG ACTATCCACC | 720 | |
| TTTGGGTCGC TTTGCTGTTC GTGATATGAG ACAGACAGTT GCGGTGGGTG TCTGGGCTCA | 780 | |
| ACATGCTA | 788 | |

(2) INFORMATION FOR SEQ ID NO: 178:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (xi) SEQUENCE DESCRIPTION: SEQ ID NO: 178:

| | |
|---|---|
| TAGCATGTTG AGCCCAGACA CCTGTGTTTC TGGGAGCTCT GGCAGTGGCG GATTCATAGG | 60 |
| CACTTGGGCT GCACTTTGAA TGACACACTT GGCTTTATTA GATTCACTAG TTTTTAAAAA | 120 |
| ATTGTTGTTC GTTTCTTTTC ATTAAAGGTT TAATCAGACA GATCAGACAG CATAATTTTG | 180 |
| TATTTAATGA CAGAAACGTT GGTACATTTC TTCATGAATG AGCTTGCATT CTGAAGCAAG | 240 |
| AGCCTACAAA AGGCACTTGT TATAAATGAA AGTTCTGGCT CTAGAGGCCA GTACTCTGGA | 300 |
| GTTTCAGAGC AGCCAGTGAT TGTTCCAGTC AGTGATGCCT AGTTATATAG AGGAGGAGTA | 360 |
| CACTGTGCAC TCTTCTAGGT GTAAGGGTAT GCAACTTTGG ATCTTAAAAT TCTGTACACA | 420 |
| TACACACTTT ATATATATGT ATGTATGTAT GAAAACATGA AATTAGTTTG TCAAATATGT | 480 |
| GTGTGTTTAG TATTTTAGCT TAGTGCAACT ATTTCCACAT TATTTATTAA ATTGATCTAA | 540 |
| GACACTTTCT TGTTGACACC TTGAATATTA ATGTTCAAGG GTGCAATGTG TATTCCTTTA | 600 |
| GATTGTTAAA GCTTAATTAC TATGATTTGT AGTAAATTAA CTTTTAAAAT GTATTTGAGC | 660 |
| CCTTCTGTAG TGTCGTAGGG CTCTTACAGG GTGGGAAAGA TTTTAATTTT CCAGTTGCTA | 720 |
| ATTGAACAGT ATGGCCTCAT TATATATTTT GATTTATAGG AGTTTGTGTC TGGGCTCAAC | 780 |
| ATGCTA | 786 |

(2) INFORMATION FOR SEQ ID NO: 179:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (xi) SEQUENCE DESCRIPTION: SEQ ID NO: 179:

| | |
|---|---|
| TAGCATGTTG AGCCCAGACA CTGGTTACAA GACCAGACCT GCTTCCTCCA TATGTAAACA | 60 |
| GCTTTTAAAA AGCCAGTGAA CCTTTTTAAT ACTTTGGCAA CCTTCTTTCA CAGGCAAAGA | 120 |
| ACACCCCCAT CCGCCCCTTG TTTGGAGTGC AGAGTTTGGC TTTGGTTCTT TGCCTTGCCT | 180 |
| GGAGTATACT TCTAATTCCT GTTGTCCTGC ACAAGCTGAA TACCGAGCTA CCCACCGCCA | 240 |
| CCCAGGCCAG GTTTCCACTC ATTTATTACT TTATGTTTCT GTTCCATTGC TGGTCCACAG | 300 |
| AAATAAGTTT TCCTTTGGAG GAATGTGATT ATACCCCTTT AATTTCCTCC TTTTGCTTTT | 360 |
| TTTTAATATC ATTGGTATGT GTTTGGCCCA GAGGAAACTG AAATTCACCA TCATCTTGAC | 420 |
| TGGCAATCCC ATTACCATGC TTTTTTTAAA AAACGTAATT TTTCTTGCCT TACATTGGCA | 480 |
| GAGTAGCCCT TCCTGGCTAC TGGCTTAATG TAGTCACTCA GTTTCTAGGT GGCATTAGGC | 540 |
| ATGAGACCTG AAGCACAGAC TGTCTTACCA CAAAAGGTGA CAAGATCTCA AACCTTAGCC | 600 |
| AAAGGGCTAT GTCAGGTTTC AATGCTATCT GCTTCTGTTC CTGCTCACTG TTCTGGATTT | 660 |
| TGTCCTTCTT CATCCCTAGC ACCAGAATTT CCCAGTCTCC CTCCCTACCT TCCCTTGTTT | 720 |

```
TAATTCTAAT CTATCAGCAA AATAACTTTT CAAATGTTTT AACCGGTATC TCCATGTGTC      780

TGGGCTCAAC ATGCTA                                                     796

(2) INFORMATION FOR SEQ ID NO: 180:

(i) SEQUENCE CHARACTERISTICS:
        (A) LENGTH: 488 base pairs
        (B) TYPE: nucleic acid
        (C) STRANDEDNESS: single
        (D) TOPOLOGY: linear (xi) SEQUENCE DESCRIPTION: SEQ ID NO: 180:

GGATGTGCTG CAAGGCGATT AAGTTGGGTA ACGCCAGGGT TTTCCCAGTC ACGACGTTGT       60

AAAACGACGG CCAGTGAATT GTAATACGAC TCACTATAGG GCGAATTGGG CCCGACGTCG      120

CATGCTCCCG GCCGCCATGG CCGCGGGATA GCATGTTGAG CCCAGACACC TGCAGGTCAT      180

TTGGAGAGAT TTTTCACGTT ACCAGCTTGA TGGTCTTTTT CAGGAGGAGA GACACTGAGC      240

ACTCCCAAGG TGAGGTTGAA GATTTCCTCT AGATAGCCGG ATAAGAAGAC TAGGAGGGAT      300

GCCTAGAAAA TGATTAGCAT GCAAATTTCT ACCTGCCATT TCAGAACTGT GTGTCAGCCC      360

ACATTCAGCT GCTTCTTGTG AACTGAAAAG AGAGAGGTAT TGAGACTTTT CTGATGGCCG      420

CTCTAACATT GTAACACAGT AATCTGTGTG TGTGTGGGTG TGTGTGTGTG TCTGGGCTCA      480

ACATGCTA                                                              488

(2) INFORMATION FOR SEQ ID NO: 181:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (xi) SEQUENCE DESCRIPTION: SEQ ID NO: 181:

TAGCATGTTG AGCCCAGACA CGGCGACGGT ACCTGATGAG TGGGGTGATG GCACCTGTGA       60

AAAGGAGGAA CGTCATCCCC CATGATATTG GGGACCCAGA TGATGAACCA TGGCTCCGCG      120

TCAATGCATA TTTAATCCAT GATACTGCTG ATTGGAAGGA CCTGAACCTG AAGTTTGTGC      180

TGCAGGTTTA TCGGGACTAT TACCTCACGG GTGATCAAAA CTTCCTGAAG GACATGTGGC      240

CTGTGTGTCT AGTAAGGGAT GCACATGCAG TGGCCAGTGT GCCAGGGGTA TGGTTGGTGT      300

CTGGGCTCAA CATGCTA                                                    317

(2) INFORMATION FOR SEQ ID NO: 182:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO: 182:

TAGCATGTTG AGCCCAGACA CTGGCTGTTA GCCAAATCCT CTCTCAGCTG CTCCCTGTGG       60

TTTGGTGACT CAGGATTACA GAGGCATCCT GTTTCAGGGA ACAAAAAGAT TTTAGCTGCC      120

AGCAGAGAGC ACCACATACA TTAGAATGGT AAGGACTGCC ACCTCCTTCA AGAACAGGAG      180

TGAGGGTGGT GGTGAATGGG AATGGAAGCC TGCATTCCCT GATGCATTTG TGCTCTCTCA      240

AATCCTGTCT TAGTCTTAGG AAAGGAAGTA AAGTTTCAAG GACGGTTCCG AACTGCTTTT      300

TGTGTCTGGG CTCAACATGC TATCCCGCGG CCATGGCGGC CGGGAGCATG CGACGTCGGG      360
```

```
CCCAATTCGC CCTATAGTGA GTCGTATTAC AATTCACTGG CCGTCGTTTT ACAACGTCGT        420

GACTGGGAAA ACCCTGGCGT TACCCAACTT AATCGCCTTG CAGCACATCC CCCTTTCCCA        480

GCTGGCGTAA TANCGAAAAG GCCCGCA                                            507
```

(2) INFORMATION FOR SEQ ID NO: 183:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (xi) SEQUENCE DESCRIPTION: SEQ ID NO: 183:

```
GATTTACGCT GCAACACTGT GGAGGTAGCC CTGGAGCAAG GCAGGCATGG ATGCTTCTGC         60

AATCCCCAAA TGGAGCCTGG TATTTCAGCC AGGAATCTGA GCAGAGCCCC CTCTAATTGT        120

AGCAATGATA AGTTATTCTC TTTGTTCTTC AACCTTCCAA TAGCCTTGAG CTTCCAGGGG        180

AGTGTCGTTA ATCATTACAG CCTGGTCTCC ACAGTGTTGC AGCGTAA                     227
```

(2) INFORMATION FOR SEQ ID NO: 184:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (xi) SEQUENCE DESCRIPTION: SEQ ID NO: 184:

```
TTACGCTGCA ACACTGTGGA GCAGATTAAC ATCAGACTTT TCTATCAACA TGACTGGGGT         60

TACTAAAAAG ACAACAAATC AATGGCTTCA AAAGTCTAAG GAATAATTTC GATACTTCAA        120

CTTTATAAAA CCTGACAAAA CTATCAATCA AGCATAAAGA CAGATGAAGA ACATTTCCAG        180

ATTTTGGCCA ATCAGATATT TTACCTCCAC AGTGTTGCAG CGTAA                       225
```

(2) INFORMATION FOR SEQ ID NO: 185:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (xi) SEQUENCE DESCRIPTION: SEQ ID NO: 185:

```
GGCCCGACGT CGCATGCTCC CGGCCGCCAT GGCCGCGGGA TTCGTTAGGG TCTCTATCCA         60

CTGGGACCCA TAGGCTAGTC AGAGTATTTA GAGTTGAGTT CCTTTCTGCT TCCCAGAATT        120

TGAAAGAAAA GGAGTGAGGT GATAGAGCTG AGAGATCAGA TTTGCCTCTG AAGCCTGTTC        180

AAGATGTATG TGCTCAGACC CCACCACTGG GGCCTGTGGG TGAGGTCCTG GGCATCTATT        240

TGAATGAATT GCTGAAGGGG AGCACTATGC CAAGGAAGGG GAACCCATCC TGGCACTGGC        300

ACAGGGTCA CCTTATCCAG TGCTCAGTGC TTCTTTGCTG CTACCTGGTT TTCTCTCATA        360

TGTGAGGGGC AGGTAAGAAG AAGTGCCCRG TGTTGTGCGA GTTTTAGAAC ATCTACCAGT        420

AAGTGGGGAA GTTTCACAAA GCAGCAGCTT TGTTTTGTGT ATTTTCACCT TCAGTTAGAA        480

GAGGAAGGCT GTGAGATGAA TGTTAGTTGA GTGGAAAAGA CGGGTAAGCT TAGTGGATAG        540

AGACCCTAAC GAATCACTAG TGCGGCCGCC TTGCAGGTCG ACCATATGGG AGAGCTC          597
```

(2) INFORMATION FOR SEQ ID NO: 186:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (xi) SEQUENCE DESCRIPTION: SEQ ID NO: 186:

| | | | | | |
|---|---|---|---|---|---|
| GGCCCGAAGT | TGCATGTTCC | CGGCCGCCAT | GGCCGCGGGA | TTCGTTAGGG | TCTCTATCCA | 60
| CTACCTAAAA | AATCCCAAAC | ATATAACTGA | ACTCCTCACA | CCCAATTGGA | CCAATCCATC | 120
| ACCCCAGAGG | CCTACAGATC | CTCCTTTGAT | ACATAAGAAA | ATTTCCCCAA | ACTACCTAAC | 180
| TATATCATTT | TGCAAGATTT | GTTTTACCAA | ATTTTGATGG | CCTTTCTGAG | CTTGTCAGTG | 240
| TGAACCACTA | TTACGAACGA | TCGGATATTA | ACTGCCCCTC | ACCGTCCAGG | TGTAGCTGGC | 300
| AACATCAAGT | GCAGTAAATA | TTCATTAAGT | TTTCACCTAC | TAAGGTGCTT | AAACACCCTA | 360
| GGGTGCCATG | TCGGTAGCAG | ATCTTTTGAT | TTGTTTTTAT | TTCCCATAAG | GGTCCTGTTC | 420
| AAGGTCAATC | ATACATGTAG | TGTGAGCAGC | TAGTCACTAT | CGCATGACTT | GGAGGGTGAT | 480
| AATAGAGGCC | TCCTTTGCTG | TTAAAGAACT | CTTGTCCCAG | CCTGTCAAAG | TGGATAGAGA | 540
| CCCTAACGAA | TCACTAGTGC | GGCCGCCTGC | AGGTCGACCA | TATGGGAGAG | CTCCCAA | 597

(2) INFORMATION FOR SEQ ID NO: 187:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (xi) SEQUENCE DESCRIPTION: SEQ ID NO: 187:

| | | | | | |
|---|---|---|---|---|---|
| TCGTTAGGGT | CTCTATCCAC | TTGCAGGTAA | AATCCAATCC | TGTGTATATC | TTATAGTCTT | 60
| CCATATGTAG | TGGTTCAAGA | GACTGCAGTT | CCAGAAAGAC | TAGCCGAGCC | CATCCATGTC | 120
| TTCCACTTAA | CCCTGCTTTG | GGTTACACAT | CTTAACTTTT | CTGTTCAAGT | TTCTCTGTGT | 180
| AGTTTATAGC | ATGAGTATTG | GGAWAATGCC | CTGAAACCTG | ACATGAGATC | TGGGAAACAC | 240
| AAACTTACTC | AATAAGAATT | TCTCCCATAT | TTTTATGATG | GAAAAATTTC | ACATGCACAG | 300
| AGGAGTGGAT | AGAGACCCTA | ACGA | | | | 324

(2) INFORMATION FOR SEQ ID NO: 188:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (xi) SEQUENCE DESCRIPTION: SEQ ID NO: 188:

| | | | | | |
|---|---|---|---|---|---|
| GCGCGGGGAT | TCGGGGTGAT | ACCTCCTCAT | GCCAAAATAC | AACGTNTAAT | TTCACAACTT | 60
| GCCTTCCAAT | TTACGCATTT | TCAATTTGCT | CTCCCCATTT | GTTGAGTCAC | AACAAACACC | 120
| ATTGCCCAGA | AACATGTATT | ACCTAACATG | CACATACTCT | TAAAACTACT | CATCCCTT | 178

(2) INFORMATION FOR SEQ ID NO: 189:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (xi) SEQUENCE DESCRIPTION: SEQ ID NO: 189:

```
TGACACCTTG TCCAGCATCT GACACAGTCT TGGCTCTTGG AAAATATTGG ATAAATGAAA      60

ATGAATTTCT TTAGCAAGTG GTATAAGCTG AGAATATACG TATCACATAT CCTCATTCTA     120

AGACACATTC AGTGTCCCTG AAATTAGAAT AGGACTTACA ATAAGTGTGT TCACTTTCTC     180

AATAGCTGTT ATTCAATTGA TGGTAGGCCT TAAAAGTCAA AGAAATGAGA GGGCATGTGA     240

AAAAAAGCTC AACATCACTG ATCATTAGAA AACTTCCATT CAAACCCCCA ATGAGATACC     300

ATCTCATACC AGTCAGAATG GCTATTATTA AAAAGTCAAA AATAACAGA TGCTGGACAA     360

GGTGTCA                                                              367
```

(2) INFORMATION FOR SEQ ID NO: 190:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (xi) SEQUENCE DESCRIPTION: SEQ ID NO: 190:

```
GACACCTTGT CCAGCATCTG ACAACGCTAA CAGCCTGAGG AGATCTTTAT TTATTTATTT     60

AGTTTTTACT CTGGCTAGGC AGATGGTGGC TAAAACATTC ATTTACCCAT TTATTCATTT    120

AATTGTTCCT GCAAGGCCTA TGGATAGAGT ATTGTCCAGC ACTGCTCTGG AAGCTAGGAG    180

CATGGGATG AACAAGATAG GCTACATCCT GTTCCCACAG AACTTCCACT TTAGTCTGGG    240

AAACAGATGA TATATACAAA TATATAAATG AATTCAGGTA GTTTTAAGTA CGAAAAGAAT    300

AAGAAAGCAG AGTCATGATT TANAATGCTG GAAACAGGGG CTATTGCTTG AGATATTGAA   360

GGTGCCCAA                                                           369
```

(2) INFORMATION FOR SEQ ID NO: 191:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (xi) SEQUENCE DESCRIPTION: SEQ ID NO: 191:

```
TGACACCTTG TCCAGCATCT GCACAGGGAA AAGAAACTAT TATCAGAGTG AACAGGCAAC     60

CTACAGAATG GGAGAAAATT TTTGCAATCT ATCCATCTGA CAAAGGGCTA ATATCCAGAA    120

TCTACAAAGA ACTTATACAA ATTTACAAGA AACAAACAAA CAAACAACTC CTCAAAAAGT    180

GGGTGAAGGA TGTGAACAGA CACTTCTCAA AAGAAGACAT TTATGGGGCC AACAAACATA    240

TGAAAAAAAG CTCATCATCA CTGGTCACTA GATAAATGCA AATCAAAACC ACAATGAGAT    300

ACCATCTCAT TCCAGTTAGA ATGGCAATCA TTAAAAAGTC AGGAAACAAC AGATGCTGGA    360

CAAGGTGTC                                                           369
```

(2) INFORMATION FOR SEQ ID NO: 192:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (xi) SEQUENCE DESCRIPTION: SEQ ID NO: 192:

```
TGACGCTTGG CCACTTGACA CTTCATCTTT GCACAGAAAA ACTTCTTTAC AGATTTAATT     60

CAAGACTGGT CTAGTGACAG TCCTCCAGAC ATTTTTTCAT TTGTTCCATA TACGTGGAAT    120
```

```
TTTAAAATCA TGTTTCATCA GTTTGAAATG ATTTGGGCTG CTAATCAACA CAATTGGATC       180

GACTGTTCTA CTAAACAACA GGAAAATGTG TATCTGGCAG CCTGTGGAGA AACACTAAAC       240

ATTGATTTTT CTTTGCCTTT TACGGACTTT GTTCCAGCTA CATGTAATAC CAAGTTCTCT       300

TTAAGAGGAG AAGATGTTGA TCTTCATTTG TTTCTACCAG ACTGCCACCC TAGTAAATAT       360

TCTTTATTTA TGCTGGTAAA AAATTGCCAT CCAAATAAGA TGATTCATGA TACTGGTATT       420

CCTGCTGAGT GTCAAGTGGC CAAGCGTCA                                        449

(2) INFORMATION FOR SEQ ID NO: 193:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (xi) SEQUENCE DESCRIPTION: SEQ ID NO: 193:

TGACGCTTGG CCACTTGACA CCAGGGATGT AKCAGTTGAA TATAATCCTG CAATTGTACA        60

TATTGGCAAT TTCCCATCAA ACATTCTAGA AAGAGACAAC CAGGATTGCT AGGCCATAAA       120

AGCTGCAATA AATAACTGGT AATTGCAGTA ATCATTTCAG GCCAATTCAA TCCAGTTTGG       180

CTCAGAGGTG CCTTTGGCTG AGAGAAGAGG TGAGATATAA TGTGTTTTCT TGCAACTTCT       240

TGGAAGAATA ACTCCACAAT AGTCTGAGGA CTAGATACAA ACCTATTTGC CATTAAAGCA       300

CCAGAGTCTG TTAATTCCAG TACTGATAAG TGTTGGAGAT TAGACTCCAG TGTGTCAAGT       360

GGCCAAGCGT CA                                                          372

(2) INFORMATION FOR SEQ ID NO: 194:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (xi) SEQUENCE DESCRIPTION: SEQ ID NO: 194:

TGACGCTTGG CCACTTGACA CTTATGTAGA ATCCATCGTG GGCTGATGCA AGCCCTTTAT        60

TTAGGCTTAG TGTTGTGGGC ACCTTCAATA TCACACTAGA GACAAACGCC ACAAGATCTG       120

CAGAAACATT CAGTTCTGAN CACTCGAATG GCAGGATAAC TTTTTGTGTT GTAATCCTTC       180

ACATATACAA AAACAAACTC TGCANTCTCA CGTTACAAAA AAACGTACTG CTGTAAAATA       240

TTAAGAAGGG GTAAAGGATA CCATCTATAA CAAAGTAACT TACAACTAGT GTCAAGTGGC       300

CAAGCGTCA                                                              309

(2) INFORMATION FOR SEQ ID NO: 195:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (xi) SEQUENCE DESCRIPTION: SEQ ID NO: 195:

TGACGCTTGG CCACTTGACA CCCAATCTCG CACTTCATCC TCCCAGCACC TGATGAAGTA        60

GGACTGCAAC TATCCCCACT TCCCAGATGA GGGGACCAAN GTACACATTA GGACCCGGAT       120

GGGAGCACAG ATTTGTCCGA TCCCAGACTC CAAGCACTCA GCGTCACTCC AGGACAGCGG       180

CTTTCAGATA AGGTCACAAA CATGAATGGC TCCGACAACC GGAGTCAGTC CGTGCTGAGT       240
```

| | |
|---|---|
| TAAGGCAATG GTGACACGGA TGCACGTGTN ACCTGTAATG GTTCATCGTA AGTGTCAAGT | 300 |
| GGCCAAGCGT CA | 312 |

(2) INFORMATION FOR SEQ ID NO: 196:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (xi) SEQUENCE DESCRIPTION: SEQ ID NO: 196:

| | |
|---|---|
| TGTATCGACG TAGTGGTCTC CTCAGCCATG CAGAACTGTG ACTCAATTAA ACCTCTTTCC | 60 |
| TTTATGAATT ACCCAATCTC GGGTAGTGTC TTTATAGTAG TGTGAGAATG GACTAATACA | 120 |
| AGTACATTTT ACTTAGTAAT AATAATAAAC AAATATATTA CATTTTTGTG TATTTACTAC | 180 |
| ACCATATTTT TTATTGTTAT TGTAGTGTAC ACCTTCTACT TATTAAAAGA AATAGGCCCG | 240 |
| AGGCGGGCAG ATCACGAGGT CAGGAGATGG AGACCACTAC GTCGATAC | 288 |

(2) INFORMATION FOR SEQ ID NO: 197:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (xi) SEQUENCE DESCRIPTION: SEQ ID NO: 197:

| | |
|---|---|
| TTGGGCACCT TCAATATCAT GACAGGTGAT GTGATAACCA AGAAGGCTAC TAAGTGATTA | 60 |
| ATGGGTGGGT AATGTATACA GAGTAGGTAC ACTGGACAGA GGGGTAATTC ATAGCCAAGG | 120 |
| CAGGAGAAGC AGAATGGCAA AACATTTCAT CACACTACTC AGGATAGCAT GCAGTTTAAA | 180 |
| ACCTATAAGT AGTTTATTTT TGGAATTTTC CACTTAATAT TTTCAGACTG CAGGTAACTA | 240 |
| AACTGTGGAA CACAAGAACA TAGATAAGGG GAGACCACTA CGTCGATAC | 289 |

(2) INFORMATION FOR SEQ ID NO: 198:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (xi) SEQUENCE DESCRIPTION: SEQ ID NO: 198:

| | |
|---|---|
| GTATCGACGT AGTGGTCTCC CAAGCAGTGG AAGAAAACG TGAACCAATT AAAATGTATC | 60 |
| AGATACCCCA AGAAAGGCG CTTGAGTAAA GATTCCAAGT GGGTCACAAT CTCAGATCTT | 120 |
| AAAATTCAGG CTGTCAAAGA GATTTGCTAT GAGGTTGCTC TCAATGACTT CAGGCACAGT | 180 |
| CGGCAGGAGA TTGAAGCCCT GGCCATTGTC AAGATGAAGG AGCTTTGTGC CATGTATGGC | 240 |
| AAGAAAGACC CCAATGAGCG GGACTCCTGG AGACCACTAC GTCGATAC | 288 |

(2) INFORMATION FOR SEQ ID NO: 199:

(i) SEQUENCE CHARACTERISTICS:
        (A) LENGTH: 1027 base pairs
        (B) TYPE: nucleic acid
        (C) STRANDEDNESS: single
        (D) TOPOLOGY: linear (xi) SEQUENCE DESCRIPTION: SEQ ID NO: 199:

| | |
|---|---|
| GCTTTTTGGG AAAAACNCAA NTGGGGGAAA GGGGGNTTNN TNGCAAGGGG ATAAAGGGGG | 60 |

```
AANCCCAGGG TTTCCCCATT CAGGGAGGTG TAAAAAGNCG GCCAGGGGAT TGTAANAGGA      120

TTCAATAATA GGGGGAATGG GCCCNGAAGT TGCAAGGTTC CNGCCCGCCA TGNCCGCGGG      180

ATTTAGTGAC ATTACGACGS TGGTAATAAA GTGGGSCCAA WAAATATTTG TGATGTGATT      240

TTTSGACCAG TGAACCCATT GWACAGGACC TCATTTCCTY TGAGATGRTA GCCATAATCA      300

GATAAAAGRT TAGAAGTYTT TCTGCACGTT AACAGCATCA TTAAATGGAG TGGCATCACC      360

AATTTCACCC TTTGTTAGCC GATACCTTCC CCTTGAAGGC ATTCAATTAA GTGACCAATC      420

GTCATACGAG AGGGGATGGC ATGGGGATTG ATGATGATAT CAGGGGTGAT ACCTTCACAG      480

GTGAAAGGCA TATCCTCTTG TCTATACTGA ATACCACAAG TACCCTTTTG ACCATGTCGA      540

CTAGCAAATT TGTCTCCAAT CTGTGTWATC CCTAACAGAG CGTACCCTTA TTTTACAAAA      600

TTTATATCCT TCCTGATTGA GAGTTACCAT AACCTGATCC ACAATGCCCG TCTCGCTWGT      660

TCTGAGAAAA GTGCTACAGT CTCTCTTGGT ATAGCGTCTA TTGGTGCTCT CCAATTCATC      720

TTCATTTTTC AGGCAAGGTG AACTGTTTTG CCTATAATAA CMTCATCTCC TGATACMCGA      780

AACCCCKGGA RCTATCAAAC CATCATCATC CAGCGTTCKT WATGTYMCTA AATCCCTATT      840

GCGGCCGCCT GCAGGTCAAC ATATNGGAAA ACCCCCCACC CCTTNGGAGC NTACCTTGAA      900

TTTTCCATAT GTCCCNTAAA TTANCTNGNC TTANCCTGGC CNTAACCTNT TCCGGTTTAA      960

ATTGTTTCCG CCCCCNTTCC CCNCCTTNNA ACCGGAAACC TTAATTTTNA ACCNGGGGTT     1020

CCTATCC                                                             1027

(2) INFORMATION FOR SEQ ID NO: 200:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (xi) SEQUENCE DESCRIPTION: SEQ ID NO: 200:

AGTGACATTA CGACGCTGGC CATCTTGAAT CCTAGGGCAT GAAGTTGCCC CAAAGTTCAG       60

CACTTGGTTA AGCCTGATCC CTCTGGTTTA TCACAAAGAA TAGGATGGGA TAAAGAAAGT      120

GGACACTTAA ATAAGCTATA AATTATATGG TCCTTGTCTA GCAGGAGACA ACTGCACAGG      180

TATACTACCA GCGTCGTAAT GTCACTA                                         207

(2) INFORMATION FOR SEQ ID NO: 201:

(i) SEQUENCE CHARACTERISTICS:
        (A) LENGTH: 209 base pairs
        (B) TYPE: nucleic acid
        (C) STRANDEDNESS: single
        (D) TOPOLOGY: linear (xi) SEQUENCE DESCRIPTION: SEQ ID NO: 201:

TGGGCACCTT CAATATCTAT TAAAAGCACA AATACTGAAG AACACACCAA GACTATCAAT       60

GAGGTTACAT CTGGAGTCCT CGATATATCA GGAAAAAATG AAGTGAACAT TCACAGAGTT      120

TTACTTCTTT GGGAACTCAA ATGCTAGAAA AGAAAAGGGT GCCCTCTTTC TCTGGCTTCC      180

TGGTCCTATC CAGCGTCGTA ATGTCACTA                                       209

(2) INFORMATION FOR SEQ ID NO: 202:

(i) SEQUENCE CHARACTERISTICS:
        (A) LENGTH: 349 base pairs
        (B) TYPE: nucleic acid
```

(C) STRANDEDNESS: single
        (D) TOPOLOGY: linear (xi) SEQUENCE DESCRIPTION: SEQ ID NO: 202:

NTACGCTGCA ACACTGTGGA GCCACTGGTT TTTATTCCCG GCAGGTTATC CAGCAAACAG      60

TCACTGAACA CACCGAAGAC CGTGGTATGG TAACCGTTCA CAGTAATCGT TCCAGTCGTC     120

TGCGGGACCC CGACGAGCGT CACTGGGTAC AGACCAGATT CAGCCGGAAG AGAAAGCGCC     180

GCAGGGAGAG ACTCGAACTC CACTCCGCTG GTGAGCAGCC CCATGTTTTC AACTCGAAGT     240

TCAAACGGCA TTGGGTTATA TACCATCAGC TGAACTTCAC ACACATCTCC TTGAACCCAC     300

TGGAAATCTA TTTTCTTGTT CCGCTCTTCT CCACAGTGTT GCAGCGTAA                349

(2) INFORMATION FOR SEQ ID NO: 203:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (xi) SEQUENCE DESCRIPTION: SEQ ID NO: 203:

TGCTCCTCTT GCCTTACCAA CCCAAAGCCC ACTGTGAAAT ATGAAGTGAA TGACAAAATT      60

CAGTTTTCAA CGCAATATAG TATAGTTTAT CTGATTCTTT TGATCTCCAG GACACTTTAA     120

ACAACTGCTA CCACCACCAC CAACCTAGGG ATTTAGGATT CTCCACAGAC CAGAAATTAT     180

TTCTCCTTTG AGTTTCAGGC TCCTCTGGGA CTCCTGTTCA TCAATGGGTG GTAAATGGCT     240

A                                                                    241

(2) INFORMATION FOR SEQ ID NO: 204:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (xi) SEQUENCE DESCRIPTION: SEQ ID NO: 204:

TAGCCATTTA CCACCCATCT GCAAACCSWG ACMWWCARGR CYWGWACKYA GGCGATTTGA      60

AGTACTGGTA ATGCTCTGAT CATGTTAGTT ACATAAGTGT GGTCAGTTTA CAAAAATTCA     120

CAGAACTAAA TACTCAATGC TATGTGTTCA TGTCTGTGTT TATGTGTGTG TAATGTTTCA     180

ATTAAGTTTT TTTAAAAAAA AGAGATGATT TCCAAATAAG AAAGCCGTGT TGGTAAGGCA     240

AGAGGAGC                                                             248

(2) INFORMATION FOR SEQ ID NO: 205:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (xi) SEQUENCE DESCRIPTION: SEQ ID NO: 205:

TACGCTGCAA CACTGTGGAG CCATTCATAC AGGTCCCTAA TTAAGGAACA AGTGATTATG      60

CTACCTTTGC ACGGTTAGGG TACCGCGGCC GTTAAACATG TGTCACTGGG CAGGCGGTGC     120

CTCTAATACT GGTGATGCTA GAGGTGATGT TTTTGGTAAA CAGGCGGGGT AAGATTTGCC     180

GAGTTCCTTT TACTTTTTTT AACCTTTCCT TATGAGCATG CCTGTGTTGG GTTGACAGTG     240

GGGTAATAA TGACTTGTTG GTTGATTGTA GATATTGGGC TGTTAATTGT CAGTTCAGTG     300

```
TTTTAATCTG ACGCAGGCTT ATGCGGAGGA GAATGTTTTC ATGTTACTTA TACTAACATT      360

AGTTCTTCTA TAGGGTGATA GATTGGTCCA ATTGGGTGTG AGGAGTTCAG TTATATGTTT      420

GGGATTTTTT AGGTAGTGGG TGTTGANCTT GAACGCTTTC TTAATTGGTG GCTGCTTTTA      480

RGCCTACTAT GGGTGGTAAA TGGCT                                            505

(2) INFORMATION FOR SEQ ID NO: 206:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (xi) SEQUENCE DESCRIPTION: SEQ ID NO: 206:

TAGACTGACT CATGTCCCCT ACCAAAGCCC ATGTAAGGAG CTGAGTTCTT AAAGACTGAA       60

GACAGACTAT TCTCTGGAGA AAAATAAAAT GGAAATTGTA CTTTAAAAAA AAAAAAAATC      120

GGCCGGGCAT GGTAGCACAC ACCTGTAATC CCAGCTACTA GGGACATGA GTCAGTCTA       179

(2) INFORMATION FOR SEQ ID NO: 207:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (xi) SEQUENCE DESCRIPTION: SEQ ID NO: 207:

AGACTGACTC ATGTCCCCTA CCCCACCTTC TGCTGTGCTG CCGTGTTCCT AACAGGTCAC       60

AGACTGGTAC TGGTCAGTGG CCTGGGGGTT GGGGACCTCT ATTATATGGG ATACAAATTT     120

AGGAGTTGGA ATTGACACGA TTTAGTGACT GATGGGATAT GGGTGGTAAA TGGCTA        176

(2) INFORMATION FOR SEQ ID NO: 208:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (xi) SEQUENCE DESCRIPTION: SEQ ID NO: 208:

AGACTGACTC ATGTCCCCTA TTTAACAGGG TCTCTAGTGC TGTGAAAAAA AAAAATGCTG       60

AACATTGCAT ATAACTTATA TTGTAAGAAA TACTGTACAA TGACTTTATT GCATCTGGGT     120

AGCTGTAAGG CATGAAGGAT GCCAAGAAGT TTAAGGAATA TGGGTGGTAA ATGGCTAGGG     180

GACATGAGTC AGTCTA                                                     196

(2) INFORMATION FOR SEQ ID NO: 209:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO: 209:

GACGCTTGGC CACTTGACAC CTTTTATTTT TTAAGGATTC TTAAGTCATT TANGTNACTT       60

TGTAAGTTTT TCCTGTGCCC CCATAAGAAT GATAGCTTTA AAAATTATGC TGGGGTAGCA     120

AAGAAGATAC TTCTAGCTTT AGAATGTGTA GGTATAGCCA GGATTCTTGT GAGGAGGGGT     180
```

```
GATTTAGAGC AAATTTCTTA TTCTCCTTGC CTCATCTGTA ACATGGGAT AATAATAGAA       240

CTGGCTTGAC AAGGTTGGAA TTAGTATTAC ATGGTAAATA CATGTAAAAT GTTTAGAATG      300

GTGCCAAGTA TCTAGGAAGT ACTTGGGCAT GGGTGGTAAA TGGCT                     345

(2) INFORMATION FOR SEQ ID NO: 210:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (xi) SEQUENCE DESCRIPTION: SEQ ID NO: 210:

GACGCTTGGC CACTTGACAC TAGAGTAGGG TTTGGCCAAC TTTTTCTATA AAGGACCAGA       60

GAGTAAATAT TTCAGGCTTT GTGGGTTGTG CAGTCTCTCT TGCAACTACT CAGCTCTGCC      120

ATTGTAGCAT AGAAATCAGC CATAGACAGG ACAGAAATGA ATGGGTGGTA AATGGCTA        178

(2) INFORMATION FOR SEQ ID NO: 211:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (xi) SEQUENCE DESCRIPTION: SEQ ID NO: 211:

TGGGCACCTT CAATATCTAT CCAGCGCATC TAAATTCGCT TTTTTCTTGA TTAAAAATTT       60

CACCACTTGC TGTTTTTGCT CATGTATACC AAGTAGCAGT GGTGTGAGGC CATGCTTGTT     120

TTTTGATTCG ATATCAGCAC CGTATAAGAG CAGTGCTTTG GCCATTAATT TATCTTCATT     180

GTAGACAGCA TAGTGTAGAG TGGTATCTCC ATACTCATCT GGAATATTTG GATCAGTGCC     240

ATGTTCCAGC AACATTAACG CACATTCATC TTCCTGGCAT TGTACGGCCT TTGTCAGAGC     300

TGTCCTCTTT TTGTTGTCAA GGACATTAAG TTGACATCGT CTGTCCAGCA CGAGTTTTAC     360

TACTTCTGAA TTCCCATTGG CAGAGGCCAG ATGTAGAGCA GTCCTCTTTT GCTTGTCCCT     420

CTTGTTCACA TCAGTGTCCC TGAGCATAAC GGAA                                 454

(2) INFORMATION FOR SEQ ID NO: 212:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (xi) SEQUENCE DESCRIPTION: SEQ ID NO: 212:

TCCGTTATGC CACCCAGAAA ACCTACTGGA GTTACTTATT AACATCAAGG CTGGAACCTA       60

TTTGCCTCAG TCCTATCTGA TTCATGAGCA CATGGTTATT ACTGATCGCA TTGAAAACAT     120

TGATCACCTG GGTTTCTTTA TTTATCGACT GTGTCATGAC AAGGAAACTT ACAAACTGCA     180

ACGCAGAGAA ACTATTAAAG GTATTCAGAA ACGTGAAGCC AGCAATTGTT TCGCAATTCG     240

GCATTTTGAA AACAAATTTG CCGTGGAAAC TTTAATTTGT TCTTGAACAG TCAAGAAAAA     300

CATTATTGAG GAAAATTAAT ATCACAGCAT AACGGAA                              337

(2) INFORMATION FOR SEQ ID NO: 213:

(i) SEQUENCE CHARACTERISTICS:
        (A) LENGTH: 715 base pairs
        (B) TYPE: nucleic acid
```

(C) STRANDEDNESS: single
        (D) TOPOLOGY: linear (xi) SEQUENCE DESCRIPTION: SEQ ID NO: 213:

TCGGGTGATG CCTCCTCAGG CATCTTCCAT CCATCTCTTC AAGATTAGCT GTCCCAAATG    60

TTTTTCCTTC TCTTCTTTAC TGATAAATTT GGACTCCTTC TTGACACTGA TGACAGCTTT   120

AGTATCCTTC TTGTCACCTT GCAGACTTTA AACATAAAAA TACTCATTGG TTTTAAAAGG   180

AAAAAAGTAT ACATTAGCAC TATTAAGCTT GGCCTTGAAA CATTTTCTAT CTTTTATTAA   240

ATGTCGGTTA GCTGAACAGA ATTCATTTTA CAATGCAGAG TGAGAAAAGA AGGGAGCTAT   300

ATGCATTTGA GAATGCAAGC ATTGTCAAAT AAACATTTTA AATGCTTTCT TAAAGTGAGC   360

ACATACAGAA ATACATTAAG ATATTAGAAA GTGTTTTTGC TTGTGTACTA CTAATTAGGG   420

AAGCACCTTG TATAGTTCCT CTTCTAAAAT TGAAGTAGAT TTTAAAAACC CATGTAATTT   480

AATTGAGCTC TCAGTTCAGA TTTTAGGAGA ATTTTAACAG GGATTTGGTT TTGTCTAAAT   540

TTTGTCAATT TNTTTAGTTA ATCTGTATAA TTTTATAAAT GTCAAACTGT ATTTAGTCCG   600

TTTTCATGCT GCTATGAAAG AAATACCCAN GACAGGGTTA TTTATAAANG GAAAGANGTT   660

AATTTGACTC CCAGTTCACA GGCCTGAGGA NGNATCNCCC GAAATCCTTA TTGCG        715

(2) INFORMATION FOR SEQ ID NO: 214:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO: 214:

GGTAANGNGC ATACNTCGGT GCTCCGGCCG CCGGAGTCGG GGGATTCGGG TGATGCCTCC    60

TCAGGCCCAC TTGGGCCTGC TTTTCCCAAA TGGCAGCTCC TCTGGACATG CCATTCCTTC   120

TCCCACCTGC CTGATTCTTC ATATGTTGGG TGTCCCTGTT TTTCTGGTGC TATTTCCTGA   180

CTGCTGTTCA GCTGCCACTG TCCTGCAAAG CCTGCCTTTT TAAATGCCTC ACCATTCCTT   240

CATTTGTTTC TTAAATATGG GAAGTGAAAG TGCCACCTGA GGCCGGGCAC AGTGGCTCAC   300

GCCTGTAATC CCAGCACTTT GGGAGCCTGA GGAGGCATCA CCCGA                   345

(2) INFORMATION FOR SEQ ID NO: 215:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (xi) SEQUENCE DESCRIPTION: SEQ ID NO: 215:

GGTGATGCCT CCTCAGGCGA AGCTCAGGGA GGACAGAAAC CTCCCGTGGA GCAGAAGGGC    60

AAAAGCTCGC TTGATCTTGA TTTTCAGTAC GAATACAGAC CGTGAAAGCG GGCCTCACG   120

ATCCTTCTGA CCTTTTGGGT TTTAAGCAGG AGGTGTCAGA AAAGTTACCA CAGGGATAAC   180

TGGCTTGTGG CGGCCAAGCG TTCATAGCGA CGTCGCTTTT TGATCCTTCG ATGTCGGCTC   240

TTCCTATCAT TGTGAAGCAG AATTCACCAA GCGTTGGATT GTTCACCCAC TAATAGGGAA   300

CGTGAGCTGG GTTTAGACCG TCGTGAGACA GGTTAGTTTT ACCCTACTGA TGATGTGTKG   360

TTGCCATGGT AATCCTGCTC AGTACGAGAG GAACCGCAGG TTCASACATT TGGTGTATGT   420

GCTTGCCTT                                                           429

(2) INFORMATION FOR SEQ ID NO: 216:

(i) SEQUENCE CHARACTERISTICS:
        (A) LENGTH: 593 base pairs
        (B) TYPE: nucleic acid
        (C) STRANDEDNESS: single
        (D) TOPOLOGY: linear (xi) SEQUENCE DESCRIPTION: SEQ ID NO: 216:

```
TGACACCTAT GTCCNGCATC TGTTCACAGT TTCCACAAAT AGCCAGCCTT TGGCCACCTC      60
TCTGTCCTGA GGTATACAAG TATATCAGGA GGTGTATACC TTCTCTTCTC TTCCCCACCA     120
AAGAGAACAT GCAGGCTCTG GAAGCTGTCT TAGGAGCCTT TGGGCTCAGA ATTTCAGAGT     180
CTTGGGTACC TTGGATGTGG TCTGGAAGGA GAAACATTGG CTCTGGATAA GGAGTACAGC     240
CGGAGGAGGG TCACAGAGCC CTCAGCTCAA GCCCCTGTGC CTTAGTCTAA AGCAGCTTT     300
GGATGAGGAA GCAGGTTAAG TAACATACGT AAGCGTACAC AGGTAGAAAG TGCTGGGAGT     360
CAGAATTGCA CAGTGTGTAG GAGTAGTACC TCAATCAATG AGGGCAAATC AACTGAAAGA     420
AGAAGACCNA TTAATGAATT GCTTANGGGG AAGGATCAAG GCTATCATGG AGATCTTTCT     480
AGGAAGATTA TTGTTTANAA TTATGAAAGG ANTAGGGCAG GGACAGGGCC AGAAGTANAA     540
GANAACATTG CCTATANCCC TTGTCTTGCA CCCAGATGCT GGACAAGGTG TCA            593
```

(2) INFORMATION FOR SEQ ID NO: 217:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (xi) SEQUENCE DESCRIPTION: SEQ ID NO: 217:

```
TGACACCTTG TCCAGCATCT GACGTGAAGA TGAGCAGCTC AGAGGAGGTG TCCTGGATTT      60
CCTGGTTCTG TGGGCTCCGT GGCAATGAAT TCTTCTGTGA AGTGGATGAA GACTACATCC     120
AGGACAAATT TAATCTTACT GGACTCAATG AGCAGGTCCC TCACTATCGA CAAGCTCTAG     180
ACATGATCTT GGACCTGGAG CCTGATGAAG AACTGGAAGA CAACCCCAAC CAGAGTGACC     240
TGATTGAGCA GGCAGCCGAG ATGCTTTATG GATTGATCCA CGCCCGCTAC ATCCTTACCA     300
ACCGTGGCAT CGCCCAGATG CTGGACAAGG TGTCA                                335
```

(2) INFORMATION FOR SEQ ID NO: 218:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (xi) SEQUENCE DESCRIPTION: SEQ ID NO: 218:

```
TACGTACTGG TCTTGAAGGT CTTAGGTAGA GAAAAAATGT GAATATTTAA TCAAAGACTA      60
TGTATGAAAT GGGACTGTAA GTACAGAGGG AAGGGTGGCC CTTATCGCCA GAAGTTGGTA     120
GATGCGTCCC CGTCATGAAA TGTTGTGTCA CTGCCCGACA TTTGCCGAAT TACTGAAATT     180
CCGTAGAATT AGTGCAAATT CTAACGTTGT TCATCTAAGA TTATGGTTCC ATGTTTCTAG     240
TACTTTTA                                                              248
```

(2) INFORMATION FOR SEQ ID NO: 219:

(i) SEQUENCE CHARACTERISTICS:

(A) LENGTH: 530 base pairs
            (B) TYPE: nucleic acid
            (C) STRANDEDNESS: single
            (D) TOPOLOGY: linear (xi) SEQUENCE DESCRIPTION: SEQ ID NO: 219:

TGACGCTTGG CCACTTGACA CAAGTAGGGG ATAAGGACAA AGACCCATNA GGTGGCCTGT       60

CAGCCTTTTG TTACTGTTGC TTCCCTGTCA CCACGGCCCC CTCTGTAGGG GTGTGCTGTG      120

CTCTGTGGAC ATTGGTGCAT TTTCACACAT ACCATTCTCT TTCTGCTTCA CAGCAGTCCT      180

GAGGCGGGAG CACACAGGAC TACCTTGTCA GATGANGATA ATGATGTCTG GCCAACTCAC      240

CCCCCAACCT TCTCACTAGT TATANGAAGA GCCANGCCTA NAACCTTCTA TCCTGNCCCC      300

TTGCCCTATG ACCTCATCCC TGTTCCATGC CCTATTCTGA TTTCTGGTGA ACTTTGGAGC      360

AGCCTGGTTT NTCCTCCTCA CTCCAGCCTC TCTCCATACC ATGGTANGGG GGTGCTGTTC      420

CACNCAAANG GTCAGGTGTG TCTGGGGAAT CCTNANANCT GCCNGGAGTT TCCNANGCAT      480

TCTTAAAAAC CTTCTTGCCT AATCANATNG TGTCCAGTGG CCAACCNTCN                530

(2) INFORMATION FOR SEQ ID NO: 220:

(i) SEQUENCE CHARACTERISTICS:
            (A) LENGTH: 531 base pairs
            (B) TYPE: nucleic acid
            (C) STRANDEDNESS: single
            (D) TOPOLOGY: linear (xi) SEQUENCE DESCRIPTION: SEQ ID NO: 220:

TGACGCTTGG CCACTTGACA CTAAATAGCA TCTTCTAAAG GCCTGATTCA GAGTTGTGGA       60

AAATTCTCCC AGTGTCAGGG ATTGTCAGGA ACAGGGCTGC TCCTGTGCTC ACTTTACCTG      120

CTGTGTTTCT GCTGGAAAAG GAGGGAAGAG GAATGGCTGA TTTTTACCTA ATGTCTCCCA      180

GTTTTTCATA TTCTTCTTGG ATCCTCTTCT CTGACAACTG TTCCCTTTTG GTCTTCTTCT      240

TCTTGCTCAG AGAGCAGGTC TCTTTAAAAC TGAGAAGGGA GAATGAGCAA ATGATTAAAG      300

AAAACACACT TCTGAGGCCC AGAGATCAAA TATTAGGTAA ATACTAAACC GCTTGCCTGC      360

TGTGGTCACT TTTCTCCTCT TTCACATGCT CTATCCCTCT ATCCCCCACC TATTCATATG      420

GCTTTTATCT GCCAAGTTAT CCGGCCTCTC ATCAACCTTC TCCCCTAGCC TACTGGGGGA      480

TATCCATCTG GGTCTGTCTC TGGTGTATTG GTGTCAAGTG GCCAAGCGTC A              531

(2) INFORMATION FOR SEQ ID NO: 221:

(i) SEQUENCE CHARACTERISTICS:
            (A) LENGTH: 530 base pairs
            (B) TYPE: nucleic acid
            (C) STRANDEDNESS: single
            (D) TOPOLOGY: linear (xi) SEQUENCE DESCRIPTION: SEQ ID NO: 221:

ATTGACGCTT GGCCACTTGA CACCCGCCTG CCTGCAATAC TGGGGCAAGG GCCTTCACTG       60

CTTTCCTGCC ACCAGCTGCC ACTGCACACA GAGATCAGAA ATGCTACCAA CCAAGACTGT      120

TGGTCCTCAG CCTCTCTGAG GAGAAAGAGC AGAAGCCTGG AAGTCAGAAG AGAAGCTAGA      180

TCGGCTACGG CCTTGGCAGC CAGCTTCCCC ACCTGTGGCA ATAAAGTCGT GCATGGCTTA      240

ACAATGGGGG CACCTCCTGA GAAACACATT GTTAGGCAAT TCGGCGTGTG TTCATCAGAG      300

CATATTTACA CAAACCTCGA TAGTGCAGCC TACTATCCAC TATTGCTCCT ACGCTGCAAA      360

CCTGAACAGC ATGGGACTGT ACTGAATACT GGAAGCAGCT GGTGATGGTA CTTATTTGTG      420

```
TATCTAAACA CAGAGAAGGT ACAGTAAGAA TATGGTATCA TAAACTTACA GGGACCGCCA      480

TCCTATATGC AGTCTGTTGT GACCAAAATG TGTCAAGTGG CCAAGCGTCA                 530

(2) INFORMATION FOR SEQ ID NO: 222:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO: 222:

TGTATCGACG TAGTGGTCTC CGGGCTACTA GGCCGTTGTG TGCTGGTAGT ACCTGGTTCA      60

CTGAAAGGCG CATCTCCCTC CCCGCGTCGC CCTGAAGCAG GGGGAGGACT TCGCCCAGCC      120

AAGGCAGTTG TATGAGTTTT AGCTGCGGCA CTTCGAGACC TCTGAGCCCA CCTCCTTCAG      180

GAGCCTTCCC CGATTAAGGA AGCCAGGGTA AGGATTCCTT CCTCCCCCAG ACACCACGAA      240

CAAACCACCA CCCCCCCTAT TCTGGCAGCC CATATACATC AGAACGAAAC AAAAATAACA      300

AATAAACNAA AACCAAAAAA AAAAGAGAAG GGGAAATGTA TATGTCTGTC CATCCTGTTG      360

CTTTAGCCTG TCAGCTCCTA NAGGGCAGGG ACCGTGTCTT CCGAATGGTC TGTGCAGCGC      420

CGACTGCGGG AAGTATCGGA GGAGGAAGCA GAGTCAGCAG AAGTTGAACG GTGGGCCCGG      480

CGGCTCTTGG GGGCTGGTGT TGTACTTCGA GACCGCTTTC GCTTTTTGTC TTAGATTTAC      540

GTTTGCTCTT TGGAGTGGGA NACCACTACN TCNATACA                             578

(2) INFORMATION FOR SEQ ID NO: 223:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO: 223:

TGTATCGACG TAGTGGTCTC CTCTTGCAAA GGACTGGCTG GTGAATGGTT TCCCTGAATT      60

ATGGACTTAC CCTAAACATA TCTTATCATC ATTACCAGTT GCAAAATATT AGAATGTGTT     120

GTCACTGTTT CATTTGATTC CTAGAAGGTT AGTCTTAGAT ATGTTACTTT AACCTGTATG     180

CTGTAGTGCT TTGAATGCAT TTTTTGTTTG CATTTTTGTT TGCCCAACCT GTCAATTATA     240

GCTGCTTAGG TCTGGACTGT CCTGGATAAA GCTGTTAAAA TATTCACCAG TCCAGCCATC     300

TTACAAGCTA ATTAAGTCAA CTAAATGCTT CCTTGTTTTG CCAGACTTGT TATGTCAATC     360

CTCAATTTCT GGGTTCATTT TGGGTGCCCT AAATCTTAGG GTGTGACTTT CTTAGCATCC     420

TGTAACATCC ATTCCCAAGC AAGCACAACT TCACATAATA CTTTCCAGAA GTTCATTGCT     480

GAAGCCTTTC CTTCACCCAG CGGAGCAACT TGATTTTCTA CAACTTCCCT CATCAGAGCC     540

ACAAGAGTAT GGGATATGGA GACCACTACG TCGATACA                            578

(2) INFORMATION FOR SEQ ID NO: 224:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO: 224:

TGTATCGACG TANTGGTCTC CCAAGGTGCT GGGATTGCAG GCATGAGCCA CCACTCCCAG      60
```

| | |
|---|---|
| GTGGATCTTT TTCTTTATAC TTACTTCATT AGGTTTCTGT TATTCAAGAA GTGTAGTGGT | 120 |
| AAAAGTCTTT TCAATCTACA TGGTTAAATA ATGATAGCCT GGGAAATAAA TAGAAATTTT | 180 |
| TTCTTTCATC TTTAGGTTGA ATAAAGAAAC AGAAAAAATA GAACATACTG AAAATAATCT | 240 |
| AAGTTCCAAC CATAGAAGAA CTGCAGAAGA AATGAAGAAA GTGATGATGA TTTAGATTTT | 300 |
| GATATTGATT TAGAAGACAC AGGAGGAGAC CACTACGTCG ATACA | 345 |

(2) INFORMATION FOR SEQ ID NO: 225:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (xi) SEQUENCE DESCRIPTION: SEQ ID NO: 225:

| | |
|---|---|
| TGTATCGACG TAGTGGTCTC CAAACTGAGG TATGTGTGCC ACTAGCACAC AAAGCCTTCC | 60 |
| AACAGGGACG CAGGCACAGG CAGTTTAAAG GGAATCTGTT TCTAAATTAA TTTCCACCTT | 120 |
| CTCTAAGTAT TCTTTCCTAA AACTGATCAA GGTGTGAAGC CTGTGCTCTT TCCCAACTCC | 180 |
| CCTTTGACAA CAGCCTTCAA CTAACACAAG AAAAGGCATG TCTGACACTC TTCCTGAGTC | 240 |
| TGACTCTGAT ACGTTGTTCT GATGTCTAAA GAGCTCCAGA ACACCAAAGG GACAATTCAG | 300 |
| AATGCTGGTG TATAACAGAC TCCAATGGAG ACCACTACGT CGATACA | 347 |

(2) INFORMATION FOR SEQ ID NO: 226:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (xi) SEQUENCE DESCRIPTION: SEQ ID NO: 226:

| | |
|---|---|
| AGGNGNGGGA NTGTATCGAC GTAGTGGTCT CCCAACAGTC TGTCATTCAG TCTGCAGGTG | 60 |
| TCAGTGTTTT GGACAATGAG GCACCATTGT CACTTATTGA CTCCTCAGCT CTAAATGCTG | 120 |
| AAATTAAATC TTGTCATGAC AAGTCTGGAA TTCCTGATGA GGTTTTACAA AGTATTTTGG | 180 |
| ATCAATACTC CAACAAATCA GAAAGCCAGA AAGAGGATCC TTTCAATATT GCAGAACCAC | 240 |
| GAGTGGATTT ACACACCTCA GGAGACCACT ACGTCGATAC A | 281 |

(2) INFORMATION FOR SEQ ID NO: 227:

(i) SEQUENCE CHARACTERISTICS:
        (A) LENGTH: 3646 base pairs
        (B) TYPE: nucleic acid
        (C) STRANDEDNESS: single
        (D) TOPOLOGY: linear (xi) SEQUENCE DESCRIPTION: SEQ ID NO: 227:

| | |
|---|---|
| GGGAAACACT TCCTCCCAGC CTTGTAAGGG TTGGAGCCCT CTCCAGTATA TGCTGCAGAA | 60 |
| TTTTTCTCTC GGTTTCTCAG AGGATTATGG AGTCCGCCTT AAAAAAGGCA AGCTCTGGAC | 120 |
| ACTCTGCAAA GTAGAATGGC CAAAGTTTGG AGTTGAGTGG CCCCTTGAAG GGTCACTGAA | 180 |
| CCTCACAATT GTTCAAGCTG TGTGGCGGGT TGTTACTGAA ACTCCCGGCC TCCCTGATCA | 240 |
| GTTTCCCTAC ATTGATCAAT GGCTGAGTTT GGTCAGGAGC ACCCCTTCCG TGGCTCCACT | 300 |
| CATGCACCAT TCATAATTTT ACCTCCAAGG TCCTCCTGAG CCAGACCGTG TTTTCGCCTC | 360 |
| GACCCTCAGC CGGTTCGGCT CGCCCTGTAC TGCCTCTCTC TGAAGAAGAG GAGAGTCTCC | 420 |

```
-continued

CTCACCCAGT CCCACCGCCT TAAAACCAGC CTACTCCCTT AGGGTCATCC CATGTCTCCT    480

CGGCTATGTC CCCTGTAGGC TCATCACCCA TTGCCTCTTG GTTGCAACCG TGGTGGGAGG    540

AAGTAGCCCC TCTACTACCA CTGAGAGAGG CACAAGTCCC TCTGGGTGAT GAGTGCTCCA    600

CCCCCTTCCT GGTTTATGTC CCTTCTTTCT ACTTCTGACT TGTATAATTG GAAAACCCAT    660

AATCCTCCCT TCTCTGAAAA GCCCCAGGCT TTGACCTCAC TGATGGAGTC TGTACTCTGG    720

ACACATTGGC CCACCTGGGA TGACTGTCAA CAGCTCCTTT TGACCCTTTT CACCTCTGAA    780

GAGAGGGAAA GTATCCAAAG AGAGGCCAAA AGTACAACC TCACATCAAC CAATAGGCCG    840

GAGGAGGAAG CTAGAGGAAT AGTGATTAGA GACCCAATTG GGACCTAATT GGGACCCAAA    900

TTTCTCAAGT GGAGGGAGAA CTTTTGACGA TTTCCACCGG TATCTCCTCG TGGGTATTCA    960

GGGAGCTGCT CAGAAACCTA TAAACTTGTC TAAGGCGACT GAAGTCGTCC AGGGGCATGA   1020

TGAGTCACCA GGAGTGTTTT TAGAGCACCT CCAGGAGGCT TATCAGATTT ACACCCCTTT   1080

TGACCTGGCA GCCCCCGAAA ATAGCCATGC TCTTAATTTG GCATTTGTGG CTCAGGCAGC   1140

CCCAGATAGT AAAAGGAAAC TCCAAAAACT AGAGGGATTT TGCTGGAATG AATACCAGTC   1200

AGCTTTTAGA GATAGCCTAA AAGGTTTTTG ACAGTCAAGA GGTTGAAAAA CAAAAACAAG   1260

CAGCTCAGGC AGCTGAAAAA AGCCACTGAT AAAGCATCCT GGAGTATCAG AGTTTACTGT   1320

TAGATCAGCC TCATTTGACT TCCCCTCCCA CATGGTGTTT AAATCCAGCT ACACTACTTC   1380

CTGACTCAAA CTCCACTATT CCTGTTCATG ACTGTCAGGA ACTGTTGGAA ACTACTGAAA   1440

CTGGCCGACC TGATCTTCAA AATGTGCCCC TAGGAAAGGT GGATGCCACC ATGTTCACAG   1500

ACAGTAGCAG CTTCCTCGAG AAGGGACTAC GAAAGGCCGG TGCAGCTGTT ACCATGGAGA   1560

CAGATGTGTT GTGGGCTCAG GCTTTACCAG CAAACACCTC AGCACAAAAG CTGAATTGA    1620

TCGCCCTCAC TCAGGCTCTC CGATGGGGTA AGGATATTAA CGTTAACACT GACAGCAGGT   1680

ACGCCTTTGC TACTGTGCAT GTACGTGGAG CCATCTACCA GGAGCGTGGG CTACTCACCT   1740

CAGCAGGTGG CTGTAATCCA CTGTAAAGGA CATCAAAAGG AAAACACGGC TGTTGCCCGT   1800

GGTAACCAGA AAGCTGATTC AGCAGCTCAA GATGCAGTGT GACTTTCAGT CACGCCTCTA   1860

AACTTGCTGC CCACAGTCTC CTTTCCACAG CCAGATCTGC CTGACAATCC CGCATACTCA   1920

ACAGAAGAAG AAAACTGGCC TCAGAACTCA GAGCCAATAA AAATCAGGAA GGTTGGTGGA   1980

TTCTTCCTGA CTCTAGAATC TTCATACCCC GAACTCTTGG GAAAACTTTA ATCAGTCACC   2040

TACAGTCTAC CACCCATTTA GGAGGAGCAA AGCTACCTCA GCTCCTCCGG AGCCGTTTTA   2100

AGATCCCCCA TCTTCAAAGC CTAACAGATC AAGCAGCTCT CCGGTGCACA ACCTGCGCCC   2160

AGGTAAATGC CAAAAAAGGT CCTAAACCCA GCCCAGGCCA CCGTCTCCAA GAAAACTCAC   2220

CAGGAGAAAA GTGGGAAATT GACTTTACAG AAGTAAAACC ACACCGGGCT GGGTACAAAT   2280

ACCTTCTAGT ACTGGTAGAC ACCTTCTCTG GATGGACTGA AGCATTTGCT ACCAAAAACG   2340

AAACTGTCAA TATGGTAGTT AAGTTTTTAC TCAATGAAAT CATCCCTCGA CATGGGCTGC   2400

CTGTTTGCCA TAGGGTCTGA TAATGGACCG GCCTTCGCCT TGTCTATAGT TTAGTCAGTC   2460

AGTAAGGCGT TAAACATTCA ATGGAAGCTC CATTGTGCCT ATCGACCCCA GAGCTCTGGG   2520

CAAGTAGAAC GCATGAACTG CACCCTAAAA AACACTCTTA CAAAATTAAT CTTAGAAACC   2580

GGTGTAAATT GTGTAAGTCT CCTTCCTTTA GCCCTACTTA GAGTAAGGTG CACCCCTTAC   2640

TGGGCTGGGT TCTTACCTTT TGAAATCATG TATGGGAGGG TGCTGCCTAT CTTGCCTAAG   2700

CTAAGAGATG CCCAATTGGC AAAAATATCA CAAACTAATT TATTACAGTA CCTACAGTCT   2760

CCCCAACAGG TACAAGATAT CATCCTGCCA CTTGTTCGAG GAACCCATCC CAATCCAATT   2820
```

```
CCTGAACAGA CAGGGCCCTG CCATTCATTC CCGCCAGGTG ACCTGTTGTT TGTTAAAAAG    2880

TTCCAGAGAG AAGGACTCCC TCCTGCTTGG AAGAGACCTC ACACCGTCAT CACGATGCCA    2940

ACGGCTCTGA AGGTGGATGG CATTCCTGCG TGGATTCATC ACTCCCGCAT CAAAAAGGCC    3000

AACAGAGCCC AACTAGAAAC ATGGGTCCCC AGGGCTGGGT CAGGCCCCTT AAAACTGCAC    3060

CTAAGTTGGG TGAAGCCATT AGATTAATTC TTTTTCTTAA TTTTGTAAAA CAATGCATAG    3120

CTTCTGTCAA ACTTATGTAT CTTAAGACTC AATATAACCC CCTTGTTATA ACTGAGGAAT    3180

CAATGATTTG ATTCCCCCAA AAACACAAGT GGGGAATGTA GTGTCCAACC TGGTTTTTAC    3240

TAACCCTGTT TTTAGACTCT CCCTTTCCTT TAATCACTCA GCTTGTTTCC ACCTGAATTG    3300

ACTCTCCCTT AGCTAAGAGC GCCAGATGGA CTCCATCTTG GCTCTTTCAC TGGCAGCCGC    3360

TTCCTCAAGG ACTTAACTTG TGCAAGCTGA CTCCCAGCAC ATCCAAGAAT GCAATTAACT    3420

GATAAGATAC TGTGGCAAGC TATATCCGCA GTTCCCAGGA ATTCGTCCAA TTGATCACAG    3480

CCCCTCTACC CTTCAGCAAC CACCACCCTG ATCAGTCAGC AGCCATCAGC ACCGAGGCAA    3540

GGCCCTCCAC CAGCAAAAAG ATTCTGACTC ACTGAAGACT TGGATGATCA TTAGTATTTT    3600

TAGCAGTAAA GTTTTTTTTT CTTTTTCTTT CTTTTTTTCT CGTGCC                   3646

(2) INFORMATION FOR SEQ ID NO: 228:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 228:

TAAGAGGGTA CAAGATCTAA GCACAGCCGT CAATGCAGAA CACAGAACGT AGCCTGGTAA      60

GTGTGTTAAG AGTGGGAATT TTTGGAGTAC AGAGTAAGGC ACCTAACCCT AGCTGGGGTT    120

TGGTGACGGT CCCAGATGGC TTACAGAAGA AAGTGTCCTG AGATGAGTTT TTAAGAATGT    180

ATAAGGATAG ACACAAGTGA GGACTGACTT GGCAGTGGTG AATGGTGGGT GGCAAAAAAA    240

TTCGCATGTA TGGAAACTGC ACGTACAGGA ATGAAGAATG AGACTGTGTG GTGTTTAATC    300

AGCTGCAAAT ACTAATTTTA TCCTGAAAGT TTTGAAGAGT TAACTAAAAA GTATTTTTTG    360

GTAAGGAAAT AACCCTACAT TTCAGGGTTA TTGTTTGTTT ANATATTGAA GGTGCCCAAA    419

(2) INFORMATION FOR SEQ ID NO: 229:

(i) SEQUENCE CHARACTERISTICS:
        (A) LENGTH: 148 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 229:

AAGAGGGTAC CTGTATGTAG CCATGGTGGC AATGAGAGAC TGATTACTAC CTGCTGGAGA     60

TTGTTTAAGT GAGTTAATAT ATTAAGGATA AAGGGAGCCA GGTTTTTTGA CTGTTGGAGA    120
```

```
AGGAAATTAC AGATATTGAA GGTCCCAA                                                148
```

(2) INFORMATION FOR SEQ ID NO: 230:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo Sapiens (xi) SEQUENCE DESCRIPTION: SEQ ID NO: 230:

```
TAAGAGGGTA CMAAAAAAA AAAATAGAAC GAATGAGTAA GACCTACTAT TTGATAGTAC    60

AACAGGGTGA CTATAGTCAA TGATAACTTA ATTATACATT TAACATAGAG TGTAATTGGA   120

TTGTTTGTAA CTCGAAGGAT AAATGCTTGA GAGGATGGAT ACCCCATTCT CCATGATGTA   180

CTTATTTCAC ATTACATGCC TGTATCAAAG CATCTCATAT ACCCTATAAA TATGTACACC   240

TACTATGTAC CCTCTTA                                                 257
```

(2) INFORMATION FOR SEQ ID NO: 231:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 231:

```
TAAGAGGGTA CGGGTATTTG CTGATGGGAT TTTTTTTTCT TTCTTTTTCT TTGGAAAACA    60

AAATGAAAGC CAGAACAAAA TTATTGAACA AAAGACAGGG ACTAAATCTG GAGAAATGAA   120

GTCCCCTCAC CTGACTGCCA TTTCATTCTA TCTGACCTTC CAGTCTAGGT TAGGAGAATA   180

GGGGGTGGAG GGGATTAATC TGATACAGGT ATATTTAAAG CAACTCTGCA TGTGTGCCAG   240

AAGTCCATGG TACCCTCTTA                                              260
```

(2) INFORMATION FOR SEQ ID NO: 232:

(i) SEQUENCE CHARACTERISTICS:
        (A) LENGTH: 596 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 232:

```
TGCTCCTCTT GCCTTACCAA CCACAAATTA GAACCATAAT GAGATGTCAC CTCATACCTG    60

GTGGGATTAA CATTATTTAA AAAATCAGAA GTATTGACAA GGATGTGAAG AAATTAGAAC   120

ATCTGTGCAC TGTTGGTGGG AATGTAAAAA AGGTGTGGCC ACTATGGGTA ACAGCATGAA   180

GGTTCCTCAA AAAAAATTTT TTTTAATCTA CTCTATGATC GATCTTGAGG TTGTTTATGC   240

AAAAGAACTG AAATCAGGAT TTTGAGGAAA TATTCACATT CCCACATCCA TTTCTGCTTT   300
```

ATTCATAATA CTCAAGAGAT GGAAACAACC TAAATGTCCA TCCCGGGATG AATGGATAAA      360

CACAGTGTGG TATATGCATA CAATGGAATA TTATTTAGTC TTTAAAAAGA AAAATTCTAT      420

CATATACTAC AACTTANATN AACCTTGAGG ACACAATGCT NAGTGAAATA AGCCACGGAA      480

GGACGAATAC TGCATTATTC CCTTATATGA AGTATCTAAA GTGGTCAAAC TCTTANAGCA      540

NAAAGTAAAA ATGGGTGGTT GCCANACAGT TGGTTAGGCN AGAAGANAAN CCTANT         596

(2) INFORMATION FOR SEQ ID NO: 233:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 233:

TCTTCTGAAG ACCTTTCGCG ACTCTTAAGC TCGTGGTTGG TAAGGCAAGA GGAGCGTTGG       60

TAAGGCAAGA GGAGCGTTGG TAAGGCAAGA GGAGCA                                96

(2) INFORMATION FOR SEQ ID NO: 234:

(i) SEQUENCE CHARACTERISTICS:
        (A) LENGTH: 313 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 234:

TGTAAGTCGA GCAGTGTGAT GATAAAACTT GAATGGATCA ATAGTTGCTT CTTATGGATG       60

AGCAAAGAAA GTAGTTTCTT GTGATGGAAT CTGCTCCTGG CAAAAATGCT GTGAACGTTG      120

TTGAAAAGAC AACAAAGAGT TTAGAGTAGT ACATAAATTT AGAATAGTAC ATAAACTTAG      180

AATAGTACAT AAACTTAGTA CATAAATAAT GCACGAAGCA GGGGCAGGGC TTGAGAGAAT      240

TGACTTCAAT TTGGAAAGAG TATCTACTGT AGGTTAGATG CTCTCAAACA GCATCACACT      300

GCTCGACTTA CAA                                                        313

(2) INFORMATION FOR SEQ ID NO: 235:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 235:

AACGAGGACA GATCCTTAAA AAGAATGTTG AGTGAAAAAA GTAGAAAATA AGATAATCTC       60

CAAAGTCCAG TAGCATTATT TAAACATTTT TAAAAAATAC ACTGATAAAA ATTTTGTACA      120

-continued

| | |
|---|---|
| TTTCCCAAAA ATACATATGG AAGCACAGCA GCATGAATGC CTATGGGRTT GAGGATAGGG | 180 |
| GTTGGGAGTA GGGATGGGGA TAAAGGGGGA AAATAAAACC AGAGAGGAGT CTTACACATT | 240 |
| TCATGAACCA AGGAGTATAA TTATTTCAAC TATTTGTACC WGAAGTCCAG AAAGAGTGGA | 300 |
| GGCAGAAGGG GGAGAAGAGG GCGAAGAAAC GTTTTTGGGA GAGGGGTCCC ASAAGAGAGA | 360 |
| TTTTCGCGAT GTGGCGCTAC ATACGTTTTT CCAGGATGCC TTAAGCTCTG CACCCTATTT | 420 |
| TTCTCATCAC TAATATTAGA TTAAACCCTT TGAAGACAGC GTCTGTGGTT TCTCTACTTC | 480 |
| AGCTTTCCCT CCGTGTCTTG CACACAGTAG CTGTTTTACA AGGGTTGAAC TGACTGAAGT | 540 |
| GAGATTATTC | 550 |

(2) INFORMATION FOR SEQ ID NO: 236:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 236:

| | |
|---|---|
| TAGACTGACT CATGTCCCCT ACCAGAGTAG CTAGAATTAA TAGCACAAGC CTCTACACCC | 60 |
| AGGAACTCAC TATTGAATAC ATAAATGGAA TTTATTCAGC CTTAAAAAGT TTGGAAGGAA | 120 |
| ATTCTGACAT ATGCTAAAAC ATGGATGAAC CTTGAAGACT TTATGATAAG TAAAAGAAGC | 180 |
| CAGTCATAAA AGGAAAAATA TTGCATGATT CCACTTATAT GAGGTACCTA GAGTAGTCAA | 240 |
| TTTCATAGAA ACACAAAATA GAATGGTGTT TGCCAGGGCT TTTGAGGAAA AGGGAATGAC | 300 |
| AAGTTAGGGG ACATGAGTCA GTCTA | 325 |

(2) INFORMATION FOR SEQ ID NO: 237:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 237:

| | |
|---|---|
| TAGACTGACT CATGTCCCCT ATCTACTCAA CATTTCCACT TGAAGTCTGA TAGGCATCTC | 60 |
| AGACTTATCT TGTCCCAAAG CAAACTCTTT ATTTCTTTTC ATCCTAGTCT TTATTTCTTG | 120 |
| TGCTGTCTTA CCCATCTCAA AAGAGTGCCA AAATCCACCA AGTTGCTGAA ACAGAAATCT | 180 |
| AAGAAATATC CTTGATTCTT CTTTTTCCCA TCTACTTCAC TTCTAATTCA TTAGTAAATA | 240 |
| ATCTGTTTCA GAAAACCAAA CACCTCATGT TCTCACTCAT AAGGGGGAGT TGAACAATGA | 300 |
| GAACACACAG ACACAGGGAG GGGAACATCA CACACCACGG CCCGTCAGGG AGTANGGGAC | 360 |
| ATGAGTCAGT CTA | 373 |

(2) INFORMATION FOR SEQ ID NO: 238:

(i) SEQUENCE CHARACTERISTICS:
        (A) LENGTH: 492 base pairs (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 238:

| TAGACTGACT CATGTCCCCT ATAATGCTCC CAGGCATCAG AAAGCATCTC AAACTGGAGC | 60 |
|---|---|
| TGACACCATG GCAGAGGTTT CAGGTAAGTC ACAAAAGGGG TCCTAAAGAA TTTGCCCTCA | 120 |
| ATATCAGAGT GATTAGAAGA AGTGGACAGA GCTACCCAAG TTAAACATAT GCGAGATAAA | 180 |
| AAAAATATGG CACTTGTGAA CACACACTAC AGGAGGAAAA TAAGGAACAT AATAGCATAT | 240 |
| TGTGCTATTA TGATGATGAA GAACCTCTCT ANAAGAAAAC ATAACCAAAG AAACAAAGAA | 300 |
| AATTCCTGCN AATGTTTAAT GCTATAGAAG AAATTAACAA AAACATATAT TCAATGAATT | 360 |
| CAGAAAAGTT AGCAGGTCAN AAGAAAACAA ATCAAAGACC AGAATAATCC CATTTTAGAT | 420 |
| TGTCGAGTAA ACTANAACAG AAAGAATACC ACTGGAAATT GAATTCCTAC GTANGGGACA | 480 |
| TGANTCANTC TA | 492 |

(2) INFORMATION FOR SEQ ID NO: 239:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 239:

| TGGAAAGTAT TTAATGATGG GCAACTTGCT GTTTACTTCC TACATATCCC ATCATCTTCT | 60 |
|---|---|
| GTATTTTTTT AAATAACTTT TTTTTGGATT TTTAAAGTAA CCTTATTCTG AGAGGTAACA | 120 |
| TGGATTACAT ACTTCTAAGC CATTAGGAGA CTCTATGTTA AACCAAAAGG AAATGTTACT | 180 |
| AGATCTTCAT TTGATCAATA GGATGTGATA ATCATCATCT TTCTGCTCTA ATGGAAAAGT | 240 |
| ACTANAAACA TGGAACCATA ATCTTAGATG AACAACGTTA GAATTTGCAC TAATTCTACG | 300 |
| GAATTTCAGT AATTCGGCAA ATGTCGGGCA GTGACACAAC ATTTCATGAC GGGGACGCAT | 360 |
| CTACCAACTT CTGGCGATAA GGGCCACCCT TCCCTCTGTA CTTACAGTCC CATTTCATAC | 420 |
| ACAGTCTTTG ATTAAATATT CACATTTTTT CTCTACCTAA AGACCTTCAA GACCAGTACG | 480 |
| TA | 482 |

(2) INFORMATION FOR SEQ ID NO: 240:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 240:

| | |
|---|---|
| TGTATCGACG TAGTGGTCTC CCCATGTGAT AGTCTGAAAT ATAGCCTCAT GGGATGAGAG | 60 |
| GCTGTGCCCC AGCCCGACAC CCGTAAAGGG TCTGTGCTGA GGTGGATTAG TAAAAGAGGA | 120 |
| AAGCCTTGCA GTTGAGATAG AGGAAGGGCA CTGTCTCCTG CCTGCCCCTG GAACTGAAT | 180 |
| GTCTCGGTAT AAAACCCGAT TGTACATTTG TTCAATTCTG AGATAGGAGA AAAACCACCC | 240 |
| TATGGCGGGA GGCGAGACAT GTTGGCAGCA ATGCTGCCTT GTTATGCTTT ACTCCACAGA | 300 |
| TGTTTGGGCG GAGGGAAACA TAAATCTGGC CTACGTGCAC ATCCAGGCAT AGTACCTCCC | 360 |
| TTTGAACTTA ATTATGACAC AGATTCCTTT GCTCACATGT TTTTTTGCTG ACCTTCTCCT | 420 |
| TATTATCACC CTGCTCTCCT ACCGCATTCC TTGTGCTGAG ATAATGAAAA TAATATCAAT | 480 |
| AAAAACTTGA NGGAACTCGG AGACCACTAC GTCGATACA | 519 |

(2) INFORMATION FOR SEQ ID NO: 241:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 241:

| | |
|---|---|
| TGTATCGACG TAGTGGTCTC CACTCCCGCC TTGACGGGGC TGCTATCTGC CTTCCAGGCC | 60 |
| ACTGTCACGG CTCCCGGGTA GAAGTCACTT ATGAGACACA CCAGTGTGGC CTTGTTGGCT | 120 |
| TGAAGCTCCT CAGAGGAGGG TGGGAACAGA GTGACCGAGG GGGCAGCCTT GGGCTGACCT | 180 |
| AGGACGGTCA GCTTGGTCCC TCCGCCAAAC ACGAGAGTGC TGCTGCTTGT ATATGAGCTG | 240 |
| CAGTAATAAT CAGCCTCGTC CTCAGCCTGG AGCCCAGAGA TGGTCAGGGA GGCCGTGTTG | 300 |
| CCANACTTGG AGCCAGAGAA GCGATTAGAA ACCCCTGAGG GCCGATTACC GACCTCATAA | 360 |
| ATCATGAATT TGGGGCTTT GCCTGGGTGC TGTTGGTACC ANGAGACATT ATTATAACCA | 420 |
| CCAACGTCAC TGCTGGTTCC ANTGCAGGGA AAATGGTTGA TCNAACTGTC CAAGAAAACC | 480 |
| ACTACGTCCA TACCAATCCA CTAATTGCCN GCCGCCTGCA GGTTCAACCA TATTGGGGAA | 540 |
| NAACTCCCCN CCGCCGTTTG GGATTGNCAT NAACCTTTGA AATTTTTTCC TATTANTTGT | 600 |
| CCCCCTAAAA TAAACCNTTG GGCNTTAATC CATTGGGTCC ATANCTTNTT TNCCCGGTTT | 660 |
| TTAAAANTTG TTTATCCCGC CNCCCNATTT CCCCCCCAAC TTTCCAAAAC CCGAAACCNT | 720 |
| TNAAATTTNT TNAAACCCTG GGGGGTTCCC NNAATTNNAN TTNAANCTNC C | 771 |

(2) INFORMATION FOR SEQ ID NO: 242:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 242:

| | |
|---|---|
| TGGGCACCTT CAATATCGGG CTCATCGATA ACATCACGCT GCTGATGCTG CTGTTGCTGG | 60 |
| TCCTCTCTAG GAACCTCTGG ATTTTCAAAT TCTTTGAGGA ATTCATCCAA ATTATCTGCC | 120 |

TCTCCTCCTT TCCTCCTTTT TCTAAGGTCT TCTGGTACAA GCGGTCA                  167

(2) INFORMATION FOR SEQ ID NO: 243:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 243:

TTGGGCACCT TCAATATCTA CTGATCTAAA TAGTGTGGTT TGAGGCCTCT TGTTCCTGGC      60

TAAAAATCCT TGGCAAGAGT CAATCTCCAC TTTACAATAG AGGTAAAAAT CTTACAATGG     120

ATATTCTTGA CAAAGCTAGC ATAGAGACAG CAATTTTACA CAAGGTATTT TTCACCTGTT     180

TAATAACAGT GGTTTTCCTA CACCCATAGG GTGCCACCAA GGGAGGAGTG CACAGTTGCA     240

GAAACAAATT AAGATACTGA AGACAACACT ACTTACCATT TCCCGTATAG CTAACCACCA     300

GTTCAACTGT ACATGTATGT TCTTATGGGC AATCAAGA                            338

(2) INFORMATION FOR SEQ ID NO: 244:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 244:

TTTTTGGCTC CCATACAGCA CACTCTCATG GGAAATGTCT GTTCTAAGGT CAACCCATAA      60

TGCAAAAATC ATCAATATAC TTGAAGATCC CCGTGTAAGG TACAATGTAT TTAATATTAT     120

CACTGATACA ATTGATCCAA TACCAGTTTT AGTCTGGCAT TGAATCAAAT CACTGTTTTT     180

GTTGTATAAA AAGAGAAATA TTTAGCTTAT ATTTAAGTAC CATATTGTAA GAAAAAAGAT     240

GCTTATCTTT ACATGCTAAA ATCATGATCT GTACATTGGT GCAGTGAATA TTACTGTAAA     300

AGGGAAGAAG GAATGAAGAC GAGCTAAGGA TATTGAAGGT GCCCAA                   346

(2) INFORMATION FOR SEQ ID NO: 245:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 245:

ACCAATCCCA CACGGATACT GAGGGACAAG TATATCATCC CATTTCATCC CTACAGCAGC      60

AACTTCATGA GGCAGGAGTT ATTAGTCCCA TTTTACAGAA GAGGAAACTG AGACTTAGGG     120

```
AGATCAAGTA ATTTGCCCAG GTCGCACAAT TAGTGATAGA GCCAGGGCTT GAAGCGACGT        180

CTGTCTTAAG CCAATGACCC CTGCAGATTA TTAGAGCAAC TGTTCTCCAC AACAGTGTAA        240

GCCTCTTGCT ANAAGCTCAG GTCCACAAGG GCAGAGATTT TTGTCTGTTT TGCTCATTGC        300

TCCTTCCCCA TTGCTTAGAG CAGGGTCTGC CACGAANCAG GTTCTCAATG CATAGTTATT        360

AAATGTATAT AAGAGCAAAC ATATGTTACA GAGAACTTTC TGTATGCTTG TCACTTACAT        420

GAATCACCTG TGANATGGGT ATGCTTGTTC CCCANTGTTG CAGATNAAGA TATTGAANGT        480

GCCCAAATCA CTANTTGCGG GCGCCTGCAN GTCCANCATA T                           521

(2) INFORMATION FOR SEQ ID NO: 246:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 246:

TGGAACCAAT CCAAATACCC ATCAATGATA GACTGGATAA AGAAAATTTG GCACATGTTC         60

ACCATGAAAT ACTATGCAGC CATAAAAAAG GATGAGTTCA TATCCTTTGC AGGGACATGG        120

ATGAAGCTGG AGACCATCAT TCTCAGCAAA CTAACAAGGG AACAGAAAAC CAAACACTGC        180

ATGTTCTCAC TCTTAAGTGG GAGCTGAACA ATGAGAACAC ATGGACACAG GGAGGGGAAC        240

ATCACACAGT GGGGCCTGCT GGTGGGTAGG GGTCTAGGGG AGGGATAGCA TTAGGAGAAA        300

TACCTAATGT AGATGACGGG TTGATGGGTG CAGCAAACCA CCATGACACG TGTATACCTA        360

TGTAACAAAC CTGCATGTTC TGCACATGTA CCCCAGAACT TAAAGTGTTA ATAAAAAAAT        420

TAAGAAAAAA GTTAAGTATG TCATAGATAC ATAAAATATT GTANATATTG AAGGTGCCCA        480

AA                                                                      482

(2) INFORMATION FOR SEQ ID NO: 247:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 247:

TTCGATACAG GCACAGAGTA AGCAGAAAAA TGGCTGTGGT TTAACCAAGT GAGTACAGTT         60

AAGTGAGAGA GGGGCAGAGA AGACAAGGGC ATATGCAGGG GGTGATTATA ACAGGTGGTT        120

GTGCTGGGAA GTGAGGGTAC TCGGGGATGA GGAACAGTGA AAAAGTGGCA AAAAGTGGTA        180

AGATCAGTGA ATTGTACTTC TCCAGAATTT GATTTCTGGN GGAGTCAAAT AACTATCCAG        240

TTTGGGGTAT CATANGGCAA CAGTTGAGGT ATAGGAGGTA GAAGTCNCAG TGGGATAATT        300

GAGGTTATGA ANGGTTTGGT ACTGACTGGT ACTGACAANG TCTGGGTTAT GACCATGGGA        360

ATGAATGACT GTANAAGCGT ANAGGATGAA ACTATTCCAC GANAAAGGGG TCCNAAAACT        420

AAAAANNNAA GNNNNNGGGG AATATTATTT ATGTGGATAT TGAANGTGCC CAAA             474
```

(2) INFORMATION FOR SEQ ID NO: 248:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (xi) SEQUENCE DESCRIPTION: SEQ ID NO: 248:

```
TTCGATACAG GCAAACATGA ACTGCAGGAG GGTGGTGACG ATCATGATGT TGCCGATGGT      60

CCGGATGGNC ACGAAGACGC ACTGGANCAC GTGCTTACGT CCTTTTGCTC TGTTGATGGC     120

CCTGAGGGGA CGCAGGACCC TTATGACCCT CAGAATCTTC ACAACGGGAG ATGGCACTGG     180

ATTGANTCCC ANTGACACCA GAGACACCCC AACCACCAGN ATATCANTAT ATTGATGTAG     240

TTCCTGTAGA NGGCCCCCTT GTGGAGGAAA GCTCCATNAG TTGGTCATCT TCAACAGGAT     300

CTCAACAGTT TCCGATGGCT GTGATGGGCA TAGTCATANT TAACCNTGTN TCGAA          355
```

(2) INFORMATION FOR SEQ ID NO: 249:

(i) SEQUENCE CHARACTERISTICS:
        (A) LENGTH: 434 base pairs
        (B) TYPE: nucleic acid
        (C) STRANDEDNESS: single
        (D) TOPOLOGY: linear (xi) SEQUENCE DESCRIPTION: SEQ ID NO: 249:

```
TTGGATTGGT CCTCCAGGAG AACAAGGGGA AAAAGGTGAC CGAGGGCTCC CTGGAACTCA      60

AGGATCTCCA GGAGCAAAAG GGGATGGGGG AATTCCTGGT CCTGCTGGTC CCTTAGGTCC     120

ACCTGGTCCT CCAGGCTTAC CAGGTCCTCA AGGCCCAAAG GGTAACAAAG GCTCTACTGG     180

ACCCGCTGGC CAGAAAGGTG ACAGTGGTCT TCCAGGGCCT CCTGGGCCTC CAGGTCCACC     240

TGGTGAAGTC ATTCAGCCTT TACCAATCTT GTCCTCCAAA AAAACGAGAA GACATACTGA     300

AGGCATGCAA GCAGATGCAG ATGATAATAT TCTTGATTAC TCGGATGGAA TGGAAGAAAT     360

ATTTGGTTCC CTCAATTCCC TGAAACAAGA CATCGAGCAT ATGAAATTTC CAATGGGTAC     420

TCAGACCAAT CCAA                                                      434
```

(2) INFORMATION FOR SEQ ID NO: 250:

(i) SEQUENCE CHARACTERISTICS:
        (A) LENGTH: 430 base pairs
        (B) TYPE: nucleic acid
        (C) STRANDEDNESS: single
        (D) TOPOLOGY: linear (xi) SEQUENCE DESCRIPTION: SEQ ID NO: 250:

```
TGGATTGGTC ACATGGCAGA GACAGGATTC CAAGGCAGTG AGAGGAGGAT ACAATGCTTC      60

TCACTAGTTA TTATTATTTA TTTTATTTTT GAGATGAAGT CTCGCTTTGT CTCCCAGGCT     120

GGAGAGCGGT GGTGCGATCT TGGCTCTCTG CAACCCCCGC CTCAAGCAAT TCTCCTGTCT     180

TAGCCTCGCG GGTAGATGGA ATTACAGGCG CCCACCGCCA TGCCCAACTA ATTTTTTTGT     240

GTCTTCAGTA GAGACAGGGT TTCGCCATGT TGGGCAGGCT GGTCTTGAAC TCCTGACCTC     300

NAGTGATCTG CCCTCCTCGG CCTCACAAAG TGCTGGAATT ACAGGCATGG GCTGCTGCAC     360

CCAGTCAACT TCTCACTAGT TATGGCCTTA TCATTTTCAC CACATTCTAT TGGCCCAAAA     420

AAAAAAAAN                                                            430
```

(2) INFORMATION FOR SEQ ID NO: 251:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (xi) SEQUENCE DESCRIPTION: SEQ ID NO: 251:

```
TGGTACTCCA CCATYATGGG GTCAACCGCC ATCCTCGCCC TCCTCCTGGC TGTTCTCCAA      60
GGAGTCTGTG CCGAGGTGCA GCTGRTGCAG TCTGGAGCAG AGGTGAAAAA GTCCGGGGAG     120
TCTCTGAAGA TCTCCTGTAA GGGTTCTGGA TACACCTTTA AGATCTACTG GATCGCCTGG    180
GTGCGCCAGT TGCCCGGGAA AGGCCTGGAG TGGATGGGGC TCATCTTTCC TGATGACTCT     240
GATACCAGAT ACAGCCCGTC CTTCCAAGGC CAGGTCACCA TCTCAGTCGA TAAGTCCATC     300
AGCACCGCCT ATCTGCAGTG GAGTACCAA                                       329
```

(2) INFORMATION FOR SEQ ID NO: 252:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (xi) SEQUENCE DESCRIPTION: SEQ ID NO: 252:

```
TGGTACTCCA CTCAGCCCAA CCTTAATTAA GAATTAAGAG GGAACCTATT ACTATTCTCC      60
CAGGCTCCTC TGCTCTAACC AGGCTTCTGG GACAGTATTA GAAAAGGATG TCTCAACAAG    120
TATGTAGATC CTGTACTGGC CTAAGAAGTT AAACTGAGAA TAGCATAAAT CAGACCAAAC    180
TTAATGGTCG TTGAGACTTG TGTCCTGGAG CAGCTGGGAT AGGAAAACTT TTGGGCAGCA    240
AGAGGAAGAA CTGCCTGGAA GGGGGCATCA TGTTAAAAAT TACAAGGGGA ACCCACACCA    300
GGCCCCCTTC CCAGCTCTCA GCCTAGAGTA TTAGCATTTC TCAGCTAGAG ACTCACAACT    360
TCCTTGCTTA GAATGTGCCA CCGGGGGGAG TCCCTGTGGG TGATGAGGCT CTCAAGAGTG    420
AGAGTGGCAT CCTATCTTCT GTGTGCCCAC AGGAGCCTGG CCCGAGACTT AGCAGGTGAA    480
GTTTCTGGTC CAGGCTTTGC CCTTGACTCA CTATGTGACC TCTGGTGGAG TACCAA        536
```

(2) INFORMATION FOR SEQ ID NO: 253:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO: 253:

```
NTGTTGCGAT CCCAGTAACT CGGGAAGCTG AGGCGGAGG ATCACCTGAG CTCAGGAGGT       60
TGAGGCCGCA GTGAGCCGGG ACCACGCCAC TACACTCCAG CCTGGGCAT AGAGTGAGAC     120
CCTCCAAGAC AGAAAAGAAA AGAAAGGAAG GGAAAGGGAA AGGGAAAAGG AAAAGGAAAA    180
GGAAAAGGAA AAGGAAAAGA CAAGACAAAA CAAGACTTGA ATTTGGATCT CCTGACTTCA   240
ATTTTATGTT CTTTCTACAC CACAATTCCT CTGCTTACTA AGATGATAAT TTAGAAACCC    300
CTCGTTCCAT TCTTTACAGC AAGCTGGAAG TTTGGTCAAG TAATTACAAT AATAGTAACA   360
AATTTGAATA TTATATGCCA GGTGTTTTTC ATTCCTGCTC TCACTTAATT CTCACCACTC    420
TGATATAAAT ACAATTGCTG CCGGGTGTGG TGGCTCATGC CTGTAATCCC GGCACTTTGG   480
GAGACCGAGG TGGGCGGATS GCAACAA                                         507
```

(2) INFORMATION FOR SEQ ID NO: 254:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (xi) SEQUENCE DESCRIPTION: SEQ ID NO: 254:

```
TTGGATTGGT CACTGTGAGG AAGCCAAATC GGATCCGAGA GTCTTTTTCT AAAGGCCAGT    60

ACTGGCCACA CTTTCTCCTG CCGCCTTCCT CAAAGCTGAA GACACACAGA GCAAGGCGCT   120

TCTGTTTTAC TCCCCAATGG TAACTCCAAA CCATAGATGG TTAGCTNCCC TGCTCATCTT   180

TCCACATCCC TGCTATTCAG TATAGTCCGT GGACCAATCC AA                     222
```

(2) INFORMATION FOR SEQ ID NO: 255:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (xi) SEQUENCE DESCRIPTION: SEQ ID NO: 255:

```
TGTTGCGATC CATAAATGCT GAAATGGAAA TAAACAACAT GATGAGGGAG GATTAAGTTG    60

GGGAGGGAGC ACATTAAGGT GGCCATGAAG TTTGTTGGAA GAAGTGACTT TTGAACAAGG   120

CCTTGGTGTT AAGAGCTGAT GAGAGTGTCC CAGACAGAGG GGCCACTGGT ACAATAGACG   180

AGATGGGAGA GGGCTTGGAA GGTGTGCGAA ATAGGAAGGA GTTTGTTCTG GTATGAGTCT   240

AGTGAACACA GAGGCGAGAG GCCCTGGTGG GTGCAGCTGG AGAGTTATGC AGAATAACAT   300

TAGGCCCTGT GGGGGACTGT AGACTGTCAG CAATAATCCA CAGTTTGGAT TTTATTCTAA   360

GAGTGATGGG AAGCCGTGGA AAGGGGGTTA AGCAAGGAGT GAAATTATCA GATTTACAGT   420

GATAAAAATA AATTGGTCTG GCTACTGGGG AAAAAAAAAA AAA                    463
```

(2) INFORMATION FOR SEQ ID NO: 256:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (xi) SEQUENCE DESCRIPTION: SEQ ID NO: 256:

```
TTGGATTGGT CAACCTGCTC AACTCTACYT TTCCTCCTTC TTCCTAAAAA ATTAATGAAT    60

CCAATACATT AATGCCAAAA CCCTTGGGTT TTATCAATAT TTCTGTTAAA AAGTATTATC   120

CAGAACTGGA CATAATACTA CATAATAATA CATAACAACC CCTTCATCTG GATGCAAACA   180

TCTATTAATA TAGCTTAAGA TCACTTTCAC TTTACAGAAG CAACATCCTG TTGATGTTAT   240

TTTGATGTTT GGACCAATCC AA                                           262
```

(2) INFORMATION FOR SEQ ID NO: 257:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (xi) SEQUENCE DESCRIPTION: SEQ ID NO: 257:

```
GNGGNNNNNN NNNCAATTCG ACTCNGTTCC CNTGGTANCC GGTCGACATG GCCGCGGGAT      60

TACCGCTTGT NNCTGGGGGT GTATGGGGGA CTATGACCGC TTGTAGCTGG GGGTGTATGG     120

GGGACTATGA CCGCTTGTAG MTGGKGGTGT ATGGGGGACT ATGACCGCTT GTCGGGTGGT     180

CGGATAAACC GACGCAAGGG ACGTGATCGA AGCTGCGTTC CCGCTCTTTC GCATCGGTAG     240

GGATCATGGA CAGCAATATC CGCATTCGYC TGAAGGCGTT CGACCATCGC GTGCTCGATC     300

AGGCGACCGG CGACATCGCC GACACCGCAC GCCGTACCGG CGCGCTCATC CGCGGTCCGA     360

TCCCGCTTCC CACGCGCATC GAGAAGTTCA CGGTCAACCG TGGCCCGCAC GTCGACAAGA     420

AGTCGCGCGA GCAGTTCGAG GTGCGTACCT ACAAGCGGTC A                        461

(2) INFORMATION FOR SEQ ID NO: 258:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (xi) SEQUENCE DESCRIPTION: SEQ ID NO: 258:

TGACCGCTTG TAGCTGGGGG TGTATGGGGG ACTACGACCG CTTGTAGCTG GGGGTGTATG      60

GGGGACTATG ACCGCTTGTA GCTGGGGGTG TATGGGGGAC TATGACCGCT TGTAGCTGGG     120

GGTGTATGGG GGACTAGGAC CGCTTGTAGC TGGGGGTGTA TGGGGGACTA TGACCGCTTG     180

TAGCTGGGGG TGTATGGGGG ACTACGACCG CTTGTAGCTG GGGGTGTATG GGGACTATG      240

ACCGCTTGTA NCTGGGGGTG TATGGGGGAC TATGACCGCT TGTGCTGCCT GGGGGATGGG     300

AGGAGAGTTG TGGTTGGGGA AAAAAAAAAA AA                                  332

(2) INFORMATION FOR SEQ ID NO: 259:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (xi) SEQUENCE DESCRIPTION: SEQ ID NO: 259:

TACCGCTTGT GACCGCTTGT GACCGCTTGT GACCGCTTGT GACCGCTTGT GACCGCTTGT      60

GACCGCTTGT GACCGCTTGT GACCGCTTGT GACCGCTTGT GACCGCTTGT GACCGCTTGT     120

GACCGCTTGT GACCGCTTGT NACNGGGGGT GTCTGGGGGA CTATGANNGA NTGTNACTGG     180

GGGTGTCTGG GGGNCTATGA NNGANTGTNA CNGGGGGTGT CTGGGGGACT ATGANNGACT     240

GTGCNNCCTG GGGGATCNGA GGAGANTNGN GGNTAGNGAT GGTTNGGGAN A              291

(2) INFORMATION FOR SEQ ID NO: 260:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (xi) SEQUENCE DESCRIPTION: SEQ ID NO: 260:

TAAGAGGGTA CTGGTTAAAA TACAGGAAAT CTGGGGTAAT GAGGCAGAGA ACCAGGATAC      60

TTTGAGGTCA GGGATGAAAA CTAGAATTTT TTTCTTTTTT TTTGCCTGAG AAACTTGCTG     120

CTCTGAAGAG GCCCATGTAT TAATTGCTTT GATCTTCCTT TTCTTACAGC CCTTTCAAGG     180

GCAGAGCCCT CCTTATCCTG AAGGAATCTT ATCCTTAGCT ATAGTATGTA CCCTCTTA       238
```

(2) INFORMATION FOR SEQ ID NO: 261:

(i) SEQUENCE CHARACTERISTICS:
        (A) LENGTH: 746 base pairs
        (B) TYPE: nucleic acid
        (C) STRANDEDNESS: single
        (D) TOPOLOGY: linear (xi) SEQUENCE DESCRIPTION: SEQ ID NO: 261:

```
TTGGGCACCT TCAATATCAA TAGCTAACAT TTATTGAGTG TTTATCGTAT CATAAAACAC      60

TGTTCTAAGC CTTTAAACGT ACTAATTCAT TTAATGCTCA TAATCACTTT AGAAGGTGGG     120

TACTAGTATT AGTCTCATTT ACAGATGCAA CATGCAGGCA CAGAGAGGTT AATTAACTTG     180

CCCAAGGTAA CACAGCTAAG AAATAGAAAA AATATTGAAT CTGGAAAGTT GGGCTTCTGG     240

GTAACCCACA GAGTCTTCAA TGAGCCTGGG GCCTCACTCA GTTTGCTTTT ACAAAGCGAA     300

TGAGTAACAT CACTTAATTC AGTGAGTAGG CCAAATGGAG GTCAGCTACG AGTTTCTGCT     360

GTTCTTGCAG TGGACTGACA GATGTTTACA ACGTCTGGCC ATCAGTWAAT GGACTGATTA     420

TCATTGGGAW GTGGGTGGGC TGAATGTTGG CCAGTGAAGT TTATTCAWGC CATATTTTTA     480

TGTTTAGGAT GACTTTTGGC TGGTCCTAGG GCAAGCTCTG TCTGSCACGG AACACAGAAT     540

WACACAGGGA CCCCCTCAAT TTCTGGTGTG GCTAGAACCA TGAACCACTG GTTGGGGGAA     600

CAAGCGGTCA AAACCTAAGT GCGGCCGGCT GGCAGGGTCC ACCCATATGG GGAAAACTCC     660

CNACGCGTTT GGAATGCCTN AGCTNGAATT ATTCTAANAG TTGTCCNCNT AAAATTAGCC     720

TGGGCGTTAA TCANGGGTCN NAAGCC                                         746
```

(2) INFORMATION FOR SEQ ID NO: 262:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (xi) SEQUENCE DESCRIPTION: SEQ ID NO: 262:

```
TGACCGCTTG TCATCTCACA TGGGGTCCTG CACGCTTTTG CCTTTGTAGG AAACCTGACA      60

TTTGTCTGTT TCTTCTTTCT CTTTTCCTTC CCATATCCTC CTAATTTACG TTTGACTTGT     120

TTGCTGAGGA GGCAGGAGCT AGAGACTGCT GTGAGCTCAT AGGGGTGGGA AGTTTATCCT     180

TCAAGTCCCG CCCACTCATC ACTGCTTCTC ACCTTCCCCT GACCAGGCTT ACAAGTGGGT     240

TCTTGCCTGC TTTCCCTTTG GACCCAACAA GCCCCTGTAA TGAGTGTGCA TGACTCTGAC     300

AGCTGTGGAC TCAGGGTCCT TGGCTACAGC TGCCATGTAA AATATCTCAT CCAGTTCTCG     360

CAAATTGTTA AAATAACCAC ATTTCTTAGA TTCCAGTACC CAAATCATGT CTTTACGAAC     420

TGCTCCTCAC ACCCAGAAGT GGCACAATAA TTCTTGGGGA ATTATTACTT TTTTTTTTCT     480

CTCTNTTNNC GNNNGNNNNG GNNNGNCCAG GAATTACCAC NTTGGAAGAC CTGGCCNGAA     540

TTTATTATAN AGGGGAGCCG ATTNTTTTTC CTAACACAAA GCGGGTCA                 588
```

(2) INFORMATION FOR SEQ ID NO: 263:

(i) SEQUENCE CHARACTERISTICS:
        (A) LENGTH: 730 base pairs
        (B) TYPE: nucleic acid
        (C) STRANDEDNESS: single
        (D) TOPOLOGY: linear (xi) SEQUENCE DESCRIPTION: SEQ ID NO: 263:

-continued

TTTTTTTTTT TTTGGCCTGA GCAACTGAAA TTATGAAATT TCCATATACT CAAAAGAGTA        60

AGACTGCAAA AAGATTAAAT GTAAAAGTTG TCTTGTATAC AGTAATGTTT AAGATACCTA       120

TTANATTTAT AAATGGAAAA TTAGGGCATT TGGATATACA AGTTGAAAAT TCAGGAGTGA       180

GGTTGGGCTG GCTGGGTATA TACTGAAAAC TGTCAGTACA CAGATGACAT CTAAAACCAC       240

AAATCTGGTT TTATTTTAGC AGTGATATGT GTCACTCCCA CAAAAGCCTT CCCAATTGGC       300

CTCAGCATAC ACAACAAGTC ACCTCCCCAC AGCCCTCTAC ACATAAACAA ATTCCTTAGT       360

TTAGTTCAGG AGGAAATGCG CCCTTTTCCT TCCGCTCTAG GTGACCGCAA GGCCCAGTTC       420

TCGTCACCAA GATGTTAAGG GAAGTCTGCC AAAGAGGCAT CTGAAAGGAA ATAAGGGGAA       480

TGGGAGTGAC CACAAAGGAA AGCCAAGGAN AAACTTTGGA GACCGTTTCT AGANCCCTGG       540

CATTTCACAA CAAAACTCNG GAACAAACCT TGTCTCATCA ATCATTTAAG CCCTTCGTTT       600

GGANNAGACT TTCTGAACTG GGCGCTGAAC ATAANCCTCA TTGAATGTCT TCACAGTCTC       660

CCAGCTGAAG GCACACCTTG GGCCAGAAGG GGAATCTTCC AGGTCCTCAA NACAGGGCTC       720

GCCCTTTGNC                                                              730

(2) INFORMATION FOR SEQ ID NO: 264:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (xi) SEQUENCE DESCRIPTION: SEQ ID NO: 264:

TTTTTTTTTT TTTGGCCAGT ATGATAGTCT CTACCACTAT ATTGAAGCTC TTAGGTCATT        60

TACACTTAAT GTGGTTATAG ATGCTGTTGA GCTTACTTCT ACCACCTTGC TATTTCTCCC       120

GTCTCTTTTT TGTTCCTTTT CTCTTCTTTT CCTCCCTTAT TTTATAATTG AATTTTTTAG       180

GATTCTATTT TATATAGATT TATCAGCTAT AACACTTTGT ATTCTTTTGT TTTGTGGTTC       240

TTCTGTCATT TCAATGTGCA TCTTAAACTC ATCACAATCT ATTTTCAAAT AATATCATAT       300

AACCTTACAT ATAATGTAAG AATCTACCAC CATATATTTC CATTTCTCCC TTCCATCCTA       360

TGTNTGTCAT ATTTTTTCCT TTATATATGT TTTAAAGACA TAATAGTATA TGGGAGGTTT       420

TTGCTTAAAA TGTGATCAAT ATTCCTTCAA NGAAACGTAA AAATTCAAAA TAAATNTCTG       480

TTTATTCTCA AATNNACCTA ATATTTCCTA CCATNTCTNA TACNTTTCAA GAATCTGAAG       540

GCATTGGTTT TTTCCGGCTT AAGAACCTCC TCTAAAGCAC TCTAAGCAGA ATTAAGTCTT       600

CTGGGAGAGG AATTCTCCCA AGCTTGGGCC TTNANNTGTA CTCCNTNANG GTTAAANTTT       660

GGCCGGGAAA TAGAAATTCC AAGTTAACAG GNTANTTTTT NTTTTTNTTN TCNCC           715

(2) INFORMATION FOR SEQ ID NO: 265:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (xi) SEQUENCE DESCRIPTION: SEQ ID NO: 265:

TTTTTTTTTT TTTCCCAACA CAAAGCACCA TTATCTTTCC TCACAATTTT CAACATAGTT        60

TGATTCCCAT GAAGAGGTTA TGATTTCTAA AGAAACATG GCTACTATAC TATCAATCAG       120

GGTTAAATCT TTTTTTTTTG AGACGGAGTT TA                                    152

(2) INFORMATION FOR SEQ ID NO: 266:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (xi) SEQUENCE DESCRIPTION: SEQ ID NO: 266:

```
TAAACTCCGT CCCCTTCTTA ATCAATATGG AGGCTACCCA CTCCACATTA CCTTCTTTTC      60

AAGGGACTGT TTCCGTAACT GTTGTGGGTA TTCACGACCA GGCTTCTAAA CCTCTTAAAA     120

CTCCCCAATT CTGGTGCCAA CTTGGACAAC ATGCTTTTTT TTTTTTTTT TTTTTTTTN      180

GAGACGGAGT TTA                                                        193
```

(2) INFORMATION FOR SEQ ID NO: 267:

(i) SEQUENCE CHARACTERISTICS:
        (A) LENGTH: 460 base pairs
        (B) TYPE: nucleic acid
        (C) STRANDEDNESS: single
        (D) TOPOLOGY: linear (xi) SEQUENCE DESCRIPTION: SEQ ID NO: 267:

```
TGTTGCGATC CCTTAAGCAT GGGTGCTATT AAAAAAATGG TGGAGAAGAA AATACCTGGA      60

ATTTACGTCT TATCTTTAGA GATTGGGAAG ACCCTGATGG AGGACGTGGA GAACAGCTTC     120

TTCTTGAATG TCAATTCCCA AGTAACAACA GTGTGTCAGG CACTTGCTAA GGATCCTAAA     180

TTGCAGCAAG GCTACAATGC TATGGGATTC TCCCAGGGAG GCCAATTTCT GAGGGCAGTG     240

GCTCAGAGAT GCCCTTCACC TCCCATGATC AATCTGATCT CGGTTGGGGG ACAACATCAA     300

GGTGTTTTTG GACTCCCTCG ATGCCCAGGA GAGAGCTCTC ACATCTGTGA CTTCATCCGA     360

AAAACACTGA ATGCTGGGGC GTACTCCAAA GTTGTTCAGG AACGCCTCGT GCAAGCCGAA     420

TACTGGCATG ACCCATAAAA GGAGGATGTG GATCGCAACA                          460
```

(2) INFORMATION FOR SEQ ID NO: 268:

(i) SEQUENCE CHARACTERISTICS:
        (A) LENGTH: 533 base pairs
        (B) TYPE: nucleic acid
        (C) STRANDEDNESS: single
        (D) TOPOLOGY: linear (xi) SEQUENCE DESCRIPTION: SEQ ID NO: 268:

```
TGTTGCGATC CGTTGATAGA ATAGCGACGT GGTAATGAGT GCATGGCACG CCTCCGACTT      60

ACCTTCGCCC GTGGGACCC CGAGTACGTC TACGGCGTCG TCACTTAGAG TACCCTCTGG     120

ACGCCCGGGC GCGTTCGATT TACCGGAAGC GCGAGCTGCA GTGGGCTTGC GCCCCCGGCC     180

AAATTCTTTG GGGGGTTTAA GGCCGCGGGG AATTTGAGGT ATCTCTATCA GTATGTAGCC     240

AAGTTGGAAC AGTCGCCATT CCCGAAATCG CTTTCTTTGA ATCCGCACCG CCTCCAGCAT     300

TGCCTCATTC ATCAACCTGA AGGCACGCAT AAGTGACGGT TGTGTCTTCA GCAGCTCCAC     360

TCCATAACTA GCGCGCTCGA CCTCGTCTTC GTACGCGCCA GGTCCGTGCG TGCGAATTCC     420

CAACTCCGGT GAGTTGCGCA TTTCAAGTTN CGAAACTGTT CGCCTCCACN ATTTGGCATG     480

TTCACGCATG ACACGGAATA AACTCGTCCA GTACCGGGAA TGGGATCGCA ACA            533
```

(2) INFORMATION FOR SEQ ID NO: 269:

(i) SEQUENCE CHARACTERISTICS:
        (A) LENGTH: 50 base pairs (B) TYPE: nucleic acid
                (C) STRANDEDNESS: single
                (D) TOPOLOGY: linear (xi) SEQUENCE DESCRIPTION: SEQ ID NO: 269:

TTTTTTTTTT TTCGCCTGAA TTAGCTACAG ATCCTCCTCA CAAGCGGTCA         50

(2) INFORMATION FOR SEQ ID NO: 270:

(i) SEQUENCE CHARACTERISTICS:
                (A) LENGTH: 519 base pairs
                (B) TYPE: nucleic acid
                (C) STRANDEDNESS: single
                (D) TOPOLOGY: linear (xi) SEQUENCE DESCRIPTION: SEQ ID NO: 270:

TGTTGCGATC CAAATAACCC ACCAGCTTCT TGCACACTTC GCAGAAGCCA CCGTCCTTTG        60

GCTGAGTCAC GTGAACGGTC AGTGCAAGCA GCCGCGTGCC AGAGCAGAGG TGCAGCATGC       120

TGCACACCAG CTCAGGGCTG ACCTCCTCCA GCAGGATGGA CAGGATGGAG CTGCCGTACG       180

TGTCCACCAC CTCCTGGCAC TCTTCCGACA GGGACTTCGG CAGCTTCGAG CACATTTTGT       240

CAAAAGCGTC GAGTATTTCT TTCTCAGTCT TGTTGTTGTC AATCAGCTTG GTCACCTCCT       300

TCACCAGGAA TTCACACACC TCACAGTAAA CATCAGACTT TGCTGGGACC TCGTGCTTCT       360

TAATGGGCTC CACCAGTTCC AGGGCAGGGA TGACATTCTT GGAGGCCACT TTGGCGGGGA       420

CCAGAGTCTG CATGGGCATC TCTTTCACCT CATCACAGAA CCCAACCAGC GCACAGATCT       480

CCTTGGGTTG CATGTGCATC ATCATCTGGG ATCGCAACA                            519

(2) INFORMATION FOR SEQ ID NO: 271:

(i) SEQUENCE CHARACTERISTICS:
                (A) LENGTH: 457 base pairs
                (B) TYPE: nucleic acid
                (C) STRANDEDNESS: single
                (D) TOPOLOGY: linear (xi) SEQUENCE DESCRIPTION: SEQ ID NO: 271:

TTTTTTTTTT TTCGGGCGGC GACCGGACGT GCACTCCTCC AGTAGCGGCT GCACGTCGTG        60

CCAATGGCCC GCTATGAGGA GGTGAGCGTG TCCGGCTTCG AGGAGTTCCA CCGGGCCGTG       120

GAACAGCACA ATGGCAAGAC CATTTTCGCC TACTTTACGG GTTCTAAGGA CGCCGGGGGG       180

AAAAGCTGGT GCCCCGACTG CGTGCAGGCT GAACCAGTCG TACGAGAGGG GCTGAAGCAC       240

ATTAGTGAAG GATGTGTGTT CATCTACTGC CAAGTAGGAG AAGAGCCTTA TTGGAAAGAT       300

CCAAATAATG ACTTCAGAAA AAACTTGAAA GTAACAGCAG TGCCTACACT ACTTAAGTAT       360

GGAACACCTC AAAAACTGGT AGAATCTGAG TGTCTTCAGG CCAACCTGGT GGAAATGTTG       420

TTCTCTGAAG ATTAAGATTT TAGGATGGCA ATCAAGA                             457

(2) INFORMATION FOR SEQ ID NO: 272:

(i) SEQUENCE CHARACTERISTICS:
                (A) LENGTH: 102 base pairs
                (B) TYPE: nucleic acid
                (C) STRANDEDNESS: single
                (D) TOPOLOGY: linear (xi) SEQUENCE DESCRIPTION: SEQ ID NO: 272:

TTTTTTTTTT TTGGGCAACA ACCTGAATAC CTTTTCAAGG CTCTGGCTTG GGCTCAAGCC        60

CGCAGGGGAA ATGCAACTGG CCAGGTCACA GGGCAATCAA GA                       102

(2) INFORMATION FOR SEQ ID NO: 273:

(i) SEQUENCE CHARACTERISTICS:
        (A) LENGTH: 455 base pairs
        (B) TYPE: nucleic acid
        (C) STRANDEDNESS: single
        (D) TOPOLOGY: linear (xi) SEQUENCE DESCRIPTION: SEQ ID NO: 273:

```
TTTTTTTTTT TTGGCAATCA ACAGGTTTAA GTCTTCGGCC GAAGTTAATC TCGTGTTTTT      60
GGCAATCAAC AGGTTTAAGT CTTCGGCCGA AGTTAATCTC GTGTTTTTGG CAATCAACAG     120
GTTTAAGTCT TCGGCCGAAG TTAATCTCGT GTTTTTGGCA ATCAACAGGT TTAAGTCTTC     180
GGCCGAAGTT AATCTCGTGT TTTTGGCAAT CAACAGGTTT AAGTCTTCGG CCGAAGTTAA     240
TCTCGTGTTT TTGGCAATCA ACAGGTTTAA GTCTTCGGCC GAAGTTAATC TCGTGTTTTT     300
GGCAATCAAG AGGTTTAAGT CTTCGGCCGA AGTTAATCTC GTGTTTTTGG CAATCAACAG     360
GTTTAAGTCT TCGGCCGAAN TTAATCTCGT GTTTTTGGCA ATCAACAGGT TTAANTCTTC     420
GGCCGAAGTT AATCTCGTGT TTTTGGCAAT CAANA                                455
```

(2) INFORMATION FOR SEQ ID NO: 274:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (xi) SEQUENCE DESCRIPTION: SEQ ID NO: 274:

```
TTTTTTTTTT TTGGCCAATA CCCTTGATGA ACATCAATGT GAAAATCCTC GGTAAAATAC      60
TGGCAAACCA AATCCAGCAG CACATCAAAA AGCTTATCCA CCATGATCAA GTGGGCTTCA     120
TCCCTGGGAT GCAAGGCTGG TTCAACATAA GAAAATCAAT AAATGTAATC CATCACATAA     180
ACAGAACCAA AGACAAAAAC CACATGATTA TCTCAATAGA TGCAGAAAAG GCCTTGGACA     240
AATTCAACAG CCCTTCATGC TAAACACTCT TAATAAACTA GATATTGATG GAATGTATCT     300
CAAAATAATA AGAGCTATTT ATGACAAACC CACAGCCAAT ATCATACTGA ATGGGCAAAG     360
ACTGGAAGCA TTCCCTTTGA AAACTGGCAC AAGACAAGGA TGCCCTCTCT CACCGCTCCT     420
ATTCAACATA GTATTGGAAG TTCTGGCCAG GGCAATCAAG A                        461
```

(2) INFORMATION FOR SEQ ID NO: 275:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (xi) SEQUENCE DESCRIPTION: SEQ ID NO: 275:

```
TTTTTTTTTT TTGGCCAACA CCAAGTCTTC CACGTGGGAG GTTTTATTAT GTTTTACAAC      60
CATGAAAACA TAGGAAGGTG GCTGTTACAG CAAACATTTC AGATAGACGA ATCGGCCAAG     120
CTCCCCAAAC CCCACCTTCA CAGCCTCTTC CACACGTCTC CCANAGATTG TTGTCCTTCA     180
CTTGCAAATT CANGGATGTT GGAAGTNGAC ATTTNNAGTN GCNGGAACCC CATCAGTGAA     240
NCANTAAGCA GAANTACGAT GACTTTGANA NACANCTGAT GAAGAACACN CTACNGANAA     300
CCCTTTCTNT CGTGTTANGA TCTCNNGTCC NTCACTAATG CGGCCCCCTG CNGGTCCACC     360
ATTTGGGAGA ACTCCCCCCN CGTTGGATCC CCCCTTGAGT NTCCCATTCT NGTCCCCCAN     420
```

```
ACCNGNCTTG NGNGNCANTN CNNCCTCNCA CCNTGTTTCC CTGNNGTNAA AATNNGTTTT        480

NCCGCCNCCC NAATTCCCAC CCNAATCACA GCGAANCCNG AAGGCCTTCN NAAGTGTTTA        540

ANGCCCNGNG GTTTCCTCNT NTANTTGCAG CCTACCCTCC CNCTTNNNNT TNCGNGTTGG        600

TCGCGCCCTG GNCNCGCCTN GTTCCTCTTT NNGGNNACAA CCTNGNTCNN NGGCNCNTCN        660

NNNCTNTTCC TNNNACTAGC TNGCCTNTCC NCNCCGNGGN NCANNGCACA TTNCNCNNAC        720

TNTGTNNCC                                                               729

(2) INFORMATION FOR SEQ ID NO: 276:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (xi) SEQUENCE DESCRIPTION: SEQ ID NO: 276:

TGACCTGACA TGTAGTAGAT ACTTAATAAA TATTTGTGGA ATGAATGGAT GAAGTGGAGT         60

TACAGAGAAA AATAGAAAAG TACAAATTGT TGTCAGTGTT TTGAAGGAAA ATTATGATCT        120

TTCCCAAAGT TCTGACTTCA TTCTAAGACA GGGTTAGTAT CTCCATACAT AATTTTACTT        180

GCTTTTGAAA ATCAAATGAG ATAATCTATT TAGATTGATA ATTTATTTAG ACTGGCTATA        240

AACTATTAAG TGCTAGCAAA TATACATTTT AATCTCATTT TCCACCTCTT GTGATATAGC        300

TATGTAGGTG TTGACTTTAA TGGATGTCAG GTCAATCCC                              339

(2) INFORMATION FOR SEQ ID NO: 277:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (xi) SEQUENCE DESCRIPTION: SEQ ID NO: 277:

TGACCTGACA TCCATAACAA AATCTTTCTC CATTATATTC TTCTAGGGGA ATTTCTTGAA         60

AAGCATCCAA AGGAAACAAA TGATGGTAAG ACCGTGCCAA GTGGGGAGCA GACACCAAAG        120

TAAGACCACA GATTTTACAT TCAACAGGTA GCTCACAGTA CTTTGCCCGA CACTGTGGGC        180

AGAAATAGCC TCCTAATGTA AGCCCTGGCT CAGTATTGCC ATCCAAATGC GCCATGCTGA        240

AAGAGGGTTT TGCATCCTGG TCAGATNAAG AAGCAATGGT GTGCTGAGGA AATCCCATAC        300

GAATAAGTGA GCATTCAGAA CTTGAGCTAG CAGGAGGAGG ACTAAGATGA TGTGTGAGCA        360

ACTCTTTGTA ATGGCTTTCA TCTAAAATAA CATGGTACGT GCCACCAGTT TCACGAGCAA        420

GTACAGTGCA AACGCGAACT TCTGCAGACA ATCCAATAAC AGATACTCTA ATTTTAGCTG        480

CCTTTAGGGT CTTGATTAAA TCATAAATAT TAGATGGATC GCAAGTTGTA AGGNTGCTAA        540

AAGATGATTA GTACTTCTCG ACTTGTATGT CCAGGCATGT TGTTTTAAAN TCTGCCTTAG        600

NCCCTGCTTA GGGGAATTTT TAAAGAAGAT GGCTCTCCAT GTTCANGGTC AATCACNAAT        660

TGCC                                                                    664

(2) INFORMATION FOR SEQ ID NO: 278:

(i) SEQUENCE CHARACTERISTICS:
        (A) LENGTH: 452 base pairs
        (B) TYPE: nucleic acid
        (C) STRANDEDNESS: single
        (D) TOPOLOGY: linear
```

(xi) SEQUENCE DESCRIPTION: SEQ ID NO: 278:

```
TGACCTGACA TTGAGGAAGA GCACACACCT CTGAAATTCC TTAGGTTCAG AAGGGCATTT      60

GACACAGAGT GGGCCTCTGA TAATTCATGA AATGCATTCT GAAGTCATCC AGAATGGAGG     120

CTGCAATCTG CTGTGCTTTG GGGGTTGCCT CACTGTGCTC CTGGATATCA CACAAAAGCT     180

GCAATCCTTC TTCTTCAACT AACATTTTGC AGTATTTGCT GGGATTTTTA CTGCAGACAT     240

GATACATAGC CCATAGTGCC CAGAGCTGAA CCTCTGGTTG AGAGAAGTTG CCAAGGAGCG     300

GGAAAAATGT CTTGAAAGAT CTATAGGTCA CCAATGCTGT CATCTTACAA CTTGAACTTG     360

GCCAATTCTG TATGGTTGCA TGCAGATCTT GGAGAAGAGT ACGCCTCTGG AAGTCACGGG     420

ATATCCAAAN CTGTCTGTCA GATGTCAGGT CA                                   452
```

(2) INFORMATION FOR SEQ ID NO: 279:

(i) SEQUENCE CHARACTERISTICS:
  (A) LENGTH: 274 base pairs
  (B) TYPE: nucleic acid
  (C) STRANDEDNESS: single
  (D) TOPOLOGY: linear (xi) SEQUENCE DESCRIPTION: SEQ ID NO: 279:

```
TTTTTTTTTT TTCGGCAAGG CAAATTTACT TCTGCAAAAG GGTGCTGCTT GCACTTTTGG      60

CCACTGCGAG AGCACACCAA ACAAAGTAGG GAAGGGGTTT TTATCCCTAA CGCGGTTATT     120

CCCTGGTTCT GTGTCGTGTC CCCATTGGCT GGAGTCAGAC TGCACAATCT ACACTGACCC     180

AACTGGCTAC TGTTTAAAAT TGAATATGAA TAATTAGGTA GGAAGGGGGA GGCTGTTTGT     240

TACGGTACAA GACGTGTTTG GGCATGTCAG GTCA                                 274
```

(2) INFORMATION FOR SEQ ID NO: 280:

(i) SEQUENCE CHARACTERISTICS:
  (A) LENGTH: 272 base pairs
  (B) TYPE: nucleic acid
  (C) STRANDEDNESS: single
  (D) TOPOLOGY: linear (xi) SEQUENCE DESCRIPTION: SEQ ID NO: 280:

```
TACCTGACAT GGAGAAATAA CTTGTAGTAT TTTGCGTGCA ATGGAATACT ATATGAGGGT      60

GAAAATGAAT GAACTAGCAA TGCGTGTATC AACATGAATA AATCCCCAAA ACATAATAAT     120

GTTGAATGGA AAAGGTGAGT TTCAGAAGGA TATATATGCC CTCTAAATCC ATTTATGTAA     180

ACCTTTAAAA AACTACATTA TTTATGGTCA TAAGTCCATC CAGAAAATAT TTAAAAACCT     240

ACATGGGATT GATAACTACT GATGTCAGGT CA                                   272
```

(2) INFORMATION FOR SEQ ID NO: 281:

(i) SEQUENCE CHARACTERISTICS:
  (A) LENGTH: 431 base pairs
  (B) TYPE: nucleic acid
  (C) STRANDEDNESS: single
  (D) TOPOLOGY: linear (xi) SEQUENCE DESCRIPTION: SEQ ID NO: 281:

```
TTTTTTTTTT TTGGCCAATA GCATGATTTA AACATTGGAA AAAGTCAAAT GAGCAATGCG      60

AATTTTTATG TTCTCTTGAA TAATCAAAAG AGTAGGCAAC ATTGGTTCCT CATTCTTGAA     120

TAGCATTAAT CAGAAAATAT TGCATAGCCT CTAGCCTCCT TAGAGTAGGT GTGCTCTCTC     180

AAATATATCA TAGTCCCACA GTTTATTTCA TGTATATTTT CTGCCTGAAT CACATAGACA     240
```

```
TTTGAATTTG CAACGCCTGA TGTAAATATA TAAATTCTTA CCAATCAGAA ACATAGCAAG      300

AAATTCAGGG ACTTGGTCAT YATCAGGGTA TGACAGCANA TCCCTGTARA AACACTGATA      360

CACACTCACA CACGTATGCA ACGTGGAGAT GTCGCYTTWW KKKTWYWCWM RMRYCRWCGN      420

AATCACTTAN N                                                          431

(2) INFORMATION FOR SEQ ID NO: 282:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (xi) SEQUENCE DESCRIPTION: SEQ ID NO: 282:

ATTCGATTCG ATGCTTGAGC CCAGGAGTTC AAGACTGCAG TGAGCCACTG CACTTCAGGC       60

TGGACAACAG AGCGAGTCCC TGTGCCAAAA AAAAAAAA                               98

(2) INFORMATION FOR SEQ ID NO: 283:

(i) SEQUENCE CHARACTERISTICS:
        (A) LENGTH: 764 base pairs
        (B) TYPE: nucleic acid
        (C) STRANDEDNESS: single
        (D) TOPOLOGY: linear (xi) SEQUENCE DESCRIPTION: SEQ ID NO: 283:

TTTTTTTTTT TTCGCAAGCA CGTGCACTTT ATTGAATGAC ACTGTAGACA GGTGTGTGGG       60

TATAAACTGC TGTATCTAGG GGCAGGACCA AGGGGGCAGG GGCAACAGCC CCAGCGTGCA      120

GGGCCASCAT TGCACAGTGG ASTGCAAAGG TTGCAGGCTA TGGGCGGCTA CTAVTAACCC      180

CGTTTTTCCT GTATTATCTG TAACATAATA TGGTAGACTG TCACAGAGCC GAATWCCART      240

HACASGATGA ATCCAAWGGT CAYGAGGATG CCCASAATCA GGGCCCASAT STTCAGGCAC      300

TTGGCGGTGG GGGCATASGC CTGKGCCCCG GTCACGTCSC CAACCWTCTY CCTGTCCCTA      360

CMCTTGAWTC CNCNCCTTNN NNTNCCNTNA TNTGCCCGCC CNCCTCCTNG NGTCAACCNG      420

NATCTGCACT ANCTCCCTCN CCCCTTNTGG ANTCTCNTCC TTCAANTAAN NTTATCCTTN      480

ACNCCCCCCT CNCCTTTCCC CTNCCNCCCN TNATCCCNGN NCCNCTATCA NTCNTNCCCT      540

CNCTNTNCTN CNNATCGTTC CNCCTNNTAA CTACNCTTTN NACNANNCCT CACTNATNCC      600

NGNNANTTCT TTCCTTCCCT CCCNACGCNN TGCGTGCGCC CGTCTNGCCT NNNCTNCGNA      660

CCCNNACTTT ATTTACCTTT NCACCCTAGC NCTCTACTTN ACCCANCCNC TCCTACCTCC      720

NGGNCCACCC NNCCCTNATC NCTNNCTCTN TCNNCTCNTT CCCC                      764

(2) INFORMATION FOR SEQ ID NO: 284:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (xi) SEQUENCE DESCRIPTION: SEQ ID NO: 284:

CAAGTGTAGG CACAGTGATG AAAGCCTGGA GCAAACACAA TCTGTGGGTA ATTAACGTTT       60

ATTTCTCCCC TTCCAGGAAC GTCTTGCATG GATGATCAAA GATCAGCTCC TGGTCAACAT      120

AAATAAGCTA GTTTAAGATA CGTTCCCCTA CACTTGA                              157

(2) INFORMATION FOR SEQ ID NO: 285:
```

(i) SEQUENCE CHARACTERISTICS:
    (A) LENGTH: 150 base pairs
    (B) TYPE: nucleic acid
    (C) STRANDEDNESS: single
    (D) TOPOLOGY: linear (xi) SEQUENCE DESCRIPTION: SEQ ID NO: 285:

```
ATTCGATTGT ACTCAGACAA CAATATGCTA AGTGGAAGAA GTCAGTCACA AAAGACCACA      60
TACTGTATGA CTTCATTTAC ATTAAGTGTC CAGAATAGGC AAATCCGTAG AGACAGAAAG     120
TAGATGAGCA GCTGCCTAGG TCTGAGTACA                                      150
```

(2) INFORMATION FOR SEQ ID NO: 286:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (xi) SEQUENCE DESCRIPTION: SEQ ID NO: 286:

```
ATTCGATTTT TTTTTTTTTG GCCATGATGA AATTCTTACT CCCTCAGATT TTTTGTCTGG      60
ATAAATGCAA GTCTCACCAC CAGATGTGAA ATTACAGTAA ACTTTGAAGG AATCTCCTGA     120
GCAACCTTGG TTAGGATCAA TCCAATATTC ACCATCTGGG AAGTCAGGAT GGCTGAGTTG     180
CAGGTCTTTA CAAGTTCGGG CTGGATTGGT CTGAGTACA                            219
```

(2) INFORMATION FOR SEQ ID NO: 287:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (xi) SEQUENCE DESCRIPTION: SEQ ID NO: 287:

```
ATTCGATTCT TGAGGCTACC AGGAGCTAGG AGAAGAGGCA TGGAACAAAT TTTCCCTCAT      60
ATCCATACTC AGAAGGAACC AACCCTGCTG ACACCTTAAT TTCAGCTTCT GGCCTCTAGA     120
ACTGTGAGAG AGTACATTTC TCTTGGTTTA AGCCAAGAGA ATCTGTCTTT TGGTACTTTA     180
TATCATAGCC TCAAGA                                                    196
```

(2) INFORMATION FOR SEQ ID NO: 288:

(i) SEQUENCE CHARACTERISTICS:
        (A) LENGTH: 199 base pairs
        (B) TYPE: nucleic acid
        (C) STRANDEDNESS: single
        (D) TOPOLOGY: linear (xi) SEQUENCE DESCRIPTION: SEQ ID NO: 288:

```
ATTCGATTTC AGTCCAGTCC CAGAACCCAC ATTGTCAATT ACTACTCTGT ARAAGATTCA      60
TTTGTTGAAA TTCATTGAGT AAAACATTTA TGATCCCTTA ATATATGCCA ATTACCATGC     120
TAGGTACTGA AGATTCAAGT GACCGAGATG CTAGCCCTTG GGTTCAAGTG ATCCCTCTCC     180
CAGAGTGCAC TGGACTGAA                                                 199
```

(2) INFORMATION FOR SEQ ID NO: 289:

(i) SEQUENCE CHARACTERISTICS:
        (A) LENGTH: 182 base pairs
        (B) TYPE: nucleic acid
        (C) STRANDEDNESS: single

```
            (D) TOPOLOGY: linear (xi) SEQUENCE DESCRIPTION: SEQ ID NO: 289:

ATTCGATTCT TGAGGCTACA AACCTGTACA GTATGTTACT CTACTGAATA CTGTAGGCAA      60

TAGTAATACA GAAGCAAGTA TCTGTATATG TAAACATTAA AAAGGTACAG TGAAACTTCA     120

GTATTATAAT CTTAGGGACC ACCATTATAT ATGTGGTCCA TCATTGGCCA AAAAAAAAAA     180

AA                                                                   182

(2) INFORMATION FOR SEQ ID NO: 290:

(i) SEQUENCE CHARACTERISTICS:
        (A) LENGTH: 1646 base pairs
        (B) TYPE: nucleic acid
        (C) STRANDEDNESS: single
        (D) TOPOLOGY: linear (xi) SEQUENCE DESCRIPTION: SEQ ID NO: 290:

GGCACGAGGA GAAATGTAAT TCCATATTTT ATTTGAAACT TATTCCATAT TTTAATTGGA      60

TATTGAGTGA TTGGGTTATC AAACACCCAC AAACTTTAAT TTTGTTAAAT TTATATGGCT     120

TTGAAATAGA AGTATAAGTT GCTACCATTT TTTGATAACA TTGAAAGATA GTATTTTACC     180

ATCTTTAATC ATCTTGGAAA ATACAAGTCC TGTGAACAAC CACTCTTTCA CCTAGCAGCA     240

TGAGGCCAAA AGTAAAGGCT TTAAATTATA ACATATGGGA TTCTTAGTAG TATGTTTTTT     300

TCTTGAAACT CAGTGGCTCT ATCTAACCTT ACTATCTCCT CACTCTTTCT CTAAGACTAA     360

ACTCTAGGCT CTTAAAAATC TGCCCACACC AATCTTAGAA GCTCTGAAAA GAATTTGTCT     420

TTAAATATCT TTTAATAGTA ACATGTATTT TATGGACCAA ATTGACATTT TCGACTATTT     480

TTTCCAAAAA AGTCAGGTGA ATTTCAGCAC ACTGAGTTGG GAATTTCTTA TCCCAGAAGA     540

CCAACCAATT TCATATTTAT TTAAGATTGA TTCCATACTC CGTTTTCAAG GAGAATCCCT     600

GCAGTCTCCT TAAAGGTAGA ACAAATACTT TCTATTTTTT TTTCACCATT GTGGGATTGG     660

ACTTTAAGAG GTGACTCTAA AAAAACAGAG AACAAATATG TCTCAGTTGT ATTAAGCACG     720

GACCCATATT ATCATATTCA CTTAAAAAAA TGATTTCCTG TGCACCTTTT GGCAACTTCT     780

CTTTTCAATG TAGGGAAAAA CTTAGTCACC CTGAAAACCC ACAAAATAAA TAAAACTTGT     840

AGATGTGGGC AGAAGGTTTG GGGGTGGACA TTGTATGTGT TTAAATTAAA CCCTGTATCA     900

CTGAGAAGCT GTTGTATGGG TCAGAGAAAA TGAATGCTTA GAAGCTGTTC ACATCTTCAA     960

GAGCAGAAGC AAACCACATG TCTCAGCTAT ATTATTATTT ATTTTTTATG CATAAAGTGA    1020

ATCATTTCTT CTGTATTAAT TTCCAAAGGG TTTTACCCTC TATTTAAATG CTTTGAAAAA    1080

CAGTGCATTG ACAATGGGTT GATATTTTTC TTTAAAAGAA AAATATAATT ATGAAAGCCA    1140

AGATAATCTG AAGCCTGTTT TATTTTAAAA CTTTTTATGT TCTGTGGTTG ATGTTGTTTG    1200

TTTGTTTGTT TCTATTTTGT TGGTTTTTTA CTTTGTTTTT TGTTTTGTTT TGTTTTGTTT    1260

KGCATACTAC ATGCAGTTCT TTAACCAATG TCTGTTTGGC TAATGTAATT AAAGTTGTTA    1320

ATTTATATGA GTGCATTTCA ACTATGTCAA TGGTTTCTTA ATATTTATTG TGTAGAAGTA    1380

CTGGTAATTT TTTTATTTAC AATATGTTTA AAGAGATAAC AGTTTGATAT GTTTTCATGT    1440

GTTTATAGCA GAAGTTATTT ATTTCTATGG CATTCCAGCG GATATTTTGG TGTTTGCGAG    1500

GCATGCAGTC AATATTTTGT ACAGTTAGTG GACAGTATTC AGCAACGCCT GATAGCTTCT    1560

TTGGCCTTAT GTTAAATAAA AAGACCTGTT TGGGATGTAT TTTTTATTTT TAAAAAAAAA    1620

AAAAAAAAAA AAAAAAAAAA AAAAA                                        1646
```

(2) INFORMATION FOR SEQ ID NO: 291:

(i) SEQUENCE CHARACTERISTICS:
        (A) LENGTH: 1851 base pairs
        (B) TYPE: nucleic acid
        (C) STRANDEDNESS: single
        (D) TOPOLOGY: linear (xi) SEQUENCE DESCRIPTION: SEQ ID NO: 291:

```
TCATCACCAT TGCCAGCAGC GGCACCGTTA GTCAGGTTTT CTGGGAATCC CACATGAGTA      60
CTTCCGTGTT CTTCATTCTT CTTCAATAGC CATAAATCTT CTAGCTCTGG CTGGCTGTTT     120
TCACTTCCTT TAAGCCTTTG TGACTCTTCC TCTGATGTCA GCTTTAAGTC TTGTTCTGGA     180
TTGCTGTTTT CAGAAGAGAT TTTTAACATC TGTTTTTCTT TGTAGTCAGA AAGTAACTGG     240
CAAATTACAT GATGATGACT AGAAACAGCA TACTCTCTGG CCGTCTTTCC AGATCTTGAG     300
AAGATACATC AACATTTTGC TCAAGTAGAG GGCTGACTAT ACTTGCTGAT CCACAACATA     360
CAGCAAGTAT GAGAGCAGTT CTTCCATATC TATCCAGCGC ATTTAAATTC GCTTTTTTCT     420
TGATTAAAAA TTTCACCACT TGCTGTTTTT GCTCATGTAT ACCAAGTAGC AGTGGTGTGA     480
GGCCATGCTT GTTTTTTGAT TCGATATCAG CACCGTATAA GAGCAGTGCT TTGGCCATTA     540
ATTTATCTTC ATTGTAGACA GCATAGTGTA GAGTGGTATT TCCATACTCA TCTGGAATAT     600
TTGGATCAGT GCCATGTTCC AGCAACATTA ACGCACATTC ATCTTCCTGG CATTGTACGG     660
CCTTTGTCAG AGCTGTCCTC TTTTTGTTGT CAAGGACATT AAGTTGACAT CGTCTGTCCA     720
GCACGAGTTT TACTACTTCT GAATTCCCAT TGGCAGAGGC CAGATGTAGA GCAGTCCTCT     780
TTTGCTTGTC CCTCTTGTTC ACATCCGTGT CCCTGAGCAT GACGATGAGA TCCTTTCTGG     840
GGACTTTACC CCACCAGGCA GCTCTGTGGA GCTTGTCCAG ATCTTCTCCA TGGACGTGGT     900
ACCTGGGATC CATGAAGGCG CTGTCATCGT AGTCTCCCCA AGCGACCACG TTGCTCTTGC     960
CGCTCCCCTG CAGCAGGGGA AGCAGTGGCA GCACCACTTG CACCTCTTGC TCCCAAGCGT    1020
CTTCACAGAG GAGTCGTTGT GGTCTCCAGA AGTGCCCACG TTGCTCTTGC CGCTCCCCCT    1080
GTCCATCCAG GGAGGAAGAA ATGCAGGAAA TGAAAGATGC ATGCACGATG GTATACTCCT    1140
CAGCCATCAA ACTTCTGGAC AGCAGGTCAC TTCCAGCAAG GTGGAGAAAG CTGTCCACCC    1200
ACAGAGGATG AGATCCAGAA ACCACAATAT CCATTCACAA ACAAACACTT TTCAGCCAGA    1260
CACAGGTACT GAAATCATGT CATCTGCGGC AACATGGTGG AACCTACCCA ATCACACATC    1320
AAGAGATGAA GACACTGCAG TATATCTGCA CAACGTAATA CTCTTCATCC ATAACAAAAT    1380
AATATAATTT TCCTCTGGAG CCATATGGAT GAACTATGAA GGAAGAACTC CCCGAAGAAG    1440
CCAGTCGCAG AGAAGCCACA CTGAAGCTCT GTCCTCAGCC ATCAGCGCCA CGGACAGGAR    1500
TGTGTTTCTT CCCCAGTGAT GCAGCCTCAA GTTATCCCGA AGCTGCCGCA GCACACGGTG    1560
GCTCCTGAGA AACACCCCAG CTCTTCCGGT CTAACACAGG CAAGTCAATA AATGTGATAA    1620
TCACATAAAC AGAATTAAAA GCAAAGTCAC ATAAGCATCT CAACAGACAC AGAAAAGGCA    1680
TTTGACAAAA TCCAGCATCC TTGTATTTAT TGTTGCAGTT CTCAGAGGAA ATGCTTCTAA    1740
CTTTTCCCCA TTTAGTATTA TGTTGGCTGT GGGCTTGTCA TAGGTGGTTT TTATTACTTT    1800
AAGGTATGTC CCTTCTATGC CTGTTTTGCT GAGGGTTTTA ATTCTCGTGC C             1851
```

(2) INFORMATION FOR SEQ ID NO: 292:

(i) SEQUENCE CHARACTERISTICS:
        (A) LENGTH: 286 base pairs
        (B) TYPE: nucleic acid

```
         (C) STRANDEDNESS: single
         (D) TOPOLOGY: linear (xi) SEQUENCE DESCRIPTION: SEQ ID NO: 292:

ACTGATGGAT GTCGCCGGAG GCGAGGGGCC TTATCTGATG CTCGGCTGCC TGTTCGTGAT      60

GTGCGCGGCG ATTGGGCTGT TTATCTCAAA CACCGCCACG GCGGTGCTGA TGGCGCCTAT     120

TGCCTTAGCG GCGGCGAAGT CAATGGGCGT CTCACCCTAT CCTTTTGCCA TGGTGGTGGC     180

GATGGCGGCT TCGGCGGCGT TTATGACCCC GGTCTCCTCG CCGGTTAACA CCCTGGTGCT     240

TGGCCCTGGC AAGTACTCAT TTAGCGATTT TGTCAAAATA GGCGTG                    286
```

What is claimed is:

1. An isolated nucleic acid molecule consisting of SEQ ID NO:147.

2. An isolated nucleic acid molecule consisting of SEQ ID NO:148.

3. An isolated nucleic acid molecule consisting of SEQ ID NO:152.

4. An isolated nucleic acid molecule consisting of SEQ ID NO:178.

5. An isolated nucleic acid molecule consisting of SEQ ID NO:239.

6. An isolated nucleic acid molecule consisting of SEQ ID NO:262.

7. A method for determining the presence of breast cancer in a patient comprising detecting within a biological sample obtained from the patient, at least one RNA molecule encoded by a nucleic acid molecule according to any one of claims 1–6, and therefrom determining the presence of breast cancer in the patient.

8. The method of claim 7, wherein the step of detecting comprises:

(a) preparing cDNA from RNA molecules within the biological sample; and (b) specifically amplifying the at least one RNA molecule, and therefrom determining the presence of breast cancer in the patient.

9. A method for monitoring the progression of breast cancer in a patient, comprising:

(a) detecting an amount within a biological sample obtained from the patient of at least one RNA molecule encoded by a nucleic acid molecule according to any one of claims 1–6 at a first point in time;

(b) repeating step (a) at a subsequent point in time; and (c) comparing the amounts of RNA molecules detected in steps (a) and (b), and therefrom monitoring the progression of breast cancer in the patient.

10. An isolated DNA or RNA molecule comprising a nucleotide sequence complementary to a DNA molecule according to any one of claims 1–6.

11. A recombinant expression vector comprising a DNA molecule according to any one of claims 1–6.

12. A host cell transformed or transfected with an expression vector according to claim 11.

13. The method of claim 7 wherein the biological sample is a portion of a breast tumor.

* * * * *

UNITED STATES PATENT AND TRADEMARK OFFICE
CERTIFICATE OF CORRECTION

PATENT NO.    : 6,225,054 B1
DATED         : May 1, 2001
INVENTOR(S)   : Tony N. Frudakis et al.

Page 1 of 1

It is certified that error appears in the above-identified patent and that said Letters Patent is hereby corrected as shown below:

Column 209, claim 7,
Line 34, "claims 1-6, and" should read -- claims 1-6; and --.

Column 210, claim 8,
Lines 17 and 18, "RNA molecule, and" should read -- RNA molecule; and --.

Column 210, claim 10,
Line 30, "molecule comprising a" should read -- molecule consisting of a --.
Line 31, "complementary to a DNA molecule" should read -- complementary to a nucleic acid molecule --.

Column 210, claim 11,
Lines 33 and 34, "vector comprising a DNA molecule" should read -- vector comprising an insert consisting of a nucleic acid molecule --.

Signed and Sealed this

Twelfth Day of March, 2002

Attest:

Attesting Officer

JAMES E. ROGAN
Director of the United States Patent and Trademark Office